(12) United States Patent
Yasumatsu et al.

(10) Patent No.: US 9,079,989 B2
(45) Date of Patent: *Jul. 14, 2015

(54) CHARGE CONTROL RESIN AND MANUFACTURING METHOD OF THE SAME

(71) Applicant: ORIENT CHEMICAL INDUSTRIES CO., LTD., Osaka (JP)

(72) Inventors: Masashi Yasumatsu, Osaka (JP); Kaori Inoue, Osaka (JP); Satoko Ozaki, Osaka (JP)

(73) Assignee: ORIENT CHEMICAL INDUSTRIES CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/507,414

(22) Filed: Oct. 6, 2014

(65) Prior Publication Data

US 2015/0025213 A1   Jan. 22, 2015

Related U.S. Application Data

(63) Continuation of application No. 14/115,450, filed as application No. PCT/JP2012/062685 on May 17, 2012, now Pat. No. 8,883,946.

(30) Foreign Application Priority Data

May 18, 2011   (JP) .................................. 2011-111796

(51) Int. Cl.
| | | |
|---|---|---|
| C08F 212/08 | (2006.01) | |
| G03G 9/087 | (2006.01) | |
| G03G 9/097 | (2006.01) | |
| C07C 69/92 | (2006.01) | |
| C08F 12/22 | (2006.01) | |
| C08F 12/32 | (2006.01) | |
| C08F 8/26 | (2006.01) | |
| C08F 8/42 | (2006.01) | |

(52) U.S. Cl.
CPC ............... C08F 212/08 (2013.01); C07C 69/92 (2013.01); C08F 12/22 (2013.01); C08F 12/32 (2013.01); G03G 9/08704 (2013.01); G03G 9/08722 (2013.01); G03G 9/08735 (2013.01); G03G 9/08791 (2013.01); G03G 9/09733 (2013.01); G03G 9/09775 (2013.01); Y10S 526/923 (2013.01)

(58) Field of Classification Search
USPC ........... 526/240, 260, 287, 292.9, 304, 307.3, 526/307.5, 312, 313, 347, 923, 342; 430/108.2, 108.4
See application file for complete search history.

(56) References Cited

U.S. PATENT DOCUMENTS

| | | | |
|---|---|---|---|
| 5,364,725 A | 11/1994 | Wilson et al. | |
| 5,612,161 A | 3/1997 | Watanabe et al. | |
| 8,883,946 B2 * | 11/2014 | Yasumatsu et al. | ........... 526/240 |
| 2009/0104554 A1 | 4/2009 | Otsuka et al. | |

(Continued)

FOREIGN PATENT DOCUMENTS

| | | |
|---|---|---|
| JP | 2 190869 | 7/1990 |
| JP | 3 105355 | 5/1991 |
| JP | 4 16858 | 1/1992 |

(Continued)

OTHER PUBLICATIONS

International Search Report Issued Aug. 21, 2012 in PCT/JP12/62685 Filed May 17, 2012.

(Continued)

*Primary Examiner* — Fred M Teskin
(74) *Attorney, Agent, or Firm* — Oblon, McClelland, Maier & Neustadt, L.L.P.

(57) ABSTRACT

Here is provided a charge control resin which is prompt in charge rising up, excellent in electrostatic charging propensity and easy in manufacturing. This charge control resin contains a polymer as an active ingredient having a constituent unit represented by following Formula (1)

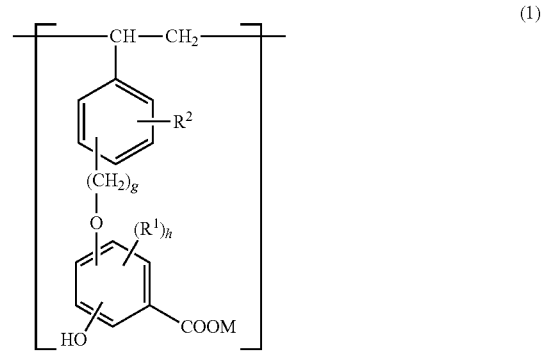

(1)

in the Formula (1), $R^1$ is independent of one another, and is a hydrogen atom, a hydroxyl group, a halogen atom, a carboxy-containing group, a straight-chained or branched alkyl group having 1-18 carbon atoms, or a straight-chained or branched alkoxy group having 1-18 carbon atoms; $R^2$ is a hydrogen atom, a hydroxyl group, a halogen atom, a carboxy-containing group, a straight-chained or branched alkyl group having 1-18 carbon atoms, or a straight-chained or branched alkoxy group having 1-18 carbon atoms; g is a number of 1-3; h is a number of 1-3; and M is a hydrogen atom, an alkali metal, a straight-chained or branched alkyl group having 1-18 carbon atoms, an ammonium radical or a mixture of any of these.

17 Claims, 18 Drawing Sheets

(56) References Cited

U.S. PATENT DOCUMENTS

2011/0159425 A1 6/2011 Itabashi et al.
2012/0295191 A1 11/2012 Itabashi et al.

FOREIGN PATENT DOCUMENTS

| | | |
|---|---|---|
| JP | 5 94018 | 4/1993 |
| JP | 8 179564 | 7/1996 |
| JP | 11 184165 | 7/1999 |
| JP | 2000 298379 | 10/2000 |
| JP | 2012 62381 | 3/2012 |

OTHER PUBLICATIONS

Machine translation of JP 05-094018A, published Apr. 1993.

* cited by examiner

Results of GPC Calculations

[Peak Information]
| Title | Time (min.) | Elution Volume (ml) | Molecular Weight | Height |
|---|---|---|---|---|
| Start | 6.292 | 3.775 | 1046748 | 1935 |
| Peak | 8.127 | 4.876 | 31130 | 17707 |
| End | 10.217 | 6.130 | 408 | 2265 |

Area : 1803637
Area %: 100.0000

[Average Molecular Weight]
 Number Average Molecular Weight (Mn) : 16160
 Weight Average Molecular Weight (Mw): 66496
 Mw/Mn : 4.11486
 % : 100.0000

Results of GPC Calculations

[Peak Information]
| Title | Time (min.) | Elution Volume (ml) | Molecular Weight | Height |
|---|---|---|---|---|
| Start | 7.408 | 4.445 | 112534 | 5637 |
| Peak | 8.660 | 5.196 | 11867 | 26121 |
| End | 10.333 | 6.200 | 299 | 6077 |

Area : 1867907
Area %: 100.0000

[Average Molecular Weight]
 Number Average Molecular Weight (Mn) : 6861
 Weight Average Molecular Weight (Mw): 14225
 Mw/Mn: 2.07333
 %: 100.0000

Results of GPC Calculations

[Peak Information]
| Title | Time (min.) | Elution Volume (ml) | Molecular Weight | Height |
|---|---|---|---|---|
| Start | 5.058 | 3.035 | 29639102 | 485 |
| Peak | 8.058 | 4.835 | 36187 | 17518 |
| End | 10.242 | 6.145 | 393 | 967 |

Area   : 2507489
Area %: 100.0000

[Average Molecular Weight]
Number Average Molecular Weight (Mn) : 22178
Weight Average Molecular Weight (Mw): 437142
Mw/Mn: 19.71023
%: 100.0000

CHARGE CONTROL RESIN AND MANUFACTURING METHOD OF THE SAME

CROSS REFERENCE TO RELATED APPLICATIONS

The present application is a continuation of U.S. patent application Ser. No. 14/115,450, now U.S. Pat. No. 8,883,946, which was filed on Nov. 4, 2013, and which is a 35 U.S.C. §371 national stage patent application of international patent application PCT/JP2012/062685, filed on May 17, 2012, which claims priority to Japanese patent application JP 2011-111796, filed on May 18, 2011.

TECHNICAL FIELD

The present invention relates to a charge control resin which is used to control an electric charge of a toner for electrophotography and that of a powdery paint for electrostatic powder coating, and which contains a polymer as its active ingredient having a constituent unit that is obtained from a particular styrene derivative or a monomer thereof.

BACKGROUND ART

Conventionally, a styrene-based resin has been widely used in household electric appliances, business machines, household utensils, food containers, packaging materials, toys and others for the reason that it is well balanced in price, transparency, mechanical strength, and formability. Also, it is possible to make a styrene-based resin through diverse methods and in general, and it is molded by means of injection molding, extrusion molding, blow molding, vacuum molding, or injection molding etc. The styrene-based resin is mainly produced by thermal polymerization or radical polymerization method, which latter makes use of an initiator. Typical manufacturing processes of it are bulk polymerization method and suspension polymerization method, and the former is more popular for the reasons of smaller product contamination with impurities such as dispersant, and lower cost with advantage.

A styrene monomer which becomes a raw material for a styrene-based resin is used as a starting material for various synthetic resins as well, and as such is an industrially important monomer. For example, in the field of electrophotography, it is used as a binding resin for toner, for example: polystyrene; poly-p-chlorostyrene; polyvinyl toluene; styrene-p-chlorostyrene copolymer; styrene-vinyl toluene copolymer; styrene-vinylnaphthalene copolymer; styrene-acrylic acid ester copolymer; styrene-methacrylic acid ester copolymer; styrene-α-chloromethacrylic acid methyl copolymer; styrene-acrylonitrile copolymer; styrene-vinylmethylether copolymer; styrene-vinylethylether copolymer; styrene-vinylmethyl ketone copolymer; styrene-butadiene copolymer; styrene-isoprene copolymer; styrene-acrylonitrile-indene copolymer; and a styrene-based copolymer which is made through a reaction between a styrene monomer and a comonomer selected from acrylamide, vinyl chloride, vinyl acetate, vinyl benzonate, ethylene, propylene, butylene, vinyl methyl ether, and vinyl isobutyl ether.

A toner for electrophotography is pre-added with a charge control agent for the purposes of increasing a rising speed of charging of the toner, improving the charging characteristics through sufficient charging of the toner and thereby properly controlling and stabilizing a electric charge amount, and increasing the rate of development of the electrostatic latent charge to thereby forming a clear image. Examples of the currently known charge control agent in the field of the technology in issue include, as negatively chargeable charge control agents, a metallic complex salt of mono azo dye, a metallic complex salt of hydroxyl carboxylic acid or dicarboxylic acid or an aromatic diol, and a resin containing an acidic component. Examples of the currently known positively chargeable charge control agents include nigrosine dyes, azine dyes, triphenylmethane-based dyes, quarternary ammonium salt, and polymers having quarternary ammonium salt on a side chain thereof. With respect to the above-named charge control agents, there is a room for improvement against the problems such as a difficulty in balancing between the image density and fogging, a difficulty in attaining a sufficient image density under a high humidity condition, a poor dispersion in the resin, and harmful effects imparted to the preservation stability, the fixity, and the anti-offset characteristic.

As a trial for attaining such improvements, there have been efforts made to improve the compatibility to the toner resin and to use a resin having charge control property as the toner for electrostatic charge image developing. For example, in Patent Document 1 there is described a toner for electrostatic charge image developing, which contains as the charge control agent a condensate of a salicylic acid having a substituent. Also, Patent Document 2 describes a toner for electrostatic charge image developing, which contains at least a salicylic acid resin. In addition, in Patent Document 3 there is described a toner for electrostatic charge image developing which contains a copolymer consisting at least of a styrene derivative and a styrene derivative having a carboxyl group and a hydroxyl group. Furthermore, Patent Document 4 describes a negatively chargeable toner containing a negatively chargeable charge control agent which consists of a polymer from a polymerizable composition containing a radical polymerizable monomer having a diphenyl group which may be substituted with a carboxyl group. Also, Patent Document 5 describes a negatively chargeable toner for electrophotography containing a charge control agent in an amount of 0.1 through 10 weight parts against 100 weight parts of a binder, wherein the charge control agent, represented by a particular chemical formula, consists of 1 through 30 weight % of sulfoalkyl(meth)acrylic acid monomers and 99 through 70 weight % of other vinyl type monomers which are capable of forming a copolymer with the former. Then, Patent Document 6 describes a toner for electrostatic image development containing a charge control agent which is a copolymer having a sulfonic acid group and which is obtained through a copolymerization among a vinyl aromatic carbon hydride and a (meth)acrylate and a sulfonic acid group-containing (meth)acrylamide, in which the copolymerization rate of the sulfonic acid group-containing (meth)acrylamide is 0.1-1.8 weight % and a weight average molecular weight of the copolymer is 2,000-15,000.

In recent years, there have been made improvements in performances of copiers and printers so that a higher resolution in the images provided by the copiers and printers are attained among other things, and also there has been an expansion of system such as electrophotography system including ones for low speed developing as well as those for high speed developing. It has been also desired to develop such a charge control agent that is designed to enable a better control of the charge risen up of the toner, to exhibit more excellent charging characteristics, to enable a formation of a clear and high resolution image, and to be manufactured with simplicity. Also, a good charge control agent has been demanded which can be used as a powdery paint, which is employed in electrostatic powder coating wherein an electrostatically charged powdery paint is adsorbed to the surface of a structure by the electric charge thereof and is burnt thereon.

PRIOR ART DOCUMENTS

Patent Documents

Patent Document 1: Japanese Patent Application Publication H02-190869
Patent Document 2: Japanese Patent Application Publication H03-105355
Patent Document 3: Japanese Patent Application Publication H04-016858
Patent Document 4: Japanese Patent Application Publication 2000-298379
Patent Document 5: Japanese Patent Application Publication H08-179564
Patent Document 6: Japanese Patent Application Publication H11-184165

SUMMARY OF THE INVENTION

Problems to be Solved by the Invention

The present invent was contrived in view of solving the above-mentioned problems, and it is a purpose of the present invention to provide a charge control resin which has a high compatibility with a toner resin, is high in the speed of being charged, exhibits excellent charging characteristics, and can be manufactured with simplicity.

Means to Solve the Problems

The charge control resin of the present invention, which is made in order to attain the above-mentioned object, is characterized by comprising a polymer as its active ingredient having a constituent unit represented by the following Formula (1):

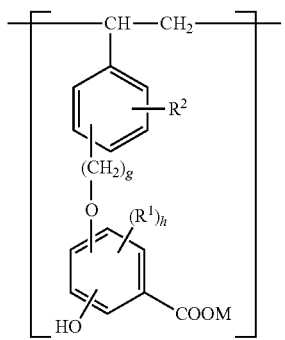

(1)

in the Formula (1), $R^1$ is independent of one another, and is a hydrogen atom, a hydroxyl group, a halogen atom, a carboxy-containing group, a straight-chained or branched alkyl group having 1-18 carbon atoms, or a straight-chained or branched alkoxy group having 1-18 carbon atoms; $R^2$ is a hydrogen atom, a hydroxyl group, a halogen atom, a carboxy-containing group, a straight-chained or branched alkyl group having 1-18 carbon atoms, or a straight-chained or branched alkoxy group having 1-18 carbon atoms; g is a number of 1-3; h is a number of 1-3; and M is a hydrogen atom, an alkali metal, a straight-chained or branched alkyl group having 1-18 carbon atoms, an ammonium radical or a mixture of any of these.

It is preferable that in the Formula (1) representing the constituent unit, $R^1$ is the hydrogen atom, the halogen atom, or the straight-chained or branched alkyl group having 1-18 carbon atoms.

It is preferable that in the Formula (1) representing the constituent unit, $R^2$ is the hydrogen atom.

It is preferable that in the Formula (1) representing the constituent unit, the hydroxyl group takes an ortho position of the —COOM group.

It is preferable that in the Formula (1) of the constituent unit M is the hydrogen atom.

It is preferable that the charge control resin contains a copolymer wherein the polymer has a constituent unit represented by the Formula (1) and a constituent unit obtained from a vinyl group-containing monomer.

Examples of the vinyl group-containing monomer, which is a monomer capable of copolymerizing with styrene derivative (ex. a styrene monomer), include a substituted or non-substituted aromatic vinyl monomer such as styrene, α-methylstyrene, p-methylstyrene, and acrylonitrile, methacrylonitrile, acrylic acid, methyl acrylate, methacrylic acid, methyl methacrylate, and a vinyl monomer such as vinyl acrylate, and also maleic anhydride and maleimide.

It is preferable that the constituent unit obtained from the vinyl group-containing monomer is one as represented by the following Formula (2):

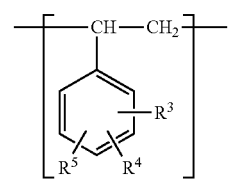

(2)

in the Formula (2), $R^3$, $R^4$ and $R^5$ are independent of one another, and are a hydrogen atom, an alkyl group, a halogen atom, or an alkoxy group.

It is preferable that the vinyl group-containing monomer is styrene.

It is preferable that the charge control resin is such that the polymer is a product of a copolymerization reaction by which a styrene derivative represented by the following Formula (3) reacts with the afore-mentioned vinyl group-containing monomer in the presence of a copolymerization initiator:

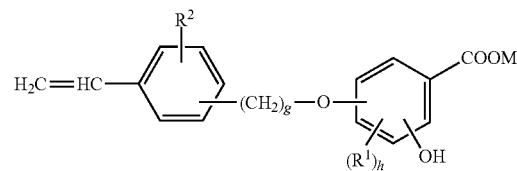

(3)

in the Formula (3), $R^1$ is independent of one another, and is a hydrogen atom, a hydroxyl group, a halogen atom, a carboxy-containing group, a straight-chained or branched alkyl group having 1-18 carbon atoms, or a straight-chained or branched alkoxy group having 1-18 carbon atoms, $R^2$ is a hydrogen atom, a hydroxyl group, a halogen atom, a carboxy-containing group, a straight-chained or branched alkyl group having 1-18 carbon atoms, or a straight-chained or branched alkoxy group having 1-18 carbon atoms, g is a number of 1-3, h is a number of 1-3, M is a hydrogen atom, an alkali metal, a straight-chained or branched alkyl group having 1-18 carbon atoms, an ammonium radical or a mixture of any of these.

The afore-mentioned charge control resin is preferably such that the afore-mentioned polymer is a copolymer which contains the constituent unit represented by the Formula (1) in an amount of 0.01 to 20 mol %.

The charge control resin is preferably such that the aforesaid polymer has a glass transition temperature of 70° C. through 150° C.

The charge control resin is preferably of a kind such that the afore-mentioned polymer shows weight decrease in a measurement of its weight at temperatures from 300° C. to 400° C. by a differential thermal thermogravimetric analysis.

The charge control resin is preferably of a kind such that the afore-mentioned polymer has a number average molecular weight (Mn) of 5000-30000 and a weight average molecular weight (Mw) of 4000-300000 as measured by gel permeation chromatography respectively, and more preferably the molecular weight distribution (Mw/Mn) is controlled to be 1-15.

It is preferable that the charge control resin is such that the afore-mentioned polymer has a volume resistive value of $0.1 \times 10^{16} - 7.0 \times 10^{17}$ Ωcm.

The charge control agent of the present invention is characteristic in that it contains as an active ingredient a styrene derivative represented by the following Formula (3) or contains as an active ingredient a charge control resin which is a polymerization product of the styrene derivative:

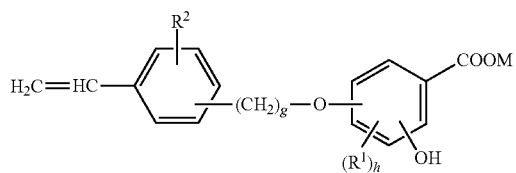

(3)

in the Formula (3), $R^1$ is independent of one another, and is a hydrogen atom, a hydroxyl group, a halogen atom, a carboxy-containing group, a straight-chained or branched alkyl group having 1-18 carbon atoms, or a straight-chained or branched alkoxy group having 1-18 carbon atoms; $R^2$ is a hydrogen atom, a hydroxyl group, a halogen atom, a carboxy-containing group, a straight-chained or branched alkyl group having 1-18 carbon atoms, or a straight-chained or branched alkoxy group having 1-18 carbon atoms; g is a number of 1-3; h is a number of 1-3; and M is a hydrogen atom, an alkali metal, a straight-chained or branched alkyl group having 1-18 carbon atoms, an ammonium radical or a mixture of any of these.

A method of using the charge control resin of the present invention is characteristic in that the charge control resin containing as an active ingredient a polymer having a constituent unit represented by the following Formula (1) is used for controlling the charge:

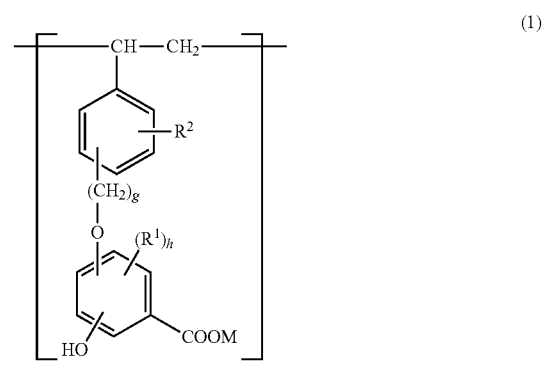

(1)

in the Formula (1), $R^1$ is independent of one another, and is a hydrogen atom, a hydroxyl group, a halogen atom, a carboxy-containing group, a straight-chained or branched alkyl group having 1-18 carbon atoms, or a straight-chained or branched alkoxy group having 1-18 carbon atoms; $R^2$ is a hydrogen atom, a hydroxyl group, a halogen atom, a carboxy-containing group, a straight-chained or branched alkyl group having 1-18 carbon atoms, or a straight-chained or branched alkoxy group having 1-18 carbon atoms; g is a number of 1-3; h is a number of 1-3; and M is a hydrogen atom, an alkali metal, a straight-chained or branched alkyl group having 1-18 carbon atoms, an ammonium radical or a mixture of any of these.

It is preferable that the method of using the charge control resin is such that the afore-mentioned polymer has a constituent unit represented by the Formula (1) and a constituent unit represented by the following Formula (2), which is obtained from a vinyl group-containing monomer:

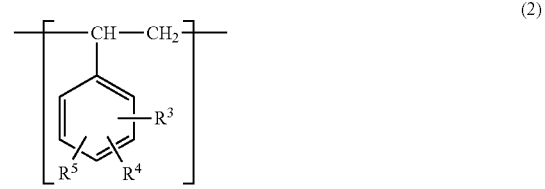

(2)

in the Formula (2), $R^3$, $R^4$ and $R^5$ are independent of one another, and are a hydrogen atom, an alkyl group, a halogen atom, or an alkoxy group.

A method for manufacturing the charge control resin of the present invention is characteristic in that, the method comprises a step for obtaining a polymer in a reaction system involving as a monomer at least a styrene derivative represented by the following Formula (3), the monomer is polymerized to thereby obtain a charge control resin which contains the thus obtained polymer as an active ingredient:

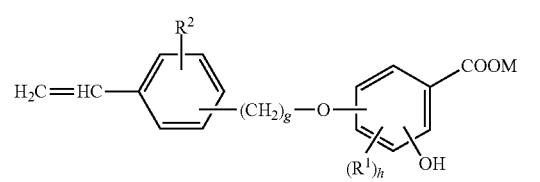

(3)

in the Formula (3), $R^1$ is independent of one another, and is a hydrogen atom, a hydroxyl group, a halogen atom, a carboxy-containing group, a straight-chained or branched alkyl group having 1-18 carbon atoms, or a straight-chained or branched alkoxy group having 1-18 carbon atoms; $R^2$ is a hydrogen atom, a hydroxyl group, a halogen atom, a carboxy-containing group, a straight-chained or branched alkyl group having 1-18 carbon atoms, or a straight-chained or branched alkoxy group having 1-18 carbon atoms; g is a number of 1-3; h is a number of 1-3; and M is a hydrogen atom, an alkali metal, a straight-chained or branched alkyl group having 1-18 carbon atoms, an ammonium radical or a mixture of any of these.

In the method for manufacturing the charge control resin, the monomer preferably involves a vinyl group-containing monomer represented by the following Formula (4):

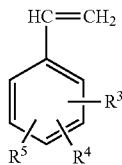

(4)

in the Formula (4), $R^3$, $R^4$ and $R^5$ are independent of one another, and are a hydrogen atom, a straight-chained or branched alkyl group having 1-8 carbon atoms, a straight-chained or branched alkoxy group having 1-8 carbon atoms, or a halogen atom.

Effects of the Invention

The charge control resin of the present invention is excellent in charge controllability, and significantly prompt in charge rise-up, and can be charged negatively and can retain the electric charge amount uniformly and stably at high level for a long time. For this reason it is possible to dependably obtain an output image which is clear and of a high resolution. This charge control resin can be used effectively for diverse toners including ones for low speed copying and ones for high speed copying. Also, this charge control resin can be employed as the powdery paint for use in electrostatic powder coating.

The polymer to constitute the active ingredient of this charge control resin has a constituent unit represented by the Formula (1), which has a charge control function and a polymerization function, and the constituent unit has a repetitive unit obtained from styrene derivatives. Or else it has the repetitive units consisting of the constituent units of the identical structure as a result of a reaction after a polymerization and a synthesis of a polymer. This polymer can have a constituent unit obtained from a vinyl group-containing monomer in addition to the afore-mentioned repetitive unit. A copolymer having the constituent unit represented by the Formula (1) and a constituent unit obtained from a vinyl group-containing monomer can be used as an effective ingredient of a charge control resin on account of its charge imparting property and charge controllability linked to the fact that they co-own the phenyl skeleton (benzene ring skeleton) and the —COOM group in the repetitive unit, especially the phenyl group, the carboxyl group (—COOM) and the hydroxyl group (—OH), and thus the polymer is usable as a charge control resin. Also, the styrene derivative to constitute the repetitive unit of the polymer can be used as the charge control monomer which constitutes the polymer of the charge control resin (styrene-based resin) containing the carboxyl group and the hydroxyl group. Furthermore, it can be used independently as a charge control agent.

The charge control agent of the present invention is high in compatibility toward a toner resin, can be uniformly dispersed, can exhibit a sufficiently high chargeability, and also is excellent in fastness and thus can retain the chargeability sustainably.

According to the method of manufacturing the charge control resin of the present invention, it is possible to make conveniently a styrene-based resin having a good charge controlling function.

MODE FOR CARRYING OUT THE INVENTION

Figure 1:
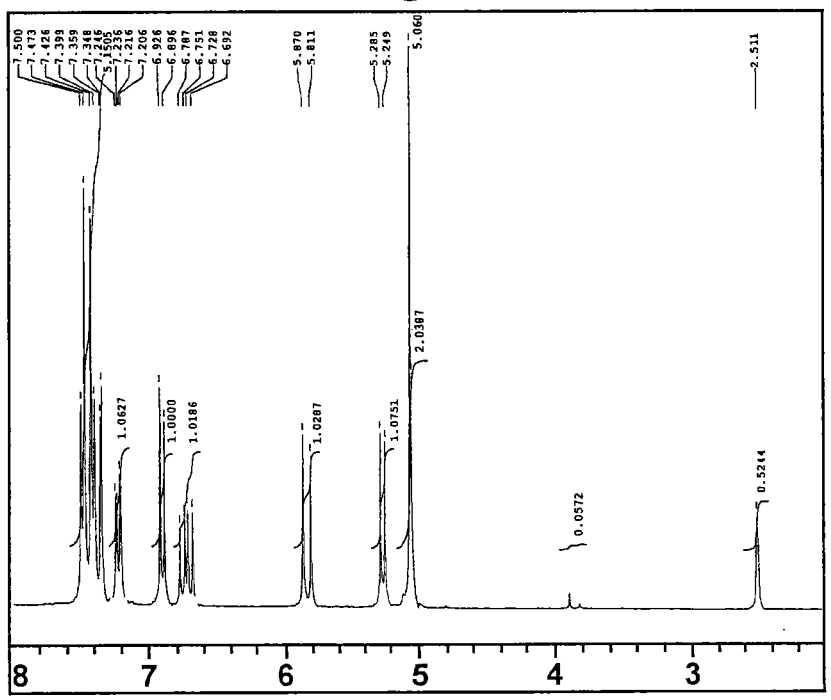
FIG. 1 is a drawing showing a chart of nuclear magnetic resonance spectrum of a styrene derivative of Example A1, used for the charge control resin to which the present invention is applied.

Hereunder, the examples, wherein the present invention is embodied, will be explained in detail. However it shall not be understood that the scope of the present invention is limited by the examples.

The charge control resin of the present invention contains as an active ingredient: a polymer having a repetition of a constituent unit represented by the afore-given Formula (1), which is obtained from a styrene derivative represented by the Formula (3) and used as a monomer; or a polymer having a repetition of a constituent unit represented by the identical Formula (1), this constituent unit of the identical structure being obtained as a result of a reaction after a polymerization and a synthesis of the polymer. The constituent unit represented by the Formula (1) and the styrene derivative to constitute the constituent unit co-own a phenyl skeleton (i.e., styrene structure) having a vinyl group in the same molecule and a phenyl skeleton (i.e., a skeleton structure of aromatic oxycarbonic acid) having a —COOM group and a hydroxyl group in the same molecule. Further, the repeated unit represented by the Formula (1) and the styrene derivative are of a structure wherein the phenyl skeletons are connected with each other through —$CH_2$—O—, —$CH_2CH_2$—O—, or —$CH_2CH_2CH_2$—O—.

This Styrene derivative's phenyl skeleton (benzene ring skeleton) having the vinyl group is an important skeleton to perform the polymerization function of the styrene derivative. Further, the combination of the phenyl group having a —COOM group and a hydroxyl group with —$CH_2$—O—, —$CH_2CH_2$—O—, or —$CH_2CH_2CH_2$—O— makes an important skeleton responsible to the exertion of charge imparting function. Then, the phenyl skeleton having a —COOM group and a hydroxyl group is a skeleton having a hydrogen bond within a molecule and between molecules which is thought to contribute to electric charging and having a function of ligand. The interplay between the two phenyl skeletons improves the electric charge retention characteristic. It is preferable that the —COOM group and the hydroxyl group (—OH) take an ortho position with respect to each other.

Therefore, the styrene derivative used in the present invention is used as a monomer for a polymer, and is useful as a styrene monomer which can control the charge controllability. The polymer including the constituent unit obtained from this styrene derivative makes a charge control resin which becomes an active ingredient for the charge control agent. This charge control resin (styrene-based resin) can be a homopolymer having the constituent unit obtained from the styrene derivative, or can be a copolymer which is a product of polymerization between the styrene derivative and another monomer. The charge control resin can contain another styrene resin besides these polymers. The constituent unit of this charge control resin is a constituent unit possessed by a polymer which is made by polymerizing or copolymerizing with the styrene derivative, and can be one obtained through a polymerization involving the styrene derivative as at least one monomer element. When used as the charge control agent, an improved dispersibility through the resin is enjoyed on account of the structural similarity to the resin, which is by virtue of the substituent effect of the styrene derivative.

The constituent unit possessed by the polymer which becomes the active ingredient of the charge control resin of the present invention is represented by the following Formula (1):

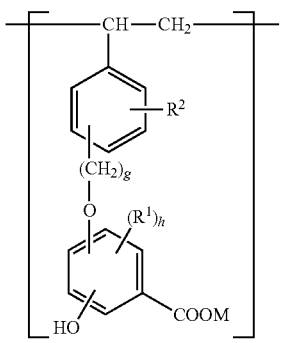

(1)

In the Formula (1), the substituent $R^1$ is independent of one another, and may for example be: a hydrogen atom; a hydroxyl group; a halogen atom such as F, Cl and Br; a carboxy-containing group such as COOH, an alkaline metal salt like COOLi, COONa and COOK, and $COONH_4$ or a mixture of any of these, a straight-chained or a branched alkyl ester group having 1-8 carbon atoms like $COOCH_3$, $COOC_2H_5$, $COOC_3H_7$, $COOC_4H_9$, $COOC_5H_{11}$, and $COOC_8H_{17}$; a straight-chained or branched alkyl group having 1-18 carbon atoms such as methyl group, ethyl group, n-propyl group, isopropyl group, n-butyl group, isobutyl group, sec-butyl group, tert-butyl group, n-pentyl group, isopentyl group, hexyl group, heptyl group, and octyl group; or a straight-chained or branched alkoxy group having 1-18 carbon atoms such as methoxy group, ethoxy group, n-propoxy group, isopropoxy group, n-butoxy group, isobutoxy group, sec-butoxy group, tert-butoxy group, n-pentoxy group, isopentoxy group, hexyloxy group, heptoxy group, octyloxy group, and 2-ethylhexyloxy group.

$R^1$ is preferably the hydrogen atom, the halogen atom, or the straight-chained or branched alkyl group having 1-18 carbon atoms. Among these hydrogen atom and straight-chained or branched alkyl group having 1-18 carbon atoms are more preferable. In particular, methyl group, ethyl group, n-propyl group, isopropyl group, n-butyl group, isobutyl group, sec-butyl group, tert-butyl group, n-pentyl group, isopentyl group, hexyl group, heptyl group and octyl group are noted.

In the Formula (1), the substituent $R^2$ may for example be: a hydrogen atom; a hydroxyl group; a halogen atom such as F, Cl and Br; a carboxy-containing group such as COOH, an alkaline metal salt like COOLi, COONa and COOK, and $COONH_4$ or a mixture of any of these, a straight-chained or a branched alkyl ester group having 1-8 carbon atoms like $COOCH_3$, $COOC_2H_5$, $COOC_3H_7$, $COOC_4H_9$, $COOC_5H_{11}$, and $COOC_8H_{17}$; a straight-chained or branched alkyl group having 1-18 carbon atoms such as methyl group, ethyl group, n-propyl group, isopropyl group, n-butyl group, isobutyl group, sec-butyl group, tert-butyl group, n-pentyl group, isopentyl group, hexyl group, heptyl group, and octyl group; or a straight-chained or branched alkoxy group having 1-18 carbon atoms such as methoxy group, ethoxy group, n-propoxy group, isopropoxy group, n-butoxy group, isobutoxy group, sec-butoxy group, tert-butoxy group, n-pentoxy group, isopentoxy group, hexyloxy group, heptoxy group, octyloxy group, and 2-ethylhexyloxy group. Of these, the hydrogen atom is more preferable.

In the Formula (1), M may for example be: a hydrogen atom; an alkaline metal such as Li, Na and K; a straight-chained or branched alkyl group having 1-18 carbon atoms such as $CH_3$, $C_2H_5$, $C_3H_7$, $C_4H_9$, $C_5H_{11}$, $C_8H_{17}$, $C_{10}H_{21}$, $C_{12}H_{25}$, and $C_{18}H_{37}$; an ammonium radical like $NH_4^+$ or mono-, di-, tri- or tetra-alkyl ammonium ion having 1-12 carbon atoms or a mixture of any of these. As for the alkyl group, a straight-chained or branched alkyl group having 1-8 carbon atoms is preferable.

In the Formula (1), g is an integer 1, 2 or 3, preferably 1 or 2, and most preferably 1. Therein, h is an integer of 1, 2 or 3, and preferably 1.

Therefore, it is preferable that the constituent unit is one represented by the following Formula (5).

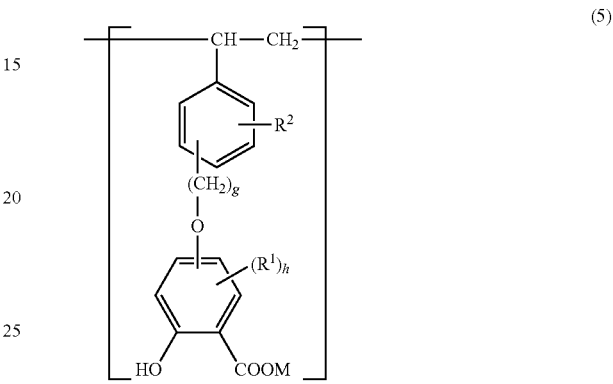

(5)

in this Formula (5), $R^1$, $R^2$, M, g, and h are defined the same as above.

It is noted that the hydroxyl group (—OH group) of the constituent unit represented by the Formula (1) and/or the Formula (5) includes free ones or instances wherein the hydrogen atom is substituted by an alkaline metal such as Li, Na and K, or by an ammonium radical like $NH_4^+$ or mono-, di-, tri- or tetra-alkyl ammonium ion having 1-12 carbon atoms or a mixture of any of these.

A polymer having a constituent unit represented by the Formula (1) and/or the Formula (5) possesses a charge control function and thus applicable as a charge control resin. The longer the carbon chain of the alkyl group in $R^1$ of the constituent unit of this polymer represented by Formula (1) and/or Formula (5) is, the higher the hydrophobicity of the polymer gets; as a result this polymer has a high saturation electrostatic propensity and thus has a good environmental stability. Therefore, a polymer obtained from a styrene derivative wherein the $R^1$ in the styrene derivative represented by Formula (3) and/or Formula (6), which is the charge control monomer making the constituent unit of the polymer, is butyl group, especially tert-butyl group, will exhibit a good electrostatic propensity.

It is preferable that this polymer is a copolymer which contains the constituent unit obtained from the styrene derivative to be a degree of 0.01-20 mol %. Furthermore, in consideration of the electrostatic propensity, it is preferable that this content is 1-15 mol %, and more preferably 2-9.5 mol %.

It is possible that the charge control resin (styrene-based resin) of the present invention possesses a constituent unit obtained from a vinyl group-containing monomer in addition to the constituent unit represented by the Formula (1) and/or the Formula (5). By virtue of possessing the constituent unit obtained from vinyl group-containing monomer, the resin can have a function of suitably controlling the electrostatic propensity. It is possible to use as charge control agents the copolymer having the constituent unit represented by the Formula (1) and/or the Formula (5) and the constituent unit obtained from vinyl group-containing monomer as well as the charge control resin (styrene-based resin) possessing such copolymer. It is preferred that the constituent unit obtained from the vinyl group-containing monomer is one represented by the following Formula (2).

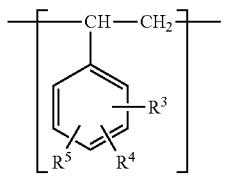

(2)

in this Formula (2), $R^3$, $R^4$ and $R^5$ are independent of one another, and are a hydrogen atom, an alkyl group, a halogen atom, or an alkoxy group.

The charge control function is improved the more with higher dispersibility through the target resin used, as occasioned by, for example, smaller particle size, and with higher compatibility to the receiving resin; the greatest charge control function is attained if the dispersion through the resin is carried out at molecular level.

The method for manufacturing the charge control resin (styrene-based resin) according to the present invention, is a method including at least a step to produce a polymer having a constituent unit represented by the Formula (1). Further, it is possible to turn the carboxyl group, which is a constituent unit, to an alkyl ester by a known method by, for example, reacting the styrene derivative wherein M of the —COOM group is either a hydrogen atom or an alkaline metal with an alcohol having 1-18 carbon atoms. One specific method for manufacturing the charge control resin, wherein a polymer having a constituent unit represented by the Formula (1), is a copolymer (Method A) is a method which includes a step to synthesize a styrene derivative by reacting vinylphenyl alkylene halide with dihydroxy aromatic carboxylic acid and a step for copolymerizing the thus obtained styrene derivative with other monomers. Another method (Method B) includes a step to copolymerize vinylphenyl alkylene halide with other monomers and a step to react the thus obtained copolymer with dihydroxy aromatic carboxylic acid or dihydroxy aromatic carboxylic acid alkyl ester.

In the present application, Method A as the chief examples will be explained. However it is possible in Method B as well to conduct the copolymerization step and the step to react the alkylene halide with the dihydroxy aromatic carboxylic acid while suitably controlling the reaction in response to the chemical properties.

Method A, which is one of the methods for manufacturing the charge control resin (styrene-based resin) of the present invention, is a method which includes a step to obtain a polymer by polymerizing a monomer which constitutes the constituent unit represented by the Formula (1) in a reaction system which has at least the styrene derivative as the monomer. It is, however, possible to conduct the alkyl-esterification after the synthesis of the polymer. In other words, it is possible to include a step to alkyl-esterify the —COOM group in the constituent unit represented by the Formula (1) and/or (5) by means of a known method such as reacting with an alcohol having 1-18 carbon atoms. A preferable method is such that the charge control monomer which is the styrene derivative constituting the constituent unit represented by the Formula (1) is mixed with a polymerization initiator and the monomer is polymerized.

A styrene derivative to be used as the monomer is represented by the following Formula (3).

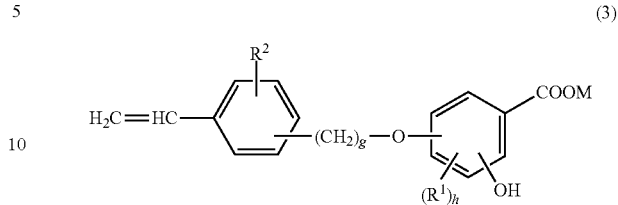

(3)

The substituent $R^1$ in Formula (3) is independent of one another, and is for example a hydrogen atom; a hydroxyl group; a halogen atom such as F, Cl and Br; a carboxy-containing group such as COOH, an alkaline metal salt like COOLi, COONa and COOK, and COONH$_4$ or a mixture of any of these, a straight-chained or a branched alkyl ester group having 1-8 carbon atoms like COOCH$_3$, COOC$_2$H$_5$, COOC$_3$H$_7$, COOC$_4$H$_9$, COOC$_5$H$_{11}$, and COOC$_8$H$_{17}$; a straight-chained or branched alkyl group having 1-18 carbon atoms such as methyl group, ethyl group, n-propyl group, isopropyl group, n-butyl group, isobutyl group, sec-butyl group, tert-butyl group, n-pentyl group, isopentyl group, hexyl group, heptyl group, and octyl group; or a straight-chained or branched alkoxy group having 1-18 carbon atoms such as methoxy group, ethoxy group, n-propoxy group, isopropoxy group, n-butoxy group, isobutoxy group, sec-butoxy group, tert-butoxy group, n-pentoxy group, isopentoxy group, hexyloxy group, heptoxy group, octyloxy group, and 2-ethylhexyloxy group.

$R^1$ is preferably the hydrogen atom, the halogen atom, or the straight-chained or branched alkyl group having 1-18 carbon atoms. Among these, the hydrogen atom and the straight-chained or branched alkyl group having 1-18 carbon atoms are more preferable. In particular, methyl group, ethyl group, n-propyl group, isopropyl group, n-butyl group, isobutyl group, sec-butyl group, tert-butyl group, n-pentyl group, isopentyl group, hexyl group, heptyl group and octyl group are noted.

The substituent $R^2$ may for example be: a hydrogen atom; a hydroxyl group; a halogen atom such as F, Cl and Br; a carboxy-containing group such as COOH, an alkaline metal salt like COOLi, COONa and COOK, and COONH$_4$ or a mixture of any of these, a straight-chained or branched alkyl ester group having 1-8 carbon atoms like COOCH$_3$, COOC$_2$H$_5$, COOC$_3$H$_7$, COOC$_4$H$_9$, COOC$_5$H$_{11}$, and COOC$_8$H$_{17}$; a straight-chained or branched alkyl group having 1-18 carbon atoms such as methyl group, ethyl group, n-propyl group, isopropyl group, n-butyl group, isobutyl group, sec-butyl group, tert-butyl group, n-pentyl group, isopentyl group, hexyl group, heptyl group, and octyl group; or a straight-chained or branched alkoxy group having 1-18 carbon atoms such as methoxy group, ethoxy group, n-propoxy group, isopropoxy group, n-butoxy group, isobutoxy group, sec-butoxy group, tert-butoxy group, n-pentoxy group, isopentoxy group, hexyloxy group, heptoxy group, octyloxy group, and 2-ethylhexyloxy group. Of these, the hydrogen atom is more preferable.

M is, for example, selected from: a hydrogen atom; an alkali metal such as Li, Na and K; an ammonium radical exemplified by NH$_4^+$ and mono-, di-, tri- or tetra-alkyl ammonium ion having an alkyl group with 1-12 carbon atoms or a mixture of any of these, and a straight-chained or branched alkyl group having 1-18 carbon atoms such as CH$_3$, C$_2$H$_5$, $C_3H_7$, $C_4H_9$, $C_5H_{11}$, $C_8H_{17}$, $C_{10}H_{21}$, $C_{12}H_{25}$, and $C_{18}H_{37}$. As for the alkyl group, the straight-chained or branched alkyl group having 1-8 carbon atoms is preferable.

In Formula (3), g is exemplified as an integer 1, 2 or 3, preferably 1 or 2, and most preferably 1. Therein, h is exemplified as an integer 1, 2 or 3, and preferably 1.

Among others, it is preferable if, as shown in under-shown Formula (6), the hydroxyl group takes an ortho position of the —COOM group, because a synergistic effect of the —COOM group and the hydroxyl group becomes stronger, which contributes to the charging effect. By polymerizing this styrene derivative, the constituent unit represented by the Formula (5) is obtained.

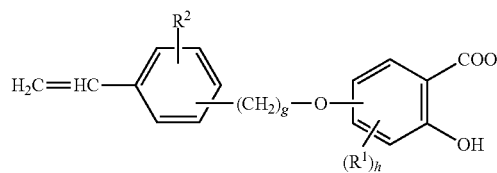

(6)

In the Formula (6), $R^2$, g, h and M are respectively the same as above.

It is noted that the hydroxyl group (—OH group) of the constituent unit represented by the Formula (3) and/or the Formula (6) includes instances wherein the hydrogen atom is substituted by an alkaline metal such as Li, Na and K, or by an ammonium radical exemplified by $NH_4^+$ or mono-, di-, tri- or tetra-alkyl ammonium ion having 1-12 carbon atoms or a mixture of any of these.

The styrene derivative represented by the Formula (3) or the Formula (6) is more specifically exemplified by the following formula. But the present invention is not limited thereby.

TABLE 1

(3-a)

| Examples of Chemical | Substitution Position of Vinyl Group | $R^2$ | g | $R^1$ | h | M |
|---|---|---|---|---|---|---|
| a1-1 | 4'- | H | 1 | H | 1 | H |
| a1-2 | 4'- | H | 1 | 5-tert-$C_4H_9$ | 1 | H |
| a1-3 | 4'- | H | 1 | 5-iso-$C_8H_{17}$ | 1 | H |
| a1-4 | 4'- | H | 1 | 5-iso-$C_3H_7$ | 1 | Na |
| a1-5 | 4'- | H | 1 | 5-$CH_3$ | 1 | H |
| a1-6 | 4'- | 3'-$OCH_3$ | 2 | 5-F 6-$OCH_3$ | 2 | $NH_4$ |
| a1-7 | 4'- | 3'-OH | 2 | 5-COOH | 1 | H |
| a1-8 | 4'- | 3'-Br | 1 | 2-$OC_2H_5$ | 1 | Na |
| a1-9 | 4'- | 3'-$CH_3$ | 3 | 6-F | 1 | K |
| a1-10 | 4'- | 3'-Cl | 1 | 5-tert-$OC_4H_9$ | 1 | H, Na |
| a1-11 | 4'- | 3'-F | 1 | 2-$OCH_3$ | 1 | Li |
| a1-12 | 4'- | 3'-tert-$C_4H_9$ | 1 | 2-OH 5-$CH_3$ | 2 | $NH_4$ |
| a1-13 | 4'- | 3'-iso-$C_8H_{17}$ | 1 | 2-$OCH_3$ | 1 | H |

TABLE 1-continued (3-a)

| Examples of Chemical | Substitution Position of Vinyl Group | $R^2$ | g | $R^1$ | h | M |
|---|---|---|---|---|---|---|
| a1-14 | 4'- | 3'-Br | 1 | 2-tert-$C_4H_9$ 5-tert-$C_4H_9$ | 2 | Na |
| a1-15 | 4'- | 3'-iso-$C_3H_7$ | 3 | 5-Br | 1 | K |
| a1-16 | 4'- | H | 2 | 5-I | 1 | H |
| a1-17 | 4'- | 3'-$CH_3$ | 1 | 5-Cl | 1 | Li |
| a1-18 | 4'- | H | 1 | 5-tert-$C_4H_9$ | 1 | H, Na |
| a1-19 | 4'- | H | 1 | H | 1 | H, Na |
| a1-20 | 4'- | H | 1 | 5-iso-$C_3H_7$ | 1 | H |
| a1-21 | 4'- | H | 2 | 5-tert-$C_4H_9$ | 1 | H |
| a1-22 | 4'- | H | 1 | 5-iso-$C_4H_9$ | 1 | H, Na |
| a1-23 | 4'- | H | 1 | 5-$CH_3$ | 1 | $NH_4$ |
| a1-24 | 4'- | H | 1 | 5-iso-$C_8H_{17}$ | 1 | K |
| a1-25 | 4'- | H | 1 | H | 1 | Na |
| a1-26 | 4'- | H | 1 | H | 1 | $CH_3$ |
| a1-27 | 4'- | H | 1 | H | 1 | $C_2H_5$ |
| a1-28 | 4'- | H | 1 | H | 1 | n-$C_4H_9$ |
| a1-29 | 4'- | H | 1 | 5-tert-$C_4H_9$ | 1 | $CH_3$ |
| a1-30 | 4'- | H | 1 | 5-iso-$C_3H_7$ | 1 | $CH_3$ |
| a1-31 | 4'- | H | 1 | 5-Cl | 1 | n-$C_8H_{17}$ |
| a1-32 | 4'- | 3'-$C_2H_5$ | 1 | 5-tert-$C_4H_9$ | 1 | $CH_3$ |
| a1-33 | 4'- | H | 1 | H | 1 | $(C_4H_9)_4N$ |
| a1-34 | 4'- | H | 1 | 5-tert-$C_4H_9$ | 1 | $(C_2H_5)_2NH_2$ |

TABLE 2

| Examples of Chemical | Substitution Position of Vinyl Group | $R^2$ | g | $R^1$ | h | M |
|---|---|---|---|---|---|---|
| a2-1 | 5'- | H | 1 | H | 1 | H |
| a2-2 | 5'- | H | 1 | 5-tert-$C_4H_9$ | 1 | H |
| a2-3 | 5'- | H | 1 | 5-iso-$C_8H_{17}$ | 1 | H |
| a2-4 | 5'- | H | 1 | 5-iso-$C_3H_7$ | 1 | H |
| a2-5 | 5'- | H | 1 | 5-$CH_3$ | 1 | H |
| a2-6 | 5'- | 4'-iso-$C_3H_7$ | 2 | 2-F 5-$OCH_3$ | 2 | H |
| a2-7 | 5'- | 4'-$OCH_3$ | 1 | 5-tert-$OC_4H_9$ | 1 | $NH_4$ |
| a2-8 | 5'- | 6'-$OC_2H_5$ | 1 | 2-$OCH_3$ | 1 | H |
| a2-9 | 5'- | 2'-COOH | 1 | 2-OH 5-$CH_3$ | 2 | H, Na |
| a2-10 | 5'- | 4'-Cl | 2 | 5-$OCH_3$ | 1 | K |
| a2-11 | 5'- | 2'-$OCH_3$ | 1 | 2-iso-$C_3H_7$ 5-iso-$C_3H_7$ | 2 | Na |
| a2-12 | 5'- | 2'-$OCH_3$ | 3 | 5-Br | 1 | Li |
| a2-13 | 5'- | 3'-OH | 1 | 5-I | 1 | $NH_4$ |
| a2-14 | 5'- | 6'-Br | 1 | 5-Cl | 1 | H |
| a2-15 | 5'- | H | 2 | H | 1 | H |
| a2-16 | 5'- | H | 2 | 5-tert-$C_4H_9$ | 1 | H |
| a2-17 | 5'- | H | 1 | 5-tert-$C_4H_9$ | 1 | H, Na |
| a2-18 | 5'- | H | 1 | 5-$CH_3$ | 1 | $NH_4$ |
| a2-19 | 5'- | H | 1 | 5-iso-$C_8H_{17}$ | 1 | K |
| a2-20 | 5'- | H | 1 | H | 1 | $CH_3$ |
| a2-21 | 5'- | H | 1 | H | 1 | $C_2H_5$ |
| a2-22 | 5'- | H | 1 | H | 1 | n-$C_4H_9$ |
| a2-23 | 5'- | H | 1 | 5-tert-$C_4H_9$ | 1 | $CH_3$ |
| a2-24 | 5'- | 4'-$C_2H_5$ | 1 | H | 1 | $C_2H_5$ |
| a2-25 | 5'- | H | 1 | H | 1 | $(C_3H_7)_4N$ |

TABLE 3

| Examples of Chemical | Substitution Position of Vinyl Group | R² | g | R¹ | h | M |
|---|---|---|---|---|---|---|
| a3-1 | 6'- | H | 1 | H | 1 | H |
| a3-2 | 6'- | H | 1 | 5-tert-$C_4H_9$ | 1 | H |
| a3-3 | 6'- | H | 1 | 5-iso-$C_8H_{17}$ | 1 | H, Na |
| a3-4 | 6'- | H | 1 | 5-iso-$C_3H_7$ | 1 | Na |
| a3-5 | 6'- | 3'-$OCH_3$ | 2 | 6-$OCH_3$ | 2 | $NH_4$ |
| a3-6 | 6'- | 3'-OH | 2 | 5-COOH | 1 | H |
| a3-7 | 6'- | 3'-Br | 1 | 2-$OC_2H_5$ | 1 | Na |
| a3-8 | 6'- | 3'-$OCH_3$ | 3 | 6-F | 1 | K |
| a3-9 | 6'- | 3'-iso-$C_8H_{17}$ | 1 | 2-$OCH_3$ | 1 | Li |
| a3-10 | 6'- | 3'-Br | 1 | 2-tert-$C_4H_9$ 5-tert-$C_4H_9$ | 2 | Na |
| a3-11 | 6'- | 3'-iso-$C_3H_7$ | 3 | 5-Br | 1 | K |
| a3-12 | 6'- | H | 2 | 5-I | 1 | H |
| a3-13 | 6'- | 3'-$CH_3$ | 1 | 5-Cl | 1 | Li |
| a3-14 | 6'- | H | 1 | 5-tert-$C_4H_9$ | 1 | H, Na |
| a3-15 | 6'- | H | 1 | H | 1 | H, Na |
| a3-16 | 6'- | H | 2 | 5-tert-$C_4H_9$ | 1 | H |
| a3-17 | 6'- | H | 1 | 5-tert-$C_4H_9$ | 1 | H, Na |
| a3-18 | 6'- | H | 1 | 5-$CH_3$ | 1 | $NH_4$ |
| a3-19 | 6'- | H | 1 | 5-iso-$C_8H_{17}$ | 1 | K |
| a3-20 | 6'- | H | 1 | H | 1 | $CH_3$ |
| a3-21 | 6'- | H | 1 | H | 1 | $C_2H_5$ |
| a3-22 | 6'- | H | 1 | H | 1 | n-$C_4H_9$ |
| a3-23 | 6'- | 2'-$CH_3$ | 1 | 5-tert-$C_4H_9$ | 1 | $CH_3$ |
| a3-24 | 6'- | H | 1 | 5-iso-$C_3H_7$ | 1 | $CH_3$ |
| a3-25 | 6'- | H | 1 | 5-Cl | 1 | n-$C_3H_7$ |
| a3-26 | 6'- | H | 1 | H | 1 | H, $NH_4$ |
| a3-27 | 6'- | 3'-Br | 1 | 2-$OC_2H_5$ | 1 | $(C_4H_9)_4N$ |

TABLE 4

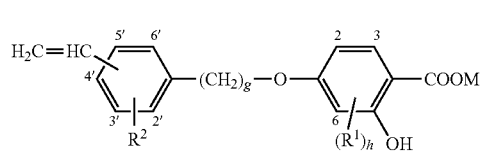

(3-b)

| Examples of Chemical | Substitution Position of Vinyl Group | R² | g | R¹ | h | M |
|---|---|---|---|---|---|---|
| b1-1 | 4'- | H | 1 | H | 1 | H |
| b1-2 | 4'- | H | 1 | 3-tert-$C_4H_9$ | 1 | H |
| b1-3 | 4'- | H | 1 | 6-iso-$C_8H_{17}$ | 1 | H |
| b1-4 | 4'- | H | 1 | 3-iso-$C_3H_7$ | 1 | H |
| b1-5 | 4'- | H | 1 | 6-$CH_3$ | 1 | H |
| b1-6 | 4'- | 3'-$OCH_3$ | 2 | 3-F 6-$OCH_3$ | 2 | $NH_4$ |
| b1-7 | 4'- | 3'-OH | 2 | 6-COOH | 1 | H |
| b1-8 | 4'- | 2'-Br | 1 | 2-$OC_2H_5$ | 1 | Na |
| b1-9 | 4'- | 3'-$OCH_3$ | 3 | 6-F | 1 | K |
| b1-10 | 4'- | 3'-Cl | 1 | 3-tert-$OC_4H_9$ | 1 | H, Na |
| b1-11 | 4'- | 3'-F | 1 | 2-$OCH_3$ | 1 | Li |
| b1-12 | 4'- | 3'-tert-$C_4H_9$ | 1 | 2-OH 3-$CH_3$ | 2 | $NH_4$ |
| b1-13 | 4'- | 3'-iso-$C_8H_{17}$ | 1 | 2-$OCH_3$ | 1 | H |
| b1-14 | 4'- | 3'-Br | 1 | 3-tert-$C_4H_9$ 6-tert-$C_4H_9$ | 2 | Na |
| b1-15 | 4'- | 3'-iso-$C_3H_7$ | 3 | 3-Br | 1 | K |
| b1-16 | 4'- | H | 2 | 3-I | 1 | H, Na |
| b1-17 | 4'- | 2'-$CH_3$ | 1 | 3-Cl | 1 | Li |
| b1-18 | 4'- | H | 1 | H | 1 | H, Na |
| b1-19 | 4'- | H | 1 | 3-tert-$C_4H_9$ | 1 | H, Na |
| b1-20 | 4'- | H | 1 | 2-Br | 1 | Na |
| b1-21 | 4'- | H | 1 | 2-Br | 1 | H |
| b1-22 | 4'- | H | 1 | 2-Cl | 1 | H |
| b1-23 | 4'- | H | 1 | H | 1 | $CH_3$ |
| b1-24 | 4'- | H | 1 | H | 1 | $C_2H_5$ |
| b1-25 | 4'- | H | 1 | H | 1 | n-$C_4H_9$ |
| b1-26 | 4'- | H | 1 | 3-iso-$C_3H_7$ | 1 | $CH_3$ |

TABLE 4-continued (3-b)

| Examples of Chemical | Substitution Position of Vinyl Group | R² | g | R¹ | h | M |
|---|---|---|---|---|---|---|
| b1-27 | 4'- | H | 1 | 3-Cl | 1 | n-$C_5H_{11}$ |
| b1-28 | 4'- | 3'-$OCH_3$ | 1 | H | 1 | $C_2H_5$ |

TABLE 5

| Examples of Chemical | Substitution Position of Vinyl Group | R² | g | R¹ | h | M |
|---|---|---|---|---|---|---|
| b2-1 | 5'- | H | 1 | H | 1 | H |
| b2-2 | 5'- | H | 1 | 3-tert-$C_4H_9$ | 1 | H |
| b2-3 | 5'- | H | 1 | 3-iso-$C_8H_{17}$ | 1 | H |
| b2-4 | 5'- | H | 1 | 3-iso-$C_3H_7$ | 1 | H, Na |
| b2-5 | 5'- | H | 1 | 3-$CH_3$ | 1 | H |
| b2-6 | 5'- | H | 2 | H | 1 | H |
| b2-7 | 5'- | 3'-OH | 2 | 3-$COONH_4$ | 1 | $NH_4$ |
| b2-8 | 5'- | 4'-Br | 1 | 2-$OC_2H_5$ | 1 | Na |
| b2-9 | 5'- | 4'-$OCH_3$ | 3 | 6-F | 1 | K |
| b2-10 | 5'- | 6'-Cl | 1 | 3-tert-$OC_4H_9$ | 1 | H |
| b2-11 | 5'- | 2'-$OC_2H_5$ | 1 | 2-$OCH_3$ | 1 | Li |
| b2-12 | 5'- | 3'-tert-$C_4H_9$ | 1 | 2-OH 3-$CH_3$ | 2 | $NH_4$ |
| b2-13 | 5'- | H | 1 | H | 1 | H, Na |
| b2-14 | 5'- | H | 1 | 3-Br | 1 | Na |
| b2-15 | 5'- | H | 1 | 2-Br | 1 | H |
| b2-16 | 5'- | H | 1 | 3-tert-$C_4H_9$ | 1 | $CH_3$ |
| b2-17 | 5'- | H | 1 | H | 1 | $C_2H_5$ |
| b2-18 | 5'- | H | 1 | H | 1 | n-$C_4H_9$ |
| b2-19 | 5'- | H | 1 | H | 1 | $CH_3$ |

TABLE 6

| Examples of Chemical | Substitution Position of Vinyl Group | R² | g | R¹ | h | M |
|---|---|---|---|---|---|---|
| b3-1 | 6'- | H | 1 | H | 1 | H |
| b3-2 | 6'- | H | 1 | 3-tert-$C_4H_9$ | 1 | H |
| b3-3 | 6'- | H | 1 | 3-iso-$C_3H_7$ | 1 | H, Na |
| b3-4 | 6'- | H | 1 | 6-$CH_3$ | 1 | Li |
| b3-5 | 6'- | 3'-$OCH_3$ | 2 | 3-$C_2H_5$ 6-$OCH_3$ | 2 | $NH_4$ |
| b3-6 | 6'- | 2'-Br | 1 | 2-$OC_2H_5$ | 1 | H, Na |
| b3-7 | 6'- | H | 2 | 3-tert-$C_4H_9$ | 1 | H |
| b3-8 | 6'- | 3'-tert-$C_4H_9$ | 1 | 2-OH 3-$CH_3$ | 2 | $NH_4$ |
| b3-9 | 6'- | H | 1 | 2-$OCH_3$ | 1 | H |
| b3-10 | 6'- | H | 1 | 3-tert-$C_4H_9$ 6-tert-$C_4H_9$ | 2 | Na |
| b3-11 | 6'- | H | 3 | 3-Br | 1 | K |
| b3-12 | 6'- | H | 2 | H | 1 | H, Na |
| b3-13 | 6'- | 2'-$CH_3$ | 1 | 3-Cl | 1 | Li |
| b3-14 | 6'- | H | 1 | H | 1 | H, Na |
| b3-15 | 6'- | 3'-iso-$C_3H_7$ | 1 | 2-Br | 1 | Na |
| b3-16 | 6'- | H | 1 | 2-Cl | 1 | H |
| b3-17 | 6'- | H | 1 | H | 1 | $CH_3$ |
| b3-18 | 6'- | H | 1 | H | 1 | $C_2H_5$ |
| b3-19 | 6'- | 2'-$CH_3$ | 1 | 3-iso-$C_3H_7$ | 1 | $CH_3$ |
| b3-20 | 6'- | H | 1 | 3-Cl | 1 | n-$C_5H_{11}$ |

TABLE 7

(3-c)

$H_2C=HC-\underset{R^2}{\underset{|}{C_6H_3}}-(CH_2)_g-O-\underset{HO}{\underset{|}{C_6H_2}}(R^1)_h-COOM$

| Examples of Chemical | Substitution Position of Vinyl Group | $R^2$ | g | $R^1$ | h | M |
|---|---|---|---|---|---|---|
| c1-1 | 4'- | H | 1 | H | 1 | H |
| c1-2 | 4'- | H | 1 | 3-tert-$C_4H_9$ | 1 | H |
| c1-3 | 4'- | H | 1 | 3-iso-$C_8H_{17}$ | 1 | H |
| c1-4 | 4'- | H | 1 | 4-iso-$C_3H_7$ | 1 | H |
| c1-5 | 4'- | H | 1 | 3-$CH_3$ | 1 | H |
| c1-6 | 4'- | H | 2 | H | 1 | H |
| c1-7 | 4'- | 3'-iso-$C_8H_{17}$ | 3 | 4-OH | 1 | K |
| c1-8 | 4'- | 2'-Br | 2 | 2-F 3-$OCH_3$ | 2 | H, Na |
| c1-9 | 4'- | 3'-iso-$C_3H_7$ | 1 | 2-COOH | 1 | H |
| c1-10 | 4'- | 3'-$OCH_3$ | 1 | 2-$OC_2H_5$ | 1 | Li |
| c1-11 | 4'- | 3'-Cl | 1 | 4-Br | 1 | H |
| c1-12 | 4'- | 2'-F | 1 | 3-tert-$C_4H_9$ | 1 | Na |
| c1-13 | 4'- | 2'-tert-$C_4H_9$ | 1 | 3-iso-$C_3H_7$ | 1 | K |
| c1-14 | 4'- | 2'-$OC_2H_5$ | 1 | 4-$OC_4H_9$ | 1 | H |
| c1-15 | 4'- | 2'-$OCH_3$ | 3 | H | 1 | H |
| c1-16 | 4'- | 2'-$OC_2H_5$ | 2 | 3-n-$C_4H_9$ | 1 | $NH_4$ |
| c1-17 | 4'- | 2'-COONa | 1 | 2-$OCH_3$ | 1 | Na |
| c1-18 | 4'- | 2'-tert-$C_4H_9$ | 1 | 2-OH | 1 | K |
| c1-19 | 4'- | H | 1 | 3-tert-$C_4H_9$ | 1 | H, Na |
| c1-20 | 4'- | H | 1 | 3-iso-$C_8H_{17}$ | 1 | H, Na |
| c1-21 | 4'- | H | 2 | 3-tert-$C_4H_9$ | 1 | H |
| c1-22 | 4'- | H | 1 | 3-$CH_3$ | 1 | $NH_4$ |
| c1-23 | 4'- | H | 1 | H | 1 | H, Na |
| c1-24 | 4'- | H | 1 | 3-Cl | 1 | H |
| c1-25 | 4'- | H | 1 | 3-n-$C_4H_9$ | 1 | H |
| c1-26 | 4'- | H | 1 | H | 1 | $CH_3$ |
| c1-27 | 4'- | H | 1 | H | 1 | $C_2H_5$ |
| c1-28 | 4'- | H | 1 | 3-Cl | 1 | n-$C_4H_9$ |
| c1-29 | 4'- | H | 1 | 3-tert-$C_4H_9$ | 1 | $CH_3$ |
| c1-30 | 4'- | 2'-$OC_2H_5$ | 1 | H | 1 | $C_2H_5$ |

TABLE 8

| Examples of Chemical | Substitution Position of Vinyl Group | $R^2$ | g | $R^1$ | h | M |
|---|---|---|---|---|---|---|
| c2-1 | 5'- | H | 1 | H | 1 | H |
| c2-2 | 5'- | H | 1 | 3-tert-$C_4H_9$ | 1 | H |
| c2-3 | 5'- | H | 1 | 3-iso-$C_8H_{17}$ | 1 | H, Na |
| c2-4 | 5'- | H | 1 | 3-iso-$C_3H_7$ | 1 | H |
| c2-5 | 5'- | H | 1 | 3-$CH_3$ | 1 | H |
| c2-6 | 5'- | H | 1 | 2-$C_2H_5$ | 1 | $NH_4$ |
| c2-7 | 5'- | 4'-iso-$C_8H_{17}$ | 3 | 4-OH | 1 | K |
| c2-8 | 5'- | H | 2 | H | 1 | H |
| c2-9 | 5'- | 4'-Br | 2 | 3-F 2-$OCH_3$ | 2 | Li |
| c2-10 | 5'- | 4'-iso-$C_3H_7$ | 1 | 3-COONa | 1 | Na |
| c2-11 | 5'- | 4'-$OCH_3$ | 1 | 2-$OC_2H_5$ | 1 | Na |
| c2-12 | 5'- | 4'-Cl | 1 | 3-Br | 1 | H |
| c2-13 | 5'- | 6'-F | 1 | 3-tert-$C_4H_9$ | 1 | Na |
| c2-14 | 5'- | 2'-OH | 2 | 2-OH 4-$CH_3$ | 2 | $NH_4$ |
| c2-15 | 5'- | H | 2 | 3-tert-$C_4H_9$ | 1 | H |
| c2-16 | 5'- | H | 1 | 3-$CH_3$ | 1 | $NH_4$ |
| c2-17 | 5'- | H | 1 | H | 1 | H, Na |
| c2-18 | 5'- | H | 1 | 3-Cl | 1 | H |
| c2-19 | 5'- | H | 1 | H | 1 | $CH_3$ |
| c2-20 | 5'- | H | 1 | H | 1 | $C_2H_5$ |
| c2-21 | 5'- | 4'-$CH_3$ | 1 | H | 1 | iso-$C_3H_7$ |

TABLE 9

| Examples of Chemical | Substitution Position of Vinyl Group | $R^2$ | g | $R^1$ | h | M |
|---|---|---|---|---|---|---|
| c3-1 | 6'- | H | 1 | H | 1 | H |
| c3-2 | 6'- | H | 1 | 3-tert-$C_4H_9$ | 1 | H |
| c3-3 | 6'- | H | 1 | 3-iso-$C_8H_{17}$ | 1 | H |
| c3-4 | 6'- | H | 2 | H | 1 | H |
| c3-5 | 6'- | 3'-iso-$C_8H_{17}$ | 3 | 4-OH | 1 | K |
| c3-6 | 6'- | H | 2 | 2-F 3-n-$C_4H_9$ | 2 | H, Na |
| c3-7 | 6'- | 3'-iso-$C_3H_7$ | 1 | 2-COOH | 1 | H |
| c3-8 | 6'- | 3'-$OCH_3$ | 1 | 2-$OC_2H_5$ | 1 | Li |
| c3-9 | 6'- | 3'-Cl | 1 | 4-Br | 1 | H |
| c3-10 | 6'- | H | 2 | 3-tert-$C_4H_9$ | 1 | Na |
| c3-11 | 6'- | 2'-tert-$C_4H_9$ | 1 | 3-iso-$C_3H_7$ | 1 | K |
| c3-12 | 6'- | H | 3 | H | 1 | H |
| c3-13 | 6'- | 2'-$OC_2H_5$ | 2 | 3-n-$C_4H_9$ | 1 | $NH_4$ |
| c3-14 | 6'- | 2'-COONa | 1 | 2-$OCH_3$ | 1 | Na |
| c3-15 | 6'- | 2'-tert-$C_4H_9$ | 1 | 2-OH | 1 | K |
| c3-16 | 6'- | H | 1 | 3-tert-$C_4H_9$ | 1 | H, Na |
| c3-17 | 6'- | H | 2 | 3-tert-$C_4H_9$ | 1 | H |
| c3-18 | 6'- | H | 1 | 3-$CH_3$ | 1 | $NH_4$ |
| c3-19 | 6'- | H | 1 | 3-Cl | 1 | H |
| c3-20 | 6'- | H | 1 | H | 1 | $CH_3$ |
| c3-21 | 6'- | H | 1 | H | 1 | $C_2H_5$ |
| c3-22 | 6'- | H | 1 | 3-Cl | 1 | n-$C_4H_9$ |
| c3-23 | 6'- | H | 1 | 3-$C_2H_5$ | 1 | $CH_3$ |

TABLE 10

(3-d)

$H_2C=HC-\underset{R^2}{\underset{|}{C_6H_3}}-(CH_2)_g-O-\underset{HO}{\underset{|}{C_6H_2}}(R^1)_h-COOM$

| Examples of Chemical | Substitution Position of Vinyl Group | $R^2$ | g | $R^1$ | h | M |
|---|---|---|---|---|---|---|
| d1-1 | 4'- | H | 1 | H | 1 | H |
| d1-2 | 4'- | H | 3 | H | 1 | H |
| d1-3 | 4'- | H | 1 | 2-tert-$C_4H_9$ | 1 | H |
| d1-4 | 4'- | H | 1 | 2-$CH_3$ | 1 | H |
| d1-5 | 4'- | H | 1 | 2-iso-$C_3H_7$ | 1 | H |
| d1-6 | 4'- | H | 1 | 2-tert-$C_8H_{17}$ | 1 | H |
| d1-7 | 4'- | H | 1 | 2-Br | 1 | H |
| d1-8 | 4'- | 2'-Cl | 1 | 2-$CH_3$ | 1 | H |
| d1-9 | 4'- | H | 2 | H | 1 | H |
| d1-10 | 4'- | H | 2 | 2-Cl | 1 | H |
| d1-11 | 4'- | 3'-$OCH_3$ | 1 | 3-$OCH_3$ | 1 | Na |
| d1-12 | 4'- | H | 1 | H | 1 | Na |
| d1-13 | 4'- | 3'-iso-$C_3H_7$ | 1 | 2-$OCH_3$ | 1 | K |
| d1-14 | 4'- | 3'-OH | 2 | 2-$OC_2H_5$ | 1 | $NH_4$ |
| d1-15 | 4'- | 3'-iso-$C_3H_7$ | 1 | 2-COOH | 1 | H, Na |
| d1-16 | 4'- | H | 1 | H | 1 | $CH_3$ |
| d1-17 | 4'- | H | 1 | H | 1 | iso-$C_3H_7$ |

TABLE 11

| Examples of Chemical | Substitution Position of Vinyl Group | $R^2$ | g | $R^1$ | h | M |
|---|---|---|---|---|---|---|
| d2-1 | 5'- | H | 1 | H | 1 | H |
| d2-2 | 5'- | H | 1 | 2-tert-$C_4H_9$ | 1 | H |
| d2-3 | 5'- | H | 1 | 2-$CH_3$ | 1 | H |
| d2-4 | 5'- | H | 1 | 2-$C_2H_5$ | 1 | H |
| d2-5 | 5'- | H | 1 | 2-iso-$C_3H_7$ | 1 | H |
| d2-6 | 5'- | H | 1 | 2-tert-$C_8H_{17}$ | 1 | H |

TABLE 11-continued

| Examples of Chemical | Substitution Position of Vinyl Group | $R^2$ | g | $R^1$ | h | M |
|---|---|---|---|---|---|---|
| d2-7 | 5'- | H | 1 | 2-Br | 1 | H |
| d2-8 | 5'- | 4'-Cl | 1 | 2-Cl | 1 | H |
| d2-9 | 5'- | H | 2 | 2-OCH$_3$ | 1 | H |
| d2-10 | 5'- | 6'-Br | 2 | 2-COOH | 1 | H, Na |
| d2-11 | 5'- | 4'-iso-C$_3$H$_7$ | 1 | 2-OC$_2$H$_5$ | 1 | Li |
| d2-12 | 5'- | 4'-OCH$_3$ | 1 | 2-Br 5-Br | 2 | Na |
| d2-13 | 5'- | 2'-Cl | 3 | 2-F 5-F 2-F | 3 | H |
| d2-14 | 5'- | 6'-F | 1 | H | 1 | Na |
| d2-15 | 5'- | 4'-OH | 1 | 2-tert-C$_4$H$_9$ | 1 | NH$_4$ |
| d2-16 | 5'- | H | 1 | H | 1 | CH$_3$ |
| d2-17 | 5'- | H | 1 | 2-tert-C$_4$H$_9$ | 1 | iso-C$_3$H$_7$ |

TABLE 12

| Examples of Chemical | Substitution Position of Vinyl Group | $R^2$ | g | $R^1$ | h | M |
|---|---|---|---|---|---|---|
| d3-1 | 6'- | H | 1 | H | 1 | H |
| d3-2 | 6'- | H | 1 | 2-tert-C$_4$H$_9$ | 1 | H |
| d3-3 | 6'- | 4'-C$_2$H$_5$ | 1 | 2-OC$_2$H$_5$ | 1 | H, Na |
| d3-4 | 6'- | H | 1 | 2-Br | 1 | H |
| d3-5 | 6'- | H | 1 | H | 1 | C$_2$H$_5$ |
| d3-6 | 6'- | H | 1 | 2-tert-C$_4$H$_9$ | 1 | tert-C$_4$H$_9$ |

TABLE 13

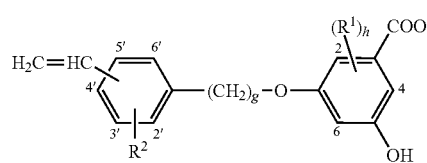

(3-e)

| Examples of Chemical | Substitution Position of Vinyl Group | $R^2$ | g | $R^1$ | h | M |
|---|---|---|---|---|---|---|
| e1-1 | 4'- | H | 1 | 6-iso-C$_3$H$_7$ | 1 | H |
| e1-2 | 4'- | H | 1 | H | 1 | H |
| e1-3 | 4'- | 2'-OH | 1 | 6-tert-C$_4$H$_9$ | 1 | H |
| e1-4 | 4'- | H | 1 | 6-CH$_3$ | 1 | H |
| e1-5 | 4'- | H | 1 | 6-Cl | 1 | H |
| e1-6 | 4'- | H | 1 | 6-tert-C$_8$H$_{17}$ | 1 | H |
| e1-7 | 4'- | H | 1 | 6-Br | 1 | H |
| e1-8 | 4'- | 2'-Cl | 1 | 6-Br | 1 | H |
| e1-9 | 4'- | H | 2 | H | 1 | H |
| e1-10 | 4'- | H | 2 | 6-F | 1 | H |
| e1-11 | 4'- | 3'-OCH$_3$ | 1 | 6-CH$_3$ | 1 | Na |
| e1-12 | 4'- | 3'-Cl | 1 | 4-F | 1 | H |
| e1-13 | 4'- | 3'-iso-C$_3$H$_7$ | 1 | 6-OCH$_3$ | 1 | K |
| e1-14 | 4'- | 3'-OH | 2 | 6-OC$_2$H$_5$ | 1 | NH$_4$ |
| e1-15 | 4'- | 3'-iso-C$_3$H$_7$ | 3 | 6-COOH | 1 | H, Na |
| e1-16 | 4'- | H | 1 | H | 1 | Na |
| e1-17 | 4'- | 3'-OC$_3$H$_7$ | 1 | 6-OC$_2$H$_5$ | 1 | H |
| e1-18 | 4'- | H | 1 | H | 1 | n-C$_4$H$_9$ |
| e1-19 | 4'- | H | 1 | H | 1 | CH$_3$ |

TABLE 14

| Examples of Chemical | Substitution Position of Vinyl Group | $R^2$ | g | $R^1$ | h | M |
|---|---|---|---|---|---|---|
| e2-1 | 5'- | H | 1 | H | 1 | H |
| e2-2 | 5'- | H | 1 | 6-CH$_3$ | 1 | H |
| e2-3 | 5'- | H | 1 | 6-iso-C$_3$H$_7$ | 1 | H |
| e2-4 | 5'- | H | 1 | 6-tert-C$_8$H$_{17}$ | 1 | H |
| e2-5 | 5'- | H | 1 | 6-Br | 1 | H |
| e2-6 | 5'- | H | 1 | 6-Cl | 1 | H |
| e2-7 | 5'- | H | 1 | 6-F | 1 | H |
| e2-8 | 5'- | H | 2 | H | 1 | H |
| e2-9 | 5'- | H | 2 | 6-iso-C$_3$H$_7$ | 1 | H |
| e2-10 | 5'- | H | 3 | H | 1 | H |
| e2-11 | 5'- | 4'-iso-C$_8$H$_{17}$ | 1 | 4-OH | 1 | Na |
| e2-12 | 5'- | H | 2 | 2-F 4-F 6-F | 3 | H |
| e2-13 | 5'- | 6'-Br | 2 | 6-F 4-OCH$_3$ | 2 | K |
| e2-14 | 5'- | 6'-F | 1 | 6-tert-C$_4$H$_9$ | 1 | NH$_4$ |
| e2-15 | 5'- | 4'-OCH$_3$ | 1 | 2-OC$_2$H$_5$ | 1 | H, Na |
| e2-16 | 5'- | H | 1 | 6-n-C$_4$H$_9$ | 1 | NH$_4$ |
| e2-17 | 5'- | H | 1 | H | 1 | CH$_3$ |

TABLE 15

| Examples of Chemical | Substitution Position of Vinyl Group | $R^2$ | g | $R^1$ | h | M |
|---|---|---|---|---|---|---|
| e3-1 | 6'- | H | 1 | H | 1 | H |
| e3-2 | 6'- | H | 2 | H | 1 | H, Na |
| e3-3 | 6'- | H | 1 | 6-iso-C$_3$H$_7$ | 1 | H |
| e3-4 | 6'- | 2'-OH | 1 | 6-tert-C$_4$H$_9$ | 1 | NH$_4$ |
| e3-5 | 6'- | H | 1 | H | 1 | C$_2$H$_5$ |

TABLE 16

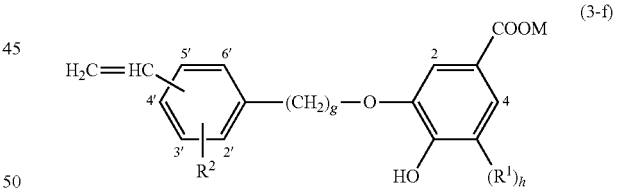

(3-f)

| Examples of Chemical | Substitution Position of Vinyl Group | $R^2$ | g | $R^1$ | h | M |
|---|---|---|---|---|---|---|
| f1-1 | 4'- | H | 1 | 5-tert-C$_4$H$_9$ | 1 | H |
| f1-2 | 4'- | H | 1 | 5-CH$_3$ | 1 | H |
| f1-3 | 4'- | H | 1 | 5-iso-C$_3$H$_7$ | 1 | H |
| f1-4 | 4'- | H | 1 | 5-tert-C$_8$H$_{17}$ | 1 | H |
| f1-5 | 4'- | H | 1 | 5-Br | 1 | H |
| f1-6 | 4'- | 2'-Cl | 1 | 5-CH$_3$ | 1 | H |
| f1-7 | 4'- | H | 2 | 5-Cl | 1 | H |
| f1-8 | 4'- | 3'-OCH$_3$ | 1 | 5-OCH$_3$ | 2 | Na |
| f1-9 | 4'- | 3'-Cl | 3 | 5-F | 2 | H |
| f1-10 | 4'- | 3'-iso-C$_3$H$_7$ | 1 | 5-OCH$_3$ | 2 | K |
| f1-11 | 4'- | 3'-OH | 2 | 5-OC$_2$H$_5$ | 1 | NH$_4$ |
| f1-12 | 4'- | 3'-iso-C$_3$H$_7$ | 1 | 5-COOH | 2 | H, Na |
| f1-13 | 4'- | H | 1 | 5-iso-C$_3$H$_7$ | 1 | C$_2$H$_5$ |

TABLE 17

| Examples of Chemical | Substitution Position of Vinyl Group | R² | g | R¹ | h | M |
|---|---|---|---|---|---|---|
| f2-1 | 5'- | H | 1 | 5-tert-C₄H₉ | 1 | H |
| f2-2 | 5'- | H | 1 | 5-CH₃ | 1 | H |
| f2-3 | 5'- | H | 1 | 5-C₂H₅ | 1 | H, Na |
| f2-4 | 5'- | H | 1 | 5-iso-C₃H₇ | 1 | H |
| f2-5 | 5'- | H | 1 | 5-tert-C₈H₁₇ | 1 | H |
| f2-6 | 5'- | H | 1 | 5-Br | 1 | H |
| f2-7 | 5'- | H | 2 | 5-OCH₃ | 1 | H |
| f2-8 | 5'- | 4'-Br | 2 | 5-COOH | 1 | H, Na |
| f2-9 | 5'- | 4'-iso-C₃H₇ | 1 | 5-OC₂H₅ | 1 | Li |
| f2-10 | 5'- | 6'-Cl | 1 | 5-tert-C₄H₉ | 1 | NH₄ |
| f2-11 | 5'- | H | 1 | 5-tert-C₄H₉ | 1 | CH₃ |

TABLE 18

| Examples of Chemical | Substitution Position of Vinyl Group | R² | g | R¹ | h | M |
|---|---|---|---|---|---|---|
| f3-1 | 6'- | H | 1 | 5-tert-C₄H₉ | 1 | H |
| f3-2 | 6'- | H | 1 | 5-C₂H₅ | 1 | H, Na |
| f3-3 | 6'- | H | 1 | 5-iso-C₃H₇ | 1 | H |
| f3-4 | 6'- | 3'-iso-C₃H₇ | 1 | 5-OCH₃ | 2 | K |
| f3-5 | 6'- | H | 1 | 5-iso-C₃H₇ | 1 | n-C₃H₇ |

In Tables 1-18, if the substituent $R^1$ is exclusively hydrogen atom, then H is entered, and if anything other than hydrogen atom is included, the substituent(s) other than hydrogen atom is entered. Also, where the substituent $R^1$ is exclusively hydrogen atom, the value of h is 1, and otherwise the value entered for h is the number of the substituents minus the number of substituent hydrogen atom(s).

These styrene derivatives can be synthesized with ease by means of any known method, such as Williamson reaction, which is described in page 187 of The 4$^{th}$ Series of Experimental Chemistry (edited by The Chemical Society of Japan and published by Maruzen Co., Ltd.).

The step of synthesizing a styrene derivative is conducted, for example, by a reaction in a solvent between a substituted or non-substituted vinyl phenyl alkyrene halide and a substituted or non-substituted dihydroxy aromatic carboxylic acid and its alkyl ester, preferably a hydroxy salicylic acid and its alkyl ester. An example is shown in following Reaction Formula (7). In the reaction between a substituted or non-substituted vinyl phenyl alkyrene halide and a substituted or non-substituted dihydroxy aromatic carboxylic acid, it is possible to select one kind each of the reactants or select mixtures of two or more kinds each of the reactants. It is also possible to obtain an alkyl ester of a styrene derivative by reacting, by means of a known method, a styrene derivative in which M of the —COOM group is a hydrogen atom or an alkaline metal with an alcohol having 1-18 carbon atoms, for example. As the alcohol having 1-18 carbon atoms, specific examples include methanol, ethanol, n-propanol, isopropanol, n-butanol, isobutanol, tert-butanol, 1-pentanol, 1-hexanol, 1-heptanol, 1-octanol, 1-ethylhexanol, 2-ethylhexanol, 1-nonyl alcohol and 1-decyl alcohol. Among these, methanol, ethanol, n-propanol, isopropanol, n-butanol, isobutanol and tert-butanol are preferable for the reasons of easy availability and high reactivity.

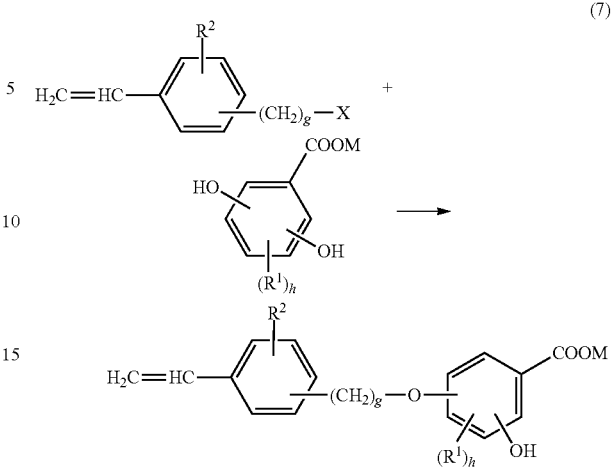

(7)

In the Reaction Formula (7), $R^1$, $R^2$, M, h and g are the same as above, and X is a halogen atom such as F, Cl and Br.

The substituted or non-substituted vinyl phenyl alkylene halide is specifically exemplified by:

p-(halogen-containing-methyl)styrene derivatives such as 4-(chloromethyl)styrene, 4-(bromomethyl)styrene, 3-methoxy-4-(chloromethyl)styrene, 3-methoxy-4-(bromomethyl)styrene, 2-hydroxy-4-(chloromethyl)styrene, 2-hydroxy-4-(bromomethyl)styrene, 3-bromo-4-(chloromethyl)styrene, 3-bromo-4-(bromomethyl)styrene, 2-methoxy-4-(chloromethyl)styrene, 2-methoxy-4-(bromomethyl)styrene, 2-chloro-4-(chloromethyl)styrene, 2-chloro-4-(bromomethyl)styrene, 3-fluoro-4-(chloromethyl)styrene, 3-fluoro-4-(bromomethyl)styrene, 2-bromo-4-(chloromethyl)styrene, 2-bromo-4-(bromomethyl)styrene, 3-tert-butyl-4-(chloromethyl)styrene, 3-tert-butyl-4-(bromomethyl)styrene, 3-isooctyl-4-(chloromethyl)styrene, 3-isooctyl-4-(bromomethyl)styrene, 3-isopropyl-4-(chloromethyl)styrene, 3-isopropyl-4-(bromomethyl)styrene, 3-methyl-4-(chloromethyl)styrene, 3-methyl-4-(bromomethyl)styrene, 3-ethoxy-4-(chloromethyl)styrene, 3-ethoxy-4-(bromomethyl)styrene, 3-carboxy-4-(chloromethyl)styrene, and 3-carboxy-4-(bromomethyl)styrene;

m-(halogen-containing-methyl)styrene derivatives such as 3-(chloromethyl)styrene, 3-(bromomethyl)styrene, 5-methyl-3-(chloromethyl)styrene, 5-methyl-3-(bromomethyl)styrene, 5-isopropyl-3-(chloromethyl)styrene, 5-isopropyl-3-(bromomethyl)styrene, 5-isooctyl-3-(chloromethyl)styrene, 5-isooctyl-3-(bromomethyl)styrene, 5-methoxy-3-(chloromethyl)styrene, 5-methoxy-3-(bromomethyl)styrene, 4-ethoxy-3-(chloromethyl)styrene, 4-ethoxy-3-(bromomethyl)styrene, 4-carboxy-3-(chloromethyl)styrene, 4-carboxy-3-(bromomethyl)styrene, 5-hydroxy-3-(chloromethyl)styrene, 5-hydroxy-3-(bromomethyl)styrene, 4-hydroxy-3-(chloromethyl)styrene, 4-hydroxy-3-(bromomethyl)styrene, 4-methoxy-3-(chloromethyl)styrene, 4-methoxy-3-(bromomethyl)styrene, 5-chloro-3-(chloromethyl)styrene, 5-chloro-3-(bromomethyl)styrene, 4-bromo-3-(chloromethyl)styrene, 4-bromo-3-(bromomethyl)styrene, 2-bromo-3-(chloromethyl)styrene, 2-bromo-3-(bromomethyl)styrene, 5-tert-butyl-3-(chloromethyl)styrene, and 5-tert-butyl-3-(bromomethyl)styrene;

o-(halogen-containing-methyl)styrene derivatives such as 2-(chloromethyl)styrene, 2-(bromomethyl)styrene, 3-tertbutyl-2-(chloromethyl)styrene, 3-tert-butyl-2-(bromomethyl)styrene, 4-chloro-2-(chloromethyl)styrene, and 4-chloro-2-(bromomethyl)styrene;

p-(halogen-containing-ethyl)styrene derivatives such as 4-(2'-bromoethyl)styrene, 4-(2'-chloroethyl)styrene, 3-methoxy-4-(2'-bromoethyl)styrene, 3-methoxy-4-(2'-chloroethyl)styrene, 2-hydroxy-4-(2'-bromoethyl)styrene, 2-hydroxy-4-(2'-chloroethyl)styrene, 3-ethoxy-4-(2'-bromoethyl)styrene, 3-ethoxy-4-(2'-chloroethyl)styrene, 3-bromo-4-(2'-bromoethyl)styrene, 3-bromo-4-(2'-chloroethyl)styrene, 3-tert-butyl-4-(2'-bromoethyl)styrene, and 3-tert-butyl-4-(2'-chloroethyl)styrene;

m-(halogen-containing-ethyl)styrene derivatives such as 3-(2'-bromoethyl)styrene, 3-(2'-chloroethyl)styrene, 5-isopropyl-3-(2'-bromoethyestyrene, 5-isopropyl-3-(2'-chloroethyl)styrene, 5-chloro-3-(2'-bromoethyl)styrene, 5-chloro-3-(2'-chloroethyl)styrene, 5-hydroxy-3-(2'-bromoethyl)styrene, 5-hydroxy-3-(2'-chloroethyl)styrene, 4-hydroxy-3-(2'-bromoethyl)styrene, 4-hydroxy-3-(2'-chloroethyl)styrene, 4-bromo-3-(2'-bromoethyl)styrene, and 4-bromo-3-(2'-chloroethyl)styrene;

o-(halogen-containing-ethyl)styrene derivatives such as 2-(2'-bromoethyl)styrene, 2-(2'-chloroethyl)styrene, 3-tert-butyl-2-(2'-bromoethyl)styrene, and 3-tert-butyl-2-(2'-chloroethyl)styrene;

p-(halogen-containing-propyl)styrene derivatives such as 4-(3'-bromopropyl)styrene, 4-(3'-chloropropyl)styrene, 2-methoxy-4-(3'-bromopropyl)styrene, 2-methoxy-4-(3'-chloropropyl)styrene, 2-isopropyl-4-(3'-bromopropyl)styrene, 2-isopropyl-4-(3'-chloropropyl)styrene, 2-isooctyl-4-(3'-bromopropyl)styrene, 2-isooctyl-4-(3'-chloropropyl)styrene, 3-methoxy-4-(3'-bromopropyl)styrene, and 3-methoxy-4-(3'-chloropropyl)styrene;

m-(halogen-containing-propyl)styrene derivatives such as 3-(3'-bromopropyl)styrene, 3-(3'-chloropropyl)styrene, 5-isooctyl-3-(3'-bromopropyl)styrene, 5-isooctyl-3-(3'-chloropropyl)styrene, 5-methoxy-3-(3'-bromopropyl)styrene, 5-methoxy-3-(3'-chloropropyl)styrene, and 2-(3'-bromopropyl)styrene;

and o-(halogen-containing-propyl)styrene derivatives such as 2-(3'-chloropropyl)styrene.

The substituted or non-substituted dihydroxy aromatic carboxylic acid is specifically exemplified by:

2,3-dihydroxy benzoic acid derivatives and their alkyl esters having 1-18 carbon atoms such as 2,3-dihydroxy benzoic acid, 5-methyl-2,3-dihydroxy benzoic acid, 5-ethyl-2,3-dihydroxy benzoic acid, 5-isopropyl-2,3-dihydroxy benzoic acid, 5-n-butyl-2,3-dihydroxy benzoic acid, 5-tert-butyl-2,3-dihydroxy benzoic acid, 5-sec-butyl-2,3-dihydroxy benzoic acid, 5-isoheptyl-2,3-dihydroxy benzoic acid, 5-isohexyl-2,3-dihydroxy benzoic acid, 5-isooctyl-2,3-dihydroxy benzoic acid, 5-fluoro-2,3-dihydroxy benzoic acid, 5-chloro-2,3-dihydroxy benzoic acid, 5-bromo-2,3-dihydroxy benzoic acid, 5-fluoro-4-methoxy-2,3-dihydroxy benzoic acid, 4-ethyl-2,3-dihydroxy benzoic acid, 4-methoxy-2,3-dihydroxy benzoic acid, 4-ethoxy-2,3-dihydroxy benzoic acid, 2,3,4-trihydroxy benzoic acid, 4-fluoro-5-methoxy-2,3-dihydroxy benzoic acid, 6-isopropyl-2,3-dihydroxy benzoic acid, and 6-butoxy-2,3-dihydroxy benzoic acid;

2,4-dihydroxy benzoic acid derivatives and their alkyl esters having 1-18 carbon atoms such as 2,4-dihydroxy benzoic acid, 6-methyl-2,4-dihydroxy benzoic acid, 6-ethyl-2,4-dihydroxy benzoic acid, 6-isopropyl-2,4-dihydroxy benzoic acid, 6-tert-butyl-2,4-dihydroxy benzoic acid, 6-sec-butyl-2,4-dihydroxy benzoic acid, 6-isohexyl-2,4-dihydroxy benzoic acid, 6-isoheptyl-2,4-dihydroxy benzoic acid, 6-isooctyl-2,4-dihydroxy benzoic acid, 5-methoxy-2,4-dihydroxy benzoic acid, 6-butoxy-2,4-dihydroxy benzoic acid, 6-chloro-2,4-dihydroxy benzoic acid, 6-bromo-2,4-dihydroxy benzoic acid, 6-iodo-2,4-dihydroxy benzoic acid, 5-n-propyl-2,4-dihydroxy benzoic acid, 5-ethoxy-2,4-dihydroxy benzoic acid, 5-chloro-2,4-dihydroxy benzoic acid, 5-bromo-2,4-dihydroxy benzoic acid, 6-methyl-2,4,5-trihydroxy benzoic acid, 5,6-di-tert-butyl-2,4-dihydroxy benzoic acid, 3-tert-butyl-2,4-dihydroxy benzoic acid, 3-isooctyl-2,4-dihydroxy benzoic acid, 3-chloro-2,4-dihydroxy benzoic acid, 3-fluoro-2,4-dihydroxy benzoic acid, and 3-bromo-2,4-dihydroxy benzoic acid;

2,5-dihydroxy benzoic acid derivatives and their alkyl esters having 1-18 carbon atoms such as 2,5-dihydroxy benzoic acid, 3-methyl-2,5-dihydroxy benzoic acid, 3-ethyl-2,5-dihydroxy benzoic acid, 3-isopropyl-2,5-dihydroxy benzoic acid, 3-tert-butyl-2,5-dihydroxy benzoic acid, 3-sec-butyl-2,5-dihydroxy benzoic acid, 3-isohexyl-2,5-dihydroxy benzoic acid, 3-isoheptyl-2,5-dihydroxy benzoic acid, 3-isooctyl-2,5-dihydroxy benzoic acid, 3-tert-butoxy-2,5-dihydroxy benzoic acid, 3-chloro-2,5-dihydroxy benzoic acid, 3-bromo-2,5-dihydroxy benzoic acid, 3-iodo-2,5-dihydroxy benzoic acid, 3-fluoro-2,5-dihydroxy benzoic acid, 6-methoxy-2,5-dihydroxy benzoic acid, 6-ethoxy-2,5-dihydroxy benzoic acid, 3-methyl-2,5,6-trihydroxy benzoic acid, 6-fluoro-4-methoxy-2,5-dihydroxy benzoic acid, 3,4-diisopropyl-2,5-dihydroxy benzoic acid, 3,4-di-tert-butyl-2,5-dihydroxy benzoic acid, 4-chloro-3-tert-butyl-2,5-dihydroxy benzoic acid, and 4-fluoro-2,5-dihydroxy benzoic acid;

2,6-dihydroxy benzoic acid derivatives and their alkyl esters having 1-18 carbon atoms such as 2,6-dihydroxy benzoic acid, 3-bromo-2,6-dihydroxy benzoic acid, 4-bromo-2,6-dihydroxy benzoic acid, 5-bromo-2,6-dihydroxy benzoic acid, 3-chloro-2,6-dihydroxy benzoic acid, 4-chloro-2,6-dihydroxy benzoic acid, 5-chloro-2,6-dihydroxy benzoic acid, 3-isopropyl-2,6-dihydroxy benzoic acid, 4-tert-butyl-2,6-dihydroxy benzoic acid, and 5-methyl-2,6-dihydroxy benzoic acid;

4,5-dihydroxy benzoic acid derivatives and their alkyl esters having 1-18 carbon atoms such as 3-methyl-4,5-dihydroxy benzoic acid, 3-tert-butyl-4,5-dihydroxy benzoic acid, 3-tert-octyl-4,5-dihydroxy benzoic acid, 3-ethoxy-4,5-dihydroxy benzoic acid, 3-methoxy-4,5-dihydroxy benzoic acid, and 3-chloro-4,5-dihydroxy benzoic acid;

3,5-dihydroxy benzoic acid derivatives and their alkyl esters having 1-18 carbon atoms such as 3,5-dihydroxy benzoic acid, 4-methyl-3,5-dihydroxy benzoic acid, 4-isopropyl-3,5-dihydroxy benzoic acid, 4-tert-butyl-3,5-dihydroxy benzoic acid, 4-ethoxy-3,5-dihydroxy benzoic acid, and 4-butoxy-3,5-dihydroxy benzoic acid; and 3,4-dihydroxy benzoic acid derivatives and their alkyl esters having 1-18 carbon atoms such as 3,4-dihydroxy benzoic acid, 2,3,4-trihydroxy benzoic acid, 6-fluoro-3,5-dihydroxy benzoic acid, 5-methyl-3,4-dihydroxy benzoic acid, 5-isopropyl-3,4-dihydroxy benzoic acid, 5-tert-butyl-3,4-dihydroxy benzoic acid, 5-tert-octyl-3,4-dihydroxy benzoic acid, 5-methoxy-3,4-dihydroxy benzoic acid, 5-ethoxy-3,4-dihydroxy benzoic acid, 5-bromo-3,4-dihydroxy benzoic acid, 5-chloro-3,4-dihydroxy benzoic acid, 6-methoxy-3,4-dihydroxy benzoic acid, 6-n-propyl-3,4-dihydroxy benzoic acid, and 6-n-butyl-3,4-dihydroxy benzoic acid.

Possible examples of reaction solvent include organic solvents such as: alcohols, ethers and glycols exemplified by methanol, ethanol, isopropanol, ethylene glycol monomethyl ether, ethylene glycol monoethyl ether, propylene glycol monomethyl ether, ethylene glycol dimethyl ether (monoglyme), diethylene glycol dimethyl ether (diglyme), ethylene glycol diethyl ether, triethylene glycol dimethyl ether (triglyme), tetraethylene glycol dimethyl ether (tetraglyme), ethylene glycol, and propylene glycol; aprotic organic polar solvents exemplified by N,N-dimethylformamide (DMF), N,N-dimethylacetamide, N-methyl-2-pyrrolidone, and dimethyl sulfoxide; ketones exemplified by acetone, methyl ethyl ketone, and methyl isobutyl ketone; esters exemplified by ethyl acetate, butyl acetate, ethyl propionate, and cellosolve acetate; hydrocarbons exemplified by hexane, octane, petroleum ether, cyclohexane, benzene, toluene, and xylene; and halogenated hydrocarbons exemplified by trichloroethylene, dichloromethane, and chloroform.

In the reaction to synthesize the styrene derivative used in the present invention, it is preferable to add a base on the occasion of reaction promotion and ether linking so as to trap hydrogen halide which is generated as a by-product.

The base that can be used for this synthesis may be any base so long as it does not complicate the reaction system by acting with a solvent or a substrate. Examples include: hydroxides of alkaline metals such as lithium hydroxide, sodium hydroxide, and potassium hydroxide; carbonates of alkaline metals such as lithium carbonate, sodium carbonate, potassium carbonate, cesium carbonate, and rubidium carbonate; and hydrides of alkaline metals such as lithium hydride, sodium hydride, and potassium hydride.

The method A, which is one of the methods for manufacturing the charge control resin of the present invention, can use, as a starting monomer, a vinyl group-containing monomer as well as the charge control monomer, which is the styrene derivative represented by the Formula (3). A preferable method is such that a polymer is obtained by effecting a polymerization among monomers, in a solvent, within a reaction system consisting of the monomers comprising at least the charge control monomer and the vinyl group-containing monomer, which becomes the constituent unit represented by the Formula (2), and a polymerization initiator. An example of this reaction system is represented by following Reaction Formula (8).

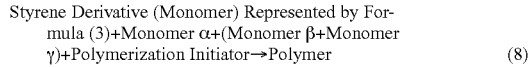

Styrene Derivative (Monomer) Represented by Formula (3)+Monomer α+(Monomer β+Monomer γ)+Polymerization Initiator→Polymer (8)

In Formula (8), the monomers α, β, γ are monomers other than the styrene derivative represented by Formula (3), and are mutually different vinyl group-containing monomers.

Examples of the vinyl group-containing monomer include: vinyl aromatic hydrocarbon-containing monomers such as styrene, α-methylstyrene, p-methylstyrene, p-tert-butylstyrene, and p-chlorostyrene; (meth)acrylic acid alkyl esters such as methyl (meth)acrylate, ethyl (meth)acrylate, n-propyl (meth)acrylate, isopropyl (meth)acrylate, n-butyl (meth)acrylate, isobutyl (meth)acrylate, tert-butyl (meth)acrylate, n-pentyl (meth)acrylate, isopentyl (meth)acrylate, neopentyl (meth)acrylate, 3-(methyl)butyl (meth)acrylate, hexyl (meth)acrylate, 2-ethylhexyl (meth)acrylate, cyclohexyl (meth)acrylate, octyl (meth)acrylate, nonyl (meth)acrylate, decyl (meth)acrylate, undecyl (meth)acrylate, lauryl (meth)acrylate, stearyl (meth)acrylate, glycidyl (meth)acrylate, β-methacryloyloxy ethylhydrogen phthalate; mono functional vinyl group-containing monomers such as vinyl chloride, vinyl acetate, vinyl benzoate, vinyl methyl ethyl ketone, vinyl hexyl ketone, vinyl methyl ether, vinyl ethyl ether, vinyl isobutyl ether, and vinyl toluene; bifunctional vinyl group-containing monomers such as divinyl benzene and diethylene glycol (meth)acrylate; and monomers having three or more reactive vinyl groups. It is possible to use any of these monomers singly or in a combination of two or more.

Preferable examples for the vinyl group-containing monomer are vinyl aromatic hydrocarbon-containing monomers represented by the following Formula (4). Examples for the vinyl aromatic hydrocarbon-containing monomers include ones represented by the Formula (4). By polymerizing this vinyl group-containing monomer, a constituent unit represented by the Formula (2) is obtained.

In the Formula (4), $R^3$, $R^4$, $R^5$ are independent of one another, and are a hydrogen atom, an alkyl group, a halogen atom, or an alkoxy group.

Examples of the substituents $R^3$, $R^4$ and $R^5$ in the case wherein they are straight-chained or branched alkyl groups having 1-8 carbon atoms include methyl group, ethyl group, propyl group, isopropyl group, n-butyl group, isobutyl group, sec-butyl group, tert-butyl group, n-pentyl group, isopentyl group, hexyl group, heptyl group, and octyl group.

Examples of the substituents $R^3$, $R^4$ and $R^5$ in the case wherein they are straight-chained or branched alkoxy groups having 1-8 carbon atoms include methoxy group, ethoxy group, n-propoxy group, isopropoxy group, n-butoxy group, isobutoxy group, sec-butoxy group, tert-butoxy group, n-pentoxy group, isopentoxy group, hexyloxy group, heptoxy group, and octyl-oxy group.

Examples of the substituents $R^3$, $R^4$ and $R^5$ in the case wherein they are halogen atoms include F, Cl and Br.

Examples of the vinyl aromatic hydrocarbon include styrene, α-methylstyrene, 2-methylstyrene, 3-methylstyrene, 4-methylstyrene, 2-ethylstyrene, 3-ethylstyrene, 4-ethylstyrene, 2-propylstyrene, 3-propylstyrene, 4-propylstyrene, 2-isopropylstyrene, 3-isopropylstyrene, 4-isopropylstyrene, 2-chlorostyrene, 3-chlorostyrene, 4-chlorostyrene, 2-methyl-α-methylstyrene, 3-methyl-α-methylstyrene, 4-methyl-α-methylstyrene, 2-ethyl-α-methylstyrene, 3-ethyl-α-methylstyrene, 4-ethyl-α-methylstyrene, 2-propyl-α-methylstyrene, 3-propyl-α-methylstyrene, 4-propyl-α-methylstyrene, 2-isopropyl-α-methylstyrene, 3-isopropyl-α-methylstyrene, 4-isopropyl-α-methylstyrene, 2-chloro-α-methylstyrene, 3-chloro-α-methylstyrene, 4-chloro-α-methylstyrene, 2,3-dimethylstyrene, 3,4-dimethylstyrene, 2,4-dimethylstyrene, 2,5-dimethylstyrene, 2,3-diethylstyrene, 3,4-diethylstyrene, 2,4-diethylstyrene, 2,5-diethylstyrene, 2-methyl-3-ethylstyrene, 2-methyl-4-ethylstyrene, 2-chloro-4-methylstyrene, 2,3-dimethyl-α-methylstyrene, 3,4-dimethyl-α-methylstyrene, 2,4-dimethylstyrene, 2,5-dimethyl-α-methyl styrene, 2,3-diethyl-α-methyl styrene, 3,4-diethyl-α-methyl styrene, 2,4-diethyl-α-methylstyrene, 2,5-diethyl-α-methylstyrene, 2-ethyl-3-methyl-α-methylstyrene, 2-methyl-4-propyl-α-methylstyrene, 2-chloro-4-ethyl-α-methylstyrene, 2-methoxystyrene, 3-ethoxystyrene, 4-ethoxystyrene, and 2-isoproxy styrene. These vinyl aromatic hydrocarbon-containing monomers can be used singly or in combination of two or more.

The vinyl aromatic hydrocarbon-containing monomer is preferably a styrene. Following Formula (9) represents a constituent unit obtained from such styrene.

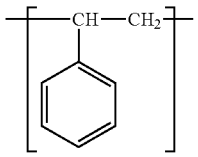

(9)

An example for the vinyl group-containing monomer to be used in the present invention is a hydrophilic unsaturated monomer. Examples of hydrophilic unsaturated monomer includes (meth)acrylic acid(s); (meth)acrylic acid alkyl esters such as hydroxyethyl (meth)acrylate, hydroxypropyl (meth)acrylate, and 2-hydroxypropyl (meth)acrylate; (meth)acrylamides such as (meth)acrylamide, N-methylol (meth)acrylamide, diacetone (meth)acrylamide, N-isopropyl (meth)acrylamide, N,N-diethyl (meth)acrylamide, N,N-dimethylaminopropyl (meth)acrylamide, and N,N-dimethyl (meth)acrylamide; alkyl(meth)acrylamide sulfonates or their esters such as ethyl(meth)acrylamide sulfonic acid(s), propyl (meth)acrylamide sulfonic acid(s), tert-butyl-(meth)acrylamidesulfonic acid(s); styrene sulfonic acid(s), metallyl sulfonic acid(s), acryloyl morpholine, acrylonitrile, monobutyl maleate, isobutyl maleate, itaconic acid, and fumaric acid. These monomers can be used singly or in combination of two or more of them. Of these monomers more preferred are (meth)acrylic acid(s), (meth)acrylic acid alkyl esters, tert-butyl-acrylamidesulfonic acid(s), and styrene sulfonic acid(s). It is noted that what is meant by (meth)acrylic acid is acrylic acids or methacrylic acids (i.e., α-methyl acrylic acid, which is an α-methyl derivative of acrylic acid). It is also noted that acid(s) is meant to include the free acids and the metal salts, the ammonium salt, and the alkyl esters of these acids, respectively.

The above-mentioned (meth)acrylic acid alkyl esters, acrylic acids and their salts, methacrylic acid (that is, α-methyl acrylic acid, which is an α-methyl derivative of acrylic acid), and their salts, and their alkyl esters with hydrophilic group substituted are usable as the vinyl group-containing monomer. These compounds are represented by the following Formula (10).

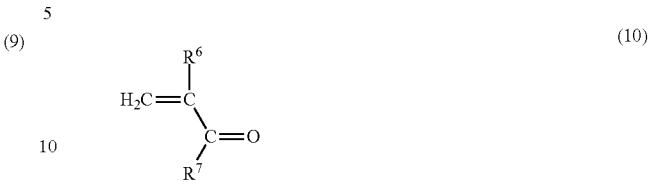

(10)

In the Formula (10), $R^6$ is either a methyl group or a hydrogen atom and $R^7$ is either a hydroxyl group or an alkoxy group with or without a substituent.

Examples of $R^7$ in the case of the alkoxy group with or without a substituent include methoxy group, ethoxy group, n-propoxy group, isopropoxy group, n-butoxy group, isobutoxy group, sec-butoxy group, tert-butoxy group, n-pentoxy group, isopentoxy group, hexyl group, heptoxy group, octyloxy group, 2-ethylhexyloxy group, nonyloxy group, and steary oxy group. Examples of a substituent that may be bonded to the alkoxy group include hydroxyl group, carboxyl group and alkoxy group.

Following Formula (11) represents a constituent unit obtained from the compound represented by the Formula (10).

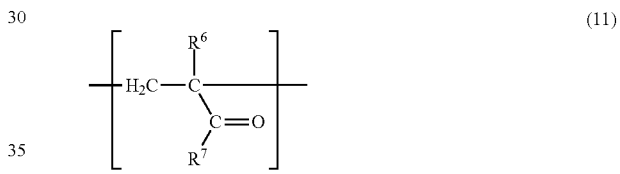

(11)

In the Formula (11), $R^6$ and $R^7$ are the same as above.

Table 19 shows specific examples of polymers which each have at least the constituent unit being obtained from the styrene derivative as the monomer represented by the Formula (3) or the Formula (6), and the constituent unit obtained from a vinyl group-containing monomer. The scope of the present invention shall not be limited by these examples.

TABLE 19

| Examples of Polymer | Constituent Unit Obtained from Styrene Derivative of Formula (3) or Formula (6) | | Constituent Unit Obtained from Monomer α | Constituent Unit Obtained from Monomer β | Constituent Unit Obtained from Monomer γ |
|---|---|---|---|---|---|
| 1 | Formula (1) | — | Formula (9) | — | — |
| 2 | Formula (1) | — | Formula (9) | Formula (2) | — |
| 3 | Formula (1) | — | Formula (9) | Formula (11) | — |
| 4 | Formula (1) | — | Formula (9) | Formula (11) | Formula (11') |
| 5 | Formula (1) | — | Formula (2) | — | — |
| 6 | Formula (1) | — | Formula (2) | Formula (11) | — |
| 7 | Formula (1) | — | Formula (2) | Formula (2') | — |
| 8 | Formula (1) | — | Formula (2) | Formula (2') | Formula (11) |
| 9 | Formula (1) | — | Formula (11) | — | — |
| 10 | Formula (1) | — | Formula (11) | Formula (11') | — |
| 11 | Formula (5) | — | Formula (9) | Formula (2) | — |
| 12 | Formula (5) | — | Formula (9) | Formula (11) | — |
| 13 | Formula (5) | — | Formula (2) | — | — |
| 14 | Formula (5) | — | Formula (2) | Formula (11) | — |
| 15 | Formula (5) | Formula (5") | Formula (9) | — | — |
| 16 | Formula (5") | — | Formula (9) | Formula (2) | — |
| 17 | Formula (1) | Formula (1") | Formula (2) | — | — |
| 18 | Formula (1") | — | Formula (2) | Formula (11) | — |

TABLE 19-continued

| Examples of Polymer | Constituent Unit Obtained from Styrene Derivative of Formula (3) or Formula (6) | | Constituent Unit Obtained from Monomer α | Constituent Unit Obtained from Monomer β | Constituent Unit Obtained from Monomer γ |
|---|---|---|---|---|---|
| 19 | Formula (1) | Formula (1') | Formula (2) | — | — |
| 20 | Formula (1") | — | Formula (2) | Formula (11) | Formula (11') |

In Table 19, styrene derivatives and monomers α, η and γ are respectively vinyl group-containing monomers different from each other. Also, the Formula (1) and Formula (1'), the Formula (2) and Formula (2'), and the Formula (11) and Formula (11'), respectively, represent compounds represented by the Formulae (1), (2) and (11) with substituents differed in the chemical structure. Also, in the Formula (1") and Formula (5"), the COOM groups have been changed to alkyl esters.

The method employed to effect the polymerization may be any of known ones such as solution polymerization, suspension polymerization, emulsion polymerization, dispersion polymerization, precipitation polymerization and bulk polymerization. It is not limited The solution polymerization is one of the methods used on an occasion of effecting a radical polymerization with a vinyl group-containing monomer such as the styrene derivative represented by the Formula (3). In this method, the monomer and polymerization initiator are dissolved in a solvent wherein the product polymer is soluble, and the polymerization is conducted by heating the solution. The polymerization initiator to be used can be benzoyl peroxide, azobis-isobutyronitrile or the like, which are soluble in the monomer or the solvent. The solution polymerization is characterized as providing lower degree of polymerization and lower polymerization velocity compared with the bulk polymerization, and since the heat of polymerization created in the polymerization system is removed by the surrounding solvent, it is easy to control the polymerization temperature. The solution polymerization is quite user-friendly if the solution is directly used as the polymer solution after the polymerization, but if the polymer is to be taken out in solid form, it is necessary to first remove the solvent and then recover the polymer.

The bulk polymerization is one of the methods to carry out a radical polymerization of monomers having a vinyl group such as the styrene derivative represented by the Formula (3). It is a method to effect polymerization without using a solvent but with heat between vinyl monomers by themselves or with a help of a small amount of a polymerization initiator. As the initiator, benzoyl peroxide or azobis-isobutyronitrile, which are soluble in the monomer is used. The bulk polymerization is characteristic in that the polymerization velocity is large and that a relatively pure polymer is obtained in blocks. The problems with this reaction are that it is difficult to remove the polymerization heat so that localized heating takes place rendering it hard to control the polymerization temperature, and that the produced polymer solidifies and sticks to the vessel rendering it hard to restore the vessel, etc. Therefore after-treatments are complicated. Industrially, the bulk polymerization is adopted in making of polystyrene pellet by continuous bulk polymerization from styrene monomers, which is a styrene-containing resin like the one of the present invention, in making of organic glass from polymethylmethacrylate, in hardening of glass fiber-reinforced unsaturated polyester, in polymerization-casting in a metal mold (casting polymerization), etc.

The precipitation polymerization is one of the methods used on an occasion of conducting a radical polymerization of monomers having a vinyl group such as the styrene derivative represented by the Formula (3). It is a method wherein a solvent is used which dissolves the monomer and the initiator, but does not dissolve or swell the product polymer almost, and wherein the polymerization is accompanied by heating. As the initiator, benzoyl peroxide or azobisisobutyronitrile or the like is used, which are soluble in the monomer or the solvent. As the polymerization proceeds and the polymer is produced, it precipitates as it is not soluble in the solvent. The precipitation polymerization is characteristic in that, as the polymerization proceeds and the produced polymer precipitates, the produced polymer is substantially similar to that of the bulk polymerization so that, in comparison to the solution polymerization, although the resulting polymerization degree and polymerization velocity are higher, the controlling of the polymerization temperature is easier because the polymerization heat which occurs in the polymerization system is removed by the surrounding solvent. With the precipitation polymerization, it is possible to obtain the polymer after the polymerization by merely isolating and drying, and thus it is possible to dispense with the use of suspension stabilizer or emulsifier which are used in suspension polymerization or emulsion polymerization, and thus pure polymer can be obtained.

The suspension polymerization is one of the methods used on an occasion of conducting a radical polymerization of monomers having a vinyl group such as the styrene derivative represented by the Formula (3). When a monomer insoluble to a medium (chiefly, water) is agitated intensely in the medium, dispersion and suspension take place and a droplet having a size of 0.01-1 mm is made. To this if a polymerization initiator soluble to the monomer (for example, benzoyl peroxide and azobisisobutyronitrile) is added, then the suspension polymerization proceeds. It is possible to conduct a polyaddition reaction in a suspended system, like in the case of polyurethane. In this polyaddition reaction, polymerization proceeds in the droplet of the monomer and a granular polymer is obtained. When a suspension polymerization is effected using vinyl acetate, styrene or methyl methacrylate as the monomer, for example, true spherical particles are obtained so that such occasion is called as pearl polymerization. The polymerization within the droplet proceeds fundamentally in the same manner as the bulk copolymerization, and the polymerization velocity and the polymerization degree are high. In the suspension polymerization, as the polymerization proceeds, the droplet of the monomer becomes a solution rich in the solute, which is the polymer, in the solvent, which is the monomer, to an extent such that the droplets are easy to unite with each other. Therefore, it is necessary to conduct this polymerization while giving an intense agitation so as to maintain thorough dispersion, and in order to stabilize the droplets, a water-soluble polymer such as gelatin, starch, polyvinyl alcohol, and carboxymethyl cellulose or water-insoluble powder such as calcium carbonate and magnesium carbonate is added. Furthermore, the size of the particle of product polymer differs depending on the agitation speed. Also, the controlling of the temperature is easy since the heat of polymerization created during the polymerization is taken away by the surrounding solvent and thus there is little localized heating. Industrially, the suspension polymerization is widely adopted in making of polymers with high polymerization degrees useful as moulding raw material to easily isolate the prepared polymer, such as polystyrene, polymethylmethacrylate, polyvinyl acetate, and polyvinyl chloride. For the purpose of the present invention, more preferable polymerization methods are solution polymerization, precipitation polymerization and bulk polymerization. It is possible to use, for example, a polymerization reaction wherein styrene is used not only as the monomer but also as the solvent, or a bulk polymerization without an addition of the solvent.

It is possible to conduct, as post-polymerization treatments, conventionally known procedures such as refining and separation and extraction. It is more preferable to program a further procedure such as a procedure wherein separation and filtration are effected with a help of an organic solvent, a refining procedure wherein the solvent fining is effected with a help of a combination of a good solvent and a poor solvent, and a procedure of reprecipitation.

As for the polymerization initiator which can be used on the occasion of polymerizing the afore-mentioned monomer, it is suitable to use a peroxide-containing polymerization initiator, an azo group-containing polymerization initiator, a redox system initiator, and various others. It is also possible to effect the polymerization with heat (natural polymerization) without a use of a polymerization initiator.

Examples of the peroxide-containing polymerization initiator include: organic ones such as peroxy ester, peroxydicarbonate, dialkyl peroxide, peroxyketal, ketone peroxide, hydroperoxide, and diacyl peroxide; inorganic ones such as persulfate and hydrogen peroxide. More specifically, examples include: peroxy esters such as tert-butyl peroxyacetate, tert-butyl peroxylaurate, tert-butyl peroxypivalate, tert-butyl peroxy-2-ethylhexanoate, tert-butyl peroxyisobutylate, tert-butyl peroxyneodecanoate, tert-hexyl peroxyacetate, tert-hexyl peroxylaurate, tert-hexyl peroxypivalate, tert-hexyl peroxy-2-ethylhexanoate, tert-hexyl peroxyisobutylate, tert-hexyl peroxyneodecanoate, tert-butyl peroxybenzoate, α,α'-bis(neodecanoilperoxy)diisopropyl benzene, cumyl peroxyneodecanoate, 1,1,3,3-tetramethylbutyl-peroxy-2-ethylhexanoate, 1,1,3,3-tetramethylbutyl-peroxyneodecanoate, 1-cyclohexyl-1-methylethyl-peroxyneodecanoate, 2,5-dimethyl-2,5-bis(2-ethylhexanoilperoxy) hexane, 1-cyclohexyl-1-methylethylperoxy-2-ethylhexanoate, tert-hexyl peroxy isopropyl monocarbonate, tert-butyl peroxy isopropyl monocarbonate, tert-butyl-peroxy-2-ethylhexyloxy monocarbonate, tert-hexyl peroxybenzoate, 2,5-dimethyl-2,5-bis(benzoilperoxy)hexane, tert-butyl peroxy-m-toluoylbenzoate, bis(tert-butylperoxy) isophthalate, tert-butyl peroxy maleic acid, tert-butyl peroxy-3,5,5-trimethylhexanoate, and 2,5-dimethyl-2,5-bis(m-toluoylperoxy)hexane; diacyl peroxides such as benzoyl peroxide, lauroyl peroxide, 2,5-dimethyl-2,5-di(tert-butylperoxy)hexyne-3, and isobutyryl peroxide; peroxydicarbonates such as diisopropylperoxydicarbonate, and bis(4-tert-butylcyclohexyl)peroxydicarbonate; peroxyketals such as 1,1-di-tert-butylperoxy cyclohexane, 1,1-di-tert-hexylperoxy cyclohexane, 1,1-di-tert-butylperoxy-3,3,5-trimethylcyclohexane, and 2,2-di-tert-butylperoxy butane; dialkyl peroxides such as di-tert-butyl peroxide, dicumyl peroxide, and tert-butyl cumyl peroxide; and others such as tert-butyl peroxy allyl monocarbonate.

Examples of azo group-containing polymerization initiator include 2,2'-azobis(2,4-dimethylvaleronitrile), 2,2'-azobis-isobutyronitrile, 1,1'-azobis(cyclohexane-1-carbonitrile), and 2,2'-azobis(4-methoxy-2,4-dimethylvaleronitrile).

Examples of the redox-type-initiator includes: a combination of a persulfate initiator such as potassium persulfate, sodium persulfate, and ammonium persulfate with a reductant such as meta sodium hydrogen sulfite and sodium hydrogen sulfite; a combination of an organic peroxide with a tertiary amine, like combining benzoyl peroxide with dimethylaniline, or cumene hydroperoxide with an aniline; and a combination of an organic peroxide with a transition metal, like combining cumene hydroperoxide with cobalt naphthate.

These polymerization initiators may be used singly or in combination of two or more if need be. The dosage of the polymerization initiator is preferably 0.1-20 weight parts against 100 weight parts of the monomer, and more preferably 1-10 weight parts thereagainst.

Examples of the solvent useful for the polymerization reaction include: ketones such as acetone, methyl ethyl ketone, and methyl isobutyl ketone; esters such as ethyl acetate, butyl acetate, ethyl propionate, and cellosolve acetate; hydrocarbons such as hexane, octane, petroleum ether, cyclohexane, styrene, toluene, and xylene; halogenated hydrocarbons such as trichloroethylene, dichloromethane, and chloroform; ethers such as ethyl ether, dimethyl glycol, trioxane, and tetrahydrofuran; acetals such as methylal, and diethyl acetal; ether alcohols such as methyl cellosolve, ethyl cellosolve, isopropyl cellosolve, butyl cellosolve, diethylene glycol, and monobutyl ether; aprotic polar solvents such as N,N-dimethylformamide, N,N-dimethylacetoamide, N-methyl-2-pyrrolidone, and dimethyl sulfoxide; and sulfur-containing and/or nitrogen-containing organic compounds such as nitropropene and nitrobenzene; and these can be used singly or in combination of two or more.

Tables 20 through 26 show specific examples of the polymerization reactions in which the reaction system consists of the styrene derivative represented by the Formula (3) or (6), monomers α, β, γ, which are different vinyl-group containing monomers, the polymerization initiator, and the solvent. The scope of the present invention is not limited by these examples.

TABLE 20

| Polymerization Examples | Styrene Derivative (wt. parts) | Monomer α (Chemical Name) (wt. parts) | Oligomer β (Chemical Name) (wt. parts) | Oligomer γ (Chemical Name) (wt. parts) | Polymerization Initiator (Chemical Name) (wt. parts) | Solvent (Chemical Name) (wt. parts) |
|---|---|---|---|---|---|---|
| 1 | a1-1 | Styrene | — | — | t-Butyl peroxy isopropyl- | DMF |
|   | (9) | (60) | (—) | (—) | (5) | (100) |
| 2 | a1-2 | α-Methylstyrene | — | — | t-Butyl peroxy isopropyl-monocarbonate | Toluene |
|   | (9) | (60) | (—) | (—) | (4) | (80) |
| 3 | a1-1 | Styrene | Acrylic acid | — | t-Butyl peroxy isopropyl-monocarbonate | DMF |
|   | (4) | (89) | (9) | (—) | (3) | (300) |

TABLE 20-continued

| Polymerization Examples | Styrene Derivative (wt. parts) | Monomer α (Chemical Name) (wt. parts) | Oligomer β (Chemical Name) (wt. parts) | Oligomer γ (Chemical Name) (wt. parts) | Polymerization Initiator (Chemical Name) (wt. parts) | Solvent (Chemical Name) (wt. parts) |
|---|---|---|---|---|---|---|
| 4 | b1-1 (10) | 2,4-Dimethylstyrene (82) | Hydroxyethyl-acrylate (10) | — (—) | t-Hexyl peroxy pivalate (6) | THF (150) |
| 5 | b1-2 (14) | 3,4-Diethyl-α-methylstyrene (75) | Isobutyl maleate (12) | 2-Ethylhexyl-acrylate (10) | t-Butyl peroxy pivalate (8) | Chloroform (300) |
| 6 | c1-1 (15) | 4-Propyl-α-methylstyrene (75) | N,N-Diethyl-methacrylamide (8) | Hydroxypropyl-acrylate (7) | 1,1-Di(t-butylperoxy)-cyclohexane (9) | 1,4-Dioxane (350) |
| 7 | c1-2 (8) | 3,4-Dimethyl-α-methylstyrene (96) | — (—) | — (—) | 2,2'-Azobis-4-methoxy-2,4-dimethyl valeronitrile (5) | Dichloromethane (250) |
| 8 | a2-1 (6) | 2-methoxystyrene (70) | Diacetone-methacrylamide (16) | — (—) | t-Butyl peroxy-2-ethylhexanoate (7) | Propanol (400) |
| 9 | a2-2 (6) | 3-Propyl-α-methylstyrene (82) | Methacrylic acid (15) | — (—) | 2,5-Dimethyl-2,5-bis-(2-Ethylhexanoilperoxy) hexane (3) | Ethyl-acetate (150) |
| 10 | b2-1 (15) | 4-Ethylstyrene (90) | Acrylonitrile (10) | 2-Ethylhexyl-acrylate (15) | t-Butyl peroxy-2-ethylhexyl-monocarbonate (8) | Diethylene-glycol (200) |
| 11 | b2-2 (8) | 2-Chlorostyrene (70) | N,N-Dimethylamino-propylacrylamide (7) | Methacrylic acid (10) | t-Butyl peroxy-maleic acid (3) | Isopropyl-cellosolve (200) |
| 12 | c2-1 (3) | 2,5-Dimethyl-α-methylstyrene (81) | 2-Hydroxypropyl-methacrylate (20) | — (—) | 2,5-Dimethyl-2,5-di-(t-butylperoxy)hexyne-3 (5) | Diethylene-glycol (300) |

TABLE 21

| Polymerization Examples | Styrene Derivative (wt. parts) | Monomer α (Chemical Name) (wt. parts) | Oligomer β (Chemical Name) (wt. parts) | Oligomer γ (Chemical Name) (wt. parts) | Polymerization Initiator (Chemical Name) (wt. parts) | Solvent (Chemical Name) (wt. parts) |
|---|---|---|---|---|---|---|
| 13 | c2-2 (12) | 3-Chloro-α-methylstyrene (60) | Hydroxypropyl-acrylate (15) | Isobutyl maleate (16) | 1,1-Di-(t-hexylperoxy) cyclohexane (6) | N-Methyl-2-pyrrolidone (250) |
| 14 | d1-1 (30) | 2,3-Diethylstyrene (50) | Itaconic acid (20) | N,N-Diethylmeth-acrylamide (20) | t-Butyl peroxyacetate (4) | Octane (400) |
| 15 | d1-3 (20) | α-Methylstyrene (60) | — (—) | — (—) | 2,2'-Azobis-(2,4-dimethylvaleronitrile) (7) | Benzene (200) |
| 16 | e1-2 (5) | Styrene (70) | Monobutyl-maleate (8) | Methacrylamide (6) | t-Butyl peroxybenzoate (3) | Methyl-cellosolve (300) |
| 17 | e1-7 (11) | 2,3-Diethylstyrene (76) | Methacrylamide (15) | — (—) | 2,2'-Azobisisobutyronitrile (7) | Toluene (150) |
| 18 | d2-1 (8) | 2-Ethyl-3-Methyl-α-methylstyrene (75) | Acrylamide (20) | 2-Hydroxypropyl-methacrylate (10) | 1,1,3,3-Tetramethylbutyl-peroxy-2-ethylhexanoate (4) | DMF (150) |
| 19 | d2-2 (3) | 3-Ethyl-α-methylstyrene (82) | n-Butyl acrylate (15) | — (—) | Bis(4-t-butylcyclohexyl)-peroxydicarbonate (5) | THF (200) |
| 20 | e2-1 (14) | 2,4-Diethylstyrene (71) | 2-Ethylhexyl-acrylate (5) | Acryloyl-morpholine (10) | Bis(4-t-butylcyclohexyl)-peroxydicarbonate (7) | Methyl-ethyl-ketone (200) |
| 21 | e2-5 (17) | 3-Methyl-α-methylstyrene (60) | — (—) | — (—) | Diisopropylperoxy-dicarbonate (5) | Dimethyl-glycol (300) |

TABLE 22

| Polymerization Examples | Styrene Derivative (wt. parts) | Monomer α (Chemical Name) (wt. parts) | Oligomer β (Chemical Name) (wt. parts) | Oligomer γ (Chemical Name) (wt. parts) | Polymerization Initiator (Chemical Name) (wt. parts) | Solvent (Chemical Name) (wt. parts) |
|---|---|---|---|---|---|---|
| 22 | e2-16 | 2,4-Diethylstyrene | Acrylic acid | Diacetone-methacrylamide | t-Butyl peroxy isopropyl-monocarbonate | N-Methyl-2-pyrrolidone |
|  | (12) | (65) | (10) | (15) | (7) | (300) |
| 23 | f1-1 | Styrene | — | — | t-Butyl peroxy isopropyl-monocarbonate | DMF |
|  | (15) | (80) | (—) | (—) | (4) | (150) |
| 24 | f1-3 | α-Methylstyrene | Methacrylic acid | — | 2,5-Dimethyl-2,5-di-(t-butylperoxy)hexyne-3 | Diethyleneglycol |
|  | (12) | (87) | (10) | (—) | (10) | (300) |
| 25 | f2-1 | 2,4-Dimethylstyrene | Acrylamide | Acrylonitrile | 2,5-Dimethyl-2,5-bis-(2-ethylhexanoilperoxy)-hexane | Methylacetate |
|  | (3) | (85) | (10) | (9) | (5) | (150) |
| 26 | f2-4 | 2-Ethyl-3-methyl-α-methylstyrene | Acrylic acid | — | 2,2'-Azobis-4-methoxy-2,4-dimethyl valeronitrile | Dichloromethane |
|  | (16) | (75) | (12) | (—) | (8) | (250) |
| 27 | a1-1 | Styrene | — | — | — | — |
|  | (2) | (98) | (—) | (—) | (—) | (—) |
| 28 | a1-1 | Styrene | — | — | t-Butyl peroxy isopropyl-monocarbonate | — |
|  | (2) | (98) | (—) | (—) | (4) | (—) |
| 29 | a3-2 | Styrene | — | — | t-Butyl peroxy isopropyl-monocarbonate | Toluene |
|  | (5) | (80) | (—) | (—) | (5) | (70) |
| 30 | a3-1 | α-Methylstyrene | Acrylic acid | — | t-Butyl peroxybenzoate | THF |
|  | (10) | (60) | (15) | (—) | (5) | (230) |

TABLE 23

| Polymerization Examples | Styrene Derivative (wt. parts) | Monomer α (Chemical Name) (wt. parts) | Oligomer β (Chemical Name) (wt. parts) | Oligomer γ (Chemical Name) (wt. parts) | Polymerization Initiator (Chemical Name) (wt. parts) | Solvent (Chemical Name) (wt. parts) |
|---|---|---|---|---|---|---|
| 31 | b3-3 | Styrene | — | — | t-Butyl peroxy isopropyl-monocarbonate | DMF |
|  | (15) | (80) | (—) | (—) | (4) | (150) |
| 32 | b3-10 | α-Methylstyrene | Methacrylic acid | — | 2,5-Dimethyl-2,5-di-(t-butylperoxy)hexyne-3 | Diethyleneglycol |
|  | (12) | (87) | (10) | (—) | (10) | (300) |
| 33 | c3-2 | 3-Methyl-α-methylstyrene | — | — | Diisopropylperoxydicarbonate | Dimethylglycol |
|  | (17) | (60) | (—) | (—) | (5) | (300) |
| 34 | b1-23 | Styrene | — | — | t-Butyl peroxy isopropyl-monocarbonate | Toluene |
|  | (5) | (80) | (—) | (—) | (5) | (70) |
| 35 | a1-26 | α-Methylstyrene | Acrylic acid | — | t-Butyl peroxybenzoate | THF |
|  | (10) | (60) | (15) | (—) | (5) | (230) |
| 36 | A2-22 | Methacrylic acid | Acrylamide | — | 1,1,3,3-Tetramethylbutyl-peroxy-2-ethylhexanoate | Dichloromethane |
|  | (8) | (70) | (15) | (—) | (7) | (300) |
| 37 | a3-24 | 2,3-Diethylstyrene | — | — | 2,5-Dimethyl-2,5-di-(t-butylperoxy)hexyne-3 | DMF |
|  | (10) | (90) | (—) | (—) | (6) | (250) |
| 38 | b1-26 | 2-Chlorostyrene | Acrylonitrile | Methacrylamide | t-Butyl peroxy maleic acid | Diethyleneglycol |
|  | (5) | (81) | (10) | (5) | (6) | (350) |
| 39 | b2-18 | 2,4-Diethylstyrene | Acrylamide | Acrylonitrile | 2,5-Dimethyl-2,5-bis-(2-ethylhexanoilperoxy)-hexane | Diethyleneglycol |
|  | (7) | (82) | (6) | (9) | (5) | (350) |
| 40 | b3-18 | 3-Methyl-α-methylstyrene | — | — | Diisopropylperoxydicarbonate | Dimethylglycol |
|  | (12) | (83) | (—) | (—) | (5) | (300) |

TABLE 24

| Polymerization Examples | Styrene Derivative (wt. parts) | Monomer α (Chemical Name) (wt. parts) | Oligomer β (Chemical Name) (wt. parts) | Oligomer γ (Chemical Name) (wt. parts) | Polymerization Initiator (Chemical Name) (wt. parts) | Solvent (Chemical Name) (wt. parts) |
|---|---|---|---|---|---|---|
| 41 | c1-28 (2) | Styrene (84) | Monobutyl maleate (8) | Methacrylamide (7) | t-Butyl peroxybenzoate (3) | Methyl-cellosolve (300) |
| 42 | c2-21 (3) | 3-Propyl-α-methylstyrene (70) | Methacrylic acid (15) | — (—) | 2,5-Dimethyl-2,5-bis-(2-ethylhexanoilperoxy)-hexane (3) | Ethyl-acetate (150) |
| 43 | d2-17 (9) | α-methylstyrene (74) | — (—) | — (—) | t-Butyl peroxy isopropyl-monocarbonate (4) | Toluene (230) |
| 44 | e1-19 (10) | 4-Propyl-α-methylstyrene (70) | N,N-Diethyl-methacrylamide (10) | Hydroxypropyl-acrylate (9) | 1,1-Di(t-butylperoxy)-cyclohexane (9) | 1,4-Dioxane (350) |
| 45 | f1-13 (12) | 3-Chloro-α-methylstyrene (57) | Hydroxypropyl-acrylate (10) | Isobutyl maleate (15) | 1,1-Di(t-hexylperoxy)-cyclohexane (6) | N-Methyl-2-pyrrolidone (250) |
| 46 | a1-2 (5) a2-2 (5) | Styrene (60) | — (—) | — (—) | t-Butyl peroxy isopropyl-monocarbonate (4) | Toluene (35) |
| 47 | b1-1 (3) b3-2 (3) | Styrene (60) | — (—) | — (—) | t-Butyl peroxy isopropyl-monocarbonate (4) | Toluene (35) |
| 48 | c1-2 (4) c2-2 (5) | 2,4-Diethylstyrene (65) | Acrylic acid (10) | Diacetone-methacrylamide (15) | t-Butyl peroxy isopropyl-monocarbonate (7) | N-Methyl-2-pyrrolidone (300) |
| 49 | d1-1 (6) d2-1 (1) | 2,5-Dimethyl-α-methylstyrene (81) | 2-Hydroxypropyl-methacrylate (20) | — (—) | 2,5-Dimethyl-2,5-di-(t-butylperoxy)hexane-3 (5) | Diethylene-glycol (300) |
| 50 | e1-2 (8) d3-2 (1) | 2,3-Diethylstyrene (50) | Itaconic acid (20) | N,N-Diethyl-methacrylamide (20) | t-Butylperoxy acetate (4) | Octane (400) |

TABLE 25

| Polymerization Examples | Styrene Derivative (wt. parts) | Monomer α (Chemical Name) (wt. parts) | Oligomer β (Chemical Name) (wt. parts) | Oligomer γ (Chemical Name) (wt. parts) | Polymerization Initiator (Chemical Name) (wt. parts) | Solvent (Chemical Name) (wt. parts) |
|---|---|---|---|---|---|---|
| 51 | f1-1 (5) f2-1 (3) | 3,4-dimethyl-α-methylstyrene (96) | — (—) | — (—) | 2,2'-Azobis-4-methoxy-2,4-dimethyl valeronitrile (5) | Dichloro-methane (250) |
| 52 | a1-2 (3) d1-1 (3) | 4-propyl-α-methylstyrene (75) | N,N-Diethyl(meth)-acrylamide (8) | Hydroxypropyl-acrylate (7) | 1,1-Di(t-butylperoxy)-cyclohexane (9) | 1,4-Dioxane (350) |
| 53 | b3-2 (7) e1-2 (3) | 2-Chlorostyrene (70) | N,N-Dimethyl-aminopropyl-acrylamide (7) | Methacrylic acid (10) | t-Butyl peroxy maleic acid (3) | Isopropyl-cellosolve (200) |
| 54 | f1-1 (3) d1-1 (3) | 2,4-Dimethylstyrene (85) | Acrylamide (10) | Acrylonitrile (9) | 2,5-Dimethyl-2,5-bis-(2-ethylhexanoilperoxy)-hexane (5) | Ethyl-acetate (150) |
| 55 | a2-1 (3) d2-1 (4) | α-Methylstyrene (87) | Methacrylic acid (10) | — (—) | 2,5-Dimethyl-2,5-di-(t-butylperoxy)hexyne-3 (10) | Diethylene-glycol (300) |

TABLE 26

| Polymerization Examples | Styrene Derivative (wt. parts) | Monomer α (Chemical Name) (wt. parts) | Oligomer β (Chemical Name) (wt. parts) | Oligomer γ (Chemical Name) (wt. parts) | Polymerization Initiator (Chemical Name) (wt. parts) | Solvent (Chemical Name) (wt. parts) |
|---|---|---|---|---|---|---|
| 56 | a1-2 (5) a2-1 (3) b3-2 (7) | Styrene (84) | Monobutyl maleate (8) | Methacrylamide (7) | t-Butyl-peroxybenzoate (3) | Methyl-cellosolve (300) |
| 57 | b1-3 (3) e3-1 (1) f2-3 (5) | 4-Propyl-α-methylstyrene (70) | N,N-Diethyl-methacrylamide (10) | Hydroxypropyl-acrylate (9) | 1,1-Di(t-butylperoxy)-cyclohexane (9) | 1,4-Dioxane (350) |
| 58 | e2-1 (2) d3-5 (2) d1-3 (5) | 2,3-Diethylstyrene (90) | — (—) | — (—) | 2,5-Dimethyl-2,5-di-(t-butylperoxy)hexane-3 (6) | DMF (250) |

The styrene derivatives in Tables 20 through 26 are the same compounds as those exemplified in Tables 1 through 18. Also in them, "tert-" is abridged to "t-", "tetrahydrofuran" to "THF", and "N,N-dimethylformamide" to "DMF".

Method B, which is another method for making the charge control resin (styrene-based resin) of the present invention, includes at least a step to obtain a polymer from vinylphenyl alkylene halide and other monomers and a step thereafter to react the thus obtained polymer with dihydroxy aromatic carboxylic acid or dihydroxy aromatic carboxylic acid alkyl ester to obtain the constituent unit represented by the Formula (1). In a preferable method of this kind, vinylphenyl alkylene halide as the starting monomer, which becomes the constituent unit represented by the Formula (1), is mixed with a polymerization initiator in a solvent, and thus the monomer is polymerized to obtain the polymer; thereafter, a reaction is conducted involving a dihydroxy aromatic carboxylic acid or a dihydroxy aromatic carboxylic acid alkyl ester to synthesize the constituent unit represented by the Formula (1).

It is possible to use, as the vinylphenyl alkylene halide, any of the vinylphenyl alkylene halides exemplified with respect to Method A. The other monomers that can be used in Method B include the vinyl group-containing monomers previously exemplified with respect to Method A. As specific examples of such reaction, wherein vinylphenyl alkylene halide is copolymerized with vinyl aromatic hydrocarbon-containing monomer represented by the Formula (4) to obtain a copolymer and then it is reacted with dihydroxy aromatic carboxylic acid derivative. It is explained by following Reaction Formulae (12) and (13) for furtherance of the explanation. However, the scope of the present invention shall not be limited by these.

The first reaction in Method B derivatizes, in the first place, a polymer by polymerizing a vinylphenyl alkylene halide having a group reactive to the dihydroxy aromatic carboxylic acid derivative with monomer α, β or γ, which are monomers containing respectively different vinyls, like in the case of the styrene monomer of the Formula (3) represented by the Reaction Formula (8). It is preferable to use a polymerization initiator in this polymerization reaction. In the following Reaction Formula (12), the vinyl aromatic hydrocarbon-containing monomer shown in the Formula (4) corresponds to the monomer α. It is possible to conduct this polymerization by any of the known methods such as solution polymerization, suspension polymerization, emulsion polymerization, dispersion polymerization, precipitation polymerization, and bulk polymerization, and the invention is not limited with regard to the method. As for the monomer, polymerization initiator, reaction solvent, reaction condition, etc. it is possible to use the same things as are exemplified with respect to Method A.

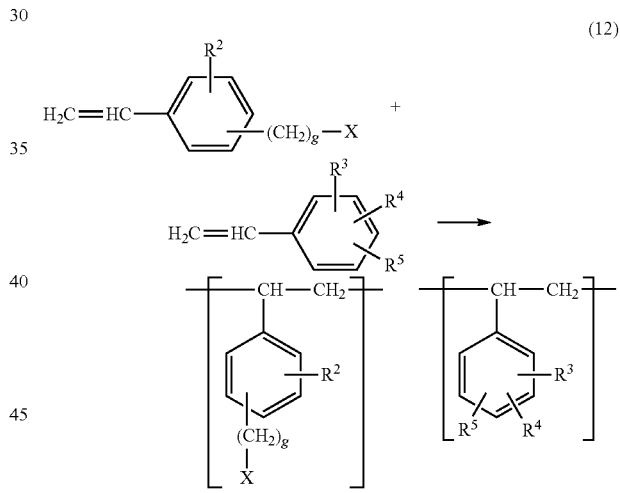

(12)

In the Reaction Formula (12), X is a halogen atom such as F, Br and Cl, and $R^2$, $R^3$, $R^4$, $R^5$ and g are the same as above.

The second reaction in Method B consists in synthesizing the constituent unit represented by the Formula (1), which is to be used in the present invention, by reacting the constituent unit in the polymer which has been obtained in the first polymerization reaction, that is the polymer obtained from the vinylphenyl alkylene halide, with dihydroxy aromatic carboxylic acid derivative. As for the dihydroxy aromatic carboxylic acid, it is possible to use the same things as are exemplified with respect to Method A. Also, as for the reaction solvent, reaction condition, etc., it is possible to use the same reaction condition described with regard to the synthesis of the styrene derivative in Method A and the same reaction solvent described with regard to the synthesis of the styrene derivative in Method A may be used. The following Reaction Formula (13) represents a case wherein the vinyl aromatic hydrocarbon-containing monomer represented by the Formula (4) is used.

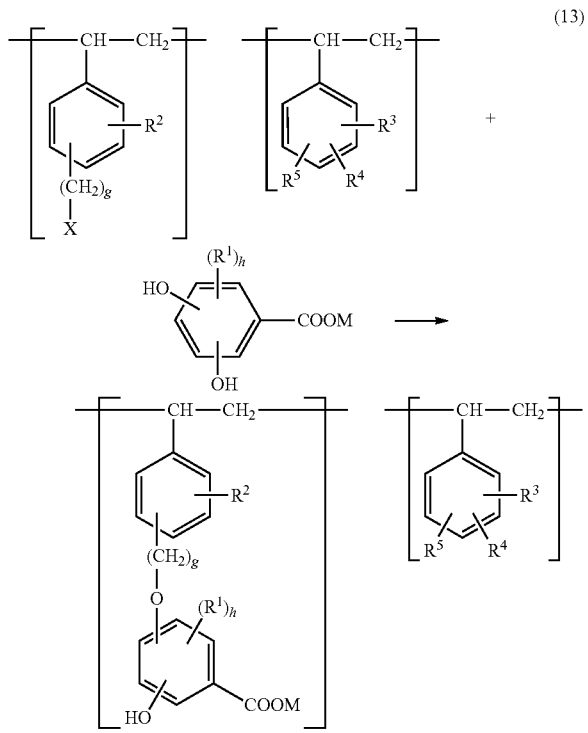

In the Reaction Formula (13), X, $R^1$, $R^2$, $R^3$, $R^4$, $R^5$, g and h are the same as above.

It is preferable that the charge control resin of the present invention has a glass transition temperature of 70-150° C. More preferably, 80-130° C. If a toner or a high molecular compound for electrostatic charge image developing containing this styrene-based resin is made by molten kneading, it is possible to effectively increase the electrification capacity by conducting the molten kneading at a temperature equal to or above the glass transition temperature, at which the fluidity of the charge control resin is increased, because the compatibility of the charge control resin to the binder resin (for example, resin for toner) is heightened and thus it becomes possible to disperse the charge control resin uniformly.

It is preferable that the number average molecular weight (Mn) of the charge control resin falls in the range of 3000-50000 and the weight average molecular weight (Mw) falls in the range of 4000-500000; and further it is preferable that the value of Mw/Mn, which is obtained by dividing the weight average molecular weight (Mw) by the number average molecular weight (Mn) and is an indicator of molecular weight distribution, is 1-25. Moreover, it is better that the number average molecular weight (Mn) is 5000 through 30000 and the weight average molecular weight (Mw) is 4000 through 300000, and that the molecular weight distribution ratio (Mw/Mn) is 1 through 15. When the value of Mw/Mn is close to 1.0, the situation is more monodisperse, and the compatibility to the binder resin is higher. For this reason, it is possible to disperse the charge control resin uniformly and thus the electrification capacity is efficiently manifested.

It is preferable that the charge control resin generates heat and loses weight in a thermogravimetric differential thermal analysis (TG-DTA) measurement when the temperature is in a range of 200-450° C. It is more preferable that the heat generation and the weight loss are observed in a range of 250-400° C. The temperature at which the heat generation and the weight loss are simultaneously observed is the temperature at which the charge control resin undergoes decomposition by combustion, and it need be equal to or higher than the temperature as of the time when the charge control resin has been added to the binder resin and thermal dispersion process is taking place.

It is preferable that the volume resistive value of the charge control resin is $0.1 \times 10^{16}$–$7.0 \times 10^{17}$ Ωcm. The binder resin containing the charge control resin would leak the electric charge it has acquired with time if the volume resistive value is lower than this range, and on the other hand if the volume resistive value is higher than this range, the electric charge acquired becomes so much that the stability is lost. It is more preferable if the volume resistive value is $0.5 \times 10^{16}$–$1.5 \times 10^{17}$ Ωcm, and even more preferable if $0.6 \times 10^{16}$–$0.5 \times 10^{17}$ Ωcm. The binder resin containing the charge control resin having such a volume resistive value acquires a sufficient amount of electric charge and exhibits a good charging speed and good temporal stability. Incidentally, the volume specific resistance is measured in accordance with JIS Standard (K6911).

The styrene derivative which makes the constituent unit of the polymer which is the active ingredient of the charge control resin of the present invention is also useful as the charge control agent besides its usefulness as the monomer used for the charge control resin.

By giving the styrene derivative used in the present invention a constituent part which gives rise to a good compatibility to the resin used in this application, it is possible to disperse it through the resin uniformly at a molecular level. In this manner, it is possible to exert the styrene derivative's charging characteristics to the utmost with the minimum dosage thereof. Furthermore, by using a styrene-based resin having a polymer which has a styrene derivative as its monomer and a copolymer of such polymer, it is possible, in applications wherein a resin having a similar or analogous composition is used, to improve the compatibility to the resin and thus to effect a uniform dispersion to obtain a good composition.

Therefore, used as the charge control agent, the substance of the present invention can exert the charging characteristics to far higher degrees compared to the conventional charge control agents. Also, the charge controllability is stable and the fastness is improved.

As a charge control agent, the styrene derivative (charge control agent) and the charge control resin (styrene-based resin) are supposed to be contained in a toner or powdery paint or the like for electrostatic charge image developing. It is preferable that the dosage of the styrene derivative (charge control monomer) or the charge control resin is 0.1 to 10 weight parts against 100 weight parts of the resin used. Furthermore, it is more preferable that the dosage of the styrene derivative (charge control monomer) or the charge control resin is 0.5 to 7 weight parts against 100 weight parts of the resin used.

It is possible to exemplify the following known resins to go with toner (binder resins) as the examples of resin for toner applicable to the present invention. Namely, thermoplastic resins such as styrene resin, styrene-acrylic resin, styrene-butadiene resin, styrene-maleic acid resin, styrene-vinylmethylether resin, styrene-methacrylic acid ester copolymer, polyester resin, and polypropylene resin can be exemplified. These resins can be used singly or in a blend of two or more.

Incidentally, it is possible to use the styrene derivative (charge control agent) and charge control resin used in the present invention for the purpose of controlling (intensifying) the chargeability of a static powdery paint by dosing it in the resin powder. In this case, examples for the resin for the paint include thermoplastic resins such as acrylic resins, polyolefin-containing resins, polyester-containing resins, and polyamide-containing resins and thermosetting resins such as phenol-containing resins, epoxy-containing resins, polyester-containing resin; and these can be used singly or in a mixture of two or more.

As the colorant for the toner, it is possible to use various dyes and pigments singly or in a blend of two or more. Examples of acceptable the colorant include organic pigments such as monoazo yellow, disazo yellow, azomethine yellow, quinophthalon yellow, quinoline yellow, isoindolinone yellow, perinone orange, perinone red, perylene maroon, rhodamine 6G lake, quinacridone red, anthrone red, rose bengal, copper phthalocyanine blue, copper phthalocyanine green, and diketo pyrrolo pyrrole-containing pigment; inorganic pigments and metal powders such as carbon black, titanium white, titanium yellow, ultramarine, cobalt blue, red ochre, aluminum powder, and bronze; various oil soluble dyestuff and disperse dyes such as azo dye, quinophthalone-containing dye, anthraquinone-containing dye, phthalocyanine-containing dye, indophenol-containing dye, and indoaniline-containing dye; and triarylmethane-containing dyes and xanthene-containing dyes such as rosin, rosin modified phenol and rosin modified maleic acid which are modified by resin. These can be used singly or in a mixture of two or more.

The toner can be made by using any of generally known methods. For example, a method for manufacturing a toner for electrostatic image development employs a mixer such as ball mill to mix together thoroughly a resin for toner, a pigment, and the styrene derivative (charge control agent) and/or charge control resin of the present invention, and, if need be, a magnetic material (for example, fine powder made of strong magnetic substance such as iron, cobalt and ferrite), a fluidity modifier (such as silica, aluminum oxide and titanium oxide), an offset inhibitor (such as wax and low molecular weight olefin wax), a dispersion stabilizer, and a light stabilizer. Thereafter, the mixture is melt and blended by means of a thermal kneading machine such as a heating roll, kneader, and extruder. Then, the mixture is cooled and solidified, and the solidified mixture is crushed and classified, and then a toner of a desired average particle size, such as 1-20 micrometers, is obtained.

It is possible to provide the styrene derivative (charge control agent) or charge control resin used in the present invention as an enhancer for charge controlling or enhancement, or as a powdery paint for electrostatic painting containing the enhancer and resin. They may contain one kind of the enhancer or may contain more kinds. A preferable dosage of the enhancer is 0.1 to 10 weight parts against 100 weight parts of the resin, or more preferably 0.5 to 5 weight parts against 100 weight parts of the resin. The resin and the pigment useful in the powdery paint for electrostatic painting can be exemplified by the ones mentioned above with regard to the toner.

Such powdery paint for the electrostatic painting is excellent in environmental resistance and durability, and by virtue of the powdery paint the coating efficiency becomes nearly 100% and the coating performance is improved, and it is possible to form a thick film free of film defect. As the enhancer is either colorless or pale-colored, color tone noise is hard to occur in the paint film.

This powdery paint for electrostatic painting may be manufactured by means of any of generally known manufacturing methods. For example, a method for manufacturing a powdery paint for electrostatic painting employs a mixer such as ball mill to mix together uniformly the added substances such as the charge enhancer and resin of the present invention, and, depending on the application and purpose, a pigment, a fluidity modifier, a powdery paint for electrostatic painting, filler, hardener, and plasticizer. Thereafter, the mixture is melt and blended by means of a thermal kneading machine such as a heating roll, kneader, and extruder. Then, the mixture is cooled and solidified, and crushed and classified, and then a powdery paint for electrostatic painting having a desired particle size, such as 10-250 micrometers, is obtained.

It is possible to conduct the painting of this powdery paint for electrostatic painting by means of any of generally employed electrostatic painting methods such as corona application method, frictional electrification method, and hybrid method.

EMBODIMENTS

Embodiments of the present invention are detailed more, but the present invention is not limited by these embodiments.

Examples of synthesis of the styrene derivative for derivation toward the charge control resin of the present invention are shown in Examples A1 through A15.

Example A1

100.0 g of 2,5-dihydroxy benzoic acid was dissolved by being stirred in 2 liters of methanol, and this was added with 88.3 g of potassium carbonate and heated to 67° C. Into this reaction liquid was dripped 102.0 g of 4-(chloromethyl)styrene in the course of 22 minutes, and a reaction was allowed to proceed for 12 hours at 67° C. This reaction liquid was cooled, and methanol was removed by distillation under a reduced pressure and was cleansed with hexane and was filtrated. The residue was dissolved in methanol and was reprecipitated by being dripped in water and the precipitate was filtered aside. This reprecipitation procedure was repeated twice, and the final residue was dried at 80° C. for 48 hours, and 48.7 g of styrene derivative (Compound Example a1-1) represented by the following Formula (A1) was obtained.

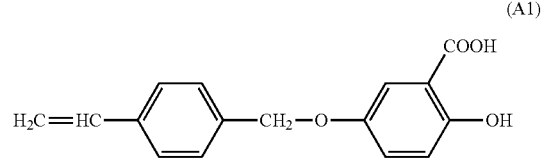 [SMILES: C=Cc1ccc(COc2ccc(O)c(C(=O)O)c2)cc1]

(A1)

Thus obtained styrene derivative (A1) was examined by high-performance liquid chromatography (HPLC: Detector SPD-M20A manufactured by Shimadzu Corporation; column oven: CTO-20A; pump: LC-20AT; degasser: DGU-20A$_3$) under the following conditions and its purity was confirmed to be 94.6%.

HPLC measurement conditions: 3 mg of the sample was dissolved in 10 ml of tetrahydrofuran (THF), to which then ultrasonic wave was applied for 30 minutes, and by filtration with a solvent-resistant membrane filter having a pore diameter of 0.5 micrometer a sample solution was obtained, and it was investigated under the following conditions.

Column: L-Column ODS (4.6×250 mm); column oven temperature: 40° C.

Flow velocity: 1.0 ml/minute; sample dosage: 3 microliters; detection wave length: 254 nm.

Elute-(1): THF:0.05 M-CH$_3$COONH$_4$ aqueous solution=4:6
Elute-(2): THF:0.05 M-CH$_3$COONH$_4$ aqueous solution=6:4
Elute-(1): Elute-(2)=100:0 then (20 minutes) then 0:100

The obtained styrene derivative (A1) was examined by means of $^1$H-nuclear magnetic resonance apparatus (NMR:

FT-NMR JNM-AL 300 manufactured by JEOL Ltd.) under conditions where the resonance frequency was 300 MHz, the measurement nuclide was $^1$H, the used solvent was heavy DMSO, and the measurement temperature was room temperature. $^1$H-NMR spectral data were as follows, and are supportive of the structure represented by the Formula (A1). The results of the measurement by $^1$H-NMR are shown in FIG. 1.

δ(ppm)=5.06 (2H, s, —CH$_2$—), 5.27 (1H, d, C—H), 5.84 (1H, d, C—H), 6.74 (1H, d-d, —CH=), 6.91 (1H, d, Ar—H), 7.23 (1H, d-d, Ar—H), 7.35 (1H, d, Ar—H), 7.41 (1H, d, Ar—H), 7.49 (2H, d, Ar—H).

Figure 2:
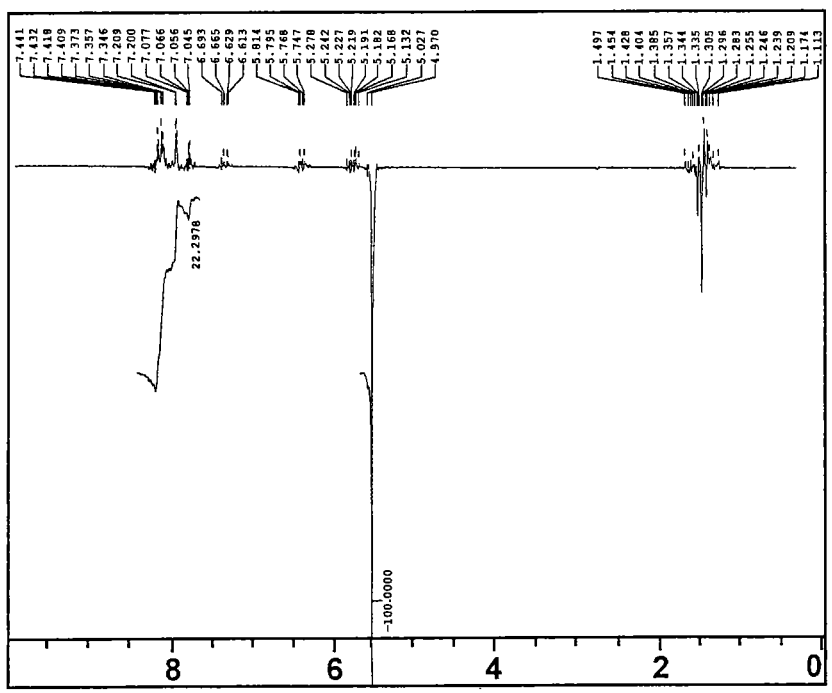
FIG. 2 is a drawing showing a chart of nuclear Overhauser effect linked to the nuclear magnetic resonance spectrum of a styrene derivative of Example A1, used for the charge control resin to which the present invention is applied.

In the $^1$H-NMR, irradiation was conducted upon the proton of 5.06 ppm (2H, s, —OCH$_2$—), a nuclear Overhauser effect (NOE) of 16.9% was observed at the aromatic proton of 7.35 (1H, d, Ar—H). The measurement result of this NOE is shown in FIG. 2.

With regard to the obtained styrene derivative (A1), the weight ratio among carbon (C), hydrogen (H) and nitrogen (N) was measured by an elemental analyzer (totally automatic elemental analyzer 2400II for CHNS/O analysis manufactured by PerkinElmer Corp.). The theoretical values and the measured values by the elemental analysis are given below.

Measured values: C, 71.61; H, 4.90; N, 0.00
Theoretical values: C, 71.10; H, 5.22; N, 0.00

With regard to the obtained styrene derivative (A1), a measurement by KBr method was conducted with a Fourier transform infrared spectrophotometer (FT-IR; JIR-SPX60S manufactured by JEOL Ltd.), and the measurement result was as follows:

ν(cm$^{-1}$)=3132, 3088, 2924, 2877, 1680, 1614, 1593, 1516, 1487, 1471, 1443, 1408, 1379, 1250, 1196, 1011, 906, 860, 831, 808, 789, 775, 744, 715, 675, 559, 492, 472.

Figure 3:
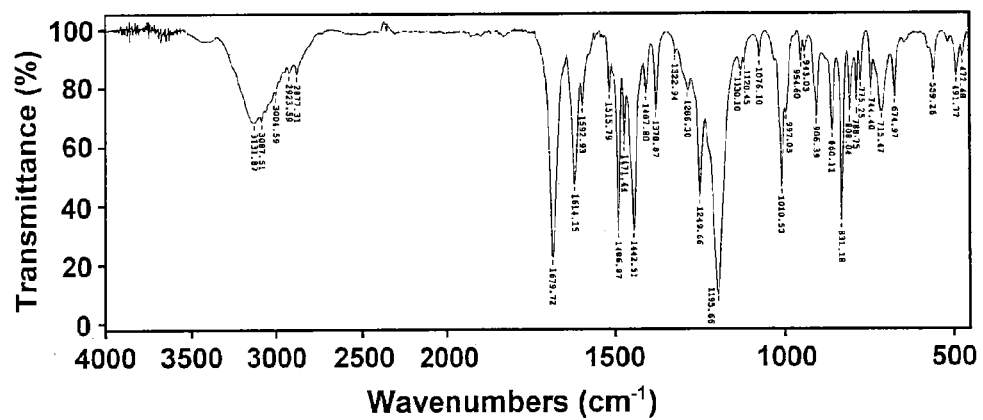
FIG. 3 is a drawing showing a chart of infrared absorption spectrum of the styrene derivative of Example A1, used for the charge control resin to which the present invention is applied.

The measurement result by FT-IR is shown in FIG. 3.

Figure 4:
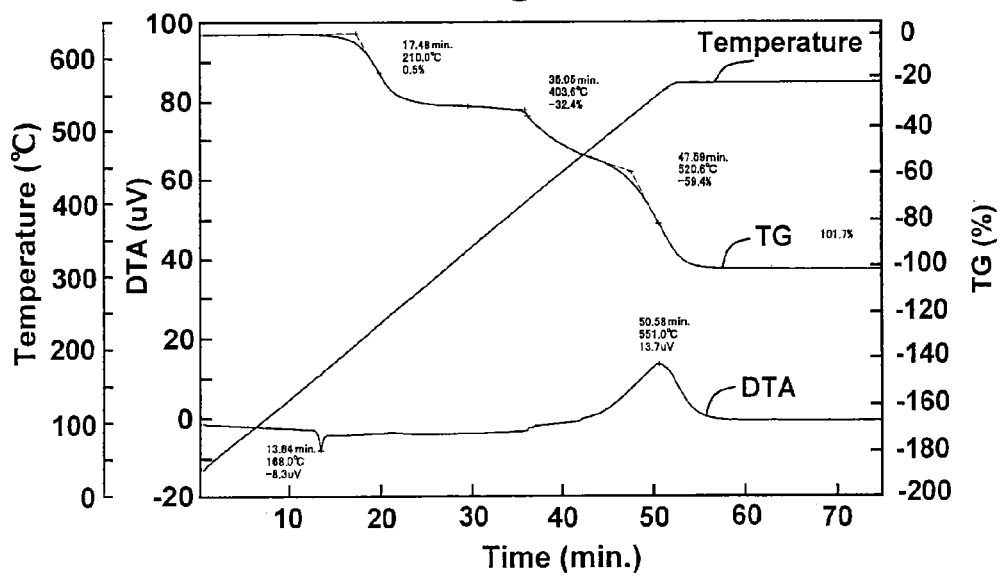
FIG. 4 is a drawing showing a chart of a result of differential thermal/thermogravimetric analysis on the styrene derivative of Example A1, used for the charge control resin to which the present invention is applied.

With regard to the obtained styrene derivative (A1), a measurement was conducted by a differential thermal/thermogravimetry simultaneous analyzer (TG-DTA6200 EXSTAR6000 manufactured by SII Nanotechnology Inc.) under a condition whereby temperature was raised from 30° C. to 550° C., at a rate of 10° C./minute. The measurement result of the simultaneous thermogravimetric and differential thermal analysis (TG-DTA) is as shown in FIG. 4. It was observed by the measurement that the melting point was 168° C., the heat generation temperature was 551° C., and the weight loss temperatures were 210° C., 404° C. and 521° C.

With regard to the obtained styrene derivative (A1), a measurement was conducted with a liquid chromatography/mass spectrometry analyzer (LC/3DQMS System M-8000 manufactured by Hitachi High-Technologies Corp.) under the following conditions.

Figure 5:
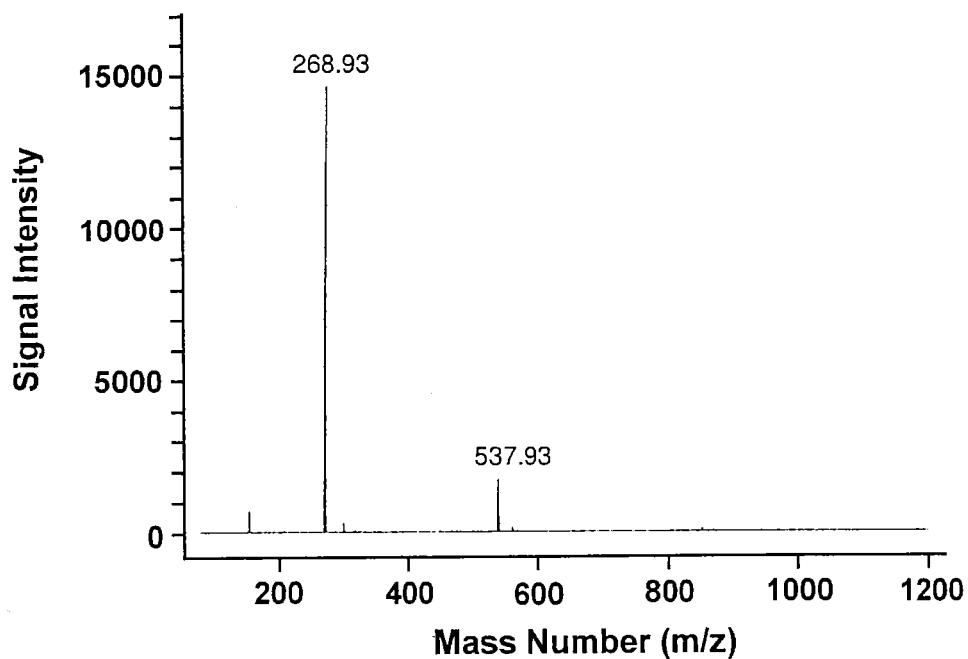
FIG. 5 is a drawing showing a chart of a result of liquid chromatography/mass spectrometry analysis on the styrene derivative of Example A1, used for the charge control resin to which the present invention is applied.

LC/MC measurement conditions were as follows:
Ionized source: ESI ionized source (measured by FI method)
Carrier: methanol for industrial electronics;
Sample preparation method: 1 mg each of the samples was dissolved in the methanol for industrial electronics. In cases of samples which did not dissolve completely, tetrahydrofuran was added to complete the dissolution.
First pore temperature: 120° C.;
Second pore temperature: 100° C.;
Desolventizing temperature: 150° C.;
Auxiliary gas temperature: 150° C.;
Focus voltage: 20 V;
Drift voltage: 20 V;

The result of the liquid chromatography/mass spectrometry analysis is shown in FIG. 5. Also, the theoretical values and the measured values by the mass spectrometry were as shown below:
measured values: LC/MS m/z=269.00 [M-H]$^-$
theoretical values: m/z=270.09

Example A2

100 g of 2,5-dihydroxy benzoic acid and 1441 g of 80% sulfuric acid were mixed and heated at a temperature of 50° C., and 144 g of tert-butanol was added to this dispersion, which was stirred for 30 minutes at a temperature of 50° C. Thereafter, this process of adding 144 g of tert-butanol to the dispersion followed by 30 minutes stirring was repeated for three times. The reaction solution was cooled to the room temperature, and was gradually poured into 1 kg of ice water, and the deposit was filtered aside, and washed with water and then with hexane. The resultant deposit was dissolved in 200 ml of methanol, and was reprecipitated in 3.6 liters of water. After filtration, the resultant deposit was dried for 24 hours at 80° C., and 74.9 g of tert-butylated salicylic acid intermediate was obtained.

25.0 g of the thus obtained salicylic acid intermediate was dissolved in 150 ml of methanol while being stirred, and 36.9 g of potassium carbonate was added and heating was conducted at 65° C. A solution obtained by dissolving 18.7 g of 4-(chloromethyl) styrene in 100 ml of methanol was dripped into this reaction liquid, and reaction was allowed to proceed for 3 hours at 65° C. This reaction liquid was cooled, filtrated, and the methanol in the filtrate was removed by distillation under a reduced pressure and a deposit was obtained.

The obtained deposit was dispersed in 1.5 liters of water of pH 2, and ethyl acetate was added and thereby an extraction was conducted. Thereafter, the solution was separated and added with water with which it was washed, and after the ethyl acetate layer was separated, it was dried with magnesium sulfate, and the ethyl acetate was removed by distillation under a reduced pressure, and a deposit was obtained. The obtained deposit was washed with hexane and was filtrated aside. The deposit was recrystallized by using a mixed solution of toluene and ethyl acetate. This was dried at 80° C. for 40 hours, and 20.1 g of styrene derivative (Compound Example a1-2) represented by the following Formula (A2) was obtained.

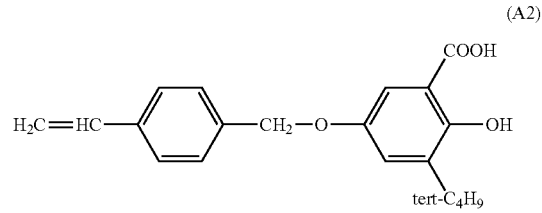

(A2)

The thus obtained styrene derivative (A2) was examined for HPLC purity under conditions described in Example A1, and it was 98.6%.

Figure 6:
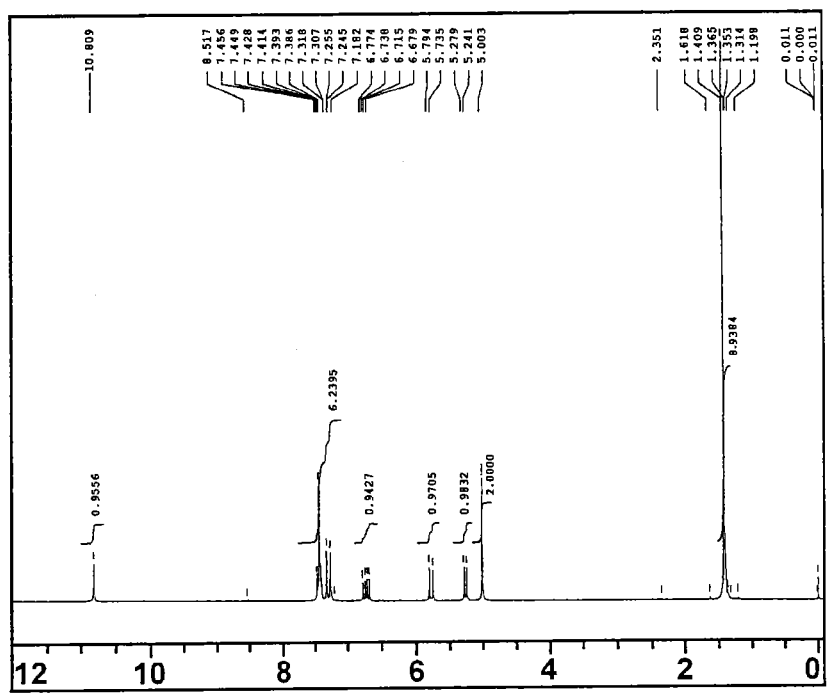
FIG. 6 is a drawing showing a chart of nuclear magnetic resonance spectrum of a styrene derivative of Example A2, used for the charge control resin to which the present invention is applied.

$^1$H-NMR measurement was conducted on the obtained styrene derivative (A2) in the same manner as described in Example A1 except that CDCl$_3$ was used as the measurement solvent. $^1$H-NMR spectrography data were as follows, and are supportive of the structure represented by the Formula (A2). FIG. 6 shows the measurement result of $^1$H-NMR.

δ(ppm)=1.41 (9H, s, —C(CH$_3$)$_3$), 5.00 (2H, s, —OCH$_2$—), 5.26 (1H, d, C—H), 5.76 (1H, d, C—H), 6.73 (1H, d-d, —CH=), 7.25 (1H, d, Ar—H), 7.31 (1H, d, Ar—H), 7.40 (1H, d, 7.44 (1H, d, Ar—H)

In the foregoing $^1$H-NMR, when the proton of 5.00 (2H, s, —OCH$_2$—) was irradiated at, a 8.1-% nuclear Overhauser effect was observed at the aromatic proton of 7.25 (1H, d, Ar—H).

The obtained styrene derivative (A2) was measured for FT-IR under the same conditions as Example A1, and the following was observed.

v(cm$^{-1}$)=3419, 3093, 3005, 2964, 2866, 2710, 2619, 1894, 1819, 1788, 1774, 1753, 1660, 1630, 1608, 1570, 1514, 1483, 1470, 1429, 1406, 1394, 1373, 1362, 1331, 1290, 1277, 1225, 1200, 1180, 1117, 1066, 1016, 985, 970, 958, 908, 889, 850, 833, 818, 806, 795, 721, 681, 658, 606, 528, 515, 494, 465, 428, 420.

Figure 7:
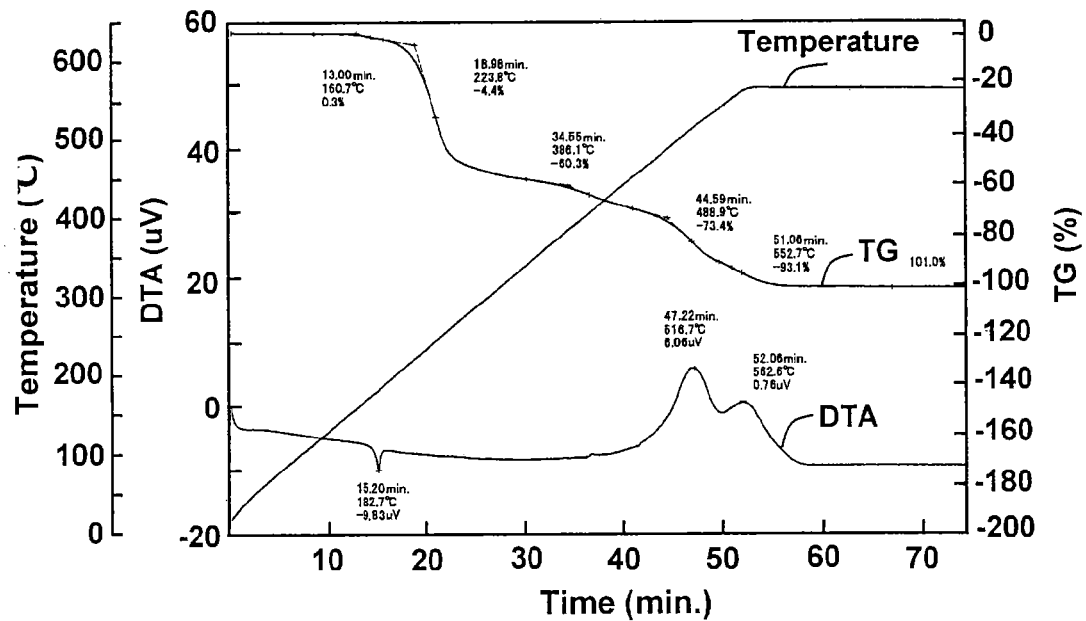
FIG. 7 is a drawing showing a chart of a result of differential thermal/thermogravimetric analysis on the styrene derivative of Example A2, used for the charge control resin to which the present invention is applied.

FIG. 7 shows the result of the measurement conducted on the obtained styrene derivative (A2) for TG-DTA under the same conditions described in Example A1. It was observed by the measurement that the melting point was 183° C., the heat generation temperatures were 517° C. and 563° C., the weight loss temperatures were 161° C., 386° C., 489° C. and 553° C.

Elementary analysis was conducted on the obtained styrene derivative (A2) under the same conditions as described in Example A1. The theoretical values and the measured values by the elemental analysis are given below.
measured values: C, 74.29; H, 6.71; N, 0.00.
theoretical values: C, 73.60; H, 6.79; N, 0.00.

On the obtained styrene derivative (A2) was conducted liquid chromatography/mass spectrometry analysis using the same conditions as described in Example A1. The theoretical values and the measured values by the mass spectrometry are given below.
measured values: LC/MC m/z=324.86 [M-H]$^-$
theoretical values: m/z=326.15

Example A3

78.63 g of 2,4-dihydroxy benzoic acid was dissolved in 400 ml of methanol with stirring, and 152.03 g of potassium carbonate was added and heated at a temperature of 60° C. A solution consisting of a mixture of 87.88 g of 4-(chloromethyl)styrene and 100 ml of methanol was dripped into the reaction liquid, and a reaction was allowed to proceed for 2.5 hours at 60° C. The resultant reaction solution was cooled, and the deposit was separated by filtration and washed with methanol.

The residue was dispersed by chloric acid in one liter of water of pH 1. Thereafter, it was filtered aside and washed with water and dried at 80° C., and 55.71 g of white styrene derivative (Compound Example b1-1) represented by the following Formula (A3) was obtained.

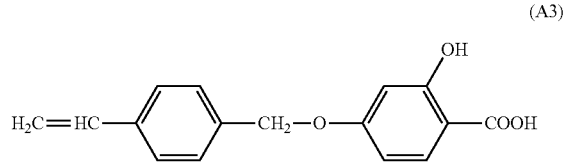 [SMILES: C=Cc1ccc(COc2ccc(C(=O)O)c(O)c2)cc1]

(A3)

The thus obtained styrene derivative (A3) was examined under the same conditions as described in Example A1 and the HPLC purity was found to be 97.7%.

With respect to the obtained styrene derivative (A3), $^1$H-NMR was conducted under the same conditions as described in Example A1. $^1$H-NMR spectral data were as described below and are supportive of the Formula (A3).

δ(ppm)=5.09 (2H, s, —CH$_2$—), 5.27 (1H, d, C—H), 5.85 (1H, d, C—H), 6.38-6.41 (2H, m, Ar—H), 6.74 (1H, d-d, C=H), 7.41 (2H, d, Ar—H), 7.49 (2H, d, Ar—H), 7.61 (1H, d, Ar—H)

In the foregoing $^1$H-NMR, when the proton of 5.09 (2H, s, —OCH$_2$—) was irradiated at, a 17.2-% nuclear Overhauser effect was observed at the aromatic proton of 6.38-6.41 (2H, m, Ar—H).

The obtained styrene derivative (A3) was measured for FT-IR under the same conditions as Example A1, and the following was observed.

v(cm$^{-1}$)=3086, 3005, 1639, 1589, 1514, 1502, 1450, 1379, 1288, 1254, 1182, 1157, 1105, 1095, 1014, 904, 827, 779, 729, 698, 649, 596, 532, 471.

A measurement was conducted on the obtained styrene derivative (A3) for TG-DTA under the same conditions described in Example A1, and it was observed by the measurement that the melting point was 184° C., the heat generation temperature was 571° C., the weight loss temperatures were 216° C., 430° C. and 554° C.

Elementary analysis was conducted on the obtained styrene derivative (A3) under the same conditions as described in Example A1. The theoretical values and the measured values by the elemental analysis are given below.
measured values: C, 64.65; H, 4.23; N, 0.00.
theoretical values: C, 71.10; H, 5.22; N, 0.00.

On the obtained styrene derivative (A3) was conducted liquid chromatography/mass spectrometry analysis using the same conditions as described in Example A1. The theoretical values and the measured values by the mass spectrometry are given below.
measured values: LC/MC m/z=269.07 [M-H]$^-$
theoretical values: m/z=270.09

Example A4

25.0 g of 2,6-dihydroxy-4-methyl benzoic acid was dissolved in 450 ml of methanol with stirring, and 40.5 g of potassium carbonate was added and heated at a temperature of 65° C. A solution consisting of a mixture of 23.4 g of 4-(chloromethyl)styrene and 100 ml of methanol was dripped into the reaction liquid, and a reaction was allowed to proceed for 5 hours at 65° C. The resultant reaction solution was cooled, and filtered and the methanol in the filtrate was removed by distillation under a reduced pressure and a deposit was obtained.

The obtained deposit was dispersed in 1.5 liters of water of pH 2, and extraction was conducted by adding ethyl acetate. Thereafter, the solution was separated and added with water for washing, and the ethyl acetate layer was removed, and drying was conducted with magnesium sulfate, and under a reduced pressure the ethyl acetate was distilled off and a deposit was obtained. The obtained deposit was cleansed with hexane, and filtrated aside. The thus obtained deposit was recrystallized by means of a mixture solution of toluene and ethyl acetate, and it was dried for 47 hours at 80° C., and 27.3 g of a styrene derivative represented by the following Formula (A4) was obtained.

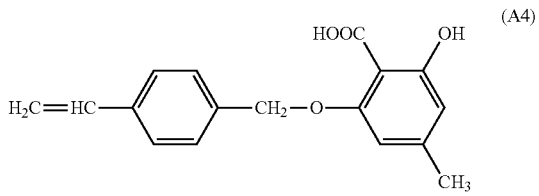 [SMILES: C=Cc1ccc(COc2cc(C)cc(O)c2C(=O)O)cc1]

(A4)

The thus obtained styrene derivative (A4) was examined for HPLC purity under conditions described in Example A1, and it was 93.7%.

With respect to the obtained styrene derivative (A4), $^1$H-NMR was conducted under the same conditions as described in Example A1, except that the measurement solvent used was $CDCl_3$. $^1$H-NMR spectral data were as given below and are supportive of the Formula (A4).

δ(ppm)=3.28 (3H, s, —$CH_3$), 4.39 (2H, s, —$OCH_2$—), 5.25 (1H, d, —C=C—H), 5.83 (1H, d, —C=C—H), 6.73 (1H, d-d, —CH=), 7.17 (1H, d, Ar—H), 7.24 (1H, d, Ar—H), 7.29 (1H, d, Ar—H), 7.45 (1H, d, Ar—H).

In the foregoing $^1$H-NMR, when the proton of 4.39 ppm (2H, s, —$OCH_2$—) was irradiated at, a 15.3-% nuclear Overhauser effect was observed at the aromatic proton of 7.29 (2H, d, Ar—H).

The obtained styrene derivative (A4) was measured for FT-IR under the same conditions as Example A1, and the following was observed.
ν($cm^{-1}$)=3417, 3097, 3007, 2969, 2863, 2621, 1664, 1611, 1516, 1434, 1371, 1333, 1295, 1279, 1228, 1202, 1114, 1064, 973, 911, 854, 836, 809, 805, 724, 684, 496, 467.

A measurement was conducted on the obtained styrene derivative (A4) for TG-DTA under the same conditions described in Example A1, and it was observed by the measurement that the melting point was 156° C., the heat generation temperatures were 509° C. and 559° C., the weight loss temperatures were 163° C., 390° C., 476° C. and 549° C.

Elementary analysis was conducted on the obtained styrene derivative (A4) under the same conditions as described in Example A1. The theoretical values and the measured values by the elemental analysis are given below.
measured values: C, 69.93; H, 5.33; N, 0.00.
theoretical values: C, 71.82; H, 5.67; N, 0.00.

On the obtained styrene derivative (A4) was conducted liquid chromatography/mass spectrometry analysis using the same conditions as described in Example A1. The theoretical values and the measured values by the mass spectrometry are given below.
measured values: LC/MC m/z=283.2 $[M-H]^-$
theoretical values: m/z=284.1

Example A5

5.53 g of 5-tert-butyl-2,3-dihydroxy benzoic acid was dissolved in 30 ml of methanol with stirring, and 8.02 g of potassium carbonate was added and heated at a temperature of 65° C. 4.12 g of 4-(chloromethyl)styrene was dripped into this reaction liquid in the course of 15 minutes, and a reaction was allowed to proceed for 3 hours at 65° C. The resultant reaction solution was cooled, and filtered. The methanol in the filtrate was removed by distillation under a reduced pressure and a deposit was obtained. The obtained deposit was dispersed in water of pH 2, and extraction was conducted by adding ethyl acetate. Thereafter, the solution was separated and added with water for washing, and the ethyl acetate layer was removed, and drying was conducted with magnesium sulfate, and under a reduced pressure the ethyl acetate was distilled off. The resultant deposit was cleansed with toluene, and filtrated aside. The residue was dried for 40 hours at 80° C., and 4.55 g of a styrene derivative (Compound Example c1-2) represented by the following Formula (A5) was obtained.

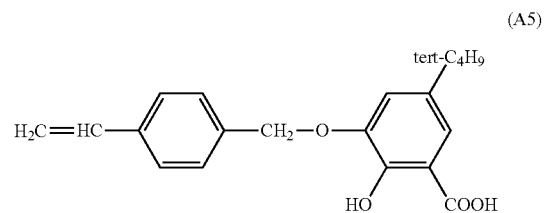

(A5)

The thus obtained styrene derivative (A5) was examined under the same conditions as described in Example A1 and the HPLC purity was found to be 99.3%.

With respect to the obtained styrene derivative (A5), $^1$H-NMR was conducted under the same conditions as described in Example A1. $^1$H-NMR spectral data were as given below and are supportive of the Formula (A5).

δ(ppm)=1.22 (9H, s, —$C(CH_3)_3$), 5.14 (2H, s, —$CH_2$—), 5.25 (1H, d, =C—H), 5.83 (1H, d, =C—H), 6.73 (1H, d-d, =C—H), 7.28 (1H, d, Ar—H), 7.32 (1H, d, Ar—H), 7.43 (1H, d, Ar—H), 7.49 (1H, d, Ar—H)

In the foregoing $^1$H-NMR, when the proton of 5.14 (2H, s, —$CH_2$—) was irradiated at, an 8.5-% nuclear Overhauser effect was observed at the aromatic proton of 7.28 (114, d, Ar—H).

The obtained styrene derivative (A5) was measured for FT-IR under the same conditions as Example A1, and the following was observed.
ν($cm^{-1}$)=3093, 3052, 2964, 2866, 2632, 1654, 1616, 1513, 1483, 1450, 1406, 1304, 1277, 1238, 1198, 1120, 1080, 1016, 982, 958, 920, 893, 858, 829, 818, 793, 710, 687, 644, 490

Figure 8:
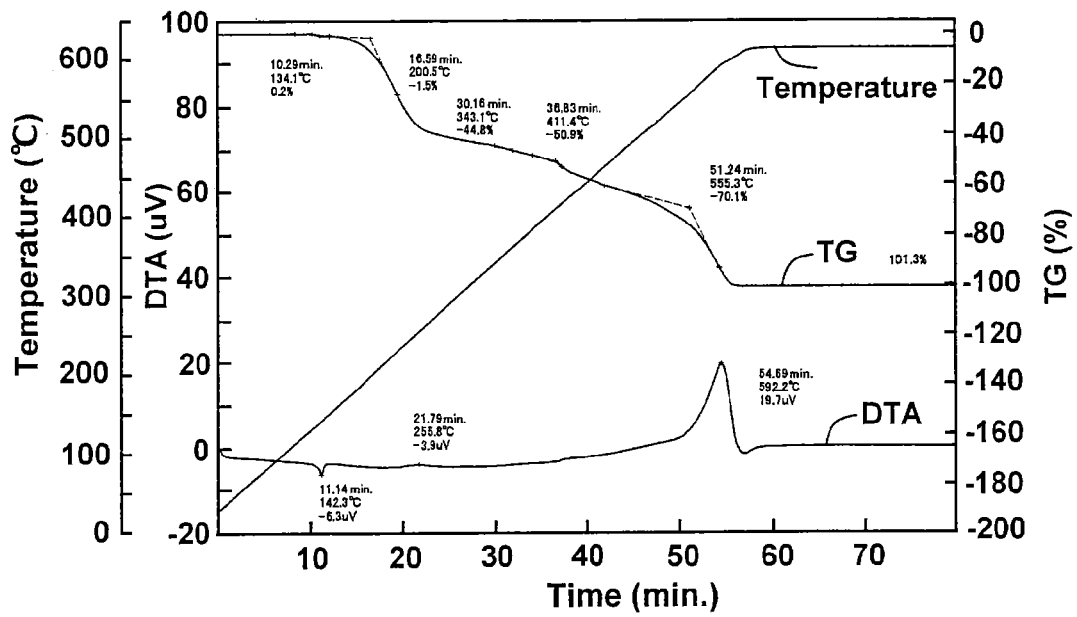
FIG. 8 is a drawing showing a chart of a result of differential thermal/thermogravimetric analysis on a styrene derivative of Example A5, used for the charge control resin to which the present invention is applied.

A measurement was conducted on the obtained styrene derivative (A5) for TG-DTA under the same conditions described in Example A1, and the result is shown in FIG. 8. It was observed by the measurement that the melting point was 142° C., the heat generation temperature was 592° C., and the weight loss temperatures were 201° C., 411° C. and 555° C.

Elementary analysis was conducted on the obtained styrene derivative (A5) under the same conditions as described in Example A1. The theoretical values and the measured values by the elemental analysis are given below.
measured values: C, 73.92; H, 6.64; N, 0.00.
theoretical values: C, 73.60; H, 6.79; N, 0.00.

On the obtained styrene derivative (A5) was conducted liquid chromatography/mass spectrometry analysis was conducted under the same conditions as described in Example A1. The theoretical values and the measured values by the mass spectrometry are given below.
measured values: LC/MC m/z=324.73 $[M-H]^-$
theoretical values: m/z=326.15

Example A6

23.8 g of 5-bromo-2,4-dihydroxy benzoic acid was dissolved in 100 ml of methanol with stirring, and 30.4 g of potassium carbonate was added and dispersed and heated at a temperature of 62° C. for 30 minutes. 17.6 g of 4-chloromethylstyrene was dripped into the reaction liquid in the course of one hour, and a reaction was allowed to proceed under reflux for 2.5 hours. After the reaction, the solution was cooled to the room temperature, and filtered. The obtained deposit was washed with methanol, and then it was added to 300 ml of water and conditioned to pH 1 with chloric acid, and dispersed for 30 minutes and filtered aside and washed with water. The residue was dried at 80° C. for 48 hours, and 13.5 g of white solid styrene derivative (Compound Example b1-21) represented by the following Formula (A6) was obtained.

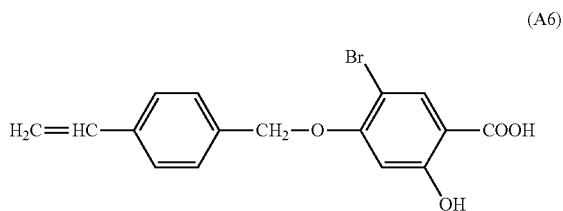 [SMILES: C=Cc1ccc(COc2cc(O)c(C(=O)O)cc2Br)cc1]

The thus obtained styrene derivative (A6) was examined under the same conditions as described in Example A1 and the HPLC purity was found to be 96.7%.

With respect to the obtained styrene derivative (A6), $^1$H-NMR was conducted under the same conditions as described in Example A1. $^1$H-NMR spectral data were as described below and are supportive of the Formula (A6).

δ(ppm)=5.27 (2H, s, —OCH$_2$—), 5.30 (1H, d, —C=C—H), 5.87 (1H, d, —C=C—H), 6.75 (1H, d-d, —C=C—H), 6.79 (1H, s, Ar—H), 7.45 (2H, d, Ar—H), 7.53 (2H, d, Ar—H), 7.90 (1H, s, Ar—H), 11.54 (1H, broad, OH)

In the foregoing $^1$H-NMR, when the proton of 5.27 (2H, s, —OCH$_2$—) was irradiated at, an 8.9-% nuclear Overhauser effect was observed at the aromatic proton of 6.79 (1H, s, Ar—H).

The obtained styrene derivative (A6) was measured for FT-IR under the same conditions as Example A1, and the following was observed.

ν(cm$^{-1}$)=3005, 2557, 1651, 1612, 1514, 1454, 1439, 1383, 1354, 1257, 1192, 1117, 1049, 1016, 1005, 985, 904, 895, 842, 822, 787, 715, 683, 606, 496, 455

A measurement was conducted on the obtained styrene derivative (A6) for TG-DTA under the same conditions described in Example A1, and it was observed by the measurement that the melting point was 232° C., the heat generation temperatures were 257° C. and 560° C., the weight loss temperatures were 227° C. and 510° C.

Elementary analysis was conducted on the obtained styrene derivative (A6) under the same conditions as described in Example A1. The theoretical values and the measured values by the elemental analysis are given below.

measured values: C, 55.35; H, 3.41; N, 0.00.
theoretical values: C, 55.04; H, 3.75; N, 0.00.

On the obtained obtained styrene derivative (A6) was conducted liquid chromatography/mass spectrometry analysis using the same conditions as described in Example A1. The theoretical values and the measured values by the mass spectrometry are given below.

measured values: LC/MC m/z=348.80 [M-H]$^-$
theoretical values: m/z=348.0

Example A7

201 g mixture of 2,5-dihydroxy benzoic acid and isopropanol was added to 1201 g of 80% sulfuric acid and stirred for 8 hours at 75° C. The solution was allowed to cool, and was added with 2 liters of ice water and 140 ml of hexane and was stirred in an ice bath. Resultant crystal deposit was filtrated, and the residue was washed with hexane. Then, it was dispersed in a mixture liquid consisting of methanol and water in a ratio of 6:4, and filtration was conducted. The substance was dried for 48 hours at 60° C., and 65.4 g of isopropyl-salicylic acid intermediate was obtained.

22.5 g of isopropyl-salicylic acid intermediate was dissolved in 450 ml of methanol with stirring, and 60 g of potassium carbonate was added and heated at a temperature of 65° C. To this reaction liquid was added by dripping 96.8 g of 4-(2-chloroethyl)styrene, which had been synthesized by the method described in Polymer Bulletin 19, 111-117 (1988) for three hours at 65° C. The resultant reaction solution was cooled and filtered. Then the methanol in the filtrate was removed by distillation under a reduced pressure and a deposit was obtained. The obtained deposit was dispersed in 1.5 liters of water of pH 2, and extraction was conducted by addition of ethyl acetate. Thereafter, the solution was separated and added with water for washing, and the ethyl acetate layer was removed, and drying was conducted with magnesium sulfate, and under a reduced pressure the ethyl acetate was distilled off and a deposit was obtained. The obtained deposit was cleansed with hexane, and filtrated aside.

The thus obtained residue was recrystallized by means of a mixture solution of toluene and ethyl acetate, and after a filtration, it was dried for 44 hours at 80° C., and 26.3 g of a styrene derivative (Compound Example a1-20) represented by the following Formula (A7) was obtained.

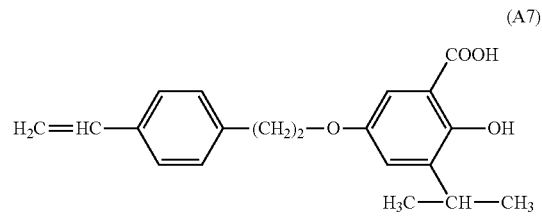

The thus obtained styrene derivative (A7) was examined for HPLC purity under conditions described in Example A1, and it was found 96.6%.

With respect to the obtained styrene derivative (A7), $^1$H-NMR was conducted under the same conditions as described in Example A1. $^1$H-NMR spectral data were as given below and are supportive of the Formula (A7).

δ(ppm)=1.24 (6H, d, —(CH$_3$)$_2$), 2.88 (1H, m, —CH—(CH$_3$)$_2$), 4.07 (2H, t, —O—CH$_2$—), 2.77 (2H, t, —O—CH$_2$—CH$_2$—), 5.25 (1H, d, —C=C—H), (1H, d, —CH=CH), 6.73 (1H, d-d, —CH=CH$_2$), 6.94 (1H, d, Ar—H), 7.26 (1H, d, Ar—H), 7.32 (2H, d, Ar—H), 7.46 (2H, d, Ar—H)

In the foregoing $^1$H-NMR, when the proton of 4.07 (2H, t, —O—CH$_2$—) was irradiated at, a 9.1-% nuclear Overhauser effect was observed at the aromatic proton of 6.94 (1H, d, Ar—H).

The obtained styrene derivative (A7) was measured for FT-IR under the same conditions as Example A1, and the following was observed.

ν(cm$^{-1}$)=3431, 3018, 2878, 1679, 1620, 1455, 1345, 1236, 1132, 1236, 1132, 1078, 930, 810, 740, 700, 506.

Elementary analysis was conducted on the obtained styrene derivative (A7) under the same conditions as described in Example A1. The theoretical values and the measured values by the elemental analysis are given below.

measured values: C, 75.60; H, 6.57; N, 0.00.
theoretical values: C, 73.60; H, 6.79; N, 0.00.

On the obtained styrene derivative (A7) was conducted liquid chromatography/mass spectrometry analysis using the same conditions as described in Example A1. The theoretical values and the measured values by the mass spectrometry are given below.
measured values: LC/MC m/z=325.8 [M-H]$^-$
theoretical values: m/z=326.1

Example A8

53.9 g of 2,3-dihydroxy benzoic acid was dissolved in 280 ml of methanol with stirring, and 106 g of $K_2CO_3$ was added and heated at a temperature of 65° C. and stirred for 30 minutes. 61.7 g of 4-chloromethylstyrene was dripped into this reaction liquid in the course of one hour. Then, a reaction was allowed to proceed under reflux for 3 hours. The reaction liquid was allowed to cool to the room temperature, and filtered; the methanol in the filtrate was removed under a reduced pressure, and a brown semi-solid was obtained. The obtained brown semi-solid was dispersed in 2 liters of water of pH 1, and ethyl acetate was added and extraction was conducted. The ethyl acetate layer was washed with a saturate saline solution and the ethyl acetate layer was removed and drying was conducted with magnesium sulfate, and the solvent was removed under a reduced pressure, and a pale yellow solid was obtained in an amount of 124.3 g. This pale yellow solid was recrystallized with toluene, and after separating the deposit by filtration, it was dried at 80° C. for 40 hours, and 54.5 g of pale yellow styrene derivative (Compound Example c1-1) represented by the following Formula (A8) was obtained.

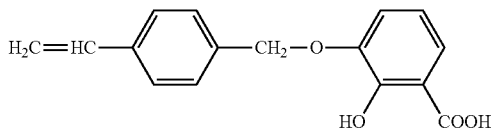

(A8)

The thus obtained Formula (A8) substance was examined under the same conditions as described in Example A1 and the HPLC purity was found to be 95.0%.

With respect to the obtained styrene derivative (A8), $^1$H-NMR was conducted under the same conditions as described in Example A1. $^1$H-NMR spectral data were as given below and are supportive of the Formula (A8).

δ(ppm)=5.11 (2H, s, —OCH$_2$—), 5.25 (1H, d, —C═C—H), 5.83 (1H, d, —C═C—H), 6.72 (1H, d-d, —C═C—H), 6.80 (1H, t, Ar—H), 7.25 (1H, d, Ar—H), 7.34-7.49 (5H, M, Ar—H)

In the foregoing $^1$H-NMR, when the proton of 5.11 (2H, s, —OCH$_2$—) was irradiated at, a 9.9% nuclear Overhauser effect was observed at the aromatic proton of 7.25 (1H, d, Ar—H).

The obtained styrene derivative (A8) was measured for FT-IR under the same conditions as Example A1, and the following was observed.
ν(cm$^{-1}$)=3236, 3032, 2879, 2719, 2594, 1666, 1612, 1581, 1464, 1443, 1385, 1306, 1246, 1234, 1178, 1162, 1087, 1026, 1018, 908, 862, 837, 827, 781, 748, 696, 653, 607, 480.

A measurement was conducted on the obtained styrene derivative (A8) for TG-DTA under the same conditions described in Example A1, and it was observed by the measurement that the melting point was 177° C., the heat generation temperature was 613° C., the weight loss temperatures were 181° C., 413° C. and 593° C.

Elementary analysis was conducted on the obtained styrene derivative (A8) under the same conditions as described in Example A1. The theoretical values and the measured values by the elemental analysis are given below.
measured values: C, 71.66; H, 4.75; N, 0.00.
theoretical values: C, 71.10; H, 5.22; N, 0.00.

On the obtained styrene derivative (A8) was conducted liquid chromatography/mass spectrometry analysis using the same conditions as described in Example A1. The theoretical values and the measured values by the mass spectrometry are given below.
measured values: LC/MC m/z=268.8 [M-H]$^-$
theoretical values: m/z=270.09

Example A9

An example of how to synthesize a mixture of 4-(4'-vinyl-benziloxy)-2-hydroxy benzoic acid and 4-(3'-vinylben-ziloxy)-2-hydroxy benzoic acid with the help of a chloromethylstyrene reagent, which is a mixture of p-chloromethylstyrene and m-chloromethylstyrene will be described.

78.6 g of 2,4-dihydroxy benzoic acid was added to 400 ml of methanol with stirring, and to this was added 152.0 g of potassium carbonate, and the solution was stirred for 30 minutes at 60° C. Then, 83.5 g of chloromethylstyrene (manufactured by AGC Seimi Chemical Co., Ltd.; product name: CMS-P), which is a mixture of p-chloromethylstyrene and m-chloromethylstyrene, was dissolved in 50 ml of methanol, and was dripped into the above-described solution in the course of one hour. After three-hour reaction under reflux, the solution was allowed to cool to room temperature, and the deposit was filtrated aside and washed with methanol. The thus obtained residue was added with one liter of water and turned to pH 1 by chloric acid and subjected to 30 minutes stirring, filtration and washing with water. It was dried at 80° C. for 48 hours, and 76.2 g of white solid styrene derivative (a mixture of Compound Example b1-1 and Compound Example b2-1) represented by the following Formula (A9) was obtained.

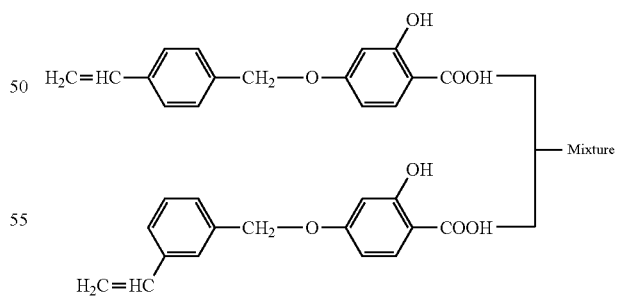

(A9)

Thus obtained styrene derivative (A9) was examined for HPLC purity under conditions described in Example A1, and it was found 97.7%.

$^1$H-NMR measurement was conducted on the obtained styrene derivative (A9) under the same conditions as described in Example A1. $^1$H-NMR spectrography data were as follows, and are supportive of the structure represented by the Formula (A9).

δ(ppm)=5.14 (12H, s, —CH$_2$—), 5.25-5.30 (1H, dX2, C—H), 5.81-5.88 (1H, dX2, C—H), 6.35-6.57 (2H, m, Ar—H), 6.68-6.79 (1H, dX2, C—H), 7.32-7.54 (4H, m, Ar—H), 7.67-7.70 (1H, dX2, Ar—H)

In the foregoing $^1$H-NMR, when the proton of 5.14 (2H, s, —OCH$_2$—) was irradiated at, a 16.8-% nuclear Overhauser effect was observed at the aromatic proton of 6.53-6.57.

The obtained styrene derivative (A9) was measured for FT-IR under the same conditions as Example A1, and the following was observed.

v(cm$^{-1}$)=3448, 3007, 2864, 2551, 2362, 1655, 1622, 1514, 1454, 1437, 1383, 1350, 1250, 1192, 1151, 1095, 1036, 1014, 991, 980, 910, 852, 835, 823, 793, 777, 681, 648, 606, 532, 496, 461.

A measurement was conducted on the obtained styrene derivative (A9) for TG-DTA under the same conditions as described in Example A1, and it was observed by the measurement that the decalescent point was 157° C., the heat generation temperatures were 440° C. and 570° C., and the weight loss temperatures were 216° C., 434° C. and 542° C.

Elementary analysis was conducted on the obtained styrene derivative (A9) under the same conditions as described in Example A1. The theoretical values and the measured values by the elemental analysis are given below.
measured values: C, 71.71; H, 5.01; N, 0.00.
theoretical values: C, 71.10; H, 5.22; N, 0.00.

On the obtained styrene derivative (A9) was conducted liquid chromatography/mass spectrometry analysis using the same conditions as described in Example A1. The theoretical values and the measured values by the mass spectrometry are given below.
measured values: LC/MC m/z=269.0 [M-H]$^-$
theoretical values: m/z=270.09

Example A10

157.3 g of 3,4-dihydroxy benzoic acid was dissolved in 1200 ml of methanol with stirring, and 304.1 g of K$_2$CO$_3$ was added and stirred at a temperature of 65° C. 175.8 g of 4-chloromethylstyrene was dripped into the reaction liquid in the course of one hour. The reaction was allowed to proceed under reflux for one hour and the resultant solution was allowed to cool to the room temperature. The thus obtained deposit was filtered aside and was washed with methanol. The residue was dispersed in 2 liters of water of pH 1, and extraction was conducted by adding ethyl acetate. Then the ethyl acetate layer was washed with saturated saline solution and the ethyl acetate layer was removed, and drying was conducted with magnesium sulfate, and under a reduced pressure the solvent was removed. The obtained deposit was recrystallized by means of ethyl acetate, and the deposit was filtered aside. The deposit was dried for 40 hours at 80° C., and 52.9 g of a white solid styrene derivative (Compound Example d1-1) represented by the following Formula (A10) was obtained.

[Chem. 37]

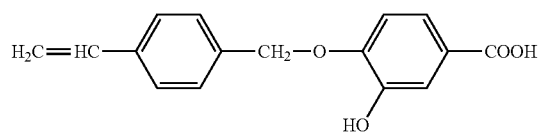
(A10)

The thus obtained Formula (A10) was examined for HPLC purity under conditions described in Example A1, and it was found 96.2%.

With respect to the obtained styrene derivative (A10), $^1$H-NMR was conducted under the same conditions as described in Example A1. $^1$H-NMR spectral data were as given below and are supportive of the Formula (A10).

δ(ppm)=5.17 (2H, s, —OCH$_2$—), 5.27 (1H, d, —C=C—H), 5.85 (1H, d, —C=C—H), 6.74 (1H, d-d, —C=C—H), 7.05 (1H, d, Ar—H), 7.35-7.38 (2H, m, Ar—H), 7.44 (2H, d, Ar—H), 7.50 (2H, d, Ar—H).

In the foregoing $^1$H-NMR, when the proton of 5.17 (2H, s, —OCH$_2$—) was irradiated at, a 12.8% nuclear Overhauser effect was observed at the aromatic proton of 7.05 (1H, d, Ar—H).

The obtained styrene derivative (A10) was measured for FT-IR under the same conditions as Example A1, and the following was observed.

v(cm$^{-1}$)=3550, 2931, 2877, 2823, 2557, 1884, 1801, 1678, 1620, 1593, 1560, 1516, 1473, 1462, 1421, 1379, 1362, 1311, 1286, 1273, 1223, 1188, 1130, 1093, 1003, 991, 943, 895, 866, 837, 825, 766, 749, 730, 650, 598, 563, 478, 438, 403.

A measurement was conducted on the obtained styrene derivative (A10) for TG-DTA under the same conditions described in Example A1, and it was observed by the measurement that the melting point was 197° C., the heat generation temperature was 611° C., the weight loss temperatures were 175° C., 230° C., 410° C. and 570° C.

Elementary analysis was conducted on the obtained styrene derivative (A10) under the same conditions as described in Example A1. The theoretical values and the measured values by the elemental analysis are as follows.
measured values: C, 73.97; H, 6.92; N, 0.00.
theoretical values: C, 73.60; H, 6.79; N, 0.00.

On the obtained styrene derivative (A10) was conducted liquid chromatography/mass spectrometry analysis using the same conditions as described in Example A1. The theoretical values and the measured values by the mass spectrometry are given below.
measured values: LC/MC m/z=268.93 [M-H]$^-$
theoretical values: m/z=270.09

Example A11

157.3 g of 3,4-dihydroxy benzoic acid and 1532.2 g of 80% sulfuric acid were mixed at a heating temperature of 60° C., and 890.5 g of tert-butanol was added to this dispersion in the course of 45 minutes, and the liquid was stirred for 30 minutes at a temperature of 65° C. Thereafter, the liquid was gradually poured into 2 kg of ice water, to which 1 liter of toluene was added, and the resultant deposit was filtered aside and washed with water. Then the deposit was filtered aside and dried at 80° C., and 160.0 g of tert-butylated salicylic acid intermediate was obtained.

63.1 g of the thus obtained salicylic acid intermediate was dissolved in 250 ml of methanol with stirring, and 91.21 g of potassium carbonate was added and heated at 62° C. To this reaction liquid was added 52.6 g of 4-(chloromethyl)styrene in the course of 45 minutes, and a reaction was allowed to proceed for three hours at 67° C. The resultant reaction solution was cooled, and the deposit was filtered aside, and washed with methanol.

The obtained residue after the filtration was dispersed in 1.5 liters of water of pH 2, and was extracted with ethyl acetate. Then the solution was separated and added with water for washing, and the ethyl acetate layer was removed and dried with magnesium sulfate, and the ethyl acetate was removed under a reduced pressure and a deposit was obtained. The thus obtained deposit was recrystallized with toluene, and the deposit was filtered aside and dried for 44 hours at 80° C., and 47.5 g of a styrene derivative (Compound Example f1-1) represented by the following Formula (A11) was obtained.

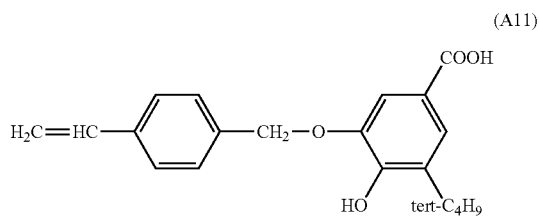

(A11)

The thus obtained styrene derivative (A11) was examined under the same conditions as described in Example A1 and the HPLC purity was found to be 97.9%.

With respect to the obtained styrene derivative (A11), $^1$H-NMR was conducted under the same conditions as described in Example A1. $^1$H-NMR spectral data were as given below and are supportive of the Formula (A11).

δ(ppm)=1.37 (9H, s, —C(CH$_3$)$_3$), 5.21 (2H, s, —OCH$_2$—), 5.26 (1H, d, —C=C—H), 5.85 (1H, d, —C=C—H), 6.73 (1H, d-d, Ar—H), 7.41, 7.49 (5H, s, Ar—H)

In the foregoing $^1$H-NMR, when the proton of 5.21 (2H, s, —OCH$_2$—) was irradiated at, an 8.3% nuclear Overhauser effect was observed at the aromatic proton of 7.41 (1H, s, Ar—H).

The obtained styrene derivative (A11) was measured for FT-IR under the same conditions as Example A1, and the following was observed.

v(cm$^{-1}$)=3518, 2956, 2598, 1678, 1630, 1605, 1516, 1489, 1427, 1387, 1360, 1302, 1255, 1215, 1171, 1117, 1047, 1018, 993, 943, 918, 858, 841, 829, 808, 769, 762, 735, 698, 652, 555, 490.

A measurement was conducted on the obtained styrene derivative (A11) for TG-DTA under the same conditions described in Example A1, and it was observed by the measurement that the melting point was 175° C., the heat generation temperature was 579° C., the weight loss temperatures were 139° C., 221° C., 300° C., 413° C., and 544° C.

Elementary analysis was conducted on the obtained styrene derivative (A11) under the same conditions as described in Example A1. The theoretical values and the measured values by the elemental analysis are given below.
measured values: C, 74.00; H, 6.92; N, 0.00.
theoretical values: C, 73.60; H, 6.79; N, 0.00.

On the obtained styrene derivative (A11) was conducted liquid chromatography/mass spectrometry analysis using the same conditions as described in Example A1. The theoretical values and the measured values by the mass spectrometry are given below.
measured values: LC/MC m/z=325.20 [M-H]$^-$
theoretical values: m/z=326.15

Example A12

46.23 g of 2,5-dihydroxy benzoic acid and 460 g of 80% sulfuric acid were mixed at heating temperature of 70° C., and to this dispersion liquid was added 78.15 g of 2-octanol in the course of 10 minutes and the liquid was stirred for 30 minutes at 70° C. Thereafter, this process of adding 78.15 g of 2-octanol to the dispersion liquid followed by 30 minutes stirring was repeated twice. After the 30 minutes stirring, the reaction liquid was cooled to the room temperature, and was gradually poured into 3 kg of ice water. The obtained deposit was filtered aside, washed with water and then with hexane. The resultant residue was dissolved in 500 ml of methanol, and reprecipitated in 4.5 liters of water. After a filtration, the residue was dried for 24 hours at 80° C., and the reaction product was subjected to silica gel column chromatography, and 29.3 g of octylated salicylic acid intermediate was obtained in a hexane:toluene fraction.

The thus obtained salicylic acid intermediate in an amount of 25.0 g was dissolved in 150 ml of methanol while being stirred, and 29.1 g of potassium carbonate was added and heating was conducted at 65° C. To this reaction liquid was dripped a mixture of 14.7 g of 4-(chloromethyl)styrene and 100 ml of methanol with stirring, and a reaction was allowed to proceed for three hours at 65° C. The thus obtained reaction liquid was cooled, filtrated, and the methanol in the filtrate was removed by distillation under a reduced pressure and a deposit was obtained.

The obtained deposit was dispersed in 1.5 liters of water of pH 2, and extraction was conducted by adding ethyl acetate. Thereafter, the solution was separated and added with water with which it was washed, and after the ethyl acetate layer was separated, it was dried with magnesium sulfate, and the ethyl acetate was removed by distillation under a reduced pressure, and a deposit was obtained. The obtained deposit was washed with hexane and filtrated aside, and the residue was recrystallized by using a mixed solution of toluene and ethyl acetate. The deposit was filtered aside and dried at 80° C. for 45 hours, and 24.1 g of styrene derivative (Compound Example a1-3) represented by the following Formula (A12) was obtained.

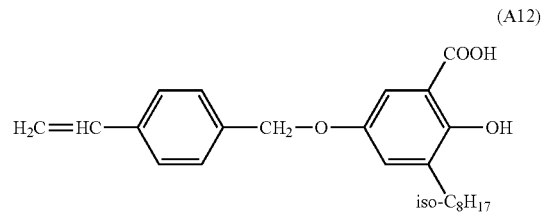

(A12)

The thus obtained styrene derivative (A12) was examined for HPLC purity under conditions described in Example A1, and it was found 96.2%.

With respect to the obtained styrene derivative (A12), $^1$H-NMR was conducted under the same conditions as described in Example A1 except that CDCl$_3$ was used as the measurement solvent. $^1$H-NMR spectral data were as given below and are supportive of the Formula (A12).

δ(ppm)=0.95 (3H, t, —CH$_3$), 1.18-1.51 (16H, broad, —(CH$_2$)$_6$—, —CH$_3$), 3.79 (1H, m, 5.02 (2H, s, —OCH$_2$—), 5.24 (1H, d, C—H), 5.78 (1H, d, C—H), 6.69 (1H, d-d, —CH=), 7.24 (1H, d, Ar—H), 7.32 (1H, d, Ar—H), 7.42 (1H, d, Ar—H), 7.44 (1H, d, Ar—H)

In the foregoing $^1$H-NMR, when the proton of 5.02 (2H, s, —OCH$_2$—) was irradiated at, a 8.1% nuclear Overhauser effect was observed at the aromatic proton of 7.24 (1H, d, Ar—H).

The obtained styrene derivative (A12) was measured for FT-IR under the same conditions as Example A1, and the following was observed.

ν(cm$^{-1}$)=3425, 3111, 3004, 2966, 2932, 2875, 2866, 2734, 2654, 1911, 1824, 1801, 1766, 1715, 1659, 1624, 1611, 1610, 1521, 1497, 1459, 1463, 1411, 1411, 1378, 1365, 1320, 1290, 1278, 1227, 1201, 1178, 1156, 1069, 1040, 986, 965, 941, 900, 893, 847, 844, 822, 808, 795, 722, 685, 660, 610, 524, 522, 499, 468, 422.

A measurement was conducted on the obtained styrene derivative (A12) for TG-DTA under the same conditions described in Example A1, and it was observed by the measurement that the melting point was 166° C., the heat generation temperatures were 514° C. and 557° C., the weight loss temperatures were 377° C. and 537° C.

Elementary analysis was conducted on the obtained styrene derivative (A12) under the same conditions as described in Example A1. The theoretical values and the measured values by the elemental analysis are given below.

measured values: C, 74.10; H, 7.85; N, 0.00.

theoretical values: C, 75.36; H, 7.91; N, 0.00.

On the obtained styrene derivative (A12) was conducted liquid chromatography/mass spectrometry analysis using the same conditions as described in Example A1. The theoretical values and the measured values by the mass spectrometry are given below.

measured values: LC/MC m/z=379.9 [M-H]$^-$ theoretical values: m/z=382.5

Example A13

An example of how to synthesize a mixture of 5-(4'-vinylbenziloxy)-3-tert-butyl-2-hydroxy benzoic acid and 5-(2'-vinylbenziloxy)-3-tert-butyl-2-hydroxy benzoic acid with the help of a chloromethylstyrene reagent, which is a mixture of p-chloromethylstyrene and m-chloromethylstyrene will be described.

25.0 g of 3-tert-butyl-2,5-dihydroxy benzoic acid, which is the salicylic acid intermediate obtained in Example A2 was dissolved in 150 ml of methanol with stirring, and to this was added 40.0 g of potassium carbonate, and the solution was stirred for one hour at 60° C. Then, 23.4 g of chloromethylstyrene (product name 4-Chloromethyl Styrene; manufactured by CHANGZHOU WUJIN LINCHUAN CHEMICAL CO., LTD.), which is a mixture of p-chloromethylstyrene and o-chloromethylstyrene, was dissolved in 100 ml of methanol, and was dripped into the above-described solution and a reaction was allowed to proceed for three hours at 65° C. The reaction liquid thus obtained was allowed to cool to room temperature, and the deposit was filtrated aside and washed with methanol. The thus obtained residue was added with one liter of water and turned to pH 1 by chloric acid and subjected to 30 minutes stirring, filtration and washing with water. It was dried at 80° C. for 48 hours, and 23.2 g of white solid styrene derivative (a mixture of Compound Example a1-2 and Compound Example a3-2) represented by the following Formula (A13) was obtained.

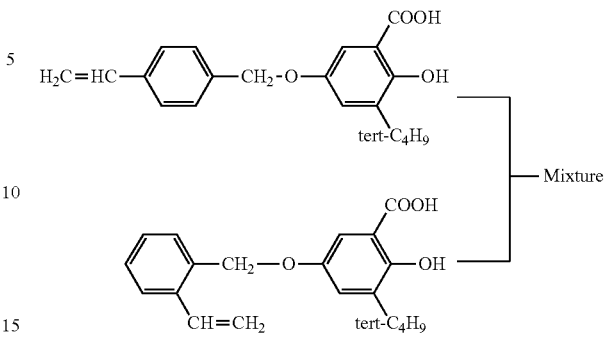

Thus obtained styrene derivative (A13) was examined for HPLC purity under conditions described in Example A1, and it was 97.7%.

$^1$H-NMR measurement was conducted on the obtained styrene derivative (A13) under the same conditions as described in Example A1 except that CDCl$_3$ was used as the measurement solvent. $^1$H-NMR spectrography data were as follows, and are supportive of the structure represented by the Formula (A13).

δ(ppm)=1.51-1.55 (9H, sx2, —C(CH$_3$)$_3$), 5.22-5.29 (1H, dx2, C—H), 5.80-5.87 (1H, dx2, C—H), 6.55-6.60 (2H, m, Ar—H), 6.70-6.81 (H, dx2, C—H), 7.36-7.58 (4H, m, Ar—H), 7.62-7.71 (1H, m, Ar—H)

In the foregoing $^1$H-NMR, when the proton of 5.22-5.29 (1H, dx2, C—H) was irradiated at, a 15.5% nuclear Overhauser effect was observed at the aromatic proton of 6.55-6.60 (2H, m, Ar—H).

The obtained styrene derivative (A13) was measured for FT-IR under the same conditions as Example A1, and the following was observed.

ν(cm$^{-1}$)=3420, 3004, 2966, 2709, 2622, 1893, 1822, 1790, 1778, 1756, 1655, 1633, 1612, 1511, 1487, 1470, 1421, 1411, 1396, 1377, 1365, 1322, 1300, 1280, 1200, 11880, 1115, 966, 957, 910, 890, 832, 811, 804, 795, 723, 678, 659, 604, 525, 514, 467, 422.

A measurement was conducted on the obtained styrene derivative (A13) for TG-DTA under the same conditions described in Example A1, and it was observed by the measurement that the decalescent point was 151° C., the heat generation temperatures were 433° C. and 549° C., and the weight loss temperatures were 209° C., 444° C. and 553° C.

Elementary analysis was conducted on the obtained styrene derivative (A13) under the same conditions as described in Example A1. The theoretical values and the measured values by the elemental analysis are given below.

measured values: C, 69.57; H, 5.61; N, 0.00.

theoretical values: C, 71.82; H, 5.67; N, 0.00.

On the obtained styrene derivative (A13) was conducted liquid chromatography/mass spectrometry analysis using the same conditions as described in Example A1. The theoretical values and the measured values by the mass spectrometry are given below.

measured values: LC/MC m/z=283.86 [M-H]$^-$ theoretical values: m/z=284.31

Examples of how to synthesize esterified styrene derivative of the present invention will be explained in Examples A14 through A15.

Example A14

50.44 g of 2,4-dihydroxy benzoic acid methyl ester was dissolved by being stirred in 300 ml of methanol, and this was added with 62.2 g of potassium carbonate and heated to 60° C. Into this reaction liquid was dripped 53.0 g of 4-(chloromethyl)styrene, and a reaction was allowed to proceed for 4.5 hours at 65° C. This reaction liquid was cooled, filtrated, and the methanol in the filtrate was removed by distillation under a reduced pressure and a deposit was obtained.

The obtained deposit was dispersed in 1.5 liters of water of pH 2, and extraction was conducted by adding ethyl acetate. Thereafter, the solution was separated and added with water with which it was washed, and after the ethyl acetate layer was separated, it was dried with magnesium sulfate, and the ethyl acetate was removed by distillation under a reduced pressure, and a deposit was obtained. The thus obtained deposit was recrystallized by using methanol. After the deposit was filtered aside, it was dried for 20 hours at 80° C., and 17.2 g of styrene derivative (Compound Example b1-23) represented by the following Formula (A14) was obtained.

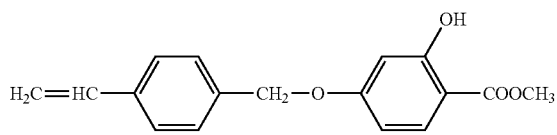

(A14)

The thus obtained styrene derivative (A14) was examined for HPLC purity under conditions described in Example A1, and it was found 98.0%.

With respect to the obtained styrene derivative (A14), $^1$H-NMR was conducted under the same conditions as described in Example A1 except that $CDCl_3$ was used as the measurement solvent. $^1$H-NMR spectral data were as given below and are supportive of the Formula (A14).

δ(ppm)=3.86 (3H, s, —OCH), 5.16 (2H, s, —OCH$_2$—), 5.28 (1H, d, C—H), 5.85 (1H, d, C—H), 6.58-6.62 (2H, m, Ar—H), 6.74 (1H, d-d, —CH=), 7.42 (2H, d, Ar—H), 7.50 (2H, d, Ar—H), 7.72 (1H, d, Ar—H), 10.77 (1H, s, —OH)

In the foregoing $^1$H-NMR, when the proton of 5.16 (2H, s, —OCH$_2$—) was irradiated at, a 12.5% nuclear Overhauser effect was observed at the aromatic proton of 7.24 (2H, d, Ar—H).

The obtained styrene derivative (A14) was measured for FT-IR under the same conditions as Example A1, and the following was observed.
ν(cm$^{-1}$)=3180, 3091, 2954, 1907, 1824, 1668, 1620, 1579, 1514, 1504, 1489, 1468, 1439, 1408, 1383, 1346, 1298, 1258, 1215, 1178, 1144, 1095, 1005, 985, 978, 958, 945, 910, 862, 843, 827, 785, 735, 702, 650, 634, 588, 532, 486, 463.

Figure 9:
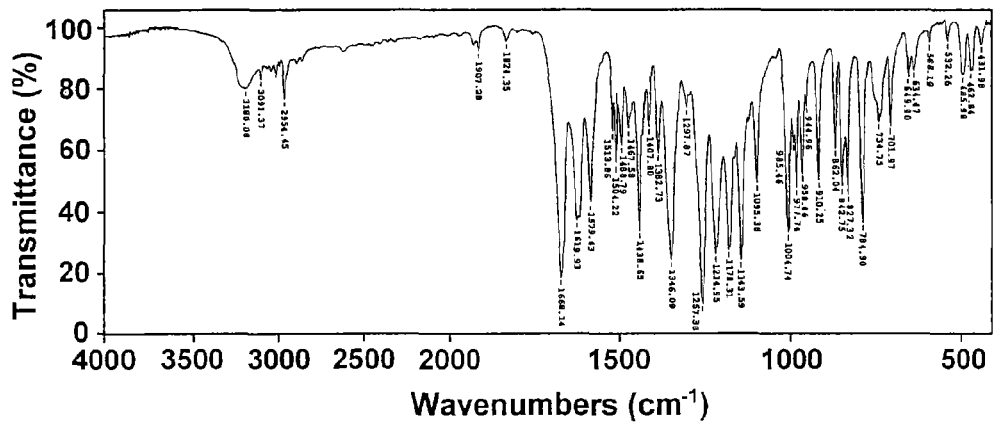
FIG. 9 is a drawing showing a chart of infrared absorption spectrum of a styrene derivative of Example A14, used for the charge control resin to which the present invention is applied.

The measurement result by FT-IR is shown in FIG. 9.

Figure 10:
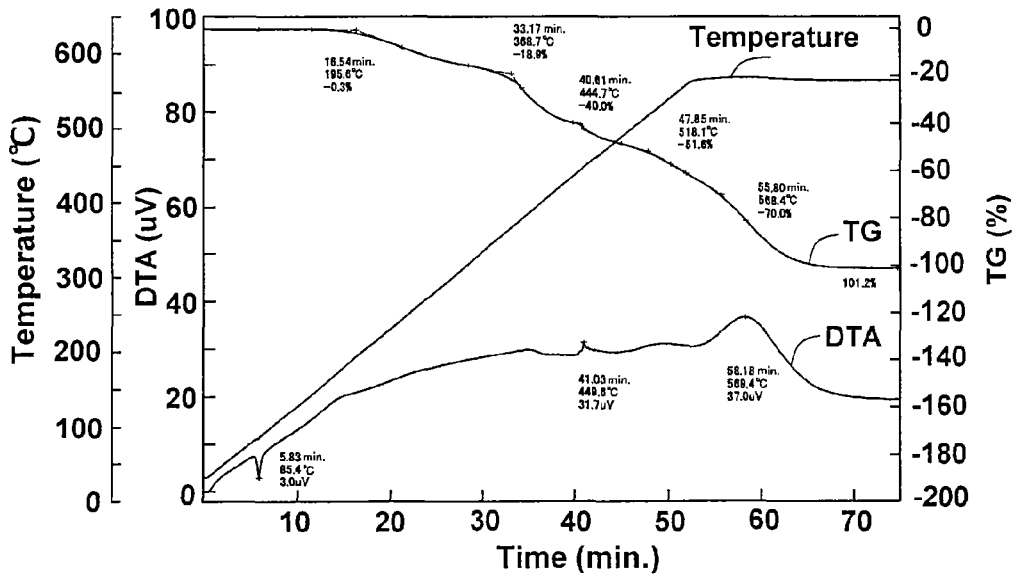
FIG. 10 is a drawing showing a chart of a result of differential thermal/thermogravimetric analysis on the styrene derivative of Example A14, used for the charge control resin to which the present invention is applied.

A measurement was conducted on the obtained styrene derivative (A14) for TG-DTA under the same conditions described in Example A1, and the result is shown in FIG. 10. It was observed by the measurement that the melting point was 85.5° C., the heat generation temperatures were 450° C. and 569° C., the weight loss temperatures were 196° C., 369° C., 445° C. and 568° C.

Elementary analysis was conducted on the obtained styrene derivative (A14) under the same conditions as described in Example A1. The theoretical values and the measured values by the elemental analysis are given below.
measured values: C, 72.03; H, 5.70; N, 0.00.
theoretical values: C, 71.82; H, 5.67; N, 0.00.

On the obtained styrene derivative (A14) was conducted liquid chromatography/mass spectrometry analysis using the same conditions as described in Example A1. The theoretical values and the measured values by the mass spectrometry are given below.
measured values: LC/MC m/z=283.1 [M-H]$^-$
theoretical values: m/z=284.1

Example A15

50.0 g of 2,5-dihydroxy benzoic acid butyl ester was dissolved in 200 ml of methanol with stirring, and 73.2 g of potassium carbonate was added and heated at 60° C. 37.0 g of 4-(chloromethyl)styrene was dripped into this reaction liquid, and a reaction was allowed to proceed for 5.0 hour at 65° C. The thus obtained reaction liquid was cooled, and filtered and the methanol in the filtrate was removed by distillation under a reduced pressure and a deposit was obtained.

The obtained deposit was dispersed in 1.5 liters of water of pH 2, and was extracted with ethyl acetate. Then, the solution was separated, and added with water for washing, and the ethyl acetate layer was separated and dried with magnesium sulfate, and the ethyl acetate was distilled off under a reduced pressure, and a deposit was obtained. The thus obtained deposit was recrystallized with methanol. After filtering aside the deposit, it was dried for 20 hours at 80° C., and 15.2 g of a styrene derivative (Compound Example a1-28) represented by the following Formula (A15).

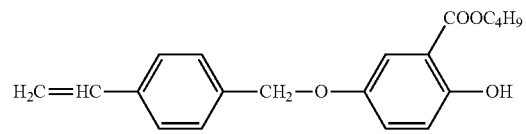

(A15)

The thus obtained styrene derivative (A15) was examined for HPLC purity under conditions described in Example A1, and it was found 97.7%.

With respect to the obtained styrene derivative (A15), $^1$H-NMR was conducted under the same conditions as described in Example A1 except that $CDCl_3$ was used as the measurement solvent. $^1$H-NMR spectral data were as given below and are supportive of the Formula (A15).

δ(ppm)=1.12 (3H, t, —CH$_3$), 1.23-1.44 (2H, m, —CH$_2$—), 1.56-1.95 (2H, m, —CH$_2$—), 4.21 (2H, t, —CH$_2$—), 5.15 (2H, s, —OCH$_2$—), 5.25 (1H, d, C—H), 5.86 (1H, d, C—H), 6.38-6.41 (2H, m, Ar—H), 6.71 (1H, d-d, —CH=), 7.40 (2H, d, Ar—H), 7.48 (2H, d, Ar—H), 7.63 (1H, d, Ar—H)

In the foregoing $^1$H-NMR, when the proton of 5.15 (2H, s, —OCH$_2$—) was irradiated at, a 13.8% nuclear Overhauser effect was observed at the aromatic proton of 7.40 (214, d, Ar—H).

The obtained styrene derivative (A15) was measured for FT-IR under the same conditions as Example A1, and the following was observed.
ν(cm$^{-1}$)=3177, 3086, 2946, 1911, 1832, 1670, 1622, 1581, 1522, 1493, 1477, 1428, 1400, 1375, 1343, 1301, 1261, 1209, 1169, 1146, 1099, 1004, 978, 936, 910, 858, 837, 789, 732, 699, 647, 629, 584, 536, 458

A measurement was conducted on the obtained styrene derivative (A15) for TG-DTA under the same conditions described in Example A1, and it was observed by the measurement that the melting point was 73.8° C., the heat generation temperatures were 443° C. and 549° C., the weight loss temperatures were 176° C., 349° C. and 558° C.

Elementary analysis was conducted on the obtained styrene derivative (A15) under the same conditions as described in Example A1. The theoretical values and the measured values by the elemental analysis are given below.
measured values: C, 72.78; H, 6.71; N, 0.00.
theoretical values: C, 73.60; H, 6.79; N, 0.00.

On the obtained styrene derivative (A15) was conducted liquid chromatography/mass spectrometry analysis using the same conditions as described in Example A1. The theoretical values and the measured values by the mass spectrometry are given below.
measured values: LC/MC m/z=325.5 [M-H]$^-$
theoretical values: m/z=326.1

Examples of how a charge control resin (copolymer) of the present invention is synthesized will be explained in Examples B1 through B26.

Example B1

Preparation of a Combination of the Formula (A2) Plus Styrene in a Molar Ratio of 5.0:95.0

9.91 g of the styrene derivative (A2) obtained in Example A2 and 60.09 g of styrene were dissolved in 42 ml of toluene and stirred for one hour. Then, this was heated to 110° C. in an atmosphere of a nitrogen gas stream (50 ml/min). To this solution was dripped in the course of 22 minutes a mixture liquid of 42 ml of toluene and 4.62 g of tert-butyl peroxy isopropyl monocarbonate (PERBUTYL I, a product name of NOF CORPORATION). After a reaction was allowed to proceed for four hours at 110° C., the liquid was cooled and dripped into one liter of methanol, and a white deposit was obtained. This reaction liquid was filtered and thus obtained deposit was dissolved in 300 ml of tetrahydrofuran. Thereafter, this was dripped into 1.5 liters of methanol and a white deposit was caused to precipitate and was filtered aside. This residue was dried at 90° C. under a reduced pressure, and 57.56 g of a copolymer (B1) was obtained from the styrene derivative and the styrene.

Figure 11:
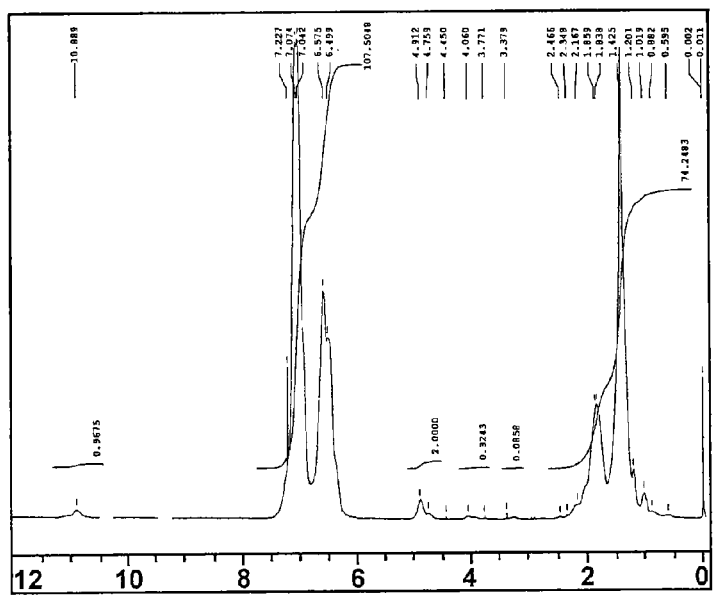
FIG. 11 is a drawing showing a chart of nuclear magnetic resonance spectrum of a copolymer of Example B1, used as the charge control resin to which the present invention is applied.

The obtained copolymer (B1) was examined by means of $^1$H-NMR (nuclear magnetic resonance apparatus: FT-NMR JNM-AL 300 manufactured by JEOL Ltd.) under conditions where the resonance frequency was 300 MHz, the measurement nuclide was $^1$H, the used solvent was CDCl$_3$, and the measurement temperature was room temperature. The result of the measurement by $^1$H-NMR is shown in FIG. 11.

There were observed no peaks that should, respectively, represent the vinyl group of the styrene and the styrene derivative (A2) represented by the Formula (A2) as a starting materials before the copolymerization reaction, and broad aromatic proton(s) and alkyl chain(s) were observed, and furthermore, a broad hydroxyl group originating from the styrene derivative A2 and a broad proton of δ(ppm)=4.9 (—CH$_2$—O—) were observed. From the integrated values of the peaks, it was confirmed that the constituent unit obtained from the styrene derivative (A2) was contained in the obtained copolymer by 4.69%.

The obtained copolymer (B1) was subjected to KBr method measurement, using an FT-IR (Fourier transform infrared spectrophotometer (JIR-SPX60S manufactured by JEOL Ltd.)), and the following observation was made.
ν(cm$^{-1}$)=3455, 3082, 3061, 3026, 2922, 2850, 1942, 1867, 1799, 1741, 1674, 1601, 1493, 1452, 1362, 1265, 1201, 1155, 1030, 906, 798, 756, 698, 540

Figure 12:
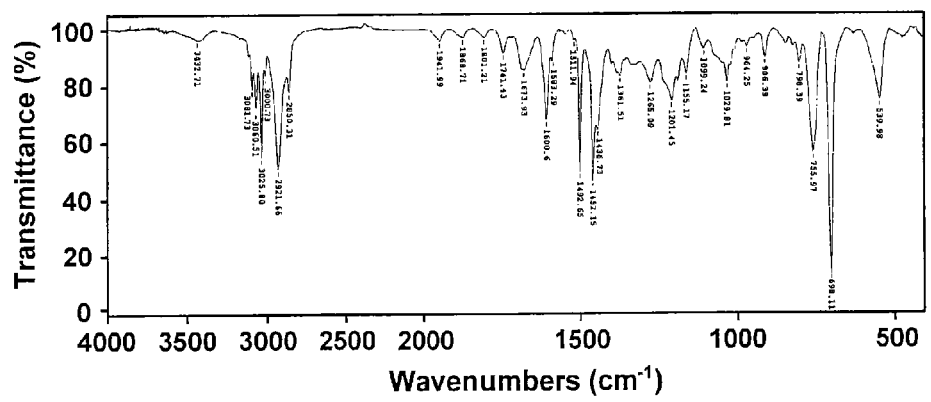
FIG. 12 is a drawing showing a chart of infrared absorption spectrum of a copolymer of Example B1, used as the charge control resin to which the present invention is applied.

The result of the measurement by the FT-IR is shown in FIG. 12.

The obtained copolymer (B1) is composed of Unit A included in the Formula (5), which is a constituent unit obtained from Compound Example a1-2, and Unit B, which is a constituent unit represented by the Formula (9).

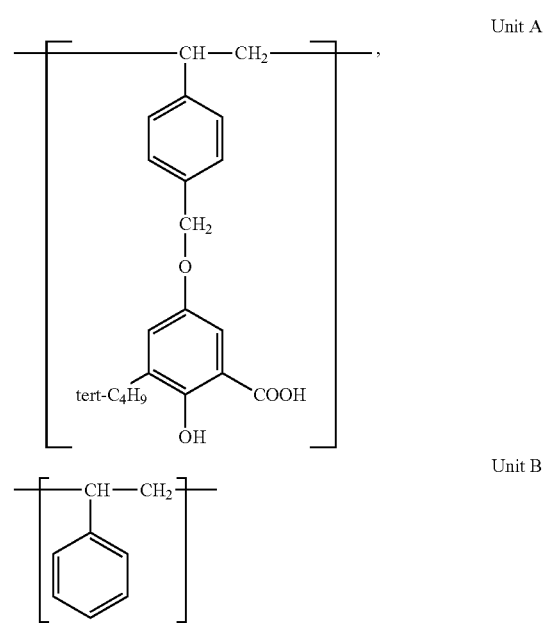

Figure 13:
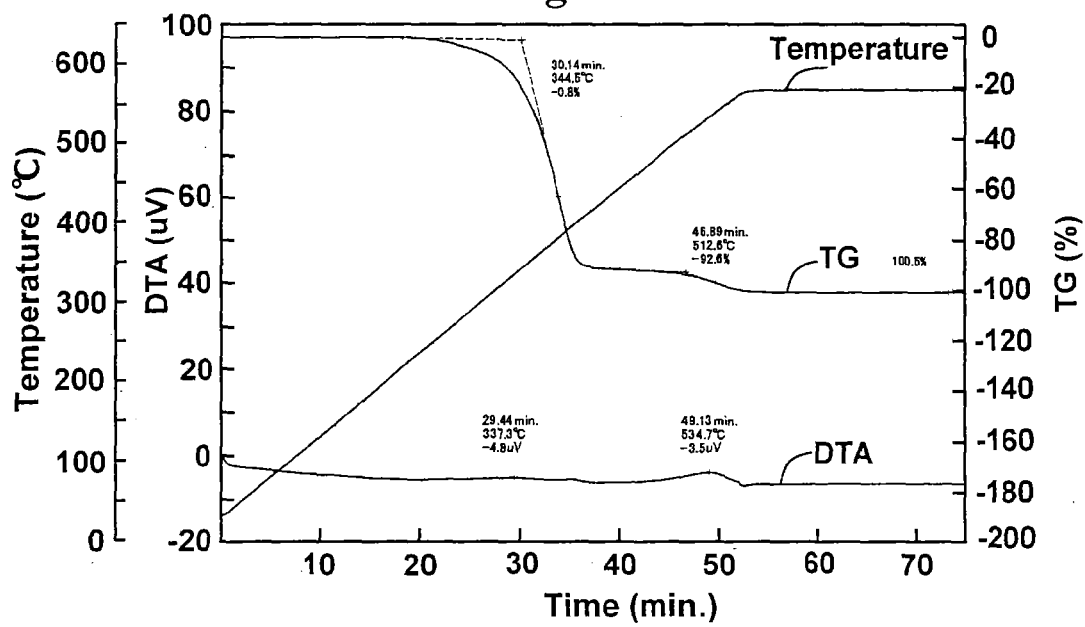
FIG. 13 is a drawing showing a chart of a result of differential thermal/thermogravimetric analysis on a copolymer of Example B1, used as the charge control resin to which the present invention is applied.

With regard to the obtained copolymer (B1), a measurement was conducted by a differential thermal/thermogravimetry simultaneous analyzer TG-DTA6200 EXSTAR6000, manufactured by SII Nanotechnology Inc., under a condition whereby temperature was raised from 30° C. to 550° C. at a rate of 10° C./minute. The measurement result of the simultaneous thermogravimetric and differential thermal analysis (TG-DTA) is as shown in FIG. 13. It was observed by the measurement that the weight loss temperatures were 345° C. and 513° C., and the heat generating temperatures were 337° C. and 535° C.

The molecular weight distribution of the obtained copolymer (B1) was measured by Gel Permeation Chromatography (manufactured by Shimadzu Corporation; detector: RID-10A; column oven: CTO-20A; pump: LC-20AT; degasser: DGU-20A$_5$) under the following conditions, and the molecular distribution, number average molecular weight, and weight average molecular weight were determined.

The GPC measurement conditions were such that 5 mg of the tested sample was dissolved in 5 ml of tetrahydrofuran, and it was passed through a solvent-resistant membrane filter having a pore diameter of 0.5 micrometer and the filtrate was used as the sample solution to be analyzed in the following manner.
column: ultra high speed SEC (size exclusion) semi-micro GPC column
elimination limit molecular quantity: polystyrene 4×10$^6$ (TSKgel Super HM-M, manufactured by Tosho Corp.) 2 units The calculation for the molecular weight of the sample was based on a calibration curve created with reference to a standard polystyrene (Shodex STANDARD SM-105 (S-3730, S-2480, S-1230, S-579, S-197, S-551, S-31.4, S-12.8, S-3.95, S-1.20) manufactured by Showa Denko K.K.)).

Figure 14:
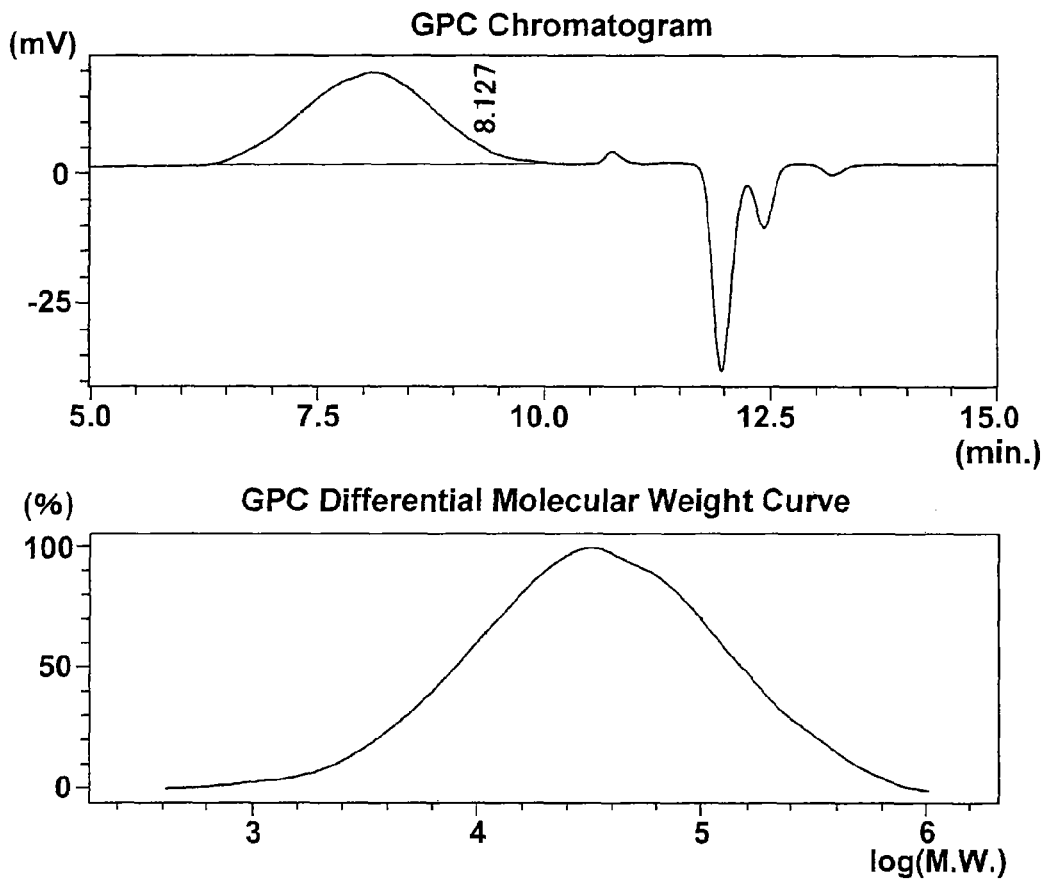
FIG. 14 is a drawing showing a chart of molecular weight distribution of the copolymer of Example B1, used as the charge control resin to which the present invention is applied.

The measurement result of the molecular weight distribution of the copolymer (B1) as measured under the above-described conditions is shown in FIG. 14. It was confirmed from the result of the measurement that the number average molecular weight (Mn) was 16160, the weight average molecular weight (Mw) was 66496, and the ratio of the molecular weight distribution (Mw/Mn) was 4.1.

In an elementary analysis, it is possible to predict a ratio of a particular monomer that would occupy the resulting copolymer from the elementary analysis measurement result of the starting monomer and that of the copolymer. Elementary analysis was conducted on the obtained copolymer (B1) under the same conditions as described in Example A1. The theoretical values and the measured values by the elemental analysis are as given below.

measured values: C, 89.45; H, 7.69; N, 0.00; O, 2.84.
theoretical values: C, 89.60; H, 7.62; N, 0.00; O, 2.78.

Here, the value for oxygen was calculated by subtracting the values for carbon (C), hydrogen (H) and nitrogen (N) from the totality of 100%. The result of the measurement was commensurate with the theoretical values predicted in the case where the styrene derivative (A2) was assumed to be contained in the copolymer by 5%.

The glass transition temperature of the obtained copolymer (B1) was measured by a differential scanning calorimeter DSC6200 EXSTAR6000 manufactured by SII Nanotechnology Inc., under following conditions, and the glass transition temperature was determined.

Figure 15:
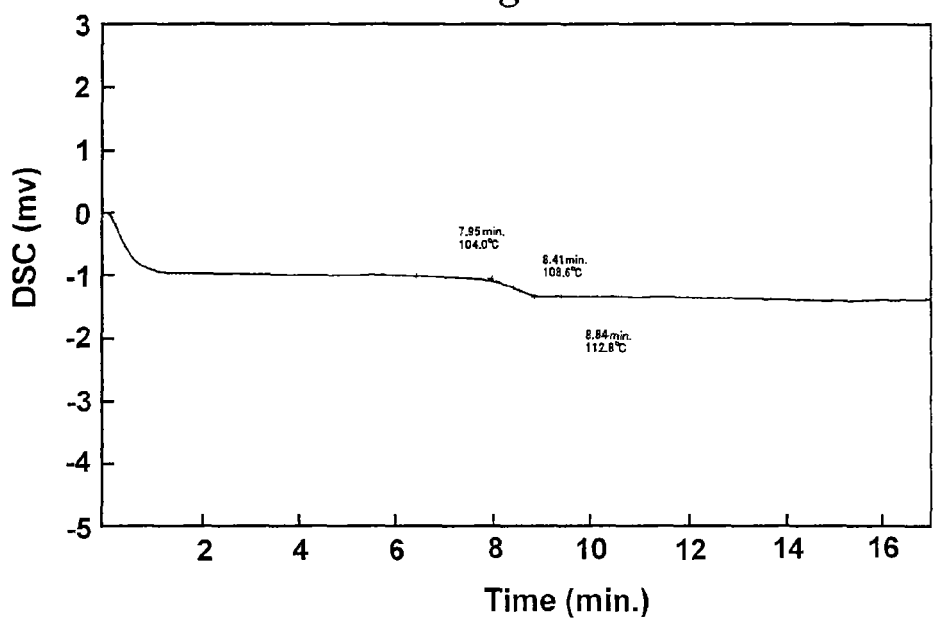
FIG. 15 is a drawing showing a chart of glass transition temperatures of the copolymer of Example B1, used as the charge control resin to which the present invention is applied.

The conditions for the measurement of the glass transition temperature were such that the measured sample was heated to 170° C., and cooled quickly, and then the temperature was raised from 30° C. to 170° C., at a rate of 10° C./minute. The result of the measurement of the glass transition temperature is shown in FIG. 15. According to the result, the glass transition temperature of the copolymer (B1) was 104.0° C.

The volume resistive value of the obtained copolymer (B1) was measured by a digital ultra-high resistance/micro ammeter R8340A manufactured by ADVANTEST CORPORATION, under the following conditions, and the volume resistive value was determined.

The conditions for the volume resistive value measurement were as prescribed in JIS (K6911) and as follows.
Applied voltage and time: 500 v; one minute
Electrode: chief electrode 38 mm diameter;
Load: 2000 kg;
Test atmosphere: temperature 23+/−2° C.;
Humidity: 50+/−5 RH.
As the result of the measurement, the copolymer (B1) was found to have a volume specific resistivity of $1.3 \times 10^{16}$ Ωcm.

Example B2

Preparation of a Combination of the Formula (A2) Plus Styrene in a Molar Ratio of 5.0:95.0

9.91 g of the styrene derivative (A2) and 60.09 g of styrene were dispersed in 42 ml of toluene, and this was heated to 110° C. in an atmosphere of a nitrogen gas stream (50 ml/min). To this solution was dripped in the course of 3 minutes a mixture liquid of 42 ml of toluene and 4.62 g of tert-butyl peroxyisopropyl monocarbonate (PERBUTYL I, a product name of NOF CORPORATION). After a reaction was allowed to proceed for four hours at 110° C., the liquid was cooled. The reaction liquid was dripped into one liter of methanol, and a white deposit was obtained, and it was filtered aside, and this residue was dried at 60° C. under a reduced pressure for 10 hours, and 29.5 g of a copolymer (B2) was obtained.

The obtained copolymer (B2) was examined by means of $^1$H-NMR under the same conditions as described in Example B1, and there were observed no peaks that should, respectively, represent the vinyl group of the styrene and the styrene derivative (A2) represented by the Formula (A2) as a starting materials before the copolymerization reaction, whereas broad aromatic proton(s) and alkyl chain(s) were observed, and furthermore, a broad hydroxyl group originating from the styrene derivative (A2) and a broad proton of δ(ppm)=4.9 (—CH$_2$—O—) were observed. From the integrated values of the peaks, it was determined that the constituent unit obtained from the styrene derivative (A2) was contained in the obtained copolymer by 4.38%.

The obtained copolymer (B2) was subjected to FT-IR analysis under the same conditions as described in Example B1, and the following observation was made.
v(cm$^{-1}$)=3425, 3081, 3061, 3025, 2922, 2850, 1942, 1869, 1801, 1741, 1673, 1603, 1493, 1452, 1363, 1265, 1201, 1155, 1030, 906, 756, 698, 540.

Figure 16:
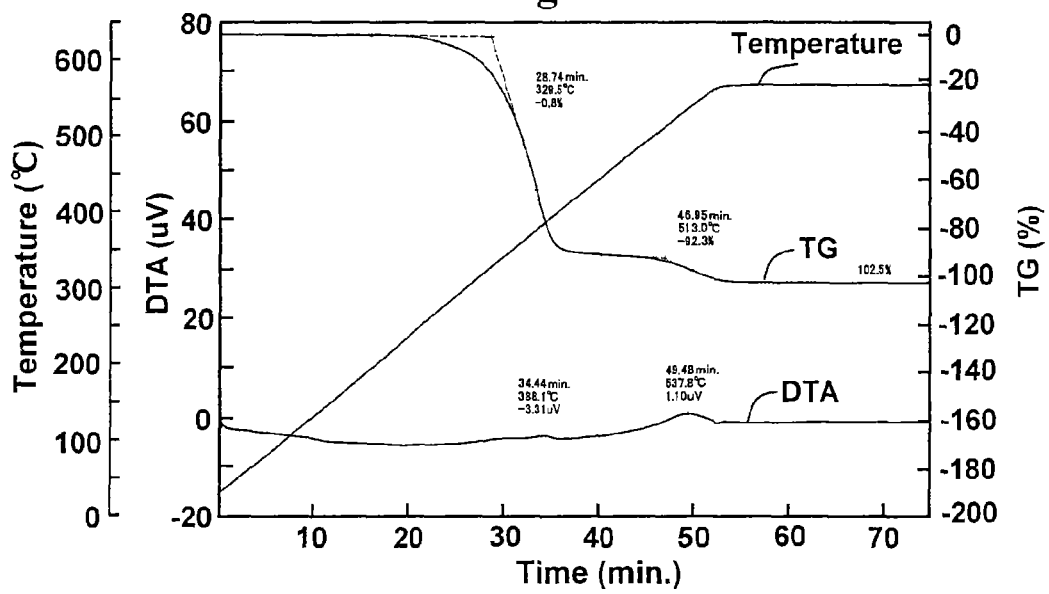
FIG. 16 is a drawing showing a chart of a result of differential thermal/thermogravimetric analysis on a copolymer of Example B2, used as the charge control resin to which the present invention is applied.

A measurement was conducted on the obtained copolymer (B2) for TG-DTA under the same conditions described in Example B1. The result of the TG-DTA measurement is shown in FIG. 16. The measurement result shows that the heat generation temperatures were 388° C. and 538° C., and the weight loss temperatures were 330° C. and 513° C.

Figure 17:
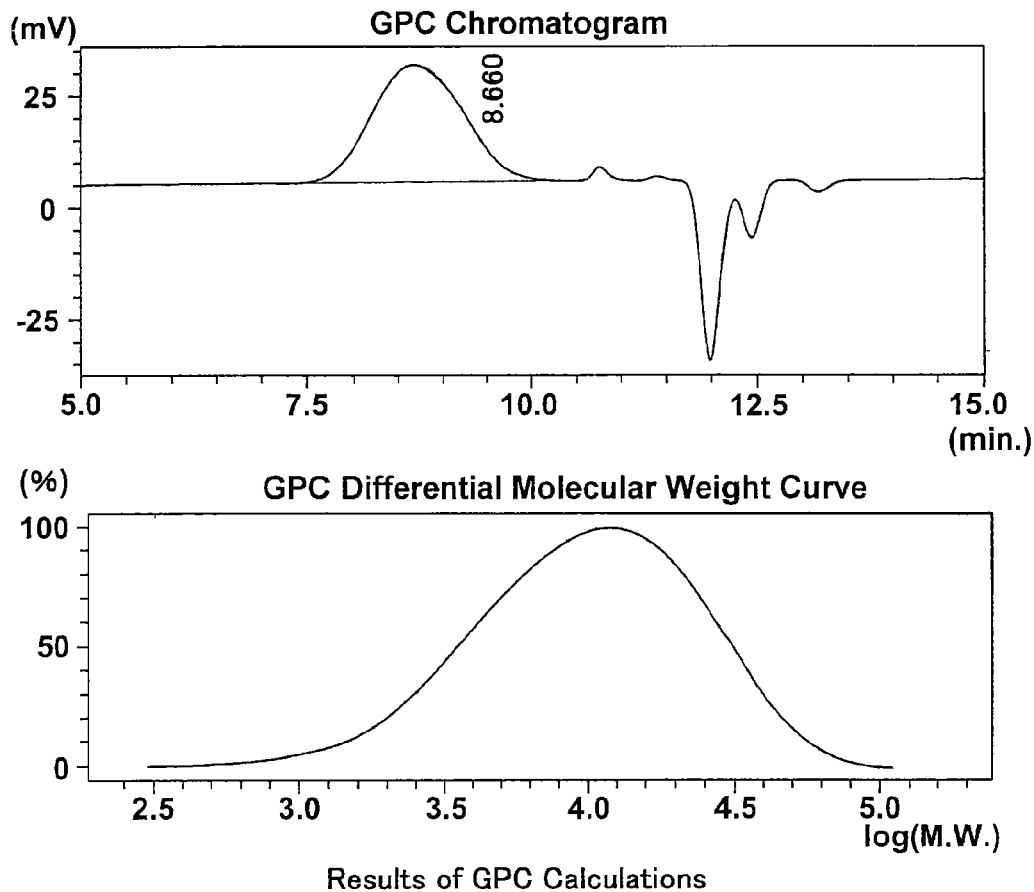
FIG. 17 is a drawing showing a chart of molecular weight distribution of the copolymer of Example B2, used as the charge control resin to which the present invention is applied.

The obtained copolymer (B2) was subjected to GPC measurement under the same conditions as described in Example B1. The measurement result of the molecular weight distribution of the copolymer (B2) as measured under the above-described conditions is shown in FIG. 17. It was confirmed from the result of the measurement that the copolymer (B2) has a number average molecular weight (Mn) of 6861, a weight average molecular weight (Mw) of 14225, and a molecular weight distribution ratio (Mw/Mn) of 2.1.

The glass transition temperature of the obtained copolymer (B2) was measured under the same conditions as described in Example B1. The result of the measurement determined the glass transition temperature of the copolymer (B2) to be 99.02° C.

Example B3

Preparation of a Combination of the Formula (A2) Plus Styrene in a Molar Ratio of 5.0:95.0

9.91 g of the styrene derivative (A2) and 60.09 g of styrene were dispersed in 21 ml of toluene, and this was heated to 110° C. in an atmosphere of a nitrogen gas stream (50 ml/min) To this solution was dripped in the course of 36 minutes a mixture liquid of 21 ml of toluene and 4.62 g of tert-butyl peroxy isopropyl monocarbonate (PERBUTYL I, a product name of NOF CORPORATION). After a reaction was allowed to proceed for 1.5 hour at 110° C., the liquid was cooled. The obtained reaction liquid was dissolved in 300 ml of tetrahydrofuran, and dripped in one liter of methanol, and a precipitate occurred. The reaction liquid was passed through a filter and the residue was dried for 20 hours at 90° C. under a reduced pressure, and 14.89 g of a copolymer (B3) was obtained.

The obtained copolymer (B3) was examined by means of $^1$H-NMR under the same conditions as described in Example B1, and there were observed no peaks that should, respectively, represent the vinyl group of the styrene and the styrene derivative (A2) represented by the Formula (A2) as a starting materials before the copolymerization reaction, whereas broad aromatic proton(s) and alkyl chain(s) were observed, and furthermore, a broad hydroxyl group originating from the styrene derivative (A2) and a broad proton of δ(ppm)=4.91 (—CH$_2$—O—) were observed. From the integrated values of the peaks, it was determined that the constituent unit obtained from the styrene derivative (A2) was contained in the obtained copolymer by 4.59%.

The obtained copolymer (B3) was subjected to FT-IR analysis under the same conditions as described in Example B1, and the following observation was made.
ν(cm$^{-1}$)=3435, 3082, 3061, 3026, 2922, 2850, 1942, 1871, 1741, 1678, 1601, 1583, 1493, 1452, 1437, 1363, 1265, 1201, 1180, 1155, 1099, 1030, 906, 798, 756, 698, 540.

Figure 18:
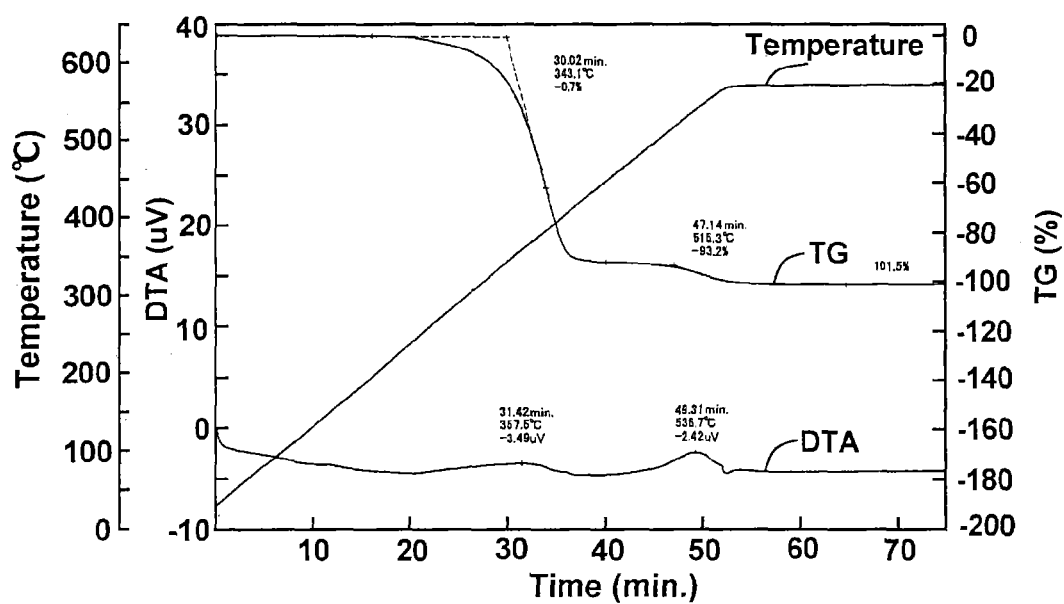
FIG. 18 is a drawing showing a chart of a result of differential thermal/thermogravimetric analysis on a copolymer of Example B3, used as the charge control resin to which the present invention is applied.

A measurement was conducted on the obtained copolymer (B3) for TG-DTA under the same conditions described in Example B1. The result of the measurement is shown in FIG. 18. The measurement result shows that the heat generation temperatures were 358° C. and 537° C., and the weight loss temperatures were 343° C. and 515° C.

Figure 19:
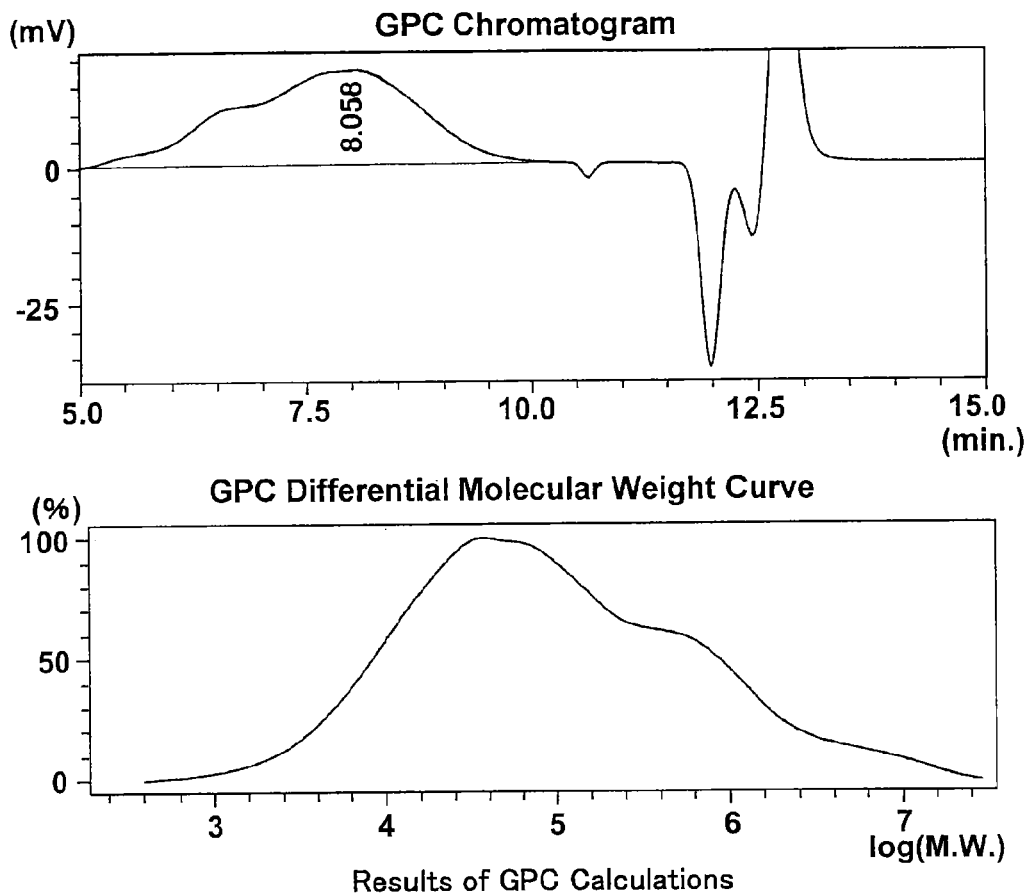
FIG. 19 is a drawing showing a chart of molecular weight distribution of the copolymer of Example B3, used as the charge control resin to which the present invention is applied.

The obtained copolymer (B3) was subjected to GPC measurement under the same conditions as described in Example B1. The measurement result of the molecular weight distribution of the copolymer (B3) as measured under the above-described conditions is shown in FIG. 19. It was confirmed from the result of the measurement that the copolymer (B3) has a number average molecular weight (Mn) of 22178, a weight average molecular weight (Mw) of 437142, and a molecular weight distribution ratio (Mw/Mn) of 19.7.

The glass transition temperature of the obtained copolymer (B3) was measured in the same manner as described in Example B1. The result of the measurement determined the glass transition temperature of the copolymer (B3) to be 102.7° C.

The volume resistive value of the copolymer (B3) was measured in the same manner as described in Example B1. The result of the measurement was that the copolymer (B3) had a volume resistive value of $1.1 \times 10^{17}$ Ωcm.

Example B4

Preparation of a Combination of the Formula (A2) Plus Styrene in a Molar Ratio of 1.0:99.0

1.07 g of the styrene derivative (A2) and 33.93 g of styrene were dispersed in 21 ml of toluene, and this was heated to 110° C. in an atmosphere of a nitrogen gas stream (50 ml/min). To this solution was dripped in the course of 17 minutes a mixture liquid of 21 ml of toluene and 2.31 g of tert-butyl peroxy isopropyl monocarbonate (PERBUTYL I, a product name of NOF CORPORATION). After a reaction was allowed to proceed for 4.0 hours at 110° C., the liquid was cooled. The obtained reaction liquid was added to 500 ml of methanol to cause a precipitation, and a highly viscous white deposit was obtained. After removing a supernatant methanol, the deposit was dissolved in 150 ml of tetrahydrofuran, and the solution was added to 2 liters of methanol to occasion a precipitation and the precipitate was filtered aside. Then, the substance was washed by being sprinkled twice with 200 ml of methanol and the residue was dried at 80° C. under a reduced pressure for 30 hours, and 32.66 g of a copolymer (B4) was obtained.

The obtained copolymer (B4) was examined by means of $^1$H-NMR under the same conditions as described in Example B1, and there were observed no peaks that should, respectively, represent the vinyl group of the styrene and the styrene derivative (A2) represented by the Formula (A2) as a starting materials before the copolymerization reaction, whereas broad aromatic proton(s) and alkyl chain(s) were observed, and furthermore, a broad hydroxyl group originating from the styrene derivative (A2) and a broad proton of δ(ppm)=4.90 (—CH$_2$—O—) were observed. From the integrated values of the peaks, it was determined that the constituent unit obtained from the styrene derivative (A2) was contained in the obtained copolymer by 0.48%.

The obtained copolymer (B4) was subjected to FT-IR analysis under the same conditions as described in Example B1, and the following observation was made.
ν(cm$^{-1}$)=3433, 3082, 3061, 3026, 3001, 2922, 2848, 1944, 1871, 1803, 1741, 1601, 1583, 1493, 1452, 1375, 1327, 1263, 1200, 1182, 1155, 1068, 1028, 980, 964, 906, 841, 756, 698, 621, 540.

A measurement was conducted on the obtained copolymer (B4) for TG-DTA under the same conditions described in Example B1. The result of the measurement shows that the heat generation temperature was 345° C., and the weight loss temperatures were 339° C. and 512° C.

The obtained copolymer (B4) was subjected to GPC measurement under the same conditions as described in Example B1. The measurement result shows that the copolymer (B4) had a number average molecular weight (Mn) of 11184, a weight average molecular weight (Mw) of 28845, and a molecular weight distribution ratio (Mw/Mn) of 2.6.

Elementary analysis was conducted on the obtained copolymer (B4) under the same conditions as described in Example A1. The theoretical values and the measured values by the elemental analysis are as given below.
measured values: C, 91.43; H, 7.76; N, 0.00; O, 0.81.
theoretical values: C, 91.67; H, 7.73; N, 0.00; O, 0.60.

The value for oxygen was calculated in the same manner as in Example B1. The result of the measurement was commensurate with the theoretical values predicted in the case where the styrene derivative (A2) was assumed to be contained in the copolymer by 1%.

The glass transition temperature of the obtained copolymer (B4) was measured in the same manner as described in Example B1. The result of the measurement determined the glass transition temperature of the copolymer (B4) to be 92.57° C.

The volume resistive value of the copolymer (B4) was measured in the same manner as described in Example B1. The result of the measurement was that the copolymer (B4) had a volume resistive value of $0.67 \times 10^{16}$ Ωcm.

Example B5

Preparation of a Combination of the Formula (A2) Plus Styrene in a Molar Ratio of 10.0:90.0

9.04 g of the styrene derivative (A2) and 25.96 g of styrene were dispersed in 21 ml of toluene, and this solution was heated to 110° C. in an atmosphere of a nitrogen gas stream (50 ml/min). To this solution was dripped in the course of 20 minutes a mixture liquid of 21 ml of toluene and 2.31 g of tert-butyl peroxy isopropyl monocarbonate (PERBUTYL I, a product name of NOF CORPORATION). After a reaction was allowed to proceed for 4.0 hours at 110° C., the liquid was cooled. The obtained reaction liquid was added to 500 ml of methanol to cause a precipitation, and a highly viscous white deposit was obtained. After removing a supernatant methanol, the deposit was dissolved in 150 ml of tetrahydrofuran, and the solution was added to 2 liters of methanol to occasion a precipitation and the precipitate was filtered aside. Then, the substance was washed by being sprinkled twice with 200 ml of methanol and the residue was dried at 90° C. under a reduced pressure for 10 hours, and 19.03 g of a copolymer (B5) was obtained.

The obtained copolymer (B5) was subjected to an examination by means of $^1$H-NMR under the same conditions as described in Example B1, but the copolymer did not solve in heavy chloroform or DMSO (dimethylsulfoxide) d-6 or the like, which were used as the measurement solvent, so that the measurement was not possible.

The obtained copolymer (B5) was subjected to FT-IR analysis under the same conditions as described in Example B1, and the following observation was made.
ν(cm$^{-1}$)=3427, 3103, 3082, 3061, 3026, 3001, 2922, 2852, 1944, 1871, 1803, 1741, 1680, 1659, 1603, 1543, 1512, 1493, 1452, 1435, 1392, 1363, 1271, 1201, 1182, 1155, 1099, 1041, 1032, 1018, 964, 906, 843, 820, 798, 758, 698, 619, 598, 540.

A measurement was conducted on the obtained copolymer (B5) for TG-DTA under the same conditions described in Example B1. The result of the measurement shows that the heat generation temperatures were 355° C. and 535° C., and the weight loss temperatures were 244° C., 342° C. and 514° C.

The obtained copolymer (B5) was subjected to GPC measurement under the same conditions as described in Example B1. The measurement result shows that the copolymer (B5) had a number average molecular weight (Mn) of 16750, a weight average molecular weight (Mw) of 61867, and a molecular weight distribution ratio (Mw/Mn) of 3.7.

Elementary analysis was conducted on the obtained copolymer (B5) under the same conditions as described in Example A1. The theoretical values and the measured values by the elemental analysis are as given below.
measured values: C, 86.49; H, 7.46; N, 0.00; O 6.05.
theoretical values: C, 86.29; H, 7.45; N, 0.00; O 6.25.

The value for oxygen was calculated in the same manner as in Example B1. The result of the measurement was commensurate with the theoretical values predicted in the case where the styrene derivative (A2) was assumed to be contained in the copolymer by 13%.

The glass transition temperature of the obtained copolymer (B5) was measured in the same manner as described in Example B1. The result of the measurement determined the glass transition temperature of the copolymer (B5) to be 118.5° C.

The volume resistive value of the copolymer (B5) was measured in the same manner as described in Example B1. The result of the measurement was that the copolymer (B5) had a volume resistive value of 0.98×10$^{16}$ Ωcm.

Example B6

Preparation of a Combination of the Formula (A3) Plus Styrene in a Molar Ratio of 5.0:95.0

4.21 g of the styrene derivative (A3) and 30.79 g of styrene were dispersed in 21 ml of DMF, and this solution was heated to 110° C. in an atmosphere of a nitrogen gas stream (50 ml/min). To this solution was dripped in the course of 18 minutes a mixture liquid of 21 ml of DMF and 2.31 g of tert-butyl peroxy isopropyl monocarbonate (PERBUTYL I, a product name of NOF CORPORATION). After a reaction was allowed to proceed for four hours at 110° C., the liquid was cooled. The obtained reaction liquid was dripped into 500 ml of methanol, whereby a precipitation of rubber-like white substance occurred. After removing a supernatant by decantation, the substance was dissolved in 150 ml of tetrahydrofuran, and the solution was added to 2 liters of methanol to occasion a precipitation and the precipitate was filtered aside. Then, the substance was dried at 90° C. under a reduced pressure for 20 hours, and 29.56 g of a copolymer (B6) was obtained.

The obtained copolymer (B6) was subjected to an examination by means of $^1$H-NMR under the same conditions as described in Example B1, and there were observed no peaks that should, respectively, represent the vinyl group of the styrene and the styrene derivative (A3) represented by the Formula (A3) as a starting materials before the copolymerization reaction, whereas broad aromatic proton(s) and alkyl chain(s) were observed, and furthermore, a broad hydroxyl group originating from the styrene derivative (A3) and a broad proton of δ(ppm)=4.97 (—CH$_2$—O—) were observed. From the integrated values of the peaks, it was determined that the constituent unit obtained from the styrene derivative (A3) was contained in the obtained copolymer by 4.68%.

The obtained copolymer (B6) was subjected to FT-IR analysis under the same conditions as described in Example B1, and the following observation was made.
ν(cm$^{-1}$)=3427, 3059, 3026, 2922, 2848, 1941, 1873, 1805, 1741, 1674, 1622, 1601, 1583, 1493, 1452, 1371, 1244, 1182, 1151, 1092, 1028, 978, 962, 906, 839, 758, 698, 540.

The obtained copolymer (B6) is composed of Unit C, which is a constituent unit obtained from the Compound Example b1-1 and is contained in the Formula (5), and Unit B, which is the constituent unit represented by the Formula (9).

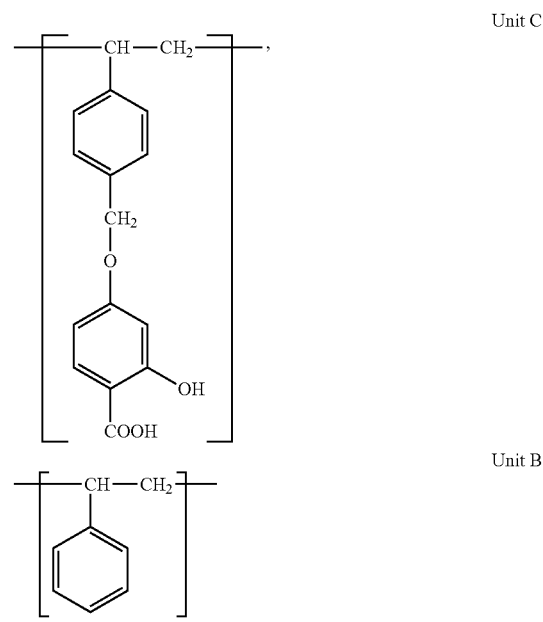

A measurement was conducted on the obtained copolymer (B6) for TG-DTA under the same conditions described in Example B1. The measurement result shows that the heat generation temperatures were 367° C. and 539° C., and the weight loss temperatures were 213° C., 344° C. and 517° C.

The obtained copolymer (B6) was subjected to GPC measurement under the same conditions as described in Example B1. The measurement result of the molecular weight distribution of the copolymer (B6) as measured under the above-described conditions showed that the copolymer (B6) had a number average molecular weight (Mn) of 7088, a weight average molecular weight (Mw) of 18085, and a molecular weight distribution ratio (Mw/Mn) of 2.6.

The glass transition temperature of the obtained copolymer (B6) was measured in the same manner as described in Example B1. The result of the measurement determined the glass transition temperature of the copolymer (B6) to be 105.2° C.

It was also determined that the volume resistive value of the copolymer (B6) was 0.61×10$^{16}$ Ωcm.

Example B7

Preparation of a Combination of the Formula (A1) Plus Styrene in a Molar Ratio of 5.0:95.0

8.41 g of the styrene derivative (A1) and 61.60 g of styrene were dispersed in 42 ml of DMF, and this was heated to 110° C. in an atmosphere of a nitrogen gas stream (50 ml/min). To this solution was dripped in the course of 24 minutes a mixture liquid of 42 ml of DMF and 4.62 g of tert-butyl peroxy isopropyl monocarbonate (PERBUTYL I, a product name of NOF CORPORATION). After a reaction was allowed to proceed for 4 hours at 110° C., the liquid was cooled. The thus obtained reaction liquid was added to 300 ml of tetrahydrofuran, and the solution was added to 3.5 liters of methanol to occasion a precipitation and the precipitate was filtered aside. Then, the residue was washed twice with 200 ml of methanol and was dried at 90° C. under a reduced pressure for 30 hours, and 59.19 g of a copolymer (B7) was obtained.

The obtained copolymer (B7) was examined by means of $^1$H-NMR under the same conditions as described in Example B1, and there were observed no peaks that should, respectively, represent the vinyl group of the styrene and the styrene derivative (A1) represented by the Formula (A1) as a starting materials before the copolymerization reaction, whereas broad aromatic proton(s) and alkyl chain(s) were observed, and furthermore, a broad hydroxyl group originating from the styrene derivative (A1) and a broad proton in the vicinity of δ(ppm)=4.9 (—CH$_2$—O—) were observed. From the integrated values of the peaks, it was determined that the constituent unit obtained from the styrene derivative (A1) was contained in the obtained copolymer by 4.73%.

The obtained copolymer (B7) was subjected to FT-IR analysis under the same conditions as described in Example B1, and the following observation was made.

v(cm$^{-1}$)=3433, 3059, 3026, 2922, 2848, 1944, 1873, 1801, 1741, 1678, 1616, 1601, 1493, 1452, 1265, 1215, 1155, 1070, 1028, 906, 758, 698, 540.

The obtained copolymer (B7) is composed of Unit D, which is a constituent unit obtained from the Compound Example a1-1 and is contained in the Formula (5), and Unit B, which is the constituent unit represented by the Formula (9).

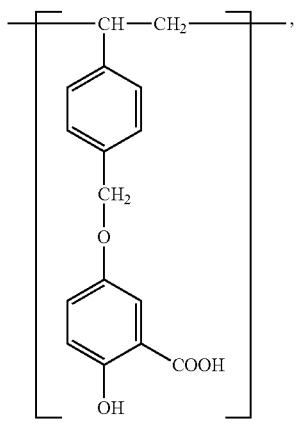

Unit D

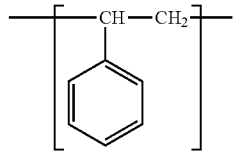

Unit B

A measurement was conducted on the obtained copolymer (B7) for TG-DTA under the same conditions as described in Example B1. The measurement result shows that the heat generation temperatures were 347° C. and 542° C., and the weight loss temperatures were 329° C., 393° C. and 520° C.

The obtained copolymer (B7) was subjected to GPC measurement under the same conditions as described in Example B1. The measurement result showed that the copolymer (B7) had a number average molecular weight (Mn) of 10118, a weight average molecular weight (Mw) of 48190, and a molecular weight distribution ratio (Mw/Mn) of 4.8.

The glass transition temperature of the obtained copolymer (B7) was measured in the same manner as described in Example B1. The result of the measurement determined the glass transition temperature of the copolymer (B7) to be 104.6° C.

Example B8

Preparation of a Combination of the Formula (A6) Plus Styrene in a Molar Ratio of 5.0:95.0

5.25 g of the styrene derivative (A6) and 29.75 g of styrene were dispersed in 21 ml of DMF, and this was heated to 110° C. in an atmosphere of a nitrogen gas stream (50 ml/min). To this solution was dripped in the course of 18 minutes a mixture liquid of 21 ml of DMF and 2.31 g of tert-butyl peroxy isopropyl monocarbonate (PERBUTYL I, a product name of NOF CORPORATION). After a reaction was allowed to proceed for 4 hours at 110° C., the liquid was cooled. The thus obtained reaction liquid was dripped into 500 ml of methanol, a precipitation of green substance occurred. This precipitate was dissolved in 150 ml of tetrahydrofuran and the solution was added to 1.5 liters of methanol to occasion a precipitation and the precipitate was filtered aside. Then, the residue was washed twice with sprinkling of 50 ml of methanol, and was dried at 90° C. under a reduced pressure for 15 hours, and 31.71 g of a copolymer (B8) was obtained.

The obtained copolymer (B8) was examined by means of $^1$H-NMR under the same conditions as described in Example B1, and there were observed no peaks that should, respectively, represent the vinyl group of the styrene and the styrene derivative (A6) represented by the Formula (A6) as a starting materials before the copolymerization reaction, whereas broad aromatic proton(s) and alkyl chain(s) were observed, and furthermore, a broad hydroxyl group originating from the styrene derivative (A6) and a broad proton in the vicinity of δ(ppm)=5.04 (—CH$_2$—O—) were observed. From the integrated values of the peaks, it was determined that the constituent unit obtained from the styrene derivative (A6) was contained in the obtained copolymer by 4.82%.

The obtained copolymer (B8) was subjected to FT-IR analysis under the same conditions as described in Example B1, and the following observation was made.

v(cm$^{-1}$)=3427, 3082, 3059, 3026, 2921, 2848, 1940, 1872, 1805, 1741, 1678, 1612, 1601, 1583, 1493, 1452, 1371, 1238, 1182, 1155, 1095, 1070, 1030, 906, 837, 756, 698, 620, 540, 449

The obtained copolymer (B8) is composed of Unit E, which is a constituent unit obtained from the Compound Example b1-21 and is contained in the Formula (5), and Unit B, which is the constituent unit represented by the Formula (9).

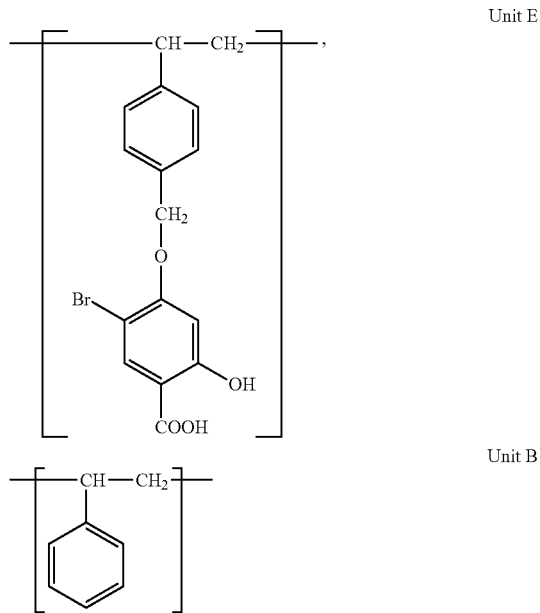

A measurement was conducted on the obtained copolymer (B8) for TG-DTA under the same conditions described in Example B1. The measurement result shows that the heat generation temperatures were 347° C. and 540° C., and the weight loss temperatures were 221° C., 324° C. and 513° C.

The obtained copolymer (B8) was subjected to GPC measurement under the same conditions as described in Example B1. It was confirmed from the result of the measurement that the copolymer (B8) has a number average molecular weight (Mn) of 10220, a weight average molecular weight (Mw) of 38008, and a molecular weight distribution ratio (Mw/Mn) of 3.7.

The glass transition temperature of the obtained copolymer (B8) was measured under the same conditions as described in Example B1. The result of the measurement determined the glass transition temperature of the copolymer (B8) to be 110.1° C.

Example B9

Preparation of a Combination of the Formula (A2) Plus Acrylic Acid Plus Styrene in a Molar Ratio of 5.0:5.0:90.0

5.03 g of the styrene derivative (A2) and 28.87 g of styrene and 1.11 g of acrylic acid and 1.75 g of 2,2'-azobis(2,4-dimethyl valeronitrile) were dissolved in 21 ml of tetrahydrofuran, and this monomer solution was stirred for 2 hours. Aside from this, 21 ml of tetrahydrofuran was stirred for one hour at 66° C. in an atmosphere of nitrogen gas stream (50 ml/min). To this tetrahydrofuran was dripped the monomer solution in the course of 37 minutes, followed by 4-hour stirring and then cooling. Thereafter the reaction liquid was dripped into 500 ml of hexane, and a highly viscous yellow deposit was obtained. The supernatant liquid was removed, and the remnant was dried for 48 hours at 70° C. under a reduced pressure, and the solid was dissolved in 100 ml of ethyl acetate, and this solution was dripped into 1.5 liters of hexane whereby some white solid material was obtained. This was filtered aside, and washed twice with 100 ml of hexane, and the residue was dried for 15 hours at 90° C. under a reduced pressure, and 18.24 g of a copolymer (B9) was obtained.

The obtained copolymer (B9) was examined by means of $^1$H-NMR under the same conditions as described in Example B1, and there were observed no peaks that should, respectively, represent the vinyl group of the styrene and the styrene derivative (A2) represented by the Formula (A2) as a starting materials before the copolymerization reaction, whereas broad aromatic proton(s) and alkyl chain(s) were observed, and furthermore, a broad hydroxyl group originating from the styrene derivative (A2) and a broad proton in the vicinity of δ(ppm)=4.92 (—CH$_2$—O—) were observed. From the integrated values of the peaks, it was determined that the constituent unit obtained from the styrene derivative (A2) was contained in the obtained copolymer by 2.31%.

The obtained copolymer (B9) was subjected to FT-IR analysis under the same conditions as described in Example B1, and the following observation was made.
ν(cm$^{-1}$)=3439, 3103, 3082, 3061, 3026, 3001, 2924, 2850, 1944, 1871, 1803, 1745, 1686, 1603, 1583, 1512, 1493, 1452, 1437, 1392, 1363, 1311, 1275, 1221, 1201, 1182, 1155, 1099, 1030, 1018, 964, 906, 843, 818, 800, 758, 698, 540

A measurement was conducted on the obtained copolymer (B9) for TG-DTA under the same conditions described in Example B1. The measurement result shows that the heat generation temperatures were 356° C. and 534° C., and the weight loss temperatures were 334° C. and 514° C.

The obtained copolymer (B9) was subjected to GPC measurement under the same conditions as described in Example B1. The measurement result showed that the copolymer (B9) had a number average molecular weight (Mn) of 6976, a weight average molecular weight (Mw) of 11333, and a molecular weight distribution ratio (Mw/Mn) of 1.6.

The glass transition temperature of the obtained copolymer (B9) was measured in the same manner as described in Example B1. The result of the measurement determined the glass transition temperature of the copolymer (B9) to be 107.7° C.

Example B10

Preparation of a Combination of the Formula (A3) Plus Acrylic Acid Plus Styrene in a Molar Ratio of 4.5:15.3:80.2

4.27 g of the styrene derivative (A3) and 29.60 g of styrene and 1.14 g of acrylic acid and 1.75 g of 2,2'-azobis(2,4-dimethyl valeronitrile) were dissolved in 21 ml of tetrahydrofuran, and this monomer solution was stirred for 2 hours. Aside from this, 21 ml of tetrahydrofuran was stirred for one hour at 66° C. in an atmosphere of nitrogen gas stream (50 ml/min). To this tetrahydrofuran was dripped the monomer solution in the course of 43 minutes, followed by 4-hour stirring and then cooling. Thereafter the reaction liquid was dripped into 500 ml of methanol, and a highly viscous white deposit was obtained. The supernatant liquid was removed, and the remnant was dried for 48 hours at 70° C. under a reduced pressure, and the solid was dissolved in 100 ml of ethyl acetate, and this solution was dripped into 1.5 liters of hexane whereby some white solid material was obtained. This was filtered aside, and washed twice with 100 ml of hexane, and the residue was dried for 15 hours at 90° C. under a reduced pressure, and 17.73 g of a copolymer (B10) was obtained.

The obtained copolymer (B10) was examined by means of $^1$H-NMR under the same conditions as described in Example B1, and there were observed no peaks that should, respectively, represent the vinyl group of the styrene and the styrene derivative (A3) represented by the Formula (A3) as a starting materials before the copolymerization reaction, whereas broad aromatic proton(s) and alkyl chain(s) were observed, and furthermore, a broad hydroxyl group originating from the styrene derivative (A3) and a broad proton in the vicinity of $\delta$(ppm)=4.97 (—CH$_2$—O—) were observed. From the integrated values of the peaks, it was determined that the constituent unit obtained from the styrene derivative (A3) was contained in the obtained copolymer by 4.88%.

The obtained copolymer (B10) was subjected to FT-IR analysis under the same conditions as described in Example B1, and the following observation was made.
$\nu$(cm$^{-1}$)=3439, 3103, 3082, 3061, 3026, 3001, 2924, 2850, 1944, 1871, 1801, 1743, 1680, 1649, 1624, 1603, 1583, 1493, 1452, 1369, 1244, 1182, 1151, 1093, 1072, 1028, 978, 962, 943, 906, 839, 822, 758, 698, 540, 457

The obtained copolymer (B10) is composed of Unit C, which is the constituent unit obtained from the Compound Example b1-1 and is contained in the Formula (5), Unit B, which is the constituent unit represented by the Formula (9), and Unit F, which is a constituent unit contained in the Formula (11).

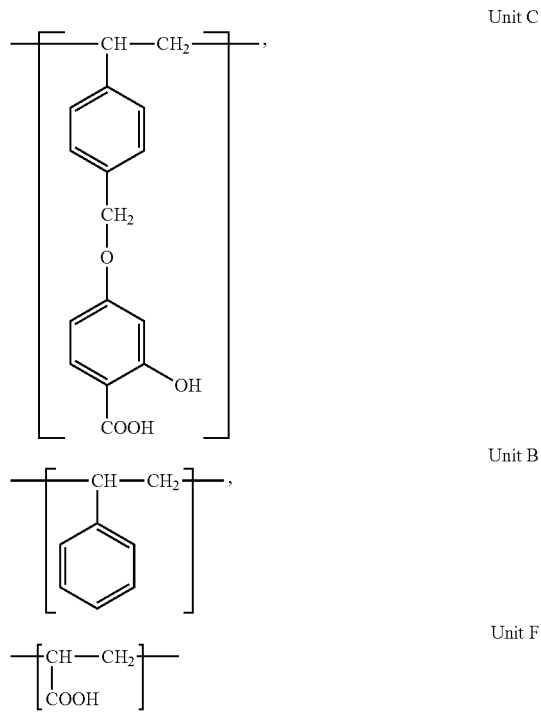

A measurement was conducted on the obtained copolymer (B10) for TG-DTA under the same conditions described in Example B1. The measurement result shows that the heat generation temperatures were 352° C. and 538° C., and the weight loss temperatures were 230° C., 337° C. and 517° C.

The obtained copolymer (B10) was subjected to GPC measurement under the same conditions as described in Example B1. It was confirmed from the result of the measurement that the copolymer (B10) has a number average molecular weight (Mn) of 7612, a weight average molecular weight (Mw) of 13037, and a molecular weight distribution ratio (Mw/Mn) of 1.7.

The glass transition temperature of the obtained copolymer (B10) was measured under the same conditions as described in Example B1. The result of the measurement determined the glass transition temperature of the copolymer (B10) to be 106.6° C.

Example B11

Preparation of a Combination of the Formula (A5) Plus Styrene in a Molar Ratio of 4.2:95.8

4.21 g of the styrene derivative (A5) and 30.80 g of styrene were dispersed in 21 ml of toluene, and this was heated to 110° C. in an atmosphere with nitrogen gas stream (50 ml/min). To this solution was dripped a mixture solution of 21 ml of toluene and 2.31 g of tert-butyl peroxy isopropyl monocarbonate (PERBUTYL I, a product name of NOF CORPORATION) in the course of 21 minutes. A consequent reaction was further allowed to proceed for 4 hours at 110° C., and was then cooled. Thereafter, the reaction liquid was dripped into 500 ml of methanol, and a viscous pale brown substance precipitated. The supernatant methanol was removed, and the deposit was dissolved in 150 ml of tetrahydrofuran, and this solution was added to 2.0 liters of methanol and a precipitation occurred, which was then filtered aside. It was washed twice with sprinkling of 200 ml of methanol, and the residue was dried for 10 hours at 90° C. under a reduced pressure, and 32.40 g of a white copolymer (B11) was obtained.

The obtained copolymer (B11) was examined by means of $^1$H-NMR under the same conditions as described in Example B1, and there were observed no peaks that should, respectively, represent the vinyl group of the styrene and the styrene derivative (A5) represented by the Formula (A5) as a starting materials before the copolymerization reaction, whereas broad aromatic proton(s) and alkyl chain(s) were observed, and furthermore, a broad hydroxyl group originating from the styrene derivative (A5) and a broad proton in the vicinity of $\delta$(ppm)=5.09 (—CH$_2$—O—) were observed. From the integrated values of the peaks, it was determined that the constituent unit obtained from the styrene derivative (A5) was contained in the obtained copolymer by 3.27%.

The obtained copolymer (B11) was subjected to FT-IR analysis under the same conditions as described in Example B1, and the following observation was made.
$\nu$(cm$^{-1}$)=3425, 3082, 3059, 3026, 2922, 2848, 1940, 1805, 1741, 1687, 1681, 1601, 1583, 1493, 1452, 1365, 1273, 1232, 1203, 1180, 1153, 1107, 1028, 906, 841, 823, 796, 756, 698, 540.

A measurement was conducted on the obtained copolymer (B11) for TG-DTA under the same conditions described in Example B1. The measurement result shows that the heat generation temperature was 539° C., and the weight loss temperatures were 232° C. and 337° C., 514° C.

The obtained copolymer (B11) was subjected to GPC measurement under the same conditions as described in Example B1. It was confirmed from the result of the measurement that the copolymer (B11) has a number average molecular weight (Mn) of 10371, a weight average molecular weight (Mw) of 28805, and a molecular weight distribution ratio (Mw/Mn) of 2.8.

The glass transition temperature of the obtained copolymer (B11) was measured in the same manner as described in Example B1. The result of the measurement determined the glass transition temperature of the copolymer (B11) to be 99.83° C.

Example B12

Preparation of a Combination of the Formula (A9) Plus Styrene in a Molar Ratio of 5.0:95.0

4.21 g of the styrene derivative (A9) and 30.80 g of styrene were dissolved in 21 ml of toluene, and this was heated to 110° C. in an atmosphere with nitrogen gas stream (50 ml/min). To this solution was dripped a mixture solution of 21 ml of toluene and 2.31 g of tert-butyl peroxy isopropyl monocarbonate (PERBUTYL I, a product name of NOF CORPORATION) in the course of 20 minutes. A consequent reaction was further allowed to proceed for 4 hours at 110° C., and was then cooled. Thereafter, the reaction liquid was dripped into 500 ml of methanol, and a viscous pale brown substance precipitated. The supernatant methanol was removed, and the deposit was dissolved in 150 ml of tetrahydrofuran, and this solution was added to 2.0 liters of methanol and a precipitation occurred, which was then filtered aside. It was washed twice with sprinkling of 200 ml of methanol, and the residue was dried for 10 hours at 90° C. under a reduced pressure, and 32.87 g of a white copolymer (B12) was obtained.

The obtained copolymer (B12) was examined by means of $^1$H-NMR under the same conditions as described in Example B1, and there were observed no peaks that should, respectively, represent the vinyl group of the styrene and the styrene derivative (A9) represented by the Formula (A9) as a starting materials before the copolymerization reaction, whereas broad aromatic proton(s) and alkyl chain(s) were observed, and furthermore, a broad hydroxyl group originating from the styrene derivative (A9) and a broad proton in the vicinity of δ(ppm)=4.97 and 4.82 (—CH$_2$—O—) were observed. From the integrated values of the peaks, it was determined that the constituent unit obtained from the styrene derivative (A9) was contained in the obtained copolymer by 4.83%.

The obtained copolymer (B12) was subjected to FT-IR analysis under the same conditions as described in Example B1, and the following observation was made.
ν(cm$^{-1}$)=3435, 3082, 3059, 3026, 2922, 2848, 1942, 1873, 1803, 1741, 1678, 1651, 1622, 1601, 1583, 1493, 1452, 1373, 1244, 1182, 1151, 1130, 1093, 1081, 1028, 978, 962, 906, 839, 756, 698, 540, 455

The obtained copolymer (B12) is composed of Unit C, which is the constituent unit obtained from the Compound Example b1-1 and is contained in the Formula (5), Unit G, which is a constituent unit obtained from the Compound Example b2-1 and is contained in the Formula (5), and Unit B, which is the constituent unit represented by the Formula (9).

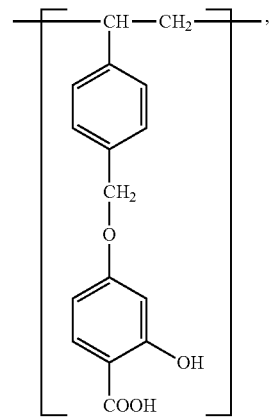
Unit C

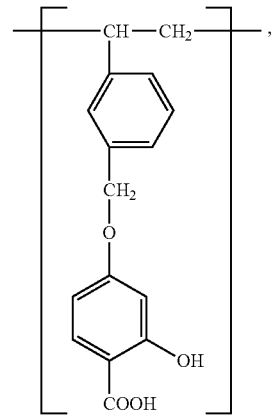
Unit G

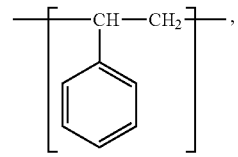
Unit B

Figure 20:
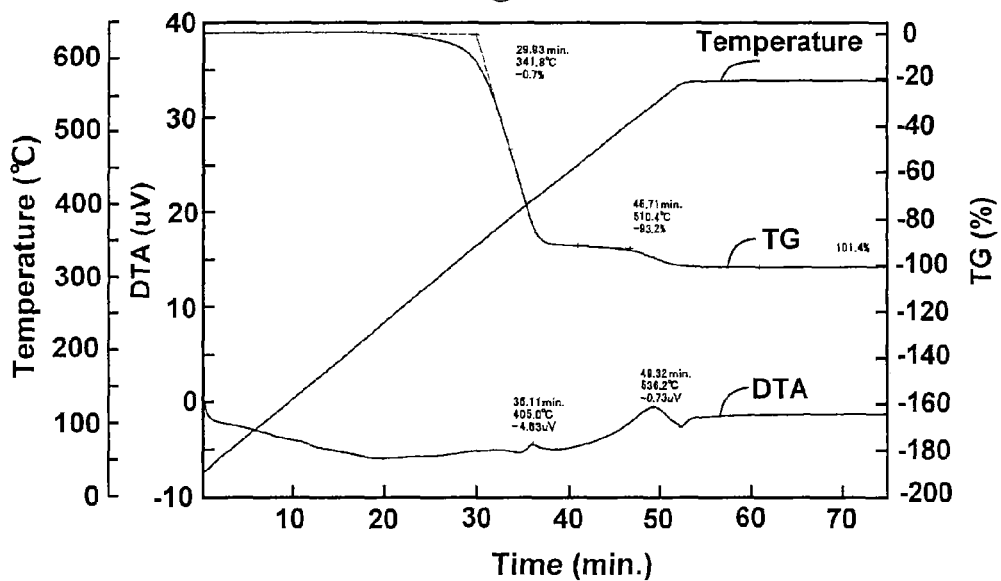
FIG. 20 is a drawing showing a chart of a result of differential thermal/thermogravimetric analysis on a copolymer of Example B12, used as the charge control resin to which the present invention is applied.

A measurement was conducted on the obtained copolymer (B12) for TG-DTA under the same conditions described in Example B1. The measurement result is shown in FIG. 20. It was observed that the heat generation temperatures were 405° C. and 536° C., and the weight loss temperatures were 342° C. and 510° C.

The obtained copolymer (B12) was subjected to GPC measurement under the same conditions as described in Example B1. It was confirmed from the result of the measurement that the copolymer (B12) has a number average molecular weight (Mn) of 11905, a weight average molecular weight (Mw) of 44906, and a molecular weight distribution ratio (Mw/Mn) of 3.8.

The glass transition temperature of the obtained copolymer (B12) was measured in the same manner as described in Example B1. The result of the measurement determined the glass transition temperature of the copolymer (B12) to be 100.7° C.

Example B13

Preparation of a Combination of the Formula (A8) Plus Styrene in a Molar Ratio of 5.0:95.0

4.21 g of the styrene derivative (A8) and 30.80 g of styrene were dissolved in 21 ml of toluene, and this was heated to 110° C. in an atmosphere with nitrogen gas stream (50 ml/min). To this solution was dripped a mixture solution of 21 ml of toluene and 2.31 g of tert-butyl peroxy isopropyl monocarbonate (PERBUTYL I, a product name of NOF CORPORATION) in the course of 19 minutes. A consequent reaction was further allowed to proceed for 4 hours at 110° C., and was then cooled. Thereafter, the reaction liquid was dripped into 500 ml of methanol, and a viscous pale brown substance precipitated. The supernatant methanol was removed, and the deposit was dissolved in 150 ml of tetrahydrofuran, and this solution was added to 2.0 liters of methanol and a precipitation occurred. This was then filtered aside, and was washed twice with sprinkling of 200 ml of methanol, and the residue was dried for 10 hours at 90° C. under a reduced pressure, and 32.26 g of a pale brown copolymer (B13) was obtained.

The obtained copolymer (B13) was examined by means of $^1$H-NMR under the same conditions as described in Example B1, and there were observed no peaks that should, respectively, represent the vinyl group of the styrene and the styrene derivative (A8) represented by the Formula (A8) as a starting materials before the copolymerization reaction, whereas broad aromatic proton(s) and alkyl chain(s) were observed, and furthermore, a broad hydroxyl group originating from the styrene derivative (A8) and a broad proton in the vicinity of δ(ppm)=5.07 (—CH$_2$—O—) were observed. From the integrated values of the peaks, it was determined that the constituent unit obtained from the styrene derivative (A8) was contained in the obtained copolymer by 4.21%.

The obtained copolymer (B13) was subjected to FT-IR analysis under the same conditions as described in Example B1, and the following observation was made.
ν(cm$^{-1}$)=3427, 3082, 3059, 3026, 2922, 2848, 1942, 1867, 1803, 1741, 1684, 1660, 1601, 1583, 1493, 1452, 1373, 1257, 1234, 1180, 1153, 1140, 1070, 1028, 906, 837, 820, 754, 698, 621, 540.

Figure 21:
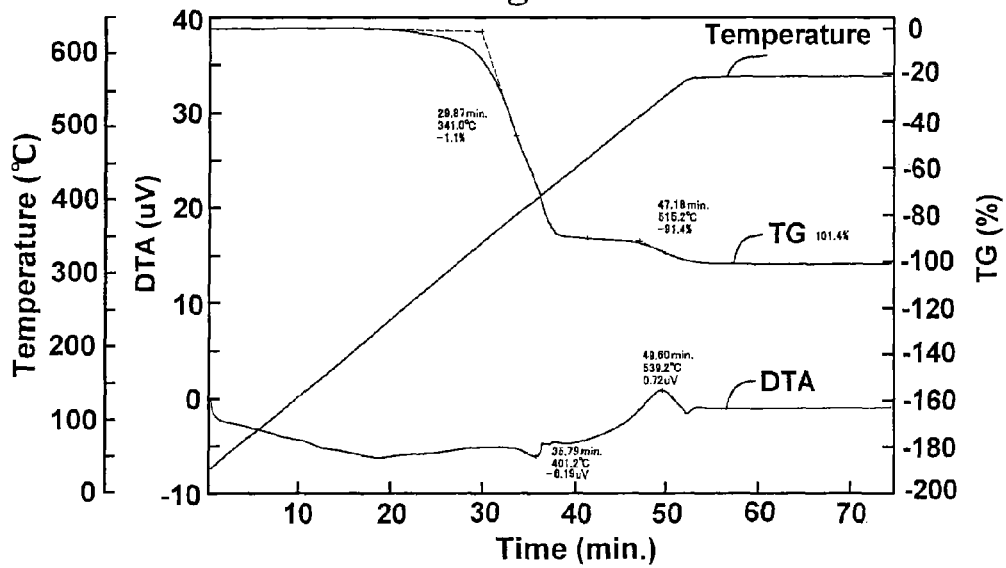
FIG. 21 is a drawing showing a chart of a result of differential thermal/thermogravimetric analysis on a copolymer of Example B13, used as the charge control resin to which the present invention is applied.

A measurement was conducted on the obtained copolymer (B13) for TG-DTA under the same conditions described in Example B1. The measurement result is shown in FIG. 21. It was observed that the heat generation temperature was 539° C., and the weight loss temperatures were 341° C. and 515° C.

The obtained copolymer (B13) was subjected to GPC measurement under the same conditions as described in Example B1. It was confirmed from the result of the measurement that the copolymer (B13) has a number average molecular weight (Mn) of 10442, a weight average molecular weight (Mw) of 52933, and a molecular weight distribution ratio (Mw/Mn) of 5.1.

The glass transition temperature of the obtained copolymer (B13) was measured in the same manner as described in Example B1. The result of the measurement determined the glass transition temperature of the copolymer (B13) to be 99.25° C.

Example B14

Preparation of a Combination of the Formula (A2) Plus Styrene in a Molar Ratio of 0.1:99.9

0.11 g of the styrene derivative (A2) and 34.89 g of styrene were dispersed in 21 ml of toluene, and this was heated to 110° C. in an atmosphere with nitrogen gas stream (50 ml/min). To this solution was dripped a mixture solution of 21 ml of toluene and 2.31 g of tert-butyl peroxy isopropyl monocarbonate (PERBUTYL I, a product name of NOF CORPORATION) in the course of 21 minutes. A consequent reaction was further allowed to proceed for 4 hours at 110° C., and was then cooled. Thereafter, the reaction liquid was dripped into 500 ml of methanol, and a viscous white substance precipitated. The supernatant liquid was removed, and the deposit was dissolved in 150 ml of tetrahydrofuran, and this solution was added to 2.0 liters of methanol and a reprecipitation occurred. This was then filtered aside, and was washed twice with sprinkling of 200 ml of methanol, and the residue was dried for 30 hours at 80° C., and 32.18 g of a copolymer (B14) was obtained.

The obtained copolymer (B14) was examined by means of $^1$H-NMR under the same conditions as described in Example B1, and there were observed no peaks that should, respectively, represent the vinyl group of the styrene and the styrene derivative (A2) represented by the Formula (A2) as a starting materials before the copolymerization reaction.

The obtained copolymer (B14) was subjected to FT-IR analysis under the same conditions as described in Example B1, and the following observation was made.
ν(cm$^{-1}$)=3439, 3103, 3082, 3061, 3026, 3001, 2922, 2848, 1942, 1871, 1801, 1741, 1601, 1583, 1541, 1493, 1452, 1373, 1329, 1311, 1263, 1182, 1155, 1068, 1028, 1003, 980, 964, 943, 906, 841, 756, 698, 621, 538.

A measurement was conducted on the obtained copolymer (B14) for TG-DTA under the same conditions described in Example B1. The measurement result indicated that the weight loss temperatures were 316° C. and 517° C.

The obtained copolymer (B14) was subjected to GPC measurement under the same conditions as described in Example B1. It was confirmed from the result of the measurement that the copolymer (B14) has a number average molecular weight (Mn) of 7968, a weight average molecular weight (Mw) of 20110, and a molecular weight distribution ratio (Mw/Mn) of 2.5.

The glass transition temperature of the obtained copolymer (B14) was measured in the same manner as described in Example B1. The result of the measurement determined the glass transition temperature of the copolymer (B14) to be 89.05° C.

Example B15

Preparation of a Combination of the Formula (A12) Plus Styrene in a Molar Ratio of 5.0:95.0

5.67 g of the styrene derivative (A12) and 29.93 g of styrene were dispersed in 21 ml of toluene, and this was heated to 110° C. in an atmosphere with nitrogen gas stream (50 ml/min). To this solution was dripped a mixture solution of 21 ml of toluene and 2.31 g of tert-butyl peroxy isopropyl monocarbonate (PERBUTYL I, a product name of NOF CORPORATION) in the course of 28 minutes. A consequent reaction was further allowed to proceed for 4 hours at 110° C., and was then cooled. Thereafter, the reaction liquid was dripped into one liter of methanol, and a highly viscous white substance precipitated. The supernatant liquid was removed, and the deposit was dissolved in 150 ml of tetrahydrofuran, and this solution was dripped into 2 liters of methanol for refinement by reprecipitation. This was then filtered aside, and was washed twice with 200 ml of methanol, and the residue was dried for 24 hours at 60° C., and 27.3 g of a copolymer (B15) was obtained.

The obtained copolymer (B15) was examined by means of $^1$H-NMR under the same conditions as described in Example B1, and there were observed no peaks that should, respectively, represent the vinyl group of the styrene and the styrene derivative (A12) represented by the Formula (A12) as a starting materials before the copolymerization reaction, whereas broad aromatic proton(s) and alkyl chain(s) were observed, and furthermore, a broad hydroxyl group originating from the styrene derivative (A12) and a broad proton in the vicinity of δ(ppm)=5.10 (—CH$_2$—O—) were observed. From the integrated values of the peaks, it was determined that the constituent unit obtained from the styrene derivative (A12) was contained in the obtained copolymer by 3.99%.

The obtained copolymer (B15) was subjected to FT-IR analysis under the same conditions as described in Example B1, and the following observation was made.

v(cm$^{-1}$)=3460, 3078, 3069, 3033, 2966, 2930, 2922, 2875, 2859, 2733, 1944, 1887, 1800, 1715, 1678, 1611, 1470, 1464, 1458, 1437, 1373, 1322, 1245, 1226, 1193, 1147, 1134, 1123, 1069, 1040, 976, 943, 911, 841, 801, 766, 701, 544.

A measurement was conducted on the obtained copolymer (B15) for TG-DTA under the same conditions described in Example B1. The measurement result indicated that the heat generation temperatures were 329° C. and 529° C., and the weight loss temperatures were 335° C. and 510° C.

The obtained copolymer (B15) was subjected to GPC measurement under the same conditions as described in Example B1. It was confirmed from the result of the measurement that the copolymer (B15) has a number average molecular weight (Mn) of 12071, a weight average molecular weight (Mw) of 52749, and a molecular weight distribution ratio (Mw/Mn) of 4.4.

The glass transition temperature of the obtained copolymer (B15) was measured in the same manner as described in Example B1. The result of the measurement determined the glass transition temperature of the copolymer (B15) to be 89.5° C.

The volume resistive value of the copolymer (B15) was 2.7×10$^{16}$ Ωcm.

Example B16

Preparation of a Combination of the Formula (A2) Plus 2-Ethylhexyl Acrylate Plus Styrene in a Molar Ratio of 5.0:5.0:90.0

4.79 g of the styrene derivative (A2) and 27.51 g of styrene and 2.70 g of 2-ethylhexyl acrylate were dissolved in a mixture solution of 1.1 g of methanol and 4.4 g of tetrahydrofuran, and to this was added 1.05 g of 2,2'-azobis(2,4-dimethyl valeronitrile). This solution was dripped into a mixture consisting of 16.4 g of methanol and 70 g of tetrahydrofuran, which mixture had been heated to 65° C. in an atmosphere with nitrogen gas stream (50 ml/min), and this dripping was completed in the course of 24 minutes. A consequent reaction was further allowed to proceed for 6 hours at 65° C., and was then cooled. Thereafter, the reaction liquid was dripped into 2 liters of methanol, and a white solid substance precipitated. After filtering, the residue was washed with methanol and the same was dried for 10 hours at 90° C. under a reduced pressure, and 10.72 g of a white copolymer (B16) was obtained.

The obtained copolymer (B16) was examined by means of $^1$H-NMR under the same conditions as described in Example B1, and there were observed no peaks that should, respectively, represent the vinyl group of the styrene and the styrene derivative (A2) represented by the Formula (A2) as a starting materials before the copolymerization reaction, whereas broad aromatic proton(s) and alkyl chain(s) were observed, and furthermore, a broad hydroxyl group originating from the styrene derivative (A2) and a broad proton in the vicinity of δ(ppm)=4.92 (—CH$_2$—O—) were observed. From the integrated values of the peaks, it was determined that the constituent unit obtained from the styrene derivative (A2) was contained in the obtained copolymer by 5.01%, and that the constituent unit obtained from the 2-ethylhexyl acrylate was contained in the same by 5.80%.

The obtained copolymer (B16) was subjected to FT-IR analysis under the same conditions as described in Example B1, and the following observation was made.

v(cm$^{-1}$)=3435, 3082, 3061, 3026, 2924, 2872, 2854, 1940, 1874, 1865, 1728, 1687, 1678, 1659, 1651, 1643, 1603, 1583, 1493, 1452, 1439, 1392, 1377, 1309, 1275, 1198, 1180, 1155, 1101, 1030, 964, 906, 843, 800, 758, 698, 540.

A measurement was conducted on the obtained copolymer (B16) for TG-DTA under the same conditions described in Example B1. The measurement result indicated that the heat generation temperature was 541° C., and the weight loss temperatures were 350° C. and 513° C.

The obtained copolymer (B16) was subjected to GPC measurement under the same conditions as described in Example B1. It was confirmed from the result of the measurement that the copolymer (B16) has a number average molecular weight (Mn) of 6720, a weight average molecular weight (Mw) of 10466, and a molecular weight distribution ratio (Mw/Mn) of 1.6.

The glass transition temperature of the obtained copolymer (B16) was measured in the same manner as described in Example B1. The result of the measurement determined the glass transition temperature of the copolymer (B16) to be 84.0° C.

Example B17

Preparation of a Combination of the Formula (A2) Plus n-Butyl Acrylate Plus Styrene in a Molar Ratio of 5.0:5.0:90.0

4.90 g of the styrene derivative (A2) and 28.17 g of styrene and 1.93 g of n-butyl acrylate were dissolved in a mixture solution of 3.35 g of methanol and 2.50 g of toluene and 4.15 g of methyl ethyl ketone, and to this was added 1.75 g of dimethyl-2,2'-azobis(2-methyl propionate). This solution was dripped into a mixture consisting of 20.10 g of methanol and 17.15 g of toluene and 24.90 g of methyl ethyl ketone, which mixture had been heated to 65° C. in an atmosphere with nitrogen gas stream (50 ml/min), and this dripping was completed in the course of 25 minutes. A consequent reaction was further allowed to proceed for 6 hours at 65° C., and was then cooled. Thereafter, the reaction liquid was dripped into 2 liters of methanol, and a white solid substance precipitated. After filtering, the residue was dissolved in 150 ml of tetrahydrofuran. This solution was added to 2 liters of methanol and obtained a precipitate and it was filtered aside. This was washed by being sprinkled twice with 200 ml of methanol, and the residue was dried for 15 hours at 70° C. under a reduced pressure, and 8.41 g of white copolymer (B17) was obtained.

The obtained copolymer (B17) was examined by means of $^1$H-NMR under the same conditions as described in Example B1, and there were observed no peaks that should, respectively, represent the vinyl group of the styrene and the styrene derivative (A2) represented by the Formula (A2) as a starting materials before the copolymerization reaction, whereas broad aromatic proton(s) and alkyl chain(s) were observed, and furthermore, a broad hydroxyl group originating from the styrene derivative (A2) and a broad proton in the vicinity of δ(ppm)=4.93 (—CH$_2$—O—) were observed. From the integrated values of the peaks, it was determined that the constituent unit obtained from the styrene derivative (A2) was contained in the obtained copolymer by 6.35%, and that the constituent unit obtained from the 2-ethylhexyl acrylate was contained in the same by 6.09%.

The obtained copolymer (B17) was subjected to FT-IR analysis under the same conditions as described in Example B1, and the following observation was made.

v(cm$^{-1}$)=3429, 3082, 3061, 3026, 3001, 2924, 2850, 1942, 1873, 1799, 1730, 1682, 1603, 1583, 1493, 1452, 1437, 1392, 1363, 1309, 1273, 1200, 1180, 1155, 1030, 906, 843, 800, 758, 698, 540.

The obtained copolymer (B17) is composed of Unit A, which is the constituent unit obtained from the Compound Example a1-2 and is contained in the Formula (5), and Unit B, which is the constituent unit represented by the Formula (9), and Unit H, which is a constituent unit included in the Formula (11).

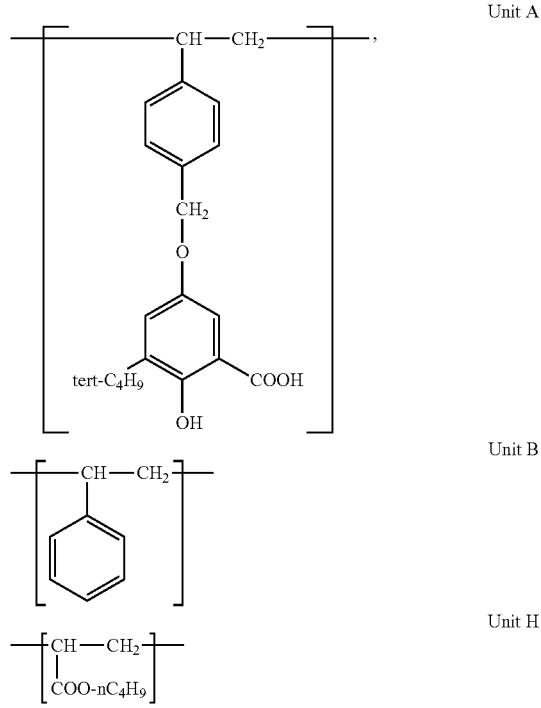

A measurement was conducted on the obtained copolymer (B17) for TG-DTA under the same conditions described in Example B1. The measurement result indicated that the heat generation temperatures were 356° C. and 532° C., and the weight loss temperatures were 246° C., 341° C. and 512° C.

The obtained copolymer (B17) was subjected to GPC measurement under the same conditions as described in Example B1. It was confirmed from the result of the measurement that the copolymer (B17) has a number average molecular weight (Mn) of 10750, a weight average molecular weight (Mw) of 16359, and a molecular weight distribution ratio (Mw/Mn) of 1.5.

The glass transition temperature of the obtained copolymer (B17) was measured in the same manner as described in Example B1. The result of the measurement determined the glass transition temperature of the copolymer (B17) to be 95.5° C.

Example B18

Preparation of a Combination of the Formula (A2) Plus Methyl Methacrylate Plus n-Butyl Acrylate Plus Styrene in a Molar Ratio of 5.0:5.0:5.0:85.0

4.94 g of the styrene derivative (A2) and 26.81 g of styrene and 1.30 g of methyl methacrylate and 1.94 g of n-butyl acrylate were dissolved in 21 ml of toluene, and this was heated to 110° C. in an atmosphere with nitrogen gas stream (50 ml/min). This solution was dripped in a solution, which had been prepared by dissolving 2.31 g of tert-butyl peroxy isopropyl monocarbonate (PERBUTYL I, a product name of NOF CORPORATION) in 21 mil of toluene, and this dripping was completed in the course of 17 minutes. A consequent reaction was further allowed to proceed for 4 hours at 110° C., and was then cooled. Thereafter, the reaction liquid was dripped into 2 liters of methanol, and a highly viscous white solid substance precipitated. The supernatant methanol was removed, and the remnant was dissolved in 150 ml of tetrahydrofuran, and this solution was added to 2 liters of methanol and obtained a precipitate, and after removing the supernatant liquid, it was filtered aside. This was washed by being sprinkled twice with 200 ml of methanol, and the residue was dried for 20 hours at 90° C. under a reduced pressure, and 28.32 g of a white copolymer (B18) was obtained.

The obtained copolymer (B18) was examined by means of $^1$H-NMR under the same conditions as described in Example B1, and there were observed no peaks that should, respectively, represent the vinyl group of the styrene and the styrene derivative (A2) represented by the Formula (A2) as a starting materials before the copolymerization reaction, whereas broad aromatic proton(s) and alkyl chain(s) were observed, and furthermore, a broad hydroxyl group originating from the styrene derivative (A2) and a broad proton in the vicinity of δ(ppm)=4.92 (—CH$_2$—O—) were observed. From the integrated values of the peaks, it was determined that the constituent unit obtained from the styrene derivative (A2) was contained in the obtained copolymer by 5.03%, and that the constituent unit obtained from the methyl methacrylate was contained in the same by 5.18%, and that the constituent unit obtained from the n-butyl acrylate was contained in the same by 3.37%.

The obtained copolymer (B18) was subjected to FT-IR analysis under the same conditions as described in Example B1, and the following observation was made.

v(cm$^{-1}$)=3437, 3082, 3061, 3026, 3001, 2924, 2850, 1940, 1873, 1805, 1730, 1687, 1680, 1601, 1493, 1452, 1435, 1392, 1362, 1265, 1219, 1201, 1180, 1155, 1101, 1064, 1030, 964, 906, 840, 800, 758, 698, 540.

The obtained copolymer (B18) is composed of Unit A, which is the constituent unit obtained from the Compound Example a1-2 and is contained in the Formula (5), and Unit B, which is the constituent unit represented by the Formula (9), Unit I, which is the constituent unit contained in the Formula (11), and Unit H, which is the constituent unit contained in the Formula (11).

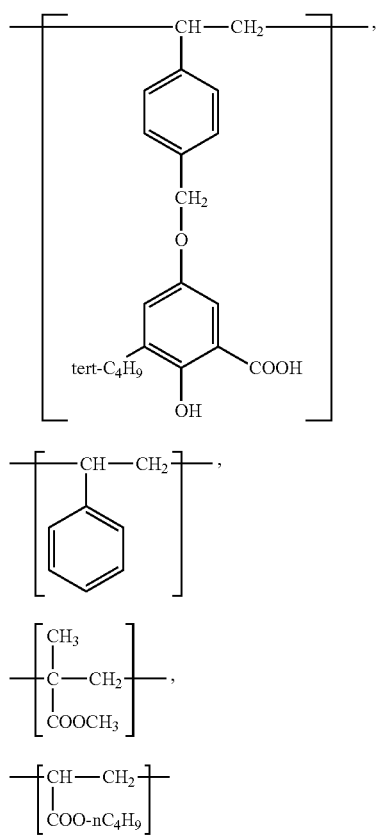

Figure 22:
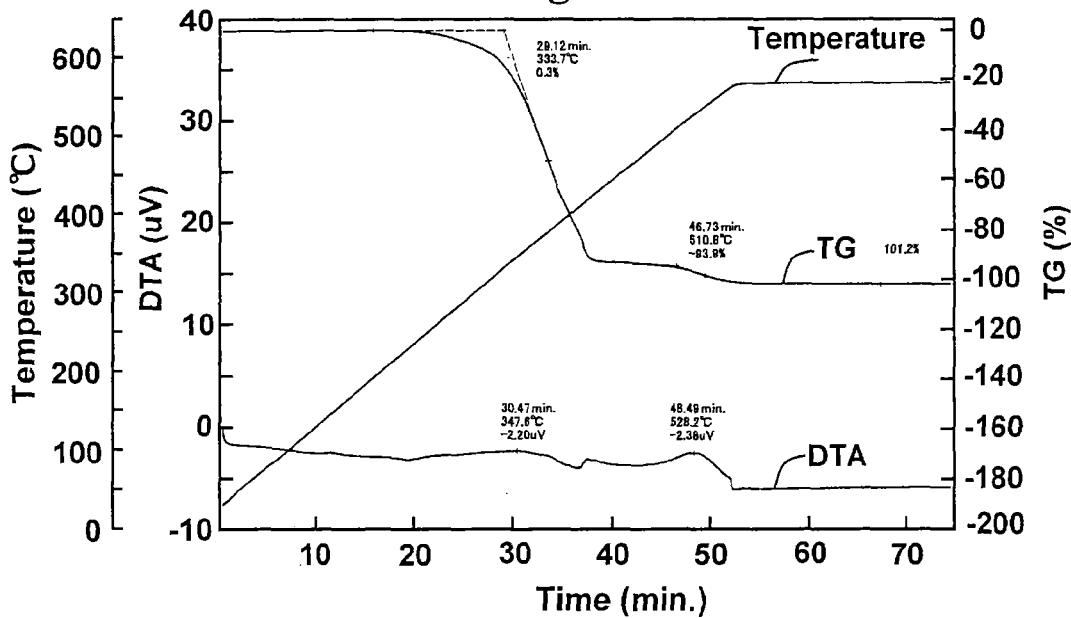
FIG. 22 is a drawing showing a chart of a result of differential thermal/thermogravimetric analysis on a copolymer of Example B18, used as the charge control resin to which the present invention is applied.

A measurement was conducted on the obtained copolymer (B18) for TG-DTA under the same conditions described in Example B1. The result of the measurement for TG-DTA is shown in FIG. 22. The measurement result indicated that the heat generation temperatures were 348° C. and 528° C., and the weight loss temperatures were 334° C. and 511° C.

The obtained copolymer (B18) was subjected to GPC measurement under the same conditions as described in Example B1. It was confirmed from the result of the measurement that the copolymer (B18) has a number average molecular weight (Mn) of 18602, a weight average molecular weight (Mw) of 72809, and a molecular weight distribution ratio (Mw/Mn) of 3.9.

The glass transition temperature of the obtained copolymer (B18) was measured in the same manner as described in Example B1. The result of the measurement determined the glass transition temperature of the copolymer (B18) to be 103.8° C.

Example B19

Preparation of a Combination of the Formula (A7) Plus Styrene in a Molar Ratio of 5.0:95.0

4.21 g of the styrene derivative (A7) and 30.80 g of styrene were dissolved in 21 ml of toluene, and heated to 110° C. in an atmosphere with nitrogen gas stream (50 ml/min). To this solution was dripped a mixture of 21 ml of toluene and 2.31 g of tert-butyl peroxy isopropyl monocarbonate (PERBUTYL I, a product name of NOF CORPORATION) and this dripping was completed in the course of 19 minutes. A consequent reaction was further allowed to proceed for 4 hours at 110° C., and was then cooled. Thereafter, the reaction liquid was dripped into 500 ml of methanol, and a viscous white substance precipitated. After the supernatant methanol was removed, the precipitate was dissolved in 150 ml of tetrahydrofuran, and this solution was added to 2.0 liters of methanol and obtained a precipitate. This was filtered aside, and was washed by being sprinkled twice with 200 ml of methanol, and the residue was dried for 10 hours at 90° C. under a reduced pressure, and 29.81 g of white copolymer (B19) was obtained.

The obtained copolymer (B19) was examined by means of $^1$H-NMR under the same conditions as described in Example B1, and there were observed no peaks that should, respectively, represent the vinyl group of the styrene and the styrene derivative (A7) represented by the Formula (A7) as a starting materials before the copolymerization reaction, whereas broad aromatic proton(s) and alkyl chain(s) were observed, and furthermore, a broad hydroxyl group originating from the styrene derivative (A7) and a broad proton in the vicinity of δ(ppm)=4.95 were observed. From the integrated values of the peaks, it was determined that the constituent unit obtained from the styrene derivative (A7) was contained in the obtained copolymer by 4.32%.

The obtained copolymer (B19) was subjected to FT-IR analysis under the same conditions as described in Example B1, and the following observation was made.
ν(cm$^{-1}$)=3435, 3455, 3081, 3061, 3025, 2922, 2850, 1941, 1866, 1779, 1741, 1673, 1600, 1492, 1452, 1361, 1265, 1201, 1155, 1029, 906, 756, 698, 540.

The obtained copolymer (B19) was subjected to GPC measurement under the same conditions as described in Example B1. It was confirmed from the result of the measurement that the copolymer (B19) has a number average molecular weight (Mn) of 15388, a weight average molecular weight (Mw) of 58200, and a molecular weight distribution ratio (Mw/Mn) of 3.8.

The glass transition temperature of the obtained copolymer (B19) was measured in the same manner as described in Example B1. The result of the measurement determined the glass transition temperature of the copolymer (B19) to be 83.2° C.

Example B20

Preparation of a Combination of the Formula (A10) Plus Styrene in a Molar Ratio of 5.0:95.0

4.21 g of the styrene derivative (A10) and 30.79 g of styrene were dispersed in 21 ml of toluene, and this was heated to 110° C. in an atmosphere of a nitrogen gas stream (50 ml/min). To this solution was dripped in the course of 22 minutes a mixture liquid of 21 ml of DMF and 2.31 g of tert-butyl peroxy isopropyl monocarbonate (PERBUTYL I, a product name of NOF CORPORATION). A consequent reaction was further allowed to proceed for 4 hours at 110° C., and was then cooled. Thereafter, the reaction liquid was dripped into 500 ml of methanol, and a white substance precipitated, and was filtered aside. The white precipitate was dissolved in 150 ml of tetrahydrofuran, and this solution was dripped into 2 liters of methanol and a white deposit was obtained. This was filtered aside, and was washed twice with 200 ml of methanol, and the residue was dried for 15 hours at 90° C. under a reduced pressure, and 29.37 g of a copolymer (B20) was obtained.

The obtained copolymer (B20) was examined by means of $^1$H-NMR under the same conditions as described in Example B1, and there were observed no peaks that should, respectively, represent the vinyl group of the styrene and the styrene derivative (A10) represented by the Formula (A10) as a starting materials before the copolymerization reaction, whereas broad aromatic proton(s) and alkyl chain(s) were observed, and furthermore, a broad hydroxyl group originating from the styrene derivative (A10) and a broad proton at δ(ppm)=5.03 (—CH$_2$—O—) were observed. From the integrated values of the peaks, it was determined that the constituent unit obtained from the styrene derivative (A10) was contained in the obtained copolymer by 3.84%.

The obtained copolymer (B20) was subjected to FT-IR analysis under the same conditions as described in Example B1, and the following observation was made.
ν(cm$^{-1}$)=3523, 3446, 3103, 3082, 3059, 3026, 3001, 2922, 2848, 1942, 1873, 1803, 1732, 1686, 1616, 1601, 1583, 1510, 1493, 1452, 1410, 1375, 1354, 1277, 1217, 1198, 1182, 1155, 1132, 1119, 1093, 1070, 1028, 1003, 964, 941, 906, 868, 841, 820, 758, 698, 623, 540, 432.

A measurement was conducted on the obtained copolymer (B20) for TG-DTA under the same conditions described in Example B1. The measurement result indicated that the heat generation temperatures were 333° C., 410° C. and 537° C., and the weight loss temperatures were 335° C., 395° C. and 515° C.

The obtained copolymer (B20) was subjected to GPC measurement under the same conditions as described in Example B1. It was confirmed from the result of the measurement that the copolymer (B20) has a number average molecular weight (Mn) of 9371, a weight average molecular weight (Mw) of 25826, and a molecular weight distribution ratio (Mw/Mn) of 2.8.

The glass transition temperature of the obtained copolymer (B20) was measured in the same manner as described in Example B1. The result of the measurement determined the glass transition temperature of the copolymer (B20) to be 108.8° C.

Example B21

Preparation of a Combination of the Formula (A2) Plus Styrene in a Molar Ratio of 5.0:95.0

4.96 g of the styrene derivative (A2) and 30.04 g of styrene were dispersed in 21 ml of toluene and heated to 110° C. in an atmosphere with nitrogen gas stream (50 ml/min). Into this solution was dripped a mixture liquid of 21 ml of toluene and 2.31 g of tert-butyl peroxy isopropyl monocarbonate (PERBUTYL I, a product name of NOF CORPORATION), and this dripping took 21 minutes. A consequent reaction was further allowed to proceed for 2.5 hours at 110° C. with vigorous stirring, and was then cooled. Thereafter, the reaction liquid was dripped into 500 ml of methanol, and a highly viscous white deposit separated. After removing the supernatant liquid, the deposit was dissolved in 150 ml of tetrahydrofuran, and this solution was dripped into 2 liters of methanol to thereby effect reprecipitation refinement. The deposit was filtered aside, and was washed twice with 200 ml of methanol, and the residue was dried for 15 hours at 90° C. under a reduced pressure, and 32.47 g of a copolymer (B21) was obtained.

The obtained copolymer (B21) was examined by means of $^1$H-NMR under the same conditions as described in Example B1, and there were observed no peaks that should, respectively, represent the vinyl group of the styrene and the styrene derivative (A2) represented by the Formula (A2) as a starting materials before the copolymerization reaction, whereas broad aromatic proton(s) and alkyl chain(s) were observed, and furthermore, a broad hydroxyl group originating from the styrene derivative (A2) and a broad proton at δ(ppm)=5.00 (—CH$_2$—O—) were observed. From the integrated values of the peaks, it was determined that the constituent unit obtained from the styrene derivative (A2) was contained in the obtained copolymer by 3.67%.

The obtained copolymer (B21) was subjected to FT-IR analysis under the same conditions as described in Example B1, and the following observation was made.
ν(cm$^{-1}$)=3491, 3103, 3082, 3061, 3026, 3001, 2922, 2848, 1942, 1871, 1803, 1726, 1684, 1639, 1601, 1583, 1547, 1512, 1493, 1452, 1431, 1363, 1348, 1300, 1255, 1221, 1180, 1153, 1105, 1066, 1043, 1028, 1018, 980, 964, 943, 906, 843, 822, 758, 698, 669, 619, 607, 596, 540, 417.

A measurement was conducted on the obtained copolymer (B21) for TG-DTA under the same conditions described in Example B1. The measurement result indicated that the heat generation temperatures were 351° C., 409° C. and 536° C., and the weight loss temperatures were 330° C., 389° C. and 515° C.

The obtained copolymer (B21) was subjected to GPC measurement under the same conditions as described in Example B1. It was confirmed from the result of the measurement that the copolymer (B21) has a number average molecular weight (Mn) of 16557, a weight average molecular weight (Mw) of 100309, and a molecular weight distribution ratio (Mw/Mn) of 6.1.

The glass transition temperature of the obtained copolymer (B21) was measured in the same manner as described in Example B1. The result of the measurement determined the glass transition temperature of the copolymer (B21) to be 109.0° C.

Example B22

Preparation of a Combination of the Formula (A13) Plus Styrene in a Molar Ratio of 5.0:95.0

4.21 g of the styrene derivative (A13) and 30.79 g of styrene were dispersed in 21 ml of DMF and heated to 110° C. in an atmosphere with nitrogen gas stream (50 ml/min). Into this solution was dripped a mixture liquid of 21 ml of DMF and 2.31 g of tert-butyl peroxy isopropyl monocarbonate (PERBUTYL I, a product name of NOF CORPORATION), and this dripping took 18 minutes. A consequent reaction was further allowed to proceed for 4 hours at 110° C., and was then cooled. Thereafter, the reaction liquid was dripped into 500 ml of methanol, and a rubber-like white deposit separated. After removing the supernatant liquid by decantation, the deposit was dissolved in 150 ml of tetrahydrofuran. This solution was dripped into 2 liters of methanol, whereby a precipitate occurred, and it was filtered aside and was dried for 20 hours at 90° C. under a reduced pressure, and 27.21 g of a copolymer (B22) was obtained.

The obtained copolymer (B22) was examined by means of $^1$H-NMR under the same conditions as described in Example B1, and there were observed no peaks that should, respectively, represent the vinyl group of the styrene and the styrene derivative (A13) represented by the Formula (A13) as a starting materials before the copolymerization reaction, whereas broad aromatic proton(s) and alkyl chain(s) were observed, and furthermore, a broad hydroxyl group originating from the styrene derivative (A13) and a broad proton at δ(ppm)=5.02 (—CH$_2$—O—) were observed. From the integrated values of the peaks, it was determined that the constituent unit obtained from the styrene derivative (A13) was contained in the obtained copolymer by 4.77%.

The obtained copolymer (B22) was subjected to FT-IR analysis under the same conditions as described in Example B1, and the following observation was made.

$\nu(cm^{-1})$=3522, 3062, 3028, 2921, 2847, 1945, 1880, 1797, 1737, 1670, 1619, 1600, 1588, 1489, 1466, 1367, 1250, 1179, 1149, 1100, 1023, 975, 966, 902, 843, 760, 701, 537.

The obtained copolymer (B22) is composed of Unit A, which is the constituent unit obtained from the Compound Example a1-2 and is contained in the Formula (5), Unit J, which is a constituent unit obtained from the Compound Example a3-2 and is contained in the Formula (5), and Unit B, which is the constituent unit represented by the Formula (9).

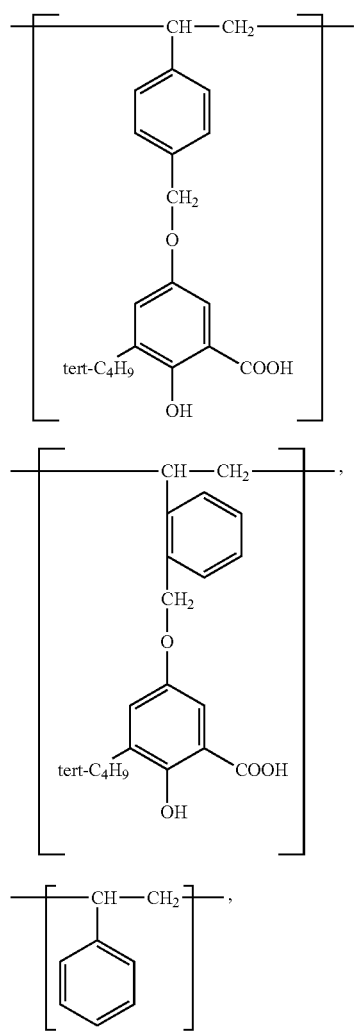

A measurement was conducted on the obtained copolymer (B22) for TG-DTA under the same conditions described in Example B1. The measurement result indicated that the heat generation temperatures were 376° C. and 541° C., and the weight loss temperatures were 222° C., 356° C. and 528° C.

The obtained copolymer (B22) was subjected to GPC measurement under the same conditions as described in Example B1. It was confirmed from the result of the molecular weight distribution measurement conducted under said conditions on the copolymer (B22) that the copolymer (B22) has a number average molecular weight (Mn) of 8327, a weight average molecular weight (Mw) of 12245, and a molecular weight distribution ratio (Mw/Mn) of 1.5.

The glass transition temperature of the obtained copolymer (B22) was measured in the same manner as described in Example B1. The result of the measurement determined the glass transition temperature of the copolymer (B22) to be 107.2° C.

Example B23

Preparation of a Combination of the Formula (A14) Plus Styrene in a Molar Ratio of 5.0:95.0

8.63 g of the styrene derivative (A14) and 60.09 g of styrene were dispersed in 42 ml of toluene, and heated to 110° C. in an atmosphere with nitrogen gas stream (50 ml/min). Into this solution was dripped a mixture liquid consisting of 42 ml of toluene and 4.54 g of tert-butyl peroxy isopropyl monocarbonate (PERBUTYL I, a product name of NOF CORPORATION), and this dripping took 20 minutes. A consequent reaction was further allowed to proceed for 4 hours at 110° C., and was then cooled. Thereafter, the reaction liquid was dripped into 500 ml of methanol, and a gelatinous white deposit separated. After removing the supernatant liquid by decantation, the deposit was dissolved in 300 ml of tetrahydrofuran. This solution was added to 1.5 liters of methanol, whereby a precipitate occurred, and it was filtered aside and was dried for 14 hours at 80° C. under a reduced pressure, and 43.12 g of a copolymer (B23) was obtained.

The obtained copolymer (B23) was examined by means of $^1$H-NMR under the same conditions as described in Example B1, and there were observed no peaks that should, respectively, represent the vinyl group of the styrene and the styrene derivative (A14) represented by the Formula (A14) as a starting materials before the copolymerization reaction, whereas broad aromatic proton(s) and alkyl chain(s) were observed, and furthermore, a broad hydroxyl group originating from the styrene derivative (A14) and a broad proton at δ(ppm)=4.94 (—CH$_2$—O—) were observed. From the integrated values of the peaks, it was determined that the constituent unit obtained from the styrene derivative (A14) was contained in the obtained copolymer by 4.30%.

The obtained copolymer (B23) was subjected to FT-IR analysis under the same conditions as described in Example B1, and the following observation was made.

$\nu(cm^{-1})$=3163, 3103, 3082, 3059, 3026, 3001, 2922, 2848, 1942, 1869, 1801, 1741, 1670, 1622, 1601, 1583, 1493, 1452, 1441, 1375, 1348, 1298, 1255, 1223, 1182, 1140, 1097, 1070, 1028, 1016, 978, 962, 951, 906, 839, 820, 758, 698, 654, 621, 540, 459.

The obtained copolymer (B23) is composed of Unit L, which is a constituent unit obtained from the Compound Example b1-23 and is contained in the Formula (5), and Unit B, which is the constituent unit represented by the Formula (9).

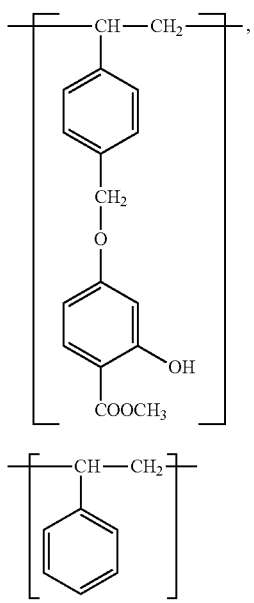

Unit L

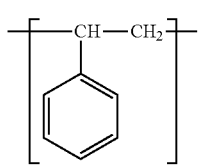

Unit B

Figure 23:
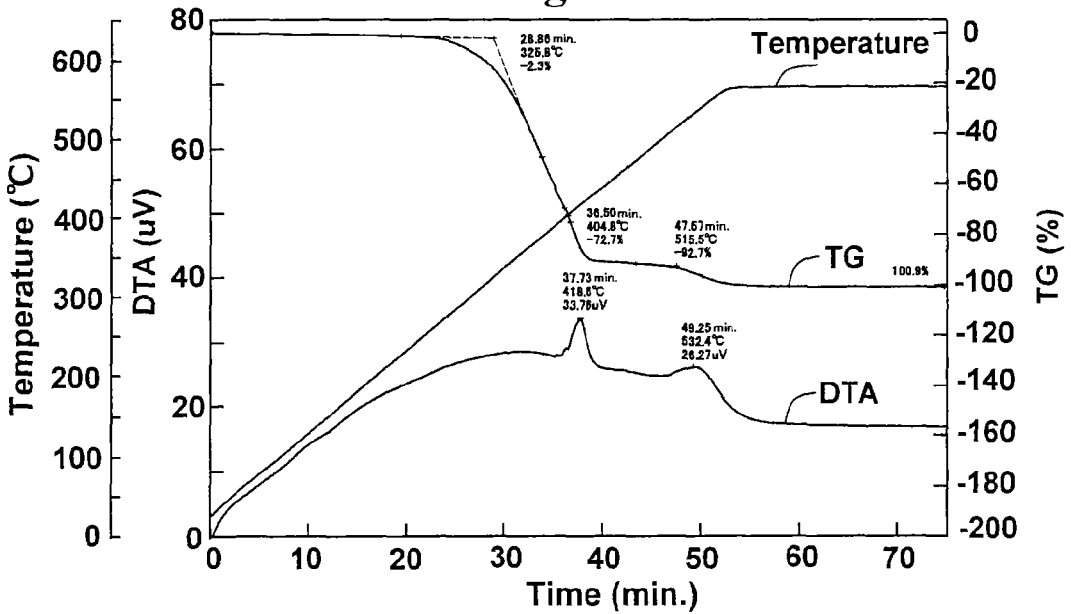
FIG. 23 is a drawing showing a chart of a result of differential thermal/thermogravimetric analysis on a copolymer of Example B23, used as the charge control resin to which the present invention is applied.

A measurement was conducted on the obtained copolymer (B23) for TG-DTA under the same conditions described in Example B1. The result of the measurement is shown in FIG. 23. The measurement result indicated that the heat generation temperatures were 419° C. and 532° C., and the weight loss temperatures were 326° C., 405° C. and 516° C.

The obtained copolymer (B23) was subjected to GPC measurement under the same conditions as described in Example B1. It was confirmed from the result of the molecular weight distribution measurement conducted under said conditions on the copolymer (B23) that the copolymer (B23) has a number average molecular weight (Mn) of 9383, a weight average molecular weight (Mw) of 36313, and a molecular weight distribution ratio (Mw/Mn) of 3.9.

The glass transition temperature of the obtained copolymer (B23) was measured in the same manner as described in Example B1. The result of the measurement determined the glass transition temperature of the copolymer (B23) to be 91.2° C.

Example B24

Preparation of a Combination of the Formula (A15) Plus Styrene in a Molar Ratio of 5.0:95.0

9.91 g of the styrene derivative (A15) and 60.09 g of styrene were dispersed in 42 ml of toluene, and heated to 110° C. in an atmosphere with nitrogen gas stream (50 ml/min). Into this solution was dripped a mixture liquid consisting of 42 ml of toluene and 4.54 g of tert-butyl peroxy isopropyl monocarbonate (PERBUTYL I, a product name of NOF CORPORATION), and this dripping took 22 minutes. A consequent reaction was further allowed to proceed for 4 hours at 110° C., and was then cooled. Thereafter, the reaction liquid was dripped into 500 ml of methanol, and a gelatinous white deposit separated. After removing the supernatant liquid by decantation, the deposit was dissolved in 300 ml of tetrahydrofuran. This solution was added to 1.5 liters of methanol, whereby a precipitate occurred, and it was filtered aside and was dried for 14 hours at 80° C. under a reduced pressure, and 42.8 g of a copolymer (B24) was obtained.

The obtained copolymer (B24) was examined by means of $^1$H-NMR under the same conditions as described in Example B1, and there were observed no peaks that should, respectively, represent the vinyl group of the styrene and the styrene derivative (A15) represented by the Formula (A15) as a starting materials before the copolymerization reaction, whereas broad aromatic proton(s) and alkyl chain(s) were observed, and furthermore, a broad hydroxyl group originating from the styrene derivative (A15) and a broad proton at δ(ppm)=5.01 (—CH$_2$—O—) were observed. From the integrated values of the peaks, it was determined that the constituent unit obtained from the styrene derivative (A15) was contained in the obtained copolymer by 4.27%.

The obtained copolymer (B24) was subjected to FT-IR analysis under the same conditions as described in Example B1, and the following observation was made.
ν(cm$^{-1}$)=3159, 3105, 3092, 3032, 3005, 2931, 2855, 1945, 1871, 1779, 1737, 1659, 1627, 1598, 1499, 1449, 1439, 1381, 1301, 1249, 1225, 1180, 1138, 1100, 1073, 1030, 1027, 1020, 981, 943, 902, 844, 814, 749, 700, 617, 535, 454.

The obtained copolymer (B24) is composed of Unit M, which is a constituent unit obtained from the Compound Example a1-28 and is contained in the Formula (5), and Unit B, which is the constituent unit represented by the Formula (9).

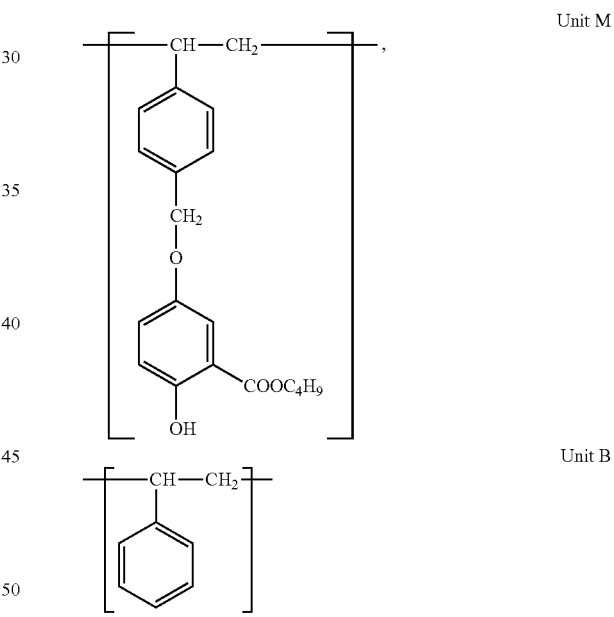

A measurement was conducted on the obtained copolymer (B24) for TG-DTA under the same conditions described in Example B1. The measurement result indicated that the heat generation temperatures were 423° C. and 544° C., and the weight loss temperatures were 319° C. and 508° C.

The obtained copolymer (B24) was subjected to GPC measurement under the same conditions as described in Example B1. It was confirmed from the result of the molecular weight distribution measurement conducted under said conditions on the copolymer (B24) that the copolymer (B24) has a number average molecular weight (Mn) of 10430, a weight average molecular weight (Mw) of 43356, and a molecular weight distribution ratio (Mw/Mn) of 4.2.

The glass transition temperature of the obtained copolymer (B24) was measured in the same manner as described in Example B1. The result of the measurement determined the glass transition temperature of the copolymer (B24) to be 89.7° C.

Example B25

The copolymer obtained in Example B7 and the copolymer obtained in Example B24 were mixed together at a weight ratio of 70:30; thus a copolymer of Example B25 was obtained.

The obtained copolymer (B25) is a mixture of a copolymer composed of Unit D, which is the constituent unit obtained from the Compound Example a1-1 and is contained in the Formula (5), and Unit B, which is the constituent unit represented by the Formula (9), and a copolymer composed of Unit M, which is the constituent unit obtained from the Compound Example a1-28 and is contained in the Formula (5) and Unit B, which is the constituent unit represented by the Formula (9).

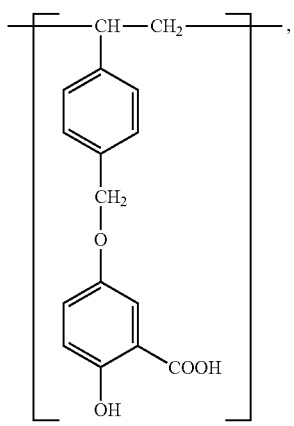
Unit D

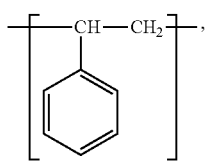
Unit B

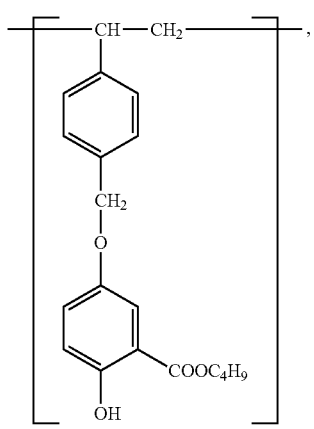
Unit M

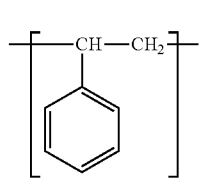
Unit B

Example B26

Preparation of a Combination of the Formula (A1) Plus Styrene in a Molar Ratio of 5.0:95.0

4.63 g of 4-chloromethylstyrene and 60.09 g of styrene were dissolved in 36.3 g of toluene, and heated to 110° C. in an atmosphere with nitrogen gas stream (50 ml/min). Into this solution was dripped a mixture liquid consisting of 33.7 g of toluene and 4.27 g of tert-butyl peroxy isopropyl monocarbonate (PERBUTYL I, a product name of NOF CORPORATION), after this mixture had been subjected to sufficient substitution with nitrogen, and this dripping took 20 minutes. A consequent reaction was further allowed to proceed for 4 hours at 110° C., and was then cooled. Thereafter, the reaction liquid was added to 1 liter of methanol, and the supernatant was decanted. The polymerized product was dissolved in 150 ml of tetrahydrofuran, and the solution was added to 1 liter of methanol to cause precipitation and the precipitate was filtered aside. The residue was washed four times with 100 ml of methanol, and was dried for 10 hours at 60° C. under a reduced pressure, and 64.1 g of a copolymerization intermediate was obtained.

The obtained copolymerization intermediate was examined by means of $^1$H-NMR under the same conditions as described in Example B1, and there were observed no peaks that should, respectively, represent the vinyl group of the styrene as a starting material before the copolymerization reaction and 4-chloromethylstyrene, whereas broad aromatic proton(s) and alkyl chain(s) and benzil proton, δ(ppm)=4.5 (—CH$_2$—Cl—), originating from the 4-chloromethylstyrene were observed. From the integrated values of the peaks, it was determined that the 4-chloromethylstyrene was contained in the obtained copolymerization intermediate by 4.33%.

The obtained copolymerization intermediate was subjected to FT-IR analysis under the same conditions as described in Example B1, and the following observation was made.

ν(cm$^{-1}$)=3103, 3082, 3059, 3026, 3001, 2976, 2924, 2848, 1942, 1869, 1801, 1741, 1601, 1583, 1506, 1493, 1452, 1423, 1385, 1373, 1363, 1352, 1329, 1313, 1263, 1182, 1155, 1105, 1070, 1028, 1003, 980, 964, 943, 906, 839, 758, 698, 621, 540.

The obtained copolymerization intermediate had the following constituent unit.

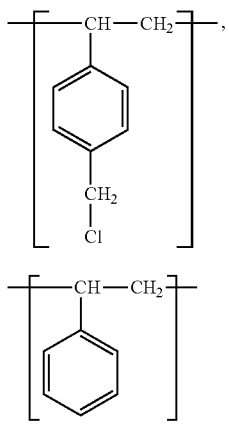

Unit S

Unit B

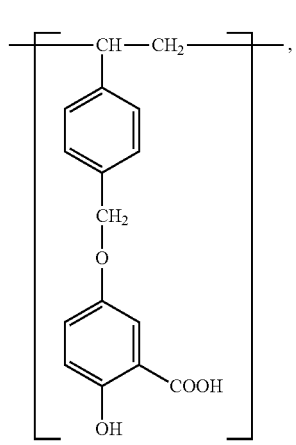

Unit D

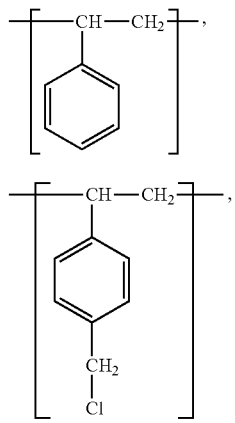

Unit B

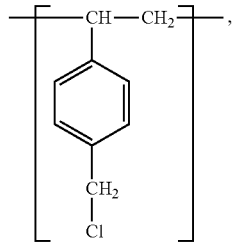

Unit S

The obtained copolymerization intermediate was subjected to GPC measurement under the same conditions as described in Example B1. It was confirmed from the result of the measurement that the copolymerization intermediate has a number average molecular weight (Mn) of 8287, a weight average molecular weight (Mw) of 20482, and a molecular weight distribution ratio (Mw/Mn) of 2.5.

10.0 g of the copolymerization intermediate was dissolved in 60 ml of tetrahydrofuran, and 4.3 g of sodium hydride was added and dispersed in this, which was then stirred for one hour at 70° C. Thereafter 3.3 g of 2,5-dihydroxy benzoic acid was added and a consequent reaction was allowed to proceed for 5 hours at 70° C., and this was cooled to the room temperature; this was gradually added and dispersed in 1 kg of ice water, and after adding chloroform, extraction was conducted. Next, this was washed with water and the chloroform layer was removed, and the remnant was dried with magnesium sulfate and the chloroform was extracted under a reduced pressure. The deposit was dried for 24 hours at 80° C. and 7.6 g of a copolymer (B26) was obtained.

The obtained copolymer (B26) was examined by means of $^1$H-NMR under the same conditions as described in Example B1, and it was confirmed from the integrated values of the peaks that the benzil proton, δ(ppm)=4.5 (—CH$_2$—Cl—), as a starting material before the reaction was contained by 0.90%. Also broad hydroxyl group(s) and broad proton(s) in the vicinity of δ(ppm)=4.9 (—CH$_2$—O—) were observed, and from the integrated values of the peaks, it was determined that the dihydroxy benzoic acid unit was contained in the obtained copolymer by 4.02%.

The obtained copolymer (B26) was subjected to FT-IR analysis under the same conditions as described in Example B1, and the following observation was made.
ν(cm$^{-1}$)=3435, 3060, 3027, 2922, 2848, 1944, 1873, 1800, 1741, 1678, 1616, 1601, 1577, 1493, 1455, 1265, 1215, 1155, 1069, 1028, 906, 758, 698, 540.

The obtained copolymer (B26) is composed of Unit D, which is the constituent unit obtained from the Compound Example a1-1 and is contained in the Formula (5), and Unit B, which is the constituent unit represented by the Formula (9), and Unit S, which originates from a copolymerization intermediate.

A measurement was conducted on the obtained copolymer (B26) for TG-DTA under the same conditions described in Example B1, and it was observed that the heat generation temperatures were 345° C. and 539° C., and the weight loss temperatures were 317° C., 389° C. and 512° C.

The obtained copolymer (B26) was subjected to GPC measurement under the same conditions as described in Example B1. It was confirmed from the result of the measurement that the copolymer (B26) has a number average molecular weight (Mn) of 8157, a weight average molecular weight (Mw) of 19775, and a molecular weight distribution ratio (Mw/Mn) of 2.4.

The glass transition temperature of the obtained copolymer (B26) was measured in the same manner as described in Example B1. The result of the measurement determined the glass transition temperature of the copolymer (B26) to be 101.6° C.

Comparative Example 1

Synthesis of the Styrene Derivative Represented by Formula (X1)

90.0 g of 2,5-dihydroxy benzoic acid was dissolved in 1200 ml of methanol, and 159.0 g of potassium carbonate was added to this and was heated to 50° C. To this reaction liquid was dripped 72.6 g of aryl bromide in the course of 90 minutes, and the reaction was allowed to proceed for 12 hours at 60° C. After cooling this reaction liquid, the methanol was distilled off under a reduced pressure, and the remnant was washed with hexane. After a filtration, the residue was dispersed in 3 liters of water of pH 2, and after adding ethyl acetate, it was extracted. Thereafter, it was washed with water and the resultant ethyl acetate was removed, drying was conducted with magnesium sulfate, and the ethyl acetate was distilled off to obtain a deposit. This deposit was dissolved in methanol and dripped into water, and was reprecipitated and the deposit was filtered aside. This reprecipitation was repeated twice, and the residue was dried for 48 hours at 80° C., and 26.5 g of a styrene derivative represented by the following Formula (X1) was obtained (yield=23.8%).

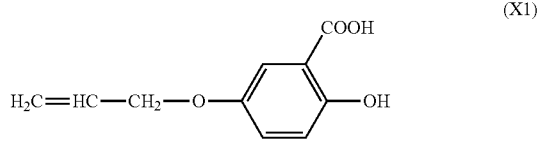

(X1)

Two kinds of polymer (Y1) made from the styrene derivative represented by the Formula (X1) and styrene
(Preparation of a Combination of the Formula (X1) Plus Styrene in a Molar Ratio of 5.0:95.0)

4.68 g of styrene derivative (X1) and 60.09 g of styrene were dispersed in 39 ml of toluene, and was heated to 110° C. in an atmosphere with nitrogen gas stream (50 ml/min). Into this solution was dripped a mixture liquid consisting of 39 ml of toluene and 4.27 g of tert-butyl peroxy isopropyl monocarbonate (PERBUTYL I, a product name of NOF CORPORATION), and this dripping took 25 minutes. A consequent reaction was further allowed to proceed for 4 hours at 110° C., and was then cooled. Thereafter, the reaction liquid was solved in 150 ml of tetrahydrofuran. This solution was dripped in methanol and a reaction product precipitated and the precipitate was filtered aside and dried for 20 hours at 90° C. under a reduced pressure, and 47.3 g of a copolymer (Y1) was obtained.

The volume resistive value was measured under the same condition as described in Example B1, and it was found that the copolymer (Y1) has a volume resistive value of $3.7 \times 10^{14}$ Ωcm.

The obtained copolymer (Y1) is composed of Unit K, which is a constituent unit shown below, and Unit B, which is the constituent unit represented by the Formula (9).

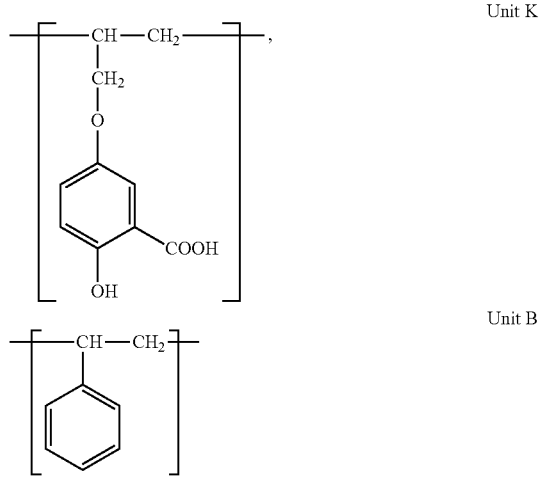

Comparative Example 2

Synthesis of Styrene Derivative Represented by Formula (X2)

50.0 g of p-cresol was dissolved in 450 ml of acetone, to which 94.5 g of potassium carbonate was added, and this was heated to 56° C. Into this reaction mixture was dripped 72.7 g of 4-(chloromethyl)styrene in the course of 30 minutes, and the consequent reaction was allowed to proceed for 12 hours at 56° C. This reaction liquid was cooled and filtered, and the acetone, which was the filtrate, was distilled off under a reduced pressure, and the resultant residue was washed with hexane. After the filtration, the residue was recrystallized with toluene. Then, filtered again, the residue was dried at 80° C. for 48 hours, and 43.2 g of a styrene derivative represented by the below formula (X2) was obtained (yield=42.5%).

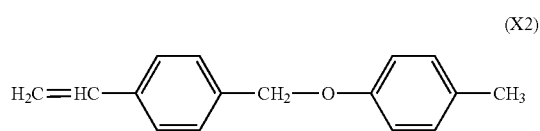 [SMILES: C=Cc1ccc(COc2ccc(C)cc2)cc1]

(X2)

Two kinds of polymer (Y2) made from the styrene derivative represented by the Formula (X2) and styrene
(Preparation of a Combination of Formula (X2) Plus Styrene in a Molar Ratio of 5.0:95.0)

3.56 g of styrene derivative (X2) and 31.44 g of styrene were dispersed in 21 ml of toluene, and was heated to 110° C. in an atmosphere with nitrogen gas stream (50 ml/min). Into this solution was dripped a mixture liquid consisting of 21 ml of toluene and 2.31 g of tert-butyl peroxy isopropyl monocarbonate (PERBUTYL I, a product name of NOF CORPORATION), and this dripping took 17 minutes. A consequent reaction was further allowed to proceed for 4 hours at 110° C., and was then cooled, and this was dissolved in 150 ml of tetrahydrofuran. This solution was dripped in methanol and a reaction product precipitated and the precipitate was filtered aside and dried for 20 hours at 90° C. under a reduced pressure, and 27.9 g of a copolymer (Y2) was obtained.

The obtained copolymer (Y2) is composed of Unit N, which is a constituent unit shown below, and Unit B, which is the constituent unit represented by the Formula (9).

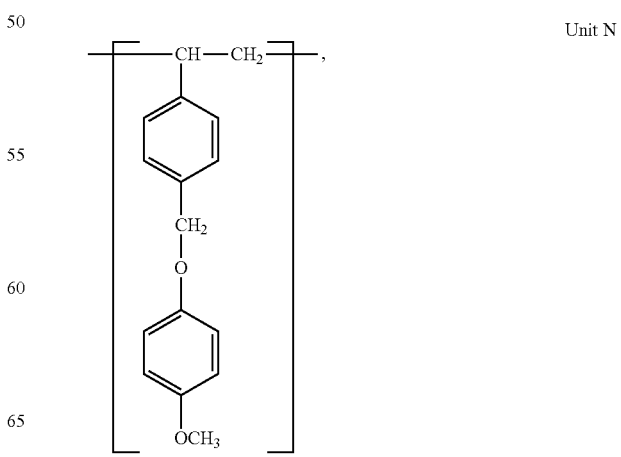

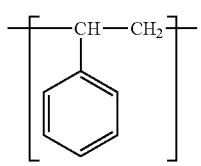

Comparative Example 3

A commercially available polyparavinylphenol represented by Formula (Y3) was used, which is the Compound Example No. 1-1 described in Japanese Patent Application Publication No. H06-95435, (manufactured by Maruzen Petrochemical Co., Ltd; product name: Maruka Lyncur M; grade name: H-2; Mw: 19800-24200; Mn: 3600-4400).

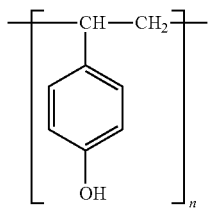

(Y3)

Comparative Example 4

A commercially available copolymer compound made from vinyl phenol and methyl methacrylate represented by Formula (Y4) was used, which is the compound No. 1-3 described in Japanese Patent Application Publication No. H06-95435, (manufactured by Maruzen Petrochemical Co., Ltd; product name. Maruka Lyncur CMM; Mw: 8000-12000; Mn: 3000-5000).

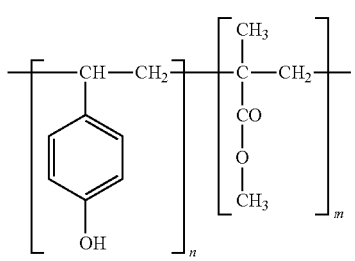

(Y4)

Comparative Example 5

A commercially available copolymer compound made from vinyl phenol and styrene represented by Formula (Y5) was used, which is the compound No. 1-4 described in Japanese Patent Application Publication No. H06-95435, (manufactured by Maruzen Petrochemical Co., Ltd; product name: Maruka Lyncur CST; Mw: 3000-5000; Mn: 1900-3300).

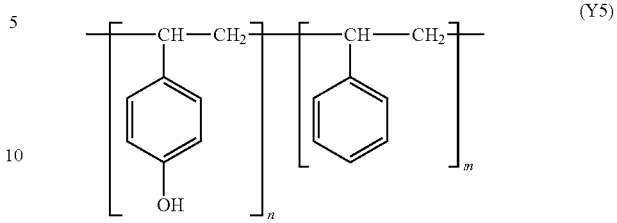

(Y5)

Example C1

Figure 24:
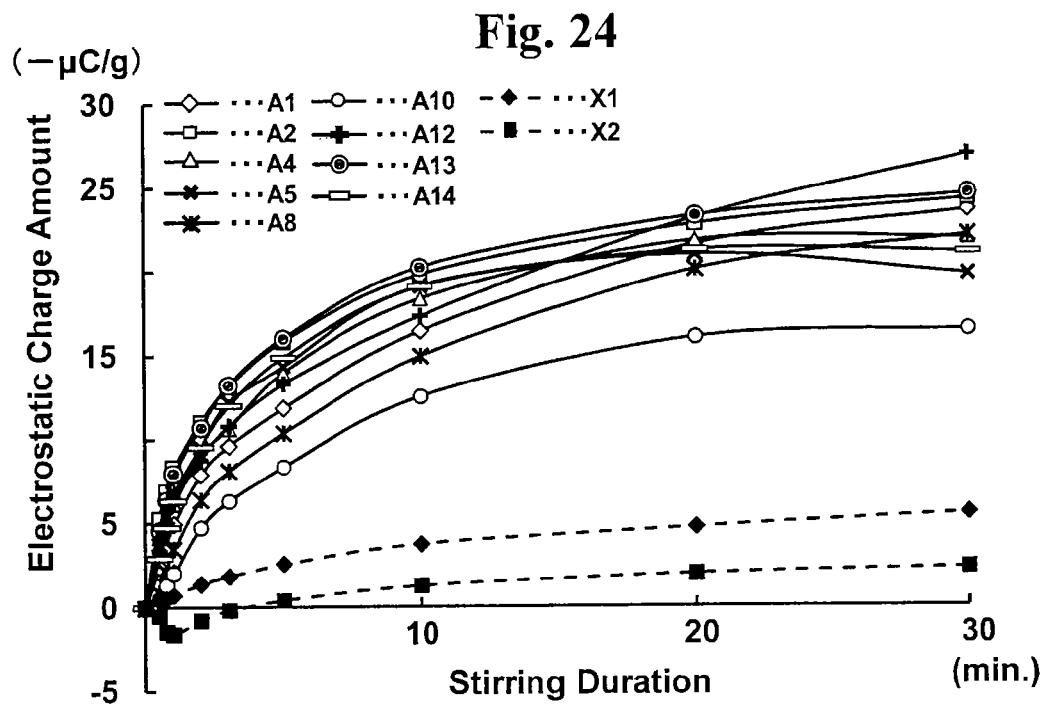
FIG. 24 is a drawing showing electric charge amounts as the result of an electrostatic propensity test A on charge control agents to which the present invention is applied and on ones to which the present invention is not applied.

Estimation of Charge Controllability of Charge Control Agents by Means of Electrostatic Propensity Test A First, one weight part of the styrene derivative (A1) obtained in the previous example and 100 weight parts of styrene-acryl copolymer resin (manufactured by Mitsui Chemicals Co., Ltd.; product name: CPR-100) were mixed together preparatively, and the mixture was melted and kneaded by a heater roller machine (manufactured by Kurimoto Ltd.; product name: S-1, KRC Kneader). After cooling, the dough was roughly pulverized by a super centrifugal pulverizer (manufactured by Retsch Inc.; product name: ULTRA CENTRIFUGAL MILL, sieve mesh size: 1.5 mm), and using an air jet mill equipped with a classifier (manufactured by SEISHIN ENTERPRISE CO., LTD.; product name: CO-JET) and a laser diffraction/light scattering-type grain diameter distribution analyzer (manufactured by HORIBA, LTD.; product name Partica LA-950), the average grain diameter was measured and then the matter was finely pulverized to have a size of 9.5-10.5 micrometers. 2.5 weight parts of this resin grain and 50.0 weight parts of iron powder carrier (manufactured by Powdertech Co., Ltd.; product name TEFV200/300) were poured into a 100-ml ointment container, and it was turned at a speed of 100 rpm on a ball mill rotary table (manufactured by ASAHI-RIKA Co., Ltd.; product name: Small-Size Ball Mill Rotary Table AV-1), and at predetermined intervals of time the mixture sample was taken, and the electrostatic charge amount was measured under the following conditions by means of a blow-off electrostatic charge amount analyzer (manufactured by Toshiba Chemical Corp.; product name: TB-200). The thus obtained results of negative chargeability verification data are shown in Table 27 and FIG. 24. Measurement conditions: metal sieve mesh size was 35 micrometers; pressure was 10.0 kPa; suction force was 10.0 kPa; suction duration was 10.0 seconds.

Next, the styrene derivatives A2, A4, A5, A8, A10, A12, A13 and A14, which were obtained in Examples and the comparative compounds X1 and X2 were subjected to the same electrostatic propensity test A, to which the styrene derivative A1 had been subjected. The results are shown in Table 27 and FIG. 24.

TABLE 27

| Stirring Duration (min.) | Electrostatic Charge Amount (−μC/g) | | | | | | | | | | |
|---|---|---|---|---|---|---|---|---|---|---|---|
| | A1 | A2 | A4 | A5 | A8 | A10 | A12 | A13 | A14 | X1 | X2 |
| 0 | 0.00 | 0.00 | 0.00 | 0.00 | 0.00 | 0.00 | 0.00 | 0.00 | 0.00 | 0.00 | 0.00 |
| 0.5 | 2.40 | 5.25 | 4.20 | 3.75 | 0.90 | 0.53 | 3.38 | 4.58 | 2.93 | 0.43 | −0.50 |
| 0.75 | 3.60 | 6.90 | 5.10 | 5.40 | 2.10 | 1.35 | 4.58 | 6.39 | 4.74 | 0.52 | −1.43 |
| 1 | 4.95 | 8.33 | 6.15 | 6.83 | 3.45 | 2.03 | 6.30 | 7.96 | 6.31 | 0.72 | −1.61 |
| 2 | 7.88 | 11.03 | 9.08 | 9.53 | 6.38 | 4.73 | 8.78 | 10.70 | 9.53 | 1.39 | −0.78 |
| 3 | 9.60 | 13.13 | 10.65 | 12.23 | 8.10 | 6.30 | 10.80 | 13.24 | 12.01 | 1.84 | −0.18 |
| 5 | 11.85 | 15.83 | 13.95 | 14.33 | 10.35 | 8.33 | 13.28 | 16.03 | 14.87 | 2.55 | 0.40 |
| 10 | 16.43 | 19.80 | 18.38 | 19.13 | 14.93 | 12.53 | 17.33 | 20.24 | 19.09 | 3.73 | 1.26 |
| 20 | 21.60 | 22.80 | 21.83 | 21.00 | 20.10 | 16.05 | 23.18 | 23.30 | 21.27 | 4.71 | 1.95 |
| 30 | 23.63 | 24.30 | 21.98 | 19.80 | 22.13 | 16.50 | 26.93 | 24.60 | 21.12 | 5.54 | 2.29 |

Example C2

Environmental Stability Rating of the Charge Control Agents which is the Resin Grain Obtained in Example C1

Using the resin grains obtained in Example C1, the styrene derivatives A1, A2, A4, A5, A8, A10, A12, A13 and A14, which had been obtained in Examples, and the comparative compounds X1 and X2 were rated in terms of environmental stability. The results are shown in Table 28.

50.0 weight parts of iron powder carrier (manufactured by Powdertech Co., Ltd.; product name TEFV200/300) plus each one, respectively, of the resin grain species prepared in the same manner as in the afore-mentioned electrostatic propensity test A were poured in a 100-ml ointment container, and a lid having a 1-cm hole in the middle was placed on it. This was set in a ball mill machine (manufactured by ASAHI-RIKA Co., Ltd.; product name: Ball Mill Rotary Table), which was installed inside a thermo-hygrostat (manufactured by Tokyo Rika Mfg. Co., Ltd.; product name: Enviros KCL-2000W), and each was let to sit for 24 hours in respective environment of a predetermined temperature and a predetermined humidity. After the 24 hours, while the 100-ml ointment container was kept rotating at 100 rpm, the respective mixture was taken out after 15-minute stirring, and the electrostatic charge amount was measured under the following conditions by means of a blow-off electrostatic charge amount analyzer (manufactured by Toshiba Chemical Corp.; product name: TB-200). Measurement conditions: metal sieve mesh size was 34 micrometers; pressure was 10.0 kPa; suction force was 10.0 kPa; suction duration was 10.0 seconds.

TABLE 28

| | Electrostatic Charge Amount (μC/g) | | | Environmental Stability | |
|---|---|---|---|---|---|
| Example No. | Saturation Charge Amount | Low Temperature & Low Humidity (LL) 20° C., 30% RH | High Temperature & High Humidity (HH) 30° C., 80% RH | \|LL val.\| − \|HH val.\| | \|LL val.\|/\|HH val.\| |
| A1 | −23.63 | −25.92 | −11.91 | 14.01 | 2.18 |
| A2 | −24.30 | −27.36 | −12.26 | 15.10 | 2.23 |
| A4 | −21.98 | −26.19 | −11.08 | 15.11 | 2.36 |
| A5 | −21.00 | −25.20 | −9.95 | 15.25 | 2.53 |
| A8 | −22.13 | −24.12 | −11.17 | 12.95 | 2.16 |
| A10 | −16.50 | −19.26 | −8.32 | 10.94 | 2.31 |
| A12 | −26.93 | −27.81 | −13.52 | 14.29 | 2.06 |
| A13 | −24.60 | −27.12 | −12.70 | 14.42 | 2.14 |
| A14 | −21.12 | −26.70 | −12.30 | 14.40 | 2.17 |
| X1 | −2.82 | −3.30 | −0.61 | 2.69 | 5.41 |
| X2 | −2.29 | −2.98 | −0.45 | 2.53 | 6.62 |

In Table 28, "LL" stands for low temperature and low humidity, and "HH" stands for high temperature and high humidity.

Example C3

Figure 25:
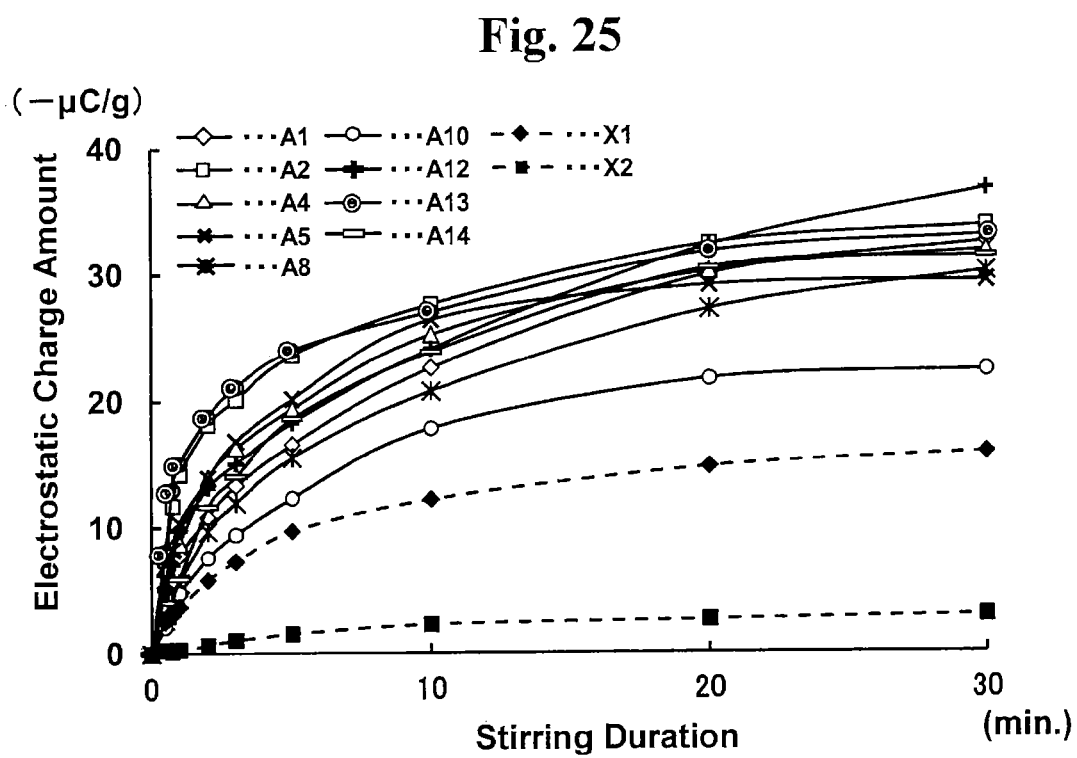
FIG. 25 is a drawing showing electric charge amounts as the result of an electrostatic propensity test B on charge control agents to which the present invention is applied and on ones to which the present invention is not applied.

Estimation of Charge Controllability of Charge Control Agents by Means of Electrostatic Propensity Test B First, one weight part of the styrene derivative (A1) obtained in the previous example and 100 weight parts of polyester resin (manufactured by Mitsubishi Rayon Co., Ltd.; product name: ER-508) were mixed together preparatively, and the mixture was melted and kneaded by a heater roller machine (manufactured by Kurimoto Ltd.; product name: S-1, KRC Kneader). After cooling, the dough was roughly pulverized by a super centrifugal pulverizer (manufactured by Retsch Inc.; product name: ULTRA CENTRIFUGAL MILL, sieve mesh size: 1.5 mm), and using an air jet mill equipped with a classifier (manufactured by SEISHIN ENTERPRISE CO., LTD.; product name: CO-JET) and a laser diffraction/light scattering-type grain diameter distribution analyzer (manufactured by HORIBA, LTD.; product name Partica LA-950), the average grain diameter was measured and then the matter was finely pulverized to have a size of 9.5-10.5 micrometers. 2.5 weight parts of this resin grain and 50.0 weight parts of iron powder carrier (manufactured by Powdertech Co., Ltd.; product name TEFV200/300) were poured into a 100-ml ointment container, and it was turned at a speed of 100 rpm on a ball mill rotary table (manufactured by ASAHI-RIKA Co., Ltd.; product name: Small-Size Ball Mill Rotary Table AV-1), and at predetermined intervals of time the mixture sample was taken, and the electrostatic charge amount was measured under the following conditions by means of a blow-off electrostatic charge amount analyzer (manufactured by Toshiba Chemical Corp.; product name: TB-200). The thus obtained results of negative chargeability verification data are shown in Table 29 and FIG. 25.
Measurement Conditions:
metal sieve mesh size was 34 micrometers; pressure was 10.0 kPa;
suction force was 10.0 kPa; suction duration was 10.0 seconds.

The styrene derivatives A2, A4, A5, A8, A10, A12, A13 and A14, which had been obtained in Examples, and the comparative compounds X1 and X2 were subjected to the same electrostatic propensity test B, to which the styrene derivative A1 had been subjected. The results are shown in Table 29 and FIG. 25.

which had been obtained in Examples, and the comparative compounds X1 and X2 were rated in terms of environmental stability. The results are shown in Table 30.

50.0 weight parts of iron powder carrier (manufactured by Powdertech Co., Ltd.; product name TEFV200/300) plus each one, respectively, of the resin grain species prepared in the same manner as in the afore-mentioned electrostatic propensity test B were poured in a 100-ml ointment container, and a lid having a 1-cm hole in the middle was placed on it. This was set in a ball mill machine (manufactured by ASAHI-RIKA Co., Ltd.; product name: Ball Mill Rotary Table), which was installed inside a thermo-hygrostat (manufactured by Tokyo Rika Mfg. Co., Ltd.; product name: Enviros KCL-2000W), and each was let to sit for 24 hours in respective environment of a predetermined temperature and a predetermined humidity. After the 24 hours, while the 100-ml ointment container was kept rotating at 100 rpm, the respective mixture was taken out after 15-minute stirring, and the electrostatic charge amount was measured under the following conditions by means of a blow-off electrostatic charge amount analyzer (manufactured by Toshiba Chemical Corp.; product name: TB-200). Measurement conditions: metal sieve mesh size was 34 micrometers; pressure was 10.0 kPa; suction force was 10.0 kPa; suction duration was 10.0 seconds.

TABLE 29

| Stirring Duration | Electrostatic Charge Amount ($-\mu C/g$) | | | | | | | | | | |
|---|---|---|---|---|---|---|---|---|---|---|---|
| (min.) | A1 | A2 | A4 | A5 | A8 | A10 | A12 | A13 | A14 | X1 | X2 |
| 0 | 0.00 | 0.00 | 0.00 | 0.00 | 0.00 | 0.00 | 0.00 | 0.00 | 0.00 | 0.00 | 0.00 |
| 0.5 | 3.78 | 7.46 | 6.76 | 5.77 | 2.68 | 2.10 | 5.05 | 8.07 | 2.58 | 2.53 | 0.29 |
| 0.75 | 5.72 | 11.70 | 8.40 | 8.20 | 3.94 | 3.25 | 7.02 | 12.96 | 4.03 | 3.03 | 0.18 |
| 1 | 7.77 | 14.20 | 8.73 | 10.37 | 5.56 | 4.78 | 9.78 | 15.06 | 5.89 | 3.68 | 0.31 |
| 2 | 10.81 | 18.10 | 13.91 | 13.91 | 9.66 | 7.56 | 13.12 | 18.76 | 11.59 | 5.79 | 0.65 |
| 3 | 13.28 | 20.10 | 16.27 | 16.80 | 11.92 | 9.40 | 15.03 | 21.10 | 14.00 | 7.26 | 1.05 |
| 5 | 16.54 | 23.60 | 19.36 | 20.14 | 15.49 | 12.28 | 18.24 | 24.00 | 18.57 | 9.66 | 1.52 |
| 10 | 22.57 | 27.60 | 25.20 | 26.38 | 20.73 | 17.79 | 24.08 | 27.00 | 23.82 | 12.14 | 2.26 |
| 20 | 29.92 | 32.38 | 30.18 | 29.07 | 27.19 | 21.68 | 32.22 | 31.72 | 30.44 | 14.71 | 2.60 |
| 30 | 32.49 | 33.79 | 31.82 | 29.40 | 30.13 | 22.31 | 36.68 | 33.01 | 31.36 | 15.82 | 2.94 |

Example C4

Environmental Stability Rating of the Charge Control Agents which is the Resin Grain Obtained in Example C3

Using the resin grains obtained in Example C3, the styrene derivatives A1, A2, A4, A5, A8, A10, A12, A13 and A14,

TABLE 30

| | Electrostatic Charge Amount ($\mu C/g$) | | | | |
|---|---|---|---|---|---|
| Example No. | Saturation Charge Amount | Low Temperature & Low Humidity (LL) 20° C., 30% RH | High Temperature & High Humidity (HH) 30° C., 80% RH | Environmental Stability | |
| | | | | \|LL val.\| − \|HH val.\| | \|LL val.\|/\|HH val.\| |
| A1 | −32.49 | −39.10 | −12.19 | 26.91 | 3.21 |
| A2 | −33.79 | −42.29 | −15.96 | 26.33 | 2.65 |
| A4 | −31.82 | −39.43 | −12.30 | 27.14 | 3.21 |
| A5 | −29.40 | −37.99 | −13.15 | 24.84 | 2.89 |
| A8 | −30.13 | −35.55 | −12.04 | 23.51 | 2.95 |
| A10 | −22.31 | −28.38 | −8.51 | 28.02 | 2.99 |

TABLE 30-continued

| Example No. | Saturation Charge Amount | Electrostatic Charge Amount (μC/g) | | Environmental Stability | |
|---|---|---|---|---|---|
| | | Low Temperature & Low Humidity (LL) 20° C., 30% RH | High Temperature & High Humidity (HH) 30° C., 80% RH | \|LL val.\| − \|HH val.\| | \|LL val.\|/\|HH val.\| |
| A12 | −36.68 | −42.09 | −14.06 | 19.88 | 3.34 |
| A13 | −33.01 | −43.56 | −18.69 | 24.87 | 2.33 |
| A14 | −31.36 | −36.35 | −14.43 | 21.92 | 2.52 |
| X1 | −15.82 | −15.60 | −2.69 | 12.91 | 5.80 |
| X2 | −2.94 | −3.81 | −0.36 | 3.45 | 10.58 |

Example C5

Figure 26:
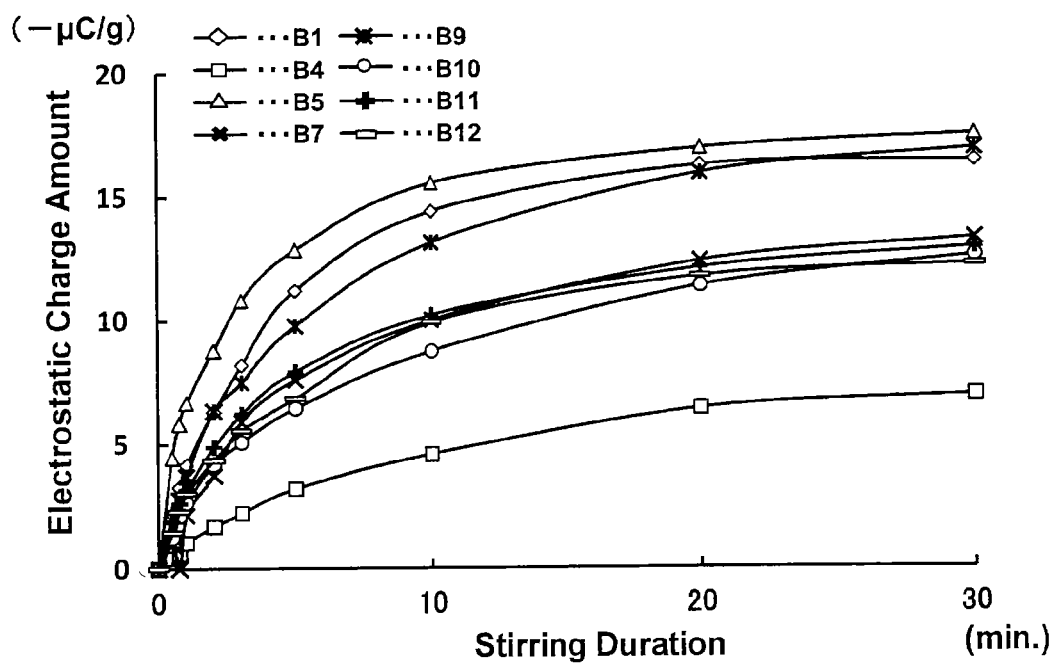
FIG. 26 is a drawing showing electric charge amounts as the result of an electrostatic propensity test A on charge control resins to which the present invention is applied and on ones to which the present invention is not applied.
Figure 27:
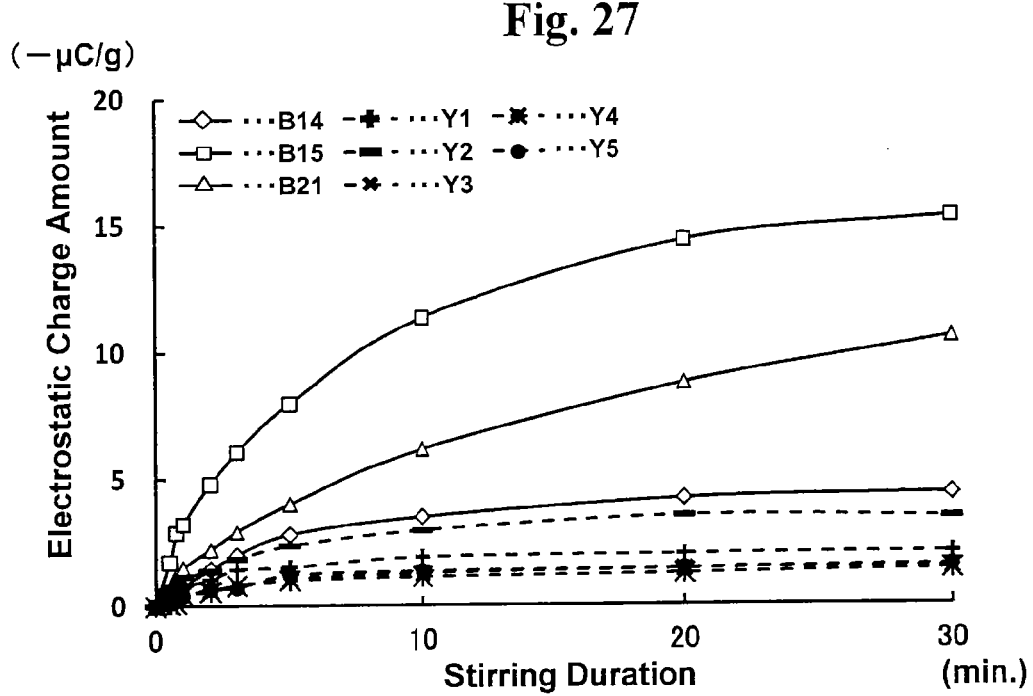
FIG. 27 is a drawing showing electric charge amounts as the result of an electrostatic propensity test A on charge control resins to which the present invention is applied and on ones to which the present invention is not applied.
Figure 28:
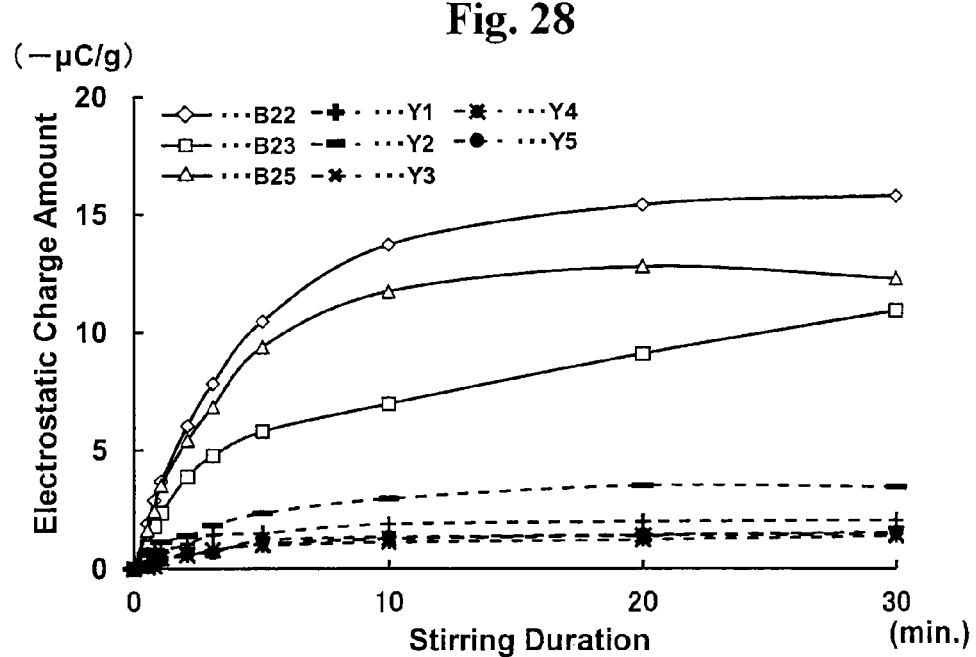
FIG. 28 is a drawing showing electric charge amounts as the result of an electrostatic propensity test A on charge control resins to which the present invention is applied and on ones to which the present invention is not applied.

Estimation of Charge Controllability of Charge Control Resins by Means of Electrostatic Propensity Test A From charge control resins, which had been obtained in Examples, such as (styrene-based resins) B1, B4, B5, B7, B9, B10, B11, B12, B14, B15, B21, B22, B23, B25 and the comparative resins such as Y1, Y2, Y3, Y4 and Y5, resin grains were obtained in the same manner as in Example C1, and their charge controllability was rated. The thus obtained results of negative chargeability verification data are shown in Table 31, Table 32, Table 33, FIG. 26, FIG. 27 and FIG. 28.

TABLE 31

| Stirring Duration (min.) | Electrostatic Charge Amount (−μC/g) | | | | | | | |
|---|---|---|---|---|---|---|---|---|
| | B1 | B4 | B5 | B7 | B9 | B10 | B11 | B12 |
| 0 | 0.00 | 0.00 | 0.00 | 0.00 | 0.00 | 0.00 | 0.00 | 0.00 |
| 0.5 | 2.19 | 0.41 | 4.47 | 1.00 | 1.68 | 1.24 | 1.88 | 1.43 |
| 0.75 | 3.27 | 0.60 | 5.82 | 1.65 | 2.78 | 2.11 | 2.62 | 2.28 |
| 1 | 4.17 | 1.04 | 6.66 | 2.15 | 3.71 | 2.66 | 3.16 | 3.01 |
| 2 | 6.29 | 1.68 | 8.77 | 3.75 | 6.33 | 4.19 | 4.88 | 4.34 |
| 3 | 8.18 | 2.22 | 10.80 | 5.89 | 7.48 | 5.07 | 6.21 | 5.53 |
| 5 | 11.20 | 3.20 | 12.84 | 7.58 | 9.77 | 6.43 | 7.91 | 6.83 |
| 10 | 14.40 | 4.58 | 15.54 | 10.00 | 13.13 | 8.73 | 10.20 | 9.90 |
| 20 | 16.23 | 6.40 | 16.92 | 12.36 | 15.92 | 11.36 | 12.09 | 11.75 |
| 30 | 16.40 | 6.93 | 17.47 | 13.27 | 16.89 | 12.56 | 12.89 | 12.23 |

TABLE 32

| Stirring Duration (min.) | Electrostatic Charge Amount (−μC/g) | | | | | | | |
|---|---|---|---|---|---|---|---|---|
| | B14 | B15 | B21 | Y1 | Y2 | Y3 | Y4 | Y5 |
| 0 | 0.00 | 0.00 | 0.00 | 0.00 | 0.00 | 0.00 | 0.00 | 0.00 |
| 0.5 | 0.50 | 1.73 | 0.66 | 0.62 | 0.61 | 0.06 | 0.08 | 0.12 |
| 0.75 | 0.61 | 2.88 | 1.24 | 0.72 | 0.77 | 0.12 | 0.11 | 0.22 |
| 1 | 0.74 | 3.23 | 1.51 | 0.78 | 1.14 | 0.46 | 0.44 | 0.40 |
| 2 | 1.44 | 4.80 | 2.21 | 1.04 | 1.38 | 0.62 | 0.56 | 0.66 |
| 3 | 2.00 | 6.06 | 2.92 | 1.43 | 1.84 | 0.82 | 0.79 | 0.70 |
| 5 | 2.80 | 7.96 | 4.00 | 1.51 | 2.35 | 1.05 | 0.99 | 1.20 |
| 10 | 3.49 | 11.35 | 6.16 | 1.90 | 2.96 | 1.28 | 1.13 | 1.35 |
| 20 | 4.20 | 14.40 | 8.76 | 2.00 | 3.52 | 1.41 | 1.23 | 1.44 |
| 30 | 4.40 | 15.32 | 10.58 | 2.07 | 3.46 | 1.49 | 1.40 | 1.56 |

TABLE 33

| Stirring Duration (min.) | Electrostatic Charge Amount (−μC/g) | | | | | | | |
|---|---|---|---|---|---|---|---|---|
| | B22 | B23 | B25 | Y1 | Y2 | Y3 | Y4 | Y5 |
| 0 | 0.00 | 0.00 | 0.00 | 0.00 | 0.00 | 0.00 | 0.00 | 0.00 |
| 0.5 | 1.92 | 0.94 | 1.64 | 0.62 | 0.61 | 0.06 | 0.08 | 0.12 |
| 0.75 | 2.89 | 1.81 | 2.45 | 0.72 | 0.77 | 0.12 | 0.11 | 0.22 |
| 1 | 3.70 | 2.36 | 3.52 | 0.78 | 1.14 | 0.46 | 0.44 | 0.40 |
| 2 | 6.04 | 3.89 | 5.43 | 1.04 | 1.38 | 0.62 | 0.56 | 0.66 |
| 3 | 7.83 | 4.77 | 6.85 | 1.43 | 1.84 | 0.82 | 0.79 | 0.70 |
| 5 | 10.47 | 5.80 | 9.39 | 1.51 | 2.35 | 1.05 | 0.99 | 1.20 |
| 10 | 13.73 | 6.98 | 11.75 | 1.90 | 2.96 | 1.28 | 1.13 | 1.35 |
| 20 | 15.42 | 9.10 | 12.80 | 2.00 | 3.52 | 1.41 | 1.23 | 1.44 |
| 30 | 15.80 | 10.94 | 12.30 | 2.07 | 3.46 | 1.49 | 1.40 | 1.56 |

Example C6

Environmental Stability Rating of the Resin Grains Obtained in Example C5

Using the resin grains of Example C5, the charge control resins, which had been obtained in Examples, such as (styrene-based resins) B1, B4, B5, B7, B9, B10, B11, B12, B14, B15, B21, B22, B23, B25 and the comparative resins such as Y1, Y2, Y3, Y4 and Y5, were rated in terms of environmental stability in the same manner as in Example C2. The results are shown in Table 34.

TABLE 34

| Example No. | Electrostatic Charge Amount (μC/g) | | | Environmental Stability | |
|---|---|---|---|---|---|
| | Saturation Charge Amount | Low Temperature & Low Humidity (LL) 20° C., 30% RH | High Temperature & High Humidity (HH) 30° C., 80% RH | \|LL val.\| − \|HH val.\| | \|LL val.\|/\|HH val.\| |
| B1 | −16.40 | −19.77 | −14.38 | 5.39 | 1.38 |
| B4 | −6.93 | −8.28 | −5.60 | 2.68 | 1.48 |
| B5 | −17.47 | −20.50 | −14.01 | 6.50 | 1.46 |
| B7 | −13.27 | −14.83 | −10.68 | 4.16 | 1.39 |
| B9 | −16.89 | −19.70 | −13.58 | 6.12 | 1.45 |
| B10 | −12.56 | −14.23 | −10.14 | 4.09 | 1.40 |
| B11 | −12.89 | −15.31 | −10.39 | 4.92 | 1.47 |
| B12 | −12.23 | −14.80 | −9.84 | 4.96 | 1.50 |
| B14 | −4.40 | −5.35 | −3.55 | 1.80 | 1.51 |
| B15 | −15.32 | −18.05 | −12.97 | 5.09 | 1.39 |
| B21 | −10.58 | −11.81 | −7.46 | 4.35 | 1.58 |
| B22 | −15.80 | −20.00 | −14.22 | 5.78 | 1.41 |
| B23 | −10.94 | −12.22 | −7.85 | 4.37 | 1.56 |
| B25 | −12.30 | −21.60 | −13.90 | 7.70 | 1.55 |
| Y1 | −2.07 | −3.70 | −0.66 | 3.04 | 5.64 |
| Y2 | −3.46 | −5.52 | −1.77 | 3.76 | 3.12 |
| Y3 | −1.49 | −2.49 | −0.19 | 2.30 | 12.98 |
| Y4 | −1.40 | −2.78 | −0.22 | 2.56 | 12.62 |
| Y5 | −1.56 | −1.73 | −0.25 | 1.48 | 6.97 |

Example C7

Figure 29:
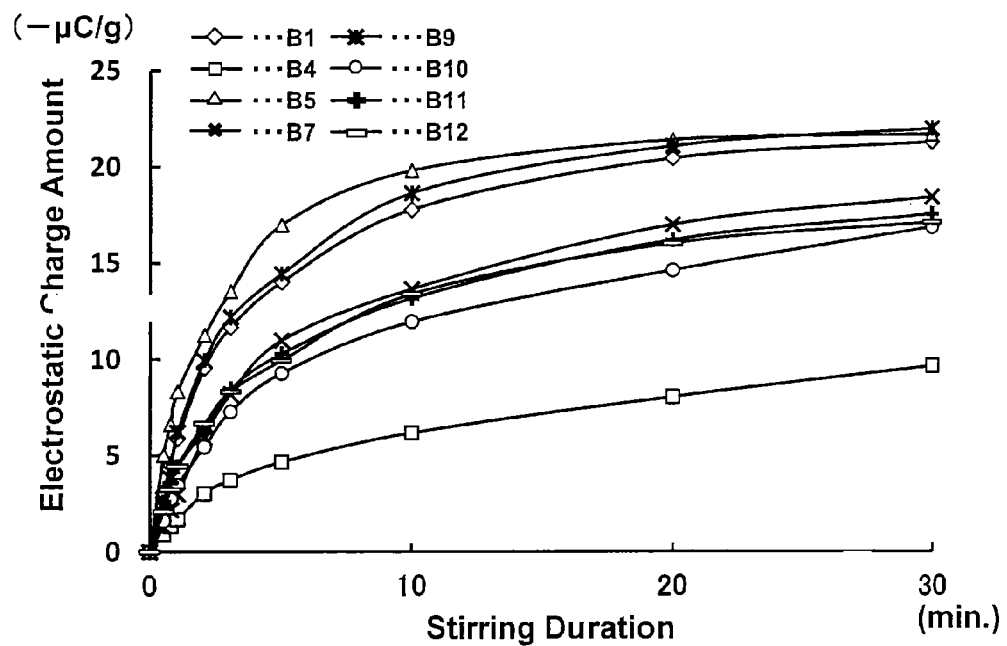
FIG. 29 is a drawing showing electric charge amounts as the result of an electrostatic propensity test B on charge control resins to which the present invention is applied and on ones to which the present invention is not applied.
Figure 30:
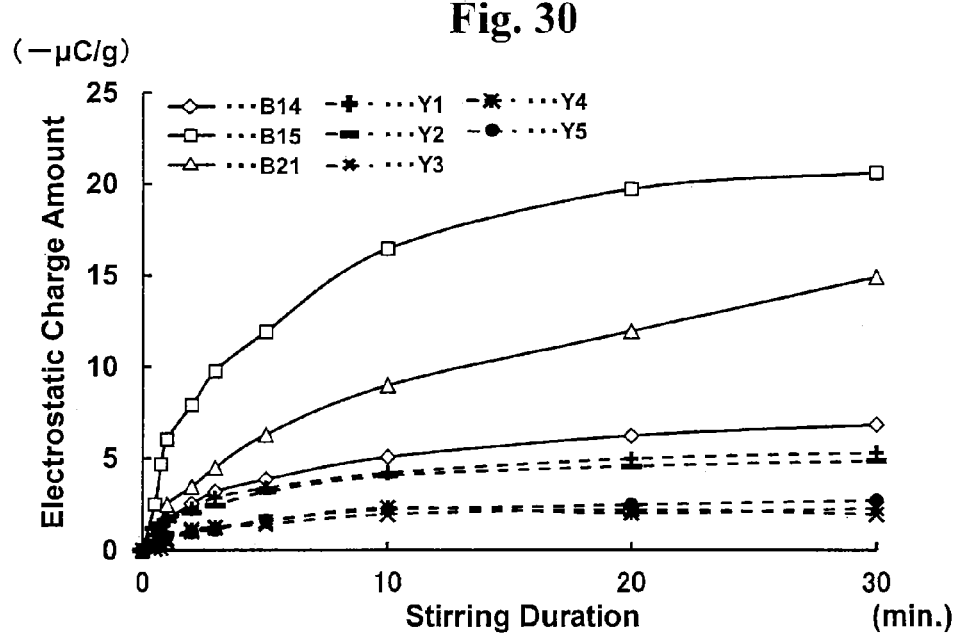
FIG. 30 is a drawing showing electric charge amounts as the result of an electrostatic propensity test B on charge control resins to which the present invention is applied and on ones to which the present invention is not applied.
Figure 31:
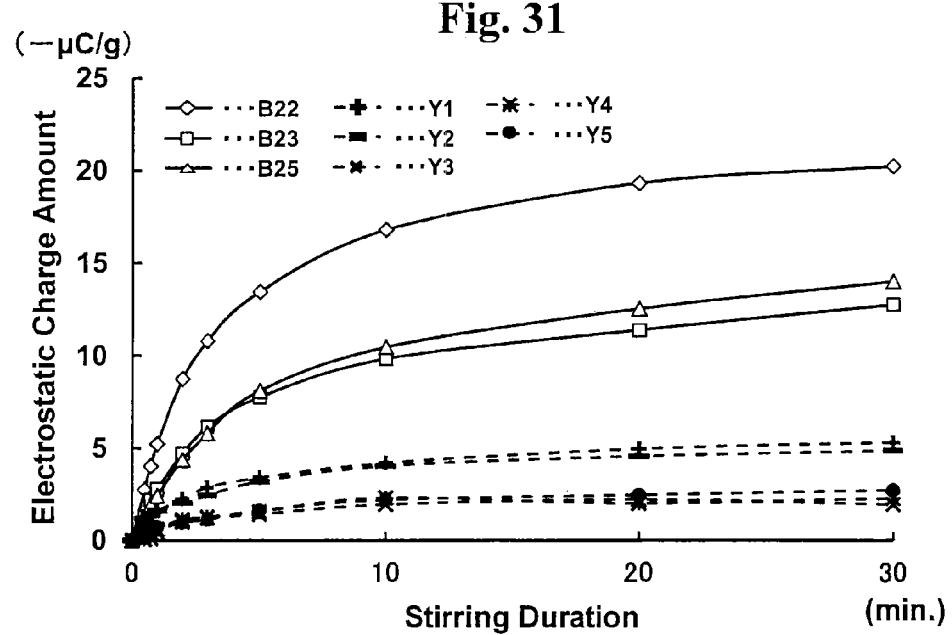
FIG. 31 is a drawing showing electric charge amounts as the result of an electrostatic propensity test B on charge control resins to which the present invention is applied and on ones to which the present invention is not applied.

Estimation of Charge Controllability of Charge Control Resins by Means of Electrostatic Propensity Test B From charge control resins, which had been obtained in Examples, such as (styrene-based resins) B1, B4, B5, B7, B9, B10, B11, B12, B14, B15, B21, B22, B23, B25 and the comparative resins such as Y1, Y2, Y3, Y4 and Y5, resin grains were obtained in the same manner as in Example C3, and their charge controllability was rated. The thus obtained results of negative chargeability verification data are shown in Table 35, Table 36, Table 37, FIG. 29, FIG. 30 and FIG. 31.

TABLE 35

| Stirring Duration | Electrostatic Charge Amount (−μC/g) | | | | | | | |
|---|---|---|---|---|---|---|---|---|
| (min.) | B1 | B4 | B5 | B7 | B9 | B10 | B11 | B12 |
| 0 | 0.00 | 0.00 | 0.00 | 0.00 | 0.00 | 0.00 | 0.00 | 0.00 |
| 0.5 | 3.08 | 0.91 | 5.03 | 1.30 | 2.50 | 1.61 | 2.60 | 2.07 |
| 0.75 | 4.51 | 1.33 | 6.62 | 2.15 | 3.80 | 2.74 | 3.58 | 3.21 |
| 1 | 5.88 | 1.67 | 8.34 | 2.96 | 6.20 | 3.46 | 4.43 | 4.45 |
| 2 | 9.54 | 3.02 | 11.24 | 5.93 | 9.94 | 5.45 | 6.34 | 6.65 |
| 3 | 11.66 | 3.72 | 13.52 | 8.20 | 12.18 | 7.27 | 8.44 | 8.32 |
| 5 | 14.00 | 4.65 | 16.97 | 10.97 | 14.42 | 9.27 | 10.28 | 9.93 |
| 10 | 17.76 | 6.16 | 19.79 | 13.64 | 18.61 | 11.94 | 13.15 | 13.38 |
| 20 | 20.42 | 8.03 | 21.38 | 16.97 | 21.06 | 14.61 | 16.18 | 16.00 |
| 30 | 21.27 | 9.65 | 21.66 | 18.41 | 21.96 | 16.85 | 17.52 | 17.10 |

TABLE 36

| Stirring Duration | Electrostatic Charge Amount (−μC/g) | | | | | | | |
|---|---|---|---|---|---|---|---|---|
| (min.) | B14 | B15 | B21 | Y1 | Y2 | Y3 | Y4 | Y5 |
| 0 | 0.00 | 0.00 | 0.00 | 0.00 | 0.00 | 0.00 | 0.00 | 0.00 |
| 0.5 | 1.02 | 2.50 | 0.86 | 0.81 | 1.16 | 0.06 | 0.25 | 0.29 |
| 0.75 | 1.36 | 4.66 | 1.38 | 1.37 | 1.39 | 0.12 | 0.43 | 0.43 |
| 1 | 1.66 | 6.03 | 2.48 | 1.59 | 1.62 | 0.46 | 0.61 | 0.72 |
| 2 | 2.52 | 7.90 | 3.45 | 2.25 | 2.03 | 1.01 | 1.12 | 0.97 |
| 3 | 3.18 | 9.75 | 4.48 | 2.86 | 2.42 | 1.22 | 1.26 | 1.12 |
| 5 | 3.84 | 11.91 | 6.28 | 3.38 | 3.17 | 1.40 | 1.55 | 1.62 |
| 10 | 5.05 | 16.43 | 8.97 | 4.19 | 4.03 | 1.94 | 2.30 | 2.19 |
| 20 | 6.21 | 19.70 | 11.93 | 4.95 | 4.55 | 2.19 | 2.00 | 2.45 |
| 30 | 6.82 | 20.60 | 14.90 | 5.30 | 4.84 | 1.94 | 2.27 | 2.70 |

TABLE 37

| Stirring Duration | Electrostatic Charge Amount (−μC/g) | | | | | | | |
|---|---|---|---|---|---|---|---|---|
| (min.) | B22 | B23 | B25 | Y1 | Y2 | Y3 | Y4 | Y5 |
| 0 | 0.00 | 0.00 | 0.00 | 0.00 | 0.00 | 0.00 | 0.00 | 0.00 |
| 0.5 | 2.74 | 1.29 | 1.13 | 0.81 | 1.16 | 0.06 | 0.25 | 0.29 |
| 0.75 | 4.01 | 2.19 | 1.92 | 1.37 | 1.39 | 0.12 | 0.43 | 0.43 |
| 1 | 5.23 | 2.77 | 2.42 | 1.59 | 1.62 | 0.46 | 0.61 | 0.72 |
| 2 | 8.74 | 4.71 | 4.37 | 2.25 | 2.03 | 1.01 | 1.12 | 0.97 |
| 3 | 10.80 | 6.15 | 5.80 | 2.86 | 2.42 | 1.22 | 1.26 | 1.12 |
| 5 | 13.45 | 7.76 | 8.10 | 3.38 | 3.17 | 1.40 | 1.55 | 1.62 |
| 10 | 16.78 | 9.83 | 10.46 | 4.19 | 4.03 | 1.94 | 2.30 | 2.19 |
| 20 | 19.31 | 11.38 | 12.53 | 4.95 | 4.55 | 2.19 | 2.00 | 2.45 |
| 30 | 20.23 | 12.76 | 14.00 | 5.30 | 4.84 | 1.94 | 2.27 | 2.70 |

Example C8

Environmental Stability Rating of the Resin Grains Obtained in Example C7

Using the resin grains of Example C7, the charge control resins, which had been obtained in Examples, such as (styrene-based resins) B1, B4, B5, B7, B9, B10, B11, B12, B14, B15, B21, B22, B23, B25 and the comparative resins such as Y1, Y2, Y3, Y4 and Y5, were rated in terms of environmental stability in the same manner as in Example C4. The results are shown in Table 38.

TABLE 38

| Example No. | Electrostatic Charge Amount (μC/g) | | | Environmental Stability | |
|---|---|---|---|---|---|
| | Saturation Charge Amount | Low Temperature & Low Humidity (LL) 20° C., 30% RH | High Temperature & High Humidity (HH) 30° C., 80% RH | \|LL val.\| − \|HH val.\| | \|LL val.\|/\|HH val.\| |
| B1 | −21.27 | −23.52 | −17.34 | 6.19 | 1.36 |
| B4 | −9.65 | −11.58 | −6.77 | 4.81 | 1.71 |
| B5 | −21.66 | −24.79 | −18.20 | 6.59 | 1.36 |
| B7 | −18.41 | −21.79 | −14.18 | 7.62 | 1.54 |
| B9 | −21.96 | −24.35 | −17.63 | 6.72 | 1.38 |
| B10 | −16.85 | −19.12 | −12.69 | 6.43 | 1.51 |
| B11 | −17.52 | −20.34 | −13.93 | 6.41 | 1.46 |
| B12 | −17.10 | −19.87 | −13.45 | 6.42 | 1.48 |
| B14 | −6.82 | −7.98 | −4.97 | 3.02 | 1.61 |
| B15 | −20.60 | −23.60 | −16.72 | 6.88 | 1.41 |
| B21 | −14.90 | −17.38 | −10.34 | 7.04 | 1.68 |
| B22 | −20.23 | −23.78 | −16.98 | 6.79 | 1.40 |
| B23 | −12.76 | −15.31 | −11.01 | 4.30 | 1.39 |
| B25 | −14.00 | −16.30 | −12.00 | 4.30 | 1.36 |
| Y1 | −5.30 | −6.36 | −2.12 | 4.24 | 3.00 |
| Y2 | −4.84 | −8.70 | −1.54 | 7.16 | 5.65 |
| Y3 | −1.94 | −3.40 | −0.21 | 3.19 | 16.19 |
| Y4 | −2.27 | −3.71 | −0.09 | 3.62 | 41.22 |
| Y5 | −2.70 | −4.02 | −0.15 | 3.87 | 26.80 |

As is clear from the figures, the charge control agent of the present invention, which is a charge control resin containing styrene derivative and copolymer as active ingredients facilitates prompt charge risen up and high charge amount irrespective of high speed rotation or low speed rotation.

INDUSTRIAL APPLICABILITY

The charge control resin of the present invention has, as the polymer to make its active ingredient, a styrene-based resin which is composed of a constituent unit having a suitable charge controllability so that the resin can be used as charge imparting agent, charge control agent and enhancer. Also, being excellent in heat resistance, electrostatic propensity and environmental stability, the resin is useful in industries wherein various electric charge and electrostatic charge are utilized, for example in commodities such as electrostatic powdery paint, electrophotography toner, electrostatic inkjet recorder, electronic paper, pressure sensitive copying paper and developing agent. The styrene derivative which is used as the charge control monomer to make this constituent unit of the styrene-based resin can be used as the charge control agent. According to the method of making the charge control resin of the present invention, it is possible to prepare the charge control resin which makes the charge control active ingredient for charge imparting agent, charge control agent and enhancer.

What is claimed is:

1. A charge control agent, comprising:
a charge control resin as an active ingredient, obtained by a process comprising polymerizing from 0.01 to 9.5 mol % of a styrene derivative with a vinyl group-containing monomer in the presence of a polymerization initiator, which is a co-polymerization product of the styrene derivative and the vinyl group-containing monomer, wherein the styrene derivative has formula (3):

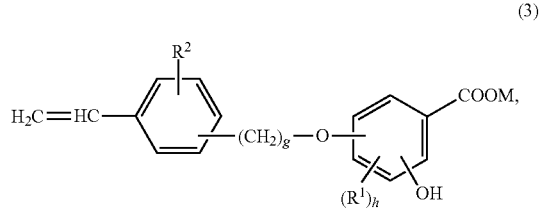

(3)

wherein, in formula (3):
each $R^1$ is independently a hydrogen atom, a hydroxyl group, a halogen atom, a carboxy-containing group, a straight-chained alkyl group having 1-18 carbon atoms, a branched alkyl group having 1-18 carbon atoms, a straight-chained alkoxy group having 1-18 carbon atoms, or a branched alkoxy group having 1-18 carbon atoms;

$R^2$ is a hydrogen atom, a hydroxyl group, a halogen atom, a carboxy-containing group, a straight-chained alkyl group having 1-18 carbon atoms, a branched alkyl group having 1-18 carbon atoms, a straight-chained alkoxy group having 1-18 carbon atoms, or a branched alkoxy group having 1-18 carbon atoms;

g is a number of 1-3;

h is a number of 1-3; and

M is a hydrogen atom, an alkali metal, a straight-chained alkyl group having 1-18 carbon atoms, a branched alkyl group having 1-18 carbon atoms, an ammonium radical, or a mixture thereof.

2. The charge control agent of claim 1, wherein the vinyl group-containing monomer has formula (4):

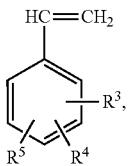

(4)

wherein, in formula (4):
$R^3$, $R^4$, and $R^5$ are each independently a hydrogen atom, a straight-chained alkyl group having 1-8 carbon atoms, a branched alkyl group having 1-8 carbon atoms, a straight-chained alkoxy group having 1-8 carbon atoms, a branched alkoxy group having 1-8 carbon atoms, or a halogen atom.

3. The charge control agent of claim 1, wherein the vinyl group-containing monomer has formula (10):

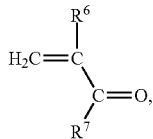

(10)

wherein, in formula (10):
$R^6$ is a methyl group or a hydrogen atom; and
$R^7$ is a hydroxyl group or an optionally substituted alkoxy group.

4. The charge control agent of claim 1, wherein the vinyl group-containing monomer is a hydrophilic unsaturated monomer.

5. The charge control agent of claim 4, wherein the hydrophilic unsaturated monomer is an acrylic acid or methacrylic acid.

6. The charge control agent of claim 4, wherein the hydrophilic unsaturated monomer is an acrylic acid alkyl ester or a methacrylic acid alkyl ester.

7. The charge control agent of claim 6, wherein the acrylic acid alkyl ester is at least one selected from the group consisting of hydroxyethyl acrylate, hydroxypropyl acrylate, and 2-hydroxypropyl acrylate, and
wherein the methacrylic acid alkyl ester is at least one selected from the group consisting of hydroxyethyl methacrylate, hydroxypropyl methacrylate, and 2-hydroxypropyl methacrylate.

8. The charge control agent of claim 4, wherein the hydrophilic unsaturated monomer is an acrylamide or a methacrylamide.

9. The charge control agent of claim 8, wherein the acrylamide is at least one selected from the group consisting of acrylamide, N-methylol acrylamide, diacetone acrylamide, N-isopropyl acrylamide, N,N-diethyl acrylamide, N,N-dimethylaminopropyl acrylamide, and N,N-dimethyl acrylamide, and
wherein the methacrylamide is at least one selected from the group consisting of methacrylamide, N-methylol methacrylamide, diacetone methacrylamide, N-isopropyl methacrylamide, N,N-diethyl methacrylamide, N,N-dimethylaminopropyl methacrylamide, and N,N-dimethyl methacrylamide.

10. The charge control agent of claim 4, wherein the hydrophilic unsaturated monomer is an alkylacrylamide sulfonate or a free acid thereof or an ester thereof, or an alkylmethacrylamide sulfonate or a free acid thereof or an ester thereof.

11. The charge control agent of claim 10, wherein the alkylacrylamide sulfonate or the free acid thereof or the ester thereof is at least one selected from the group consisting of an ethylacrylamide sulfonic acid, a propylacrylamide sulfonic acid, and a tert-butyl-acrylamidesulfonic acid, and
wherein the alkylmethacrylamide sulfonate or the free acid thereof or the ester thereof is at least one selected from the group consisting of an ethylmethacrylamide sulfonic acid, a propylmethacrylamide sulfonic acid, and a tert-butyl-methacrylamidesulfonic acid.

12. The charge control agent of claim 11, wherein the alkylacrylamide sulfonate or the free acid thereof or the ester thereof is a tert-butylacrylamidesulfonic acid, and
wherein the alkylmethacrylamide sulfonate or the free acid thereof or the ester thereof is a tert-butylmethacrylamidesulfonic acid.

13. The charge control agent of claim 4, wherein the hydrophilic unsaturated monomer is a styrene sulfonic acid.

14. The charge control agent of claim 4, wherein the hydrophilic unsaturated monomer is a metallyl sulfonic acid.

15. The charge control agent of claim 4, wherein the hydrophilic unsaturated monomer is acryloyl morpholine.

16. The charge control agent of claim 4, wherein the hydrophilic unsaturated monomer is acrylonitrile.

17. The charge control agent of claim 4, wherein the hydrophilic unsaturated monomer is at least one selected from the group consisting of monobutyl maleate, isobutyl maleate, itaconic acid, and fumaric acid.

* * * * *